US007776560B2

(12) United States Patent
Ni et al.

(10) Patent No.: US 7,776,560 B2
(45) Date of Patent: *Aug. 17, 2010

(54) HUMAN TUMOR NECROSIS FACTOR RECEPTOR TR9 ANTIBODY

(75) Inventors: Jian Ni, Germantown, MD (US); Guo-Liang Yu, Berkeley, CA (US); Ping Fan, Rockville, MD (US); Reiner L. Gentz, Belo Horizonte-Mg (BR)

(73) Assignee: Human Genome Scienes, Inc., Rockville, MD (US)

( * ) Notice: Subject to any disclaimer, the term of this patent is extended or adjusted under 35 U.S.C. 154(b) by 199 days.

This patent is subject to a terminal disclaimer.

(21) Appl. No.: 11/780,643

(22) Filed: Jul. 20, 2007

(65) Prior Publication Data

US 2007/0298459 A1 Dec. 27, 2007

Related U.S. Application Data

(60) Continuation of application No. 10/834,966, filed on Apr. 30, 2004, now abandoned, which is a division of application No. 10/041,574, filed on Jan. 10, 2002, now Pat. No. 6,919,078, which is a division of application No. 09/527,236, filed on Mar. 16, 2000, now Pat. No. 6,358,508, and a continuation-in-part of application No. 09/095,094, filed on Jun. 10, 1998, now Pat. No. 6,949,358.

(60) Provisional application No. 60/126,019, filed on Mar. 24, 1999, provisional application No. 60/134,220, filed on May 14, 1999, provisional application No. 60/052,991, filed on Jun. 11, 1997.

(51) Int. Cl.
C07K 14/705 (2006.01)
C07K 16/28 (2006.01)
C12N 5/12 (2006.01)
G01N 33/53 (2006.01)

(52) U.S. Cl. ............... 435/7.21; 435/7.9; 435/7.92; 435/328; 435/334; 435/346; 530/350; 530/387.3; 530/388.22; 530/389.1; 530/388.15; 530/391.1; 530/391.3; 424/185.1

(58) Field of Classification Search .......... None
See application file for complete search history.

(56) References Cited

U.S. PATENT DOCUMENTS

| | | | |
|---|---|---|---|
| 5,112,954 A | 5/1992 | Abrams et al. | |
| 5,563,039 A | 10/1996 | Goeddel et al. | |
| 5,856,161 A | 1/1999 | Aggarwal et al. | |
| 5,876,691 A | 3/1999 | Chester et al. | |
| 6,013,476 A | 1/2000 | Deen et al. | |
| 6,235,883 B1 | 5/2001 | Jakobovits et al. | |
| 6,358,508 B1 | 3/2002 | Ni et al. | |
| 6,667,390 B2 | 12/2003 | Ni et al. | |
| 6,919,078 B2 | 7/2005 | Ni et al. | |
| 6,949,358 B1 | 9/2005 | Ni et al. | |
| 2004/0197870 A1 | 10/2004 | Ni et al. | |
| 2005/0239123 A1 | 10/2005 | Ni et al. | |

FOREIGN PATENT DOCUMENTS

| | | |
|---|---|---|
| EP | 0 869 179 | 10/1998 |
| WO | WO-98/45437 | 10/1998 |
| WO | WO-98/56892 | 12/1998 |
| WO | WO-99/11790 | 3/1999 |
| WO | WO-99/15663 | 4/1999 |
| WO | WO-99/31128 | 6/1999 |
| WO | WO-99/46281 | 9/1999 |
| WO | WO-99/54447 | 10/1999 |
| WO | WO-99/66039 | 12/1999 |
| WO | WO-00/01817 | 1/2000 |
| WO | WO-00/24771 | 5/2000 |
| WO | WO-00/34294 | 6/2000 |
| WO | WO-00/34335 | 6/2000 |
| WO | WO-00/37643 | 6/2000 |
| WO | WO-00/53756 | 9/2000 |

OTHER PUBLICATIONS

U.S. Appl. No. 09/912,293, Rosen et al.
U.S. Appl. No. 09/912,292, Rosen et al.
U.S. Appl. No. 60/041,796, Hurle.
GenBank Accession No. AAC34583 (Sep. 5, 1998).
GenBank Accession No. AF068868 (Sep. 5, 1998).
GenBank Accession No. AL096801 (Nov. 29, 1999).
GenBank Accession No. AA156356 (Dec. 11, 1996).
GenBank Accession No. N49208 (Feb. 14, 1996).
GenBank Accession No. AA351536 (Apr. 21, 1997).
GenBank Accession No. AA155873 (Dec. 11, 1996).
GenBank Accession No. D59902 (Aug. 28, 1995).
GenBank Accession No. H41872 (Jul. 31, 1995).
GenBank Accession No. AA357231 (Apr. 21, 1997).
GenBank Accession No. H41873 (Jul. 31, 1995).
GenBank Accession No. T17352 (Feb. 14, 1997).
GenBank Accession No. AA374471 (Apr. 21, 1997).
GenBank Accession No. AA918818 (Apr. 13, 1998).
Genbank Accession No. AA186423 (Jan. 6, 1997).
GenBank Accession No. AA072902 (Oct. 1, 1996).
GeneSeq (Version 67.0) Abstract of German Document DE198 18 619 (Aug. 7, 2001).
Dietrich, F.S., Accession No. S50578, EMBL Data Library, the sequence of *S. Cerevisiae* lambda clone 3612 and cosmid 9794, superfamily protein-tyrosine-phosphatase homology, (Dec. 1994).
Pan et al., "Identification and functional characterization of DR6, a novel death domain-containing TNF receptor," FEBS Letters 431:351-356 (1998).
Yoshimatsu et al., "Control of Gene Expression by Artificial Introns in *Saccharomyces cerevisiae*,," Science 244:1346-1348, (1989).
International Search Report mailed on Aug. 28, 2000, in connection with a copending International Application, PCT/US98/11932.

(Continued)

Primary Examiner—Lorraine Spector
Assistant Examiner—Claire Kaufman

(57) ABSTRACT

The present invention relates to a novel member of the tumor necrosis factor family of receptors. In particular, isolated nucleic acid molecules are provided encoding the human TR9 receptor. TR9 polypeptides are also provided as are vectors, host cells and recombinant methods for producing the same. The invention further relates to screening methods for identifying agonists and antagonists of TR9 receptor activity.

16 Claims, 11 Drawing Sheets

OTHER PUBLICATIONS

P. Mottram, Immunology and Cell Biology (2003) 81, pp. 350-353.
Mouzaki et al., Current Medicinal Chemistry (2005) 12, pp. 1537-1550.
Lee et al., Basic and Clinical Immunology (2005) 116, No. 4, pp. 900-905.
Foell et al., Springer Seminars in Immunology (2006) 28, pp. 153-162.
Decision on Deen Preliminary Motions and Ni Motion, *Deen et al.* v. *Ni et al.*, Patent Interference No. 104,784 (Jul. 9, 2003).
Decision on Request for Reconsideration and Final Judgment, *Deen et al.* v. *Ni et al.*, Patent Interference No. 104,784 (Oct. 29, 2003).
New England Biolabs 1993/94 Catalog, Random Primer, p. 91.
GenBank Accession No. AA555059 (Sep. 8, 1997).
GenBank Accession No. AA181032 (Mar. 10, 1998).
GenBank Accession No. AA621819 (Oct. 31, 1997).
GenBank Accession No. AA554244 (Sep. 9, 1997).
GenBank Accession No. AA662654 (Nov. 12, 1997).
International Search Report mailed on Oct. 13, 1998, in connection with International Application No. PCT/US98/11932.
Liu et al., "Enhanced CD4$^+$T Cell Proliferation and Th2 Cytokine Production in *DR6*-Deficient Mice" *Immunity* 15:23-24 (Jul. 2001).
Zhao et al, "Impaired c-Jun Amino Terminal Kinase Activity and T Cell Differentiation in Death Receptor 6-deficient Mice" *J. Exp. Med.* 194:1441-1448 (Nov. 19, 2001).
Chinnaiyan et al., "Signal Transduction by DR3, a Death Domain-Containing Receptor Related to TNFR-1 and CD95" *Science* 274:990-992 (Nov. 8, 1996).
Nagata, Shigekazu, "Apoptosis by Death Factor" *Cell* 88:355-365 (Feb. 7, 1997).
Kohno et al., "A second tumor necrosis factor receptor gene product can shed a naturally occurring tumor necrosis factor inhibitor" *Proc. Natl. Acad. Sci. USA*, 87:8331-8335 (Nov. 1990).

Figure 1A

```
                10                      30                      50
       GCGGGCTGCAGTCGCGGCGGCTTCTCCCCGCCTGGGCGGCCGCGCCGCTGGGCAGGTGCT
                70                      90                     110
       GAGCGCCCCTAGAGCCTCCCTTGCCGCCTCCCTCCTCTGCCCGGCCGCAGCAGTGCACAT
               130                     150                     170
       GGGGTGTTGGAGGTAGATGGGCTCCCGGCCCGGGAGGCGGCGGTGGATGCGGCGCTGGGC
               190                     210                     230
       AGAAGCAGCCGCCGATTCCAGCTGCCCCGCGCGCCCCGGGCGCCCCTGCGAGTCCCCGGT
               250                     270                     290
       TCAGCCATGGGGACCTCTCCGAGCAGCAGCACCGCCCTCGCCTCCTGCAGCCGCATCGCC
                 M  G  T  S  P  S  S  S  T  A  L  A  S  C  S  R  I  A
               310                     330                     350
       CGCCGAGCCACAGCCACGATGATCGCGGGCTCCCTTCTCCTGCTTGGATTCCTTAGCACC
        R  R  A  T  A  T  M  I  A  G  S  L  L  L  L  G  F  L  S  T
               370                     390                     410
       ACCACAGCTCAGCCAGAACAGAAGGCCTCGAATCTCATTGGCACATACCGCCATGTTGAC
        T  T  A  Q  P  E  Q  K  A  S  N  L  I  G  T  Y  R  H  V  D
               430                     450                     470
       CGTGCCACCGGCCAGGTGCTAACCTGTGACAAGTGTCCAGCAGGAACCTATGTCTCTGAG
        R  A  T  G  Q  V  L  T  C  D  K  C  P  A  G  T  Y  V  S  E
               490                     510                     530
       CATTGTACCAACACAAGCCTGCGCGTCTGCAGCAGTTGCCCTGTGGGGACCTTTACCAGG
        H  C  T  N  T  S  L  R  V  C  S  S  C  P  V  G  T  F  T  R
               550                     570                     590
       CATGAGAATGGCATAGAGAAATGCCATGACTGTAGTCAGCCATGCCCATGGCCAATGATT
        H  E  N  G  I  E  K  C  H  D  C  S  Q  P  C  P  W  P  M  I
               610                     630                     650
       GAGAAATTACCTTGTGCTGCCTTGACTGACCGAGAATGCACTTGCCCACCTGGCATGTTC
        E  K  L  P  C  A  A  L  T  D  R  E  C  T  C  P  P  G  M  F
               670                     690                     710
       CAGTCTAACGCTACCTGTGCCCCCCATACGGTGTGTCCTGTGGGTTGGGGTGTGCGGAAG
        Q  S  N  A  T  C  A  P  H  T  V  C  P  V  G  W  G  V  R  K
               730                     750                     770
       AAAGGGACAGAGACTGAGGATGTGCGGTGTAAGCAGTGTGCTCGGGGTACCTTCTCAGAT
        K  G  T  E  T  E  D  V  R  C  K  Q  C  A  R  G  T  F  S  D
               790                     810                     830
       GTGCCTTCTAGTGTGATGAAATGCAAAGCATACACAGACTGTCTGAGTCAGAACCTGGTG
        V  P  S  S  V  M  K  C  K  A  Y  T  D  C  L  S  Q  N  L  V
               850                     870                     890
       GTGATCAAGCCGGGGACCAAGGAGACAGACAACGTCTGTGGCACACTCCCGTCCTTCTCC
        V  I  K  P  G  T  K  E  T  D  N  V  C  G  T  L  P  S  F  S
               910                     930                     950
       AGCTCCACCTCACCTTCCCCTGGCACAGCCATCTTTCCACGCCCTGAGCACATGGAAACC
        S  S  T  S  P  S  P  G  T  A  I  F  P  R  P  E  H  M  E  T
               970                     990                    1010
       CATGAAGTCCCTTCCTCCACTTATGTTCCCAAAGGCATGAACTCAACAGAATCCAACTCT
        H  E  V  P  S  S  T  Y  V  P  K  G  M  N  S  T  E  S  N  S
```

Figure 1B

```
           1030                1050                1070
TCTGCCTCTGTTAGACCAAAGGTACTGAGTAGCATCCAGGAAGGGACAGTCCCTGACAAC
 S   A   S   V   R   P   K   V   L   S   S   I   Q   E   G   T   V   P   D   N
           1090                1110                1130
ACAAGCTCAGCAAGGGGGAAGGAAGACGTGAACAAGACCCTCCCAAACCTTCAGGTAGTC
 T   S   S   A   R   G   K   E   D   V   N   K   T   L   P   N   L   Q   V   V
           1150                1170                1190
AACCACCAGCAAGGCCCCCACCACAGACACATCCTGAAGCTGCTGCCGTCCATGGAGGCC
 N   H   Q   Q   G   P   H   H   R   H   I   L   K   L   L   P   S   M   E   A
           1210                1230                1250
ACTGGGGGCGAGAAGTCCAGCACGCCCATCAAGGGCCCCAAGAGGGGACATCCTAGACAG
 T   G   G   E   K   S   S   T   P   I   K   G   P   K   R   G   H   P   R   Q
           1270                1290                1310
AACCTACACAAGCATTTTGACATCAATGAGCATTTGCCCTGGATGATTGTGCTTTTCCTG
 N   L   H   K   H   F   D   I   N   E   H   L   P   W   M   I   V   L   F   L
           1330                1350                1370
CTGCTGGTGCTTGTGGTGATTGTGGTGTGCAGTATCCGGAAAAGCTCGAGGACTCTGAAA
 L   L   V   L   V   V   I   V   V   C   S   I   R   K   S   S   R   T   L   K
           1390                1410                1430
AAGGGGCCCCGGCAGGATCCCAGTGCCATTGTGGAAAAGGCAGGGCTGAAGAAATCCATG
 K   G   P   R   Q   D   P   S   A   I   V   E   K   A   G   L   K   K   S   M
           1450                1470                1490
ACTCCAACCCAGAACCGGGAGAAATGGATCTACTACTGCAATGGCCATGGTATCGATATC
 T   P   T   Q   N   R   E   K   W   I   Y   Y   C   N   G   H   G   I   D   I
           1510                1530                1550
CTGAAGCTTGTAGCAGCCCAAGTGGGAAGCCAGTGGAAAGATATCTATCAGTTTCTTTGC
 L   K   L   V   A   A   Q   V   G   S   Q   W   K   D   I   Y   Q   F   L   C
           1570                1590                1610
AATGCCAGTGAGAGGGAGGTTGCTGCTTTCTCCAATGGGTACACAGCCGACCACGAGCGG
 N   A   S   E   R   E   V   A   A   F   S   N   G   Y   T   A   D   H   E   R
           1630                1650                1670
GCCTACGCAGCTCTGCAGCACTGGACCATCCGGGGCCCCGAGGCCAGCCTCGCCCAGCTA
 A   Y   A   A   L   Q   H   W   T   I   R   G   P   E   A   S   L   A   Q   L
           1690                1710                1730
ATTAGCGCCCTGCGCCAGCACCGGAGAAACGATGTTGTGGAGAAGATTCGTGGGCTGATG
 I   S   A   L   R   Q   H   R   R   N   D   V   V   E   K   I   R   G   L   M
           1750                1770                1790
GAAGACACCACCCAGCTGGAAACTGACAAACTAGCTCTCCCGATGAGCCCCAGCCCGCTT
 E   D   T   T   Q   L   E   T   D   K   L   A   L   P   M   S   P   S   P   L
           1810                1830                1850
AGCCCGAGCCCCATCCCCAGCCCCAACGCGAAACTTGAGAATTCCGCTCTCCTGACGGTG
 S   P   S   P   I   P   S   P   N   A   K   L   E   N   S   A   L   L   T   V
           1870                1890                1910
GAGCCTTCCCCACAGGACAAGAACAAGGGCTTCTTCGTGGATGAGTCGGAGCCCCTTCTC
 E   P   S   P   Q   D   K   N   K   G   F   F   V   D   E   S   E   P   L   L
           1930                1950                1970
CGCTGTGACTCTACATCCAGCGGCTCCTCCGCGCTGAGCAGGAACGGTTCCTTTATTACC
 R   C   D   S   T   S   S   G   S   S   A   L   S   R   N   G   S   F   I   T
```

Figure 1C

```
            1990                2010                2030
AAAGAAAAGAAGGACACAGTGTTGCGGCAGGTACGCCTGGACCCCTGTGACTTGCAGCCT
 K  E  K  K  D  T  V  L  R  Q  V  R  L  D  P  C  D  L  Q  P
            2050                2070                2090
ATCTTTGATGACATGCTCCACTTTCTAAATCCTGAGGAGCTGCGGGTGATTGAAGAGATT
 I  F  D  D  M  L  H  F  L  N  P  E  E  L  R  V  I  E  E  I
            2110                2130                2150
CCCCAGGCTGAGGACAAACTAGACCGGCTATTCGAAATTATTGGAGTCAAGAGCCAGGAA
 P  Q  A  E  D  K  L  D  R  L  F  E  I  I  G  V  K  S  Q  E
            2170                2190                2210
GCCAGCCAGACCCTCCTGGACTCTGTTTATAGCCATCTTCCTGACCTGCTGTAGAACATA
 A  S  Q  T  L  L  D  S  V  Y  S  H  L  P  D  L  L  *
            2230                2250                2270
GGGATACTGCATTCTGGAAATTACTCAATTTAGTGGCAGGGTGGTTTTTTAATTTTCTTC
            2290                2310                2330
TGTTTCTGATTTTTGTTGTTTGGGGTGTGTGTGTGTGTTTGTGTGTGTGTGTGTGTGTGT
            2350                2370                2390
GTGTGTGTGTGTGTGTGTGTTTAACAGAGAATATGGCCAGTGCTTGAGTTCTTTCTCC
            2410                2430                2450
TTCTCTCTCTCTTTTTTTTTAAATAACTCTTCTGGGAAGTTGGTTTATAAGCCTTTGCC
            2470                2490                2510
AGGTGTAACTGTTGTGAAATACCCACCACTAAAGTTTTTTAAGTTCCATATTTTCTCCAT
            2530                2550                2570
TTTGCCTTCTTATGTATTTTCGAGATTATTCTGTGCACTTTAAATTTACTTAACTTACCA
            2590                2610                2630
TAAATGCAGTGTGACTTTTCCCACACACTGGATTGTGAGGCTCTTAACTTCTTAAAAGTA
            2650                2670                2690
TAATGGCATCTTGTGAATCCTATAAGCAGTCTTTATGTCTCTTAACATTCACACCTACTT
            2710                2730                2750
TTTAAAAACAAATATTATTACTATTTTTATTATTGTTTGTCCTTTATAAATTTTCTTAAA
            2770                2790                2810
GATTAAGAAAATTTAAGACCCCATTGAGTTACTGTAATGCAATTCAACTTTGAGTTATCT
            2830                2850                2870
TTTAAATATGTCTTGTATAGTTCATATTCATGGCTGAAACTTGACCACACTATTGCTGAT
            2890                2910                2930
TGTATGGTTTTCACCTGGACACCGTGTAGAATGCTTGATTACTTGTACTCTTCTTATGCT
            2950                2970                2990
AATATGCTCTGGGCTGGAGAAATGAAATCCTCAAGCCATCAGGATTTGCTATTTAAGTGG
            3010                3030                3050
CTTGACAACTGGGCCACCAAAGAACTTGAACTTCACCTTTTAGGATTTGAGCTGTTCTGG
            3070                3090                3110
AACACATTGCTGCACTTTGGAAAGTCAAAATCAAGTGCCAGTGGCGCCCTTTCCATAGAG
            3130                3150                3170
AATTTGCCCAGCTTTGCTTTAAAAGATGTCTTGTTTTTTATATACACATAATCAATAGGT
            3190                3210                3230
CCAATCTGCTCTCAAGGCCTTGGTCCTGGTGGGATTCCTTCACCAATTACTTTAATTAAA
            3250                3270                3290
AATGGCTGCAACTGTAAGAACCCTTGTCTGATATATTTGCAACTATGCTCCCATTTACAA
```

Figure 1D

```
          3310                    3330                    3350
ATGTACCTTCTAATGCTCAGTTGCCAGGTTCCAATGCAAAGGTGGCGTGGACTCCCTTTG
          3370                    3390                    3410
TGTGGGTGGGGTTTGTGGGTAGTGGTGAAGGACCGATATCAGAAAAATGCCTTCAAGTGT
          3430                    3450                    3470
ACTAATTTATTAATAAACATTAGGTGTTTGTTAAAAAAAAAAAAAAAAAAAAA
```

```
  1  MGTSPSSSTALASCSRIARRATATMIAGSLLLLGFLSTTTAQPEQKASNLIGTYRHVDRATGQVLTCDKC    70
     ────────────────────────────────▲
     PAGTYVSEHCTNTSLRVCSSCPVGTETRHENGIEKCHDCSQPCPWPMIEKLPCAALTDRECTCPPGMFQS   140

NATCAPHTVCPVGWGVRKKGTETEDVRCKQCARGTFSDVPSSVMKCKAYTDCLSQNLVVIKPGTKETDNV   210

CGTLPSFSSSTSPSPGTAIFPRPEHMETHEVPSSTYVPKGMNSTESNSSASVRPKVLSSIQEGTVPDNTS   280

SARGKEDVNKTLPNLQVVNHQQGPHHRHILKLLPSMEATGGEKSSTPIKGPKRGHPRQNLHKHFDINEHL   350

PWMIVLFLLLVLVIVVCSIRKSSRTLKKGPRQDPSAIVEKAGLKKSMTPTQNREKWIYYCNGHGIDILK   420
     ══════════════════
     LVAAQVGS|QWKDIYQFLCNASEREVAAFSNGYTADHERAYAALQHWTIRGPEASLAQLISALRQHRRNDV   490
     ══════════
     VEKIR|GLMEDTTQLETDKLALPMSPSPLSPSPIPSPNAKLENSALLTVEPSPQDKNKGFFVDESEPLLRC   560
     ─────
     DSTSSGSSALSRNGSFITKEKKDTVLRQVRLDPCDLQPIFDDMLHFLNPEELRVIEEIPQAEDKLDRLFE   630

IIGVKSQEASQTLLDSVYSHLPDLL                                                655
```

Figure 4B

```
T C D K K C A G T Y V S E H C T N T S E R V G S S C P V G T F T R H E N G I E K   TR9
  G D K C G P G T Y L K Q H C T A K W K T V C A P C P D H Y Y T D S W H T S D E   OPG

C H D C S Q P C P W P M I E K L P C A L T D R E C T C P P G M F Q S N A T C A K   TR9
  G L Y G S P C V P C E K Q Y E Q Y K K C N R T H N R V C E C K E G R Y L E F G L  OPG

P H V G P C V G W R K G T E T D V R C Q C A Q G R G P D G F F S N E T S K A P K   TR9
  K H R S C P P G F G V V Q A G T P E R N T V C K R C P D G F F S N E T S S K A P  OPG

C K A Y T D C L S Q N L V L I K P G T K E T D N V C G                              TR9
  C R K H T N C S V F G L L L T Q K G N A T H D N I C S                            OPG
```

Figure 4C

SEQUENCE LISTING

```
<160> NUMBER OF SEQ ID NOS: 27

<210> SEQ ID NO 1
<211> LENGTH: 3474
<212> TYPE: DNA
<213> ORGANISM: Homo sapiens
<220> FEATURE:
<221> NAME/KEY: CDS
<222> LOCATION: (247)..(2211)
<220> FEATURE:
<221> NAME/KEY: sig_peptide
<222> LOCATION: (247)..(366)
<220> FEATURE:
<221> NAME/KEY: mat_peptide
<222> LOCATION: (367)..(2211)

<400> SEQUENCE: 1
gcgggctgca gtcgcggcgg cttctccccg cctgggcggc cgcgccgctg ggcaggtgct      60
gagcgcccct agagcctccc ttgccgcctc cctcctctgc ccggccgcag cagtgcacat     120
ggggtgttgg aggtagatgg gctcccgccc cgggaggcgg cggtggatgc ggcgctgggc     180
agaagcagcc gccgattcca gctgcccgc gcgccccggg cgcccctgcg agtccccggt      240 tcagcc atg ggg acc tct ccg agc agc agc acc gcc ctc gcc tcc tgc         288
       Met Gly Thr Ser Pro Ser Ser Ser Thr Ala Leu Ala Ser Cys
       -40             -35                 -30 agc cgc atc gcc cgc cga gcc aca gcc acg atg atc gcg ggc tcc ctt        336
Ser Arg Ile Ala Arg Arg Ala Thr Ala Thr Met Ile Ala Gly Ser Leu
    -25                 -20                 -15 ctc ctg ctt gga ttc ctt agc acc acc aca gct cag cca gaa cag aag        384
Leu Leu Leu Gly Phe Leu Ser Thr Thr Thr Ala Gln Pro Glu Gln Lys
-10                  -5                  -1   1                  5 gcc tcg aat ctc att ggc aca tac cgc cat gtt gac cgt gcc acc ggc        432
Ala Ser Asn Leu Ile Gly Thr Tyr Arg His Val Asp Arg Ala Thr Gly
                10                  15                  20 cag gtg cta acc tgt gac aag tgt cca gca gga acc tat gtc tct gag        480
Gln Val Leu Thr Cys Asp Lys Cys Pro Ala Gly Thr Tyr Val Ser Glu
            25                  30                  35 cat tgt acc aac aca agc ctg cgc gtc tgc agc agt tgc cct gtg ggg        528
His Cys Thr Asn Thr Ser Leu Arg Val Cys Ser Ser Cys Pro Val Gly
         40                  45                  50 acc ttt acc agg cat gag aat ggc ata gag aaa tgc cat gac tgt agt        576
Thr Phe Thr Arg His Glu Asn Gly Ile Glu Lys Cys His Asp Cys Ser
55                  60                  65                  70 cag cca tgc cca tgg cca atg att gag aaa tta cct tgt gct gcc ttg        624
Gln Pro Cys Pro Trp Pro Met Ile Glu Lys Leu Pro Cys Ala Ala Leu
                75                  80                  85 act gac cga gaa tgc act tgc cca cct ggc atg ttc cag tct aac gct        672
Thr Asp Arg Glu Cys Thr Cys Pro Pro Gly Met Phe Gln Ser Asn Ala
            90                  95                 100
```

-continued

```
acc tgt gcc ccc cat acg gtg tgt cct gtg ggt tgg ggt gtg cgg aag       720
Thr Cys Ala Pro His Thr Val Cys Pro Val Gly Trp Gly Val Arg Lys
        105                 110                 115 aaa ggg aca gag act gag gat gtg cgg tgt aag cag tgt gct cgg ggt       768
Lys Gly Thr Glu Thr Glu Asp Val Arg Cys Lys Gln Cys Ala Arg Gly
    120                 125                 130 acc ttc tca gat gtg cct tct agt gtg atg aaa tgc aaa gca tac aca       816
Thr Phe Ser Asp Val Pro Ser Ser Val Met Lys Cys Lys Ala Tyr Thr
135                 140                 145                 150 gac tgt ctg agt cag aac ctg gtg gtg atc aag ccg ggg acc aag gag       864
Asp Cys Leu Ser Gln Asn Leu Val Val Ile Lys Pro Gly Thr Lys Glu
                155                 160                 165 aca gac aac gtc tgt ggc aca ctc ccg tcc ttc tcc agc tcc acc tca       912
Thr Asp Asn Val Cys Gly Thr Leu Pro Ser Phe Ser Ser Ser Thr Ser
            170                 175                 180 cct tcc cct ggc aca gcc atc ttt cca cgc cct gag cac atg gaa acc       960
Pro Ser Pro Gly Thr Ala Ile Phe Pro Arg Pro Glu His Met Glu Thr
        185                 190                 195 cat gaa gtc cct tcc tcc act tat gtt ccc aaa ggc atg aac tca aca      1008
His Glu Val Pro Ser Ser Thr Tyr Val Pro Lys Gly Met Asn Ser Thr
    200                 205                 210 gaa tcc aac tct tct gcc tct gtt aga cca aag gta ctg agt agc atc      1056
Glu Ser Asn Ser Ser Ala Ser Val Arg Pro Lys Val Leu Ser Ser Ile
215                 220                 225                 230 cag gaa ggg aca gtc cct gac aac aca agc tca gca agg ggg aag gaa      1104
Gln Glu Gly Thr Val Pro Asp Asn Thr Ser Ser Ala Arg Gly Lys Glu
                235                 240                 245 gac gtg aac aag acc ctc cca aac ctt cag gta gtc aac cac cag caa      1152
Asp Val Asn Lys Thr Leu Pro Asn Leu Gln Val Val Asn His Gln Gln
            250                 255                 260 ggc ccc cac cac aga cac atc ctg aag ctg ctg ccg tcc atg gag gcc      1200
Gly Pro His His Arg His Ile Leu Lys Leu Leu Pro Ser Met Glu Ala
        265                 270                 275 act ggg ggc gag aag tcc agc acg ccc atc aag ggc ccc aag agg gga      1248
Thr Gly Gly Glu Lys Ser Ser Thr Pro Ile Lys Gly Pro Lys Arg Gly
    280                 285                 290 cat cct aga cag aac cta cac aag cat ttt gac atc aat gag cat ttg      1296
His Pro Arg Gln Asn Leu His Lys His Phe Asp Ile Asn Glu His Leu
295                 300                 305                 310 ccc tgg atg att gtg ctt ttc ctg ctg ctg gtg ctt gtg gtg att gtg      1344
Pro Trp Met Ile Val Leu Phe Leu Leu Leu Val Leu Val Val Ile Val
                315                 320                 325 gtg tgc agt atc cgg aaa agc tcg agg act ctg aaa aag ggg ccc cgg      1392
Val Cys Ser Ile Arg Lys Ser Ser Arg Thr Leu Lys Lys Gly Pro Arg
            330                 335                 340 cag gat ccc agt gcc att gtg gaa aag gca ggg ctg aag aaa tcc atg      1440
Gln Asp Pro Ser Ala Ile Val Glu Lys Ala Gly Leu Lys Lys Ser Met
        345                 350                 355 act cca acc cag aac cgg gag aaa tgg atc tac tac tgc aat ggc cat      1488
Thr Pro Thr Gln Asn Arg Glu Lys Trp Ile Tyr Tyr Cys Asn Gly His
    360                 365                 370 ggt atc gat atc ctg aag ctt gta gca gcc caa gtg gga agc cag tgg      1536
Gly Ile Asp Ile Leu Lys Leu Val Ala Ala Gln Val Gly Ser Gln Trp
375                 380                 385                 390 aaa gat atc tat cag ttt ctt tgc aat gcc agt gag agg gag gtt gct      1584
Lys Asp Ile Tyr Gln Phe Leu Cys Asn Ala Ser Glu Arg Glu Val Ala
                395                 400                 405 gct ttc tcc aat ggg tac aca gcc gac cac gag cgg gcc tac gca gct      1632
Ala Phe Ser Asn Gly Tyr Thr Ala Asp His Glu Arg Ala Tyr Ala Ala
            410                 415                 420
```

-continued

| | | |
|---|---|---|
| ctg cag cac tgg acc atc cgg ggc ccc gag gcc agc ctc gcc cag cta<br>Leu Gln His Trp Thr Ile Arg Gly Pro Glu Ala Ser Leu Ala Gln Leu<br>425 430 435 | | 1680 |
| att agc gcc ctg cgc cag cac cgg aga aac gat gtt gtg gag aag att<br>Ile Ser Ala Leu Arg Gln His Arg Arg Asn Asp Val Val Glu Lys Ile<br>440 445 450 | | 1728 |
| cgt ggg ctg atg gaa gac acc acc cag ctg gaa act gac aaa cta gct<br>Arg Gly Leu Met Glu Asp Thr Thr Gln Leu Glu Thr Asp Lys Leu Ala<br>455 460 465 470 | | 1776 |
| ctc ccg atg agc ccc agc ccg ctt agc ccg agc ccc atc ccc agc ccc<br>Leu Pro Met Ser Pro Ser Pro Leu Ser Pro Ser Pro Ile Pro Ser Pro<br>475 480 485 | | 1824 |
| aac gcg aaa ctt gag aat tcc gct ctc ctg acg gtg gag cct tcc cca<br>Asn Ala Lys Leu Glu Asn Ser Ala Leu Leu Thr Val Glu Pro Ser Pro<br>490 495 500 | | 1872 |
| cag gac aag aac aag ggc ttc ttc gtg gat gag tcg gag ccc ctt ctc<br>Gln Asp Lys Asn Lys Gly Phe Phe Val Asp Glu Ser Glu Pro Leu Leu<br>505 510 515 | | 1920 |
| cgc tgt gac tct aca tcc agc ggc tcc tcc gcg ctg agc agg aac ggt<br>Arg Cys Asp Ser Thr Ser Ser Gly Ser Ser Ala Leu Ser Arg Asn Gly<br>520 525 530 | | 1968 |
| tcc ttt att acc aaa gaa aag aag gac aca gtg ttg cgg cag gta cgc<br>Ser Phe Ile Thr Lys Glu Lys Lys Asp Thr Val Leu Arg Gln Val Arg<br>535 540 545 550 | | 2016 |
| ctg gac ccc tgt gac ttg cag cct atc ttt gat gac atg ctc cac ttt<br>Leu Asp Pro Cys Asp Leu Gln Pro Ile Phe Asp Asp Met Leu His Phe<br>555 560 565 | | 2064 |
| cta aat cct gag gag ctg cgg gtg att gaa gag att ccc cag gct gag<br>Leu Asn Pro Glu Glu Leu Arg Val Ile Glu Glu Ile Pro Gln Ala Glu<br>570 575 580 | | 2112 |
| gac aaa cta gac cgg cta ttc gaa att att gga gtc aag agc cag gaa<br>Asp Lys Leu Asp Arg Leu Phe Glu Ile Ile Gly Val Lys Ser Gln Glu<br>585 590 595 | | 2160 |
| gcc agc cag acc ctc ctg gac tct gtt tat agc cat ctt cct gac ctg<br>Ala Ser Gln Thr Leu Leu Asp Ser Val Tyr Ser His Leu Pro Asp Leu<br>600 605 610 | | 2208 |
| ctg tagaacatag ggatactgca ttctggaaat tactcaattt agtggcaggg<br>Leu<br>615 | | 2261 |
| tggttttta atttcttct gtttctgatt tttgttgttt ggggtgtgtg tgtgtgtttg | | 2321 |
| tgtgtgtgtg tgtgtgtgtg tgtgtgtgtg tgtgtgtgtg tttaacagag aatatggcca | | 2381 |
| gtgcttgagt tctttctcct tctctctctc tttttttttt aaataactct tctgggaagt | | 2441 |
| tggtttataa gcctttgcca ggtgtaactg ttgtgaaata cccaccacta aagttttta | | 2501 |
| agttccatat tttctccatt ttgccttctt atgtatttc gagattattc tgtgcacttt | | 2561 |
| aaatttactt aacttaccat aaatgcagtg tgactttcc cacacactgg attgtgaggc | | 2621 |
| tcttaacttc ttaaaagtat aatggcatct tgtgaatcct ataagcagtc tttatgtctc | | 2681 |
| ttaacattca cacctacttt ttaaaaacaa atattattac tatttttatt attgtttgtc | | 2741 |
| ctttataaat tttcttaaag attaagaaaa tttaagaccc cattgagtta ctgtaatgca | | 2801 |
| attcaacttt gagttatctt ttaaatatgt cttgtatagt tcatattcat ggctgaaact | | 2861 |
| tgaccacact attgctgatt gtatggtttt cacctgaca ccgtgtagaa tgcttgatta | | 2921 |
| cttgtactct tcttatgcta atatgctctg ggctggagaa atgaaatcct caagccatca | | 2981 |
| ggatttgcta tttaagtggc ttgacaactg ggccaccaaa gaacttgaac ttcaccttt | | 3041 |

```
aggatttgag ctgttctgga acacattgct gcactttgga aagtcaaaat caagtgccag   3101
tggcgccctt tccatagaga atttgcccag ctttgcttta aaagatgtct tgtttttat    3161 atacacataa tcataggtc caatctgctc tcaaggcctt ggtcctggtg ggattccttc    3221
accaattact ttaattaaaa atggctgcaa ctgtaagaac ccttgtctga tatatttgca   3281
actatgctcc catttacaaa tgtaccttct aatgctcagt tgccaggttc caatgcaaag   3341
gtggcgtgga ctcccttgt gtgggtgggg tttgtgggga gtggtgaagg accgatatca    3401
gaaaaatgcc ttcaagtgta ctaatttatt aataaacatt aggtgtttgt taaaaaaaaa   3461
aaaaaaaaaa aaa                                                      3474
```

<210> SEQ ID NO 2
<211> LENGTH: 655
<212> TYPE: PRT
<213> ORGANISM: Homo sapiens

<400> SEQUENCE: 2

```
Met Gly Thr Ser Pro Ser Ser Thr Ala Leu Ala Ser Cys Ser Arg
-40              -35              -30              -25

Ile Ala Arg Arg Ala Thr Ala Thr Met Ile Ala Gly Ser Leu Leu Leu
              -20              -15              -10

Leu Gly Phe Leu Ser Thr Thr Thr Ala Gln Pro Glu Gln Lys Ala Ser
          -5                   -1   1                5

Asn Leu Ile Gly Thr Tyr Arg His Val Asp Arg Ala Thr Gly Gln Val
         10                  15                  20

Leu Thr Cys Asp Lys Cys Pro Ala Gly Thr Tyr Val Ser Glu His Cys
 25                  30                  35                  40

Thr Asn Thr Ser Leu Arg Val Cys Ser Ser Cys Pro Val Gly Thr Phe
                 45                  50                  55

Thr Arg His Glu Asn Gly Ile Glu Lys Cys His Asp Cys Ser Gln Pro
             60                  65                  70

Cys Pro Trp Pro Met Ile Glu Lys Leu Pro Cys Ala Ala Leu Thr Asp
         75                  80                  85

Arg Glu Cys Thr Cys Pro Pro Gly Met Phe Gln Ser Asn Ala Thr Cys
 90                  95                 100

Ala Pro His Thr Val Cys Pro Val Gly Trp Gly Val Arg Lys Lys Gly
105                 110                 115                 120

Thr Glu Thr Glu Asp Val Arg Cys Lys Gln Cys Ala Arg Gly Thr Phe
                125                 130                 135

Ser Asp Val Pro Ser Ser Val Met Lys Cys Lys Ala Tyr Thr Asp Cys
            140                 145                 150

Leu Ser Gln Asn Leu Val Val Ile Lys Pro Gly Thr Lys Glu Thr Asp
        155                 160                 165

Asn Val Cys Gly Thr Leu Pro Ser Phe Ser Ser Ser Thr Ser Pro Ser
170                 175                 180

Pro Gly Thr Ala Ile Phe Pro Arg Pro Glu His Met Glu Thr His Glu
185                 190                 195                 200

Val Pro Ser Ser Thr Tyr Val Pro Lys Gly Met Asn Ser Thr Glu Ser
                205                 210                 215

Asn Ser Ser Ala Ser Val Arg Pro Lys Val Leu Ser Ser Ile Gln Glu
            220                 225                 230

Gly Thr Val Pro Asp Asn Thr Ser Ser Ala Arg Gly Lys Glu Asp Val
        235                 240                 245

Asn Lys Thr Leu Pro Asn Leu Gln Val Val Asn His Gln Gln Gly Pro
```

```
               250                 255                 260
His His Arg His Ile Leu Lys Leu Leu Pro Ser Met Glu Ala Thr Gly
265                 270                 275                 280

Gly Glu Lys Ser Ser Thr Pro Ile Lys Gly Pro Lys Arg Gly His Pro
                285                 290                 295

Arg Gln Asn Leu His Lys His Phe Asp Ile Asn Glu His Leu Pro Trp
            300                 305                 310

Met Ile Val Leu Phe Leu Leu Val Leu Val Ile Val Val Cys
            315                 320                 325

Ser Ile Arg Lys Ser Ser Arg Thr Leu Lys Lys Gly Pro Arg Gln Asp
330                 335                 340

Pro Ser Ala Ile Val Glu Lys Ala Gly Leu Lys Lys Ser Met Thr Pro
345                 350                 355                 360

Thr Gln Asn Arg Glu Lys Trp Ile Tyr Tyr Cys Asn Gly His Gly Ile
                365                 370                 375

Asp Ile Leu Lys Leu Val Ala Ala Gln Val Gly Ser Gln Trp Lys Asp
            380                 385                 390

Ile Tyr Gln Phe Leu Cys Asn Ala Ser Glu Arg Glu Val Ala Ala Phe
        395                 400                 405

Ser Asn Gly Tyr Thr Ala Asp His Glu Arg Ala Tyr Ala Ala Leu Gln
    410                 415                 420

His Trp Thr Ile Arg Gly Pro Glu Ala Ser Leu Ala Gln Leu Ile Ser
425                 430                 435                 440

Ala Leu Arg Gln His Arg Arg Asn Asp Val Val Glu Lys Ile Arg Gly
                445                 450                 455

Leu Met Glu Asp Thr Thr Gln Leu Glu Thr Asp Lys Leu Ala Leu Pro
            460                 465                 470

Met Ser Pro Ser Pro Leu Ser Pro Ser Pro Ile Pro Ser Pro Asn Ala
        475                 480                 485

Lys Leu Glu Asn Ser Ala Leu Leu Thr Val Glu Pro Ser Pro Gln Asp
    490                 495                 500

Lys Asn Lys Gly Phe Phe Val Asp Glu Ser Glu Pro Leu Leu Arg Cys
505                 510                 515                 520

Asp Ser Thr Ser Ser Gly Ser Ser Ala Leu Ser Arg Asn Gly Ser Phe
                525                 530                 535

Ile Thr Lys Glu Lys Lys Asp Thr Val Leu Arg Gln Val Arg Leu Asp
            540                 545                 550

Pro Cys Asp Leu Gln Pro Ile Phe Asp Asp Met Leu His Phe Leu Asn
        555                 560                 565

Pro Glu Glu Leu Arg Val Ile Glu Glu Ile Pro Gln Ala Glu Asp Lys
    570                 575                 580

Leu Asp Arg Leu Phe Glu Ile Ile Gly Val Lys Ser Gln Glu Ala Ser
585                 590                 595                 600

Gln Thr Leu Leu Asp Ser Val Tyr Ser His Leu Pro Asp Leu Leu
                605                 610                 615

<210> SEQ ID NO 3
<211> LENGTH: 281
<212> TYPE: PRT
<213> ORGANISM: Homo sapiens

<400> SEQUENCE: 3

Met Leu Gly Ile Trp Thr Leu Leu Pro Leu Val Leu Thr Ser Val Ala
1               5                   10                  15
```

Arg Leu Ser Ser Lys Ser Val Asn Ala Gln Val Thr Asp Ile Asn Ser
                20                  25                  30

Lys Gly Leu Glu Leu Arg Lys Thr Val Thr Val Glu Thr Gln Asn
        35                  40                  45

Leu Glu Gly Leu His His Asp Gly Gln Phe Cys His Lys Pro Cys Pro
    50                  55                  60

Pro Gly Glu Arg Lys Ala Arg Asp Cys Thr Val Asn Gly Asp Glu Pro
65                  70                  75                  80

Asp Cys Val Pro Cys Gln Glu Gly Lys Glu Tyr Thr Asp Lys Ala His
                85                  90                  95

Phe Ser Ser Lys Cys Arg Arg Cys Arg Leu Cys Asp Glu Gly His Gly
            100                 105                 110

Leu Glu Val Glu Ile Asn Cys Thr Arg Thr Gln Asn Thr Lys Cys Arg
        115                 120                 125

Cys Lys Pro Asn Phe Phe Cys Asn Ser Thr Val Cys Glu His Cys Asp
    130                 135                 140

Pro Cys Thr Lys Cys Glu His Gly Ile Ile Lys Glu Cys Thr Leu Thr
145                 150                 155                 160

Ser Asn Thr Lys Cys Lys Glu Glu Gly Ser Arg Ser Asn Leu Gly Trp
                165                 170                 175

Leu Cys Leu Leu Leu Leu Pro Ile Pro Leu Ile Val Trp Val Lys Arg
            180                 185                 190

Lys Glu Val Gln Lys Thr Cys Arg Lys His Arg Lys Glu Asn Gln Gly
        195                 200                 205

Ser His Glu Ser Pro Thr Leu Asn Pro Glu Thr Val Ala Ile Asn Leu
    210                 215                 220

Ser Asp Val Asp Leu Ser Lys Tyr Ile Thr Thr Ile Ala Gly Val Met
225                 230                 235                 240

Thr Leu Ser Gln Val Lys Ala Asn Leu Cys Thr Leu Ala Glu Lys Ile
                245                 250                 255

Gln Thr Ile Ile Leu Lys Asp Ile Thr Ser Asp Ser Glu Asn Ser Asn
            260                 265                 270

Phe Arg Asn Glu Ile Gln Ser Leu Val
        275                 280

<210> SEQ ID NO 4
<211> LENGTH: 455
<212> TYPE: PRT
<213> ORGANISM: Homo sapiens

<400> SEQUENCE: 4

Met Gly Ala Gly Ala Thr Gly Arg Ala Met Asp Gly Pro Arg Leu Leu
1               5                   10                  15

Leu Leu Leu Leu Leu Gly Val Ser Leu Gly Gly Ala Lys Glu Ala Cys
                20                  25                  30

Pro Thr Gly Leu Tyr Thr His Ser Gly Glu Cys Cys Lys Ala Cys Asn
            35                  40                  45

Leu Gly Glu Gly Val Ala Gln Pro Cys Gly Ala Asn Gln Thr Val Cys
    50                  55                  60

Glu Pro Cys Leu Asp Ser Val Thr Phe Ser Asp Val Val Ser Ala Thr
65                  70                  75                  80

Glu Pro Cys Lys Pro Cys Thr Glu Cys Val Gly Leu Gln Ser Met Ser
                85                  90                  95

Ala Pro Cys Val Glu Ala Asp Asp Ala Val Cys Arg Cys Ala Tyr Gly
            100                 105                 110

-continued

```
Tyr Tyr Gln Asp Glu Thr Thr Gly Arg Cys Glu Ala Cys Arg Val Cys
        115                 120                 125

Glu Ala Gly Ser Gly Leu Val Phe Ser Cys Gln Asp Lys Gln Asn Thr
    130                 135                 140

Val Cys Glu Glu Cys Pro Asp Gly Thr Tyr Ser Asp Glu Ala Asn His
145                 150                 155                 160

Val Asp Pro Cys Leu Pro Cys Thr Val Cys Glu Asp Thr Glu Arg Gln
                165                 170                 175

Leu Arg Glu Cys Thr Arg Trp Ala Asp Ala Glu Cys Glu Glu Ile Pro
            180                 185                 190

Gly Arg Trp Ile Thr Arg Ser Thr Pro Pro Glu Gly Ser Asp Ser Thr
        195                 200                 205

Ala Pro Ser Thr Gln Glu Pro Glu Ala Pro Pro Glu Gln Asp Leu Ile
    210                 215                 220

Ala Ser Thr Val Ala Gly Val Val Thr Thr Val Met Gly Ser Ser Gln
225                 230                 235                 240

Pro Val Val Thr Arg Gly Thr Thr Asp Asn Leu Ile Pro Val Tyr Cys
                245                 250                 255

Ser Ile Leu Ala Ala Val Val Gly Leu Val Ala Tyr Ile Ala Phe
            260                 265                 270

Lys Arg Trp Asn Ser Cys Lys Gln Asn Lys Gln Gly Ala Asn Ser Arg
        275                 280                 285

Pro Val Asn Gln Thr Pro Pro Pro Glu Gly Glu Lys Leu His Ser Asp
    290                 295                 300

Ser Gly Ile Ser Val Asp Ser Gln Ser Leu His Asp Gln Gln Pro His
305                 310                 315                 320

Thr Gln Thr Ala Ser Gly Gln Ala Leu Lys Gly Asp Gly Gly Leu Tyr
                325                 330                 335

Ser Ser Leu Pro Pro Ala Lys Arg Glu Glu Val Glu Lys Leu Leu Asn
            340                 345                 350

Gly Ser Ala Gly Asp Thr Trp Arg His Leu Ala Gly Glu Leu Gly Tyr
        355                 360                 365

Gln Pro Glu His Ile Asp Ser Phe Thr His Glu Ala Cys Pro Val Arg
    370                 375                 380

Ala Leu Leu Ala Ser Trp Ala Thr Gln Asp Ser Ala Thr Leu Pro Arg
385                 390                 395                 400

Arg Glu Val Ala Pro Pro Tyr Gln Gly Ala Asp Pro Ile Leu Ala Thr
                405                 410                 415

Ala Leu Ala Ser Asp Pro Ile Pro Asn Pro Leu Gln Lys Trp Glu Asp
            420                 425                 430

Ser Ala His Lys Pro Gln Ser Leu Asp Thr Asp Asp Pro Cys Ser Glu
        435                 440                 445

Ser Thr Ala Thr Ser Pro Val
    450                 455

<210> SEQ ID NO 5
<211> LENGTH: 455
<212> TYPE: PRT
<213> ORGANISM: Homo sapiens

<400> SEQUENCE: 5

Met Gly Leu Ser Thr Val Pro Asp Leu Leu Leu Pro Leu Val Leu Leu
  1               5                  10                  15

Glu Leu Leu Val Gly Ile Tyr Pro Ser Gly Val Ile Gly Leu Val Pro
```

-continued

```
                20                  25                  30
His Leu Gly Asp Arg Glu Lys Arg Asp Ser Val Cys Pro Gln Gly Lys
            35                  40                  45

Tyr Ile His Pro Gln Asn Asn Ser Ile Cys Cys Thr Lys Cys His Lys
        50                  55                  60

Gly Thr Tyr Leu Tyr Asn Asp Cys Pro Gly Pro Gly Gln Asp Thr Asp
65                  70                  75                  80

Cys Arg Glu Cys Glu Ser Gly Ser Phe Thr Ala Ser Glu Asn His Leu
                85                  90                  95

Arg His Cys Leu Ser Cys Ser Lys Cys Arg Lys Glu Met Gly Gln Val
            100                 105                 110

Glu Ile Ser Ser Cys Thr Val Asp Arg Asp Thr Val Cys Gly Cys Arg
        115                 120                 125

Lys Asn Gln Tyr Arg His Tyr Trp Ser Glu Asn Leu Phe Gln Cys Phe
130                 135                 140

Asn Cys Ser Leu Cys Leu Asn Gly Thr Val His Leu Ser Cys Gln Glu
145                 150                 155                 160

Lys Gln Asn Thr Val Cys Thr Cys His Ala Gly Phe Phe Leu Arg Glu
                165                 170                 175

Asn Glu Cys Val Ser Cys Ser Asn Cys Lys Lys Ser Leu Glu Cys Thr
            180                 185                 190

Lys Leu Cys Leu Pro Gln Ile Glu Asn Val Lys Gly Thr Glu Asp Ser
        195                 200                 205

Gly Thr Thr Val Leu Leu Pro Leu Val Ile Phe Phe Gly Leu Cys Leu
210                 215                 220

Leu Ser Leu Leu Phe Ile Gly Leu Met Tyr Arg Tyr Gln Arg Trp Lys
225                 230                 235                 240

Ser Lys Leu Tyr Ser Ile Val Cys Gly Lys Ser Thr Pro Glu Lys Glu
                245                 250                 255

Gly Glu Leu Glu Gly Thr Thr Thr Lys Pro Leu Ala Pro Asn Pro Ser
            260                 265                 270

Phe Ser Pro Thr Pro Gly Phe Thr Pro Thr Leu Gly Phe Ser Pro Val
        275                 280                 285

Pro Ser Ser Thr Phe Thr Ser Ser Ser Thr Tyr Thr Pro Gly Asp Cys
290                 295                 300

Pro Asn Phe Ala Ala Pro Arg Arg Glu Val Ala Pro Pro Tyr Gln Gly
305                 310                 315                 320

Ala Asp Pro Ile Leu Ala Thr Ala Leu Ala Ser Asp Pro Ile Pro Asn
                325                 330                 335

Pro Leu Gln Lys Trp Glu Asp Ser Ala His Lys Pro Gln Ser Leu Asp
            340                 345                 350

Thr Asp Asp Pro Ala Thr Leu Tyr Ala Val Val Glu Asn Val Pro Pro
        355                 360                 365

Leu Arg Trp Lys Glu Phe Val Arg Arg Leu Gly Leu Ser Asp His Glu
370                 375                 380

Ile Asp Arg Leu Glu Leu Gln Asn Gly Arg Cys Leu Arg Glu Ala Gln
385                 390                 395                 400

Tyr Ser Met Leu Ala Thr Trp Arg Arg Arg Thr Pro Arg Arg Glu Ala
                405                 410                 415

Thr Leu Glu Leu Leu Gly Arg Val Leu Arg Asp Met Asp Leu Leu Gly
            420                 425                 430

Cys Leu Glu Asp Ile Glu Glu Ala Leu Cys Gly Pro Ala Ala Leu Pro
        435                 440                 445
```

Pro Ala Pro Ser Leu Leu Arg
    450             455

<210> SEQ ID NO 6
<211> LENGTH: 365
<212> TYPE: DNA
<213> ORGANISM: Homo sapiens

<400> SEQUENCE: 6

```
tcggctgtgt acccattgga gaaagcagca acctccctct cactggcatt gcaaagaaac      60
tgatagatat ctttccactg gcttcccact tgggctgcta caagcttcag gatatcgata     120
ccatggccat tgcagtagta gatccatttt cccggttctg ggttggagtc atggattttt     180
cagccctgcc ttttccacaa tggcactggg atcctgccgg ggccccttt tagagtcctc      240
gagcttttcc ggatactgca caccacaatc accacaagca ccagcagcag gaaaagcaca     300
atcatccagg gcaaatgctc attgatgtca aaatgcttgt gtaggttctg tctaggatgt     360
cccct                                                                 365
```

<210> SEQ ID NO 7
<211> LENGTH: 378
<212> TYPE: DNA
<213> ORGANISM: Homo sapiens

<400> SEQUENCE: 7

```
agaaacgatg ttgtggagaa gattcgtggg ctgatggaag acaccaccca gctggaaact      60
gacaaactag ctctcccgat gagccccagc ccgcttagcc cgagccccat ccccagcccc     120
aacgcgaaac ttgagaattc cgctctcctg acggtggagc cttccccaca ggacaagaac     180
aagggcttct tcgtggatga gtcggagccc cttctccgct gtactctaca tccagcggct     240
cctccgcgct gagcaggaac ggttccttta ttaccaaaga aaagaaggac acagtgttgc     300
ggcaggtacg cctggacccc tgtaaatttg cagcctatct ttgattgaca tgttccactt     360
tctaaatcct gaggagtt                                                   378
```

<210> SEQ ID NO 8
<211> LENGTH: 345
<212> TYPE: DNA
<213> ORGANISM: Homo sapiens

<400> SEQUENCE: 8

```
ggcagaggca caaggtaatt tctcaatcat tggccatggg catggctgac tacagtcatg      60
gcatttctct atgccattct catgcctggt aaaggtcccc acagggcaac tgctgacaga     120
cgcgcggctt gtgttggtac atgctcagag acataggttc ctgctggaca cttgtcacag     180
gttagcacct agccggtggc acggtcaaca tggcggtatg tgccaatgag attcgaggcc     240
ttctgttctg gctgagctgt ggtggtgcta aggaatccaa gcggagaagg gagcccagat     300
catcgtggct gtggctggcg ggcgatgcgg ttcaggaggc cgagg                     345
```

<210> SEQ ID NO 9
<211> LENGTH: 316
<212> TYPE: DNA
<213> ORGANISM: Homo sapiens

<400> SEQUENCE: 9

```
gctaattagc gccctgccag accggagaaa cgatgtttgg agaagattcg tgggctgatg      60
gaagacacca cccagctgga aactgacaaa ctagctctcc cgatgagccc cagcccgctt     120
```

```
agcccgagcc ccatcccag ccccaacgcg aaacttgaga attccgctct cctgacggtg    180
gagcctttcc cacaggacaa gaacaagggc ttcttcgtgg atgagtcgga gcccctttcc    240
cgctgtactc tacatccagc ggctcctccg gctgagcagg aacggttcct ttattaccaa    300
gaaaagaagg acacag                                                     316
```

```
<210> SEQ ID NO 10
<211> LENGTH: 489
<212> TYPE: DNA
<213> ORGANISM: Homo sapiens

<400> SEQUENCE: 10
aattcggcac gaggaatcct ataagcagtc tttatgtctc ttaacattca cacctacttt     60
ttaaaaacaa atattattac tatttttatt attgtttgtc ctttataaat tttcttaaag    120
attaagaaaa tttaagaccc cattgagtta ctgtaatgca attcaacttt gagttatctt    180
ttaaatatgt cttgtatagt tcatattcat ggctgaaact tgaccacact attgctgatt    240
gtatggttca cctggcaccg tgtagatgct tgattacttg tactctctta tgtaaatgct    300
ctgggctggg gaatgaatcc caggctcagg tttccctatt aaggggttca ctggccccaa    360
gactgactcc cttggggttg ggtttggaca atgtcttggg agaaaagccg gggcttccag    420
ggttcccctt gtaagggttt taaaaaaaag ccattctgag ctcgccgggg tcccatttaa    480
aagggcccg                                                            489
```

```
<210> SEQ ID NO 11
<211> LENGTH: 26
<212> TYPE: DNA
<213> ORGANISM: Homo sapiens

<400> SEQUENCE: 11
cgcccatggc tcagccagaa cagaag                                          26
```

```
<210> SEQ ID NO 12
<211> LENGTH: 28
<212> TYPE: DNA
<213> ORGANISM: Homo sapiens

<400> SEQUENCE: 12
cgcaagcttt tagggcaaat gctcattg                                        28
```

```
<210> SEQ ID NO 13
<211> LENGTH: 33
<212> TYPE: DNA
<213> ORGANISM: Homo sapiens

<400> SEQUENCE: 13
cgccccgggg ccatcatggg gacctctccg agc                                  33
```

```
<210> SEQ ID NO 14
<211> LENGTH: 28
<212> TYPE: DNA
<213> ORGANISM: Homo sapiens

<400> SEQUENCE: 14
cgcggtacct tagggcaaat gctcattg                                        28
```

```
<210> SEQ ID NO 15
<211> LENGTH: 55
<212> TYPE: DNA
```

<210> SEQ ID NO 15
<211> LENGTH: 55
<212> TYPE: DNA
<213> ORGANISM: Homo sapiens

<400> SEQUENCE: 15
cgctctagat caagcgtagt ctgggacgtc gtatgggtag ggcaaatgct cattg                55

<210> SEQ ID NO 16
<211> LENGTH: 31
<212> TYPE: DNA
<213> ORGANISM: Homo sapiens

<400> SEQUENCE: 16
ggaagatctg ccagaacaga aggcctcgaa t                                          31

<210> SEQ ID NO 17
<211> LENGTH: 31
<212> TYPE: DNA
<213> ORGANISM: Homo sapiens

<400> SEQUENCE: 17
ccatcttcct gacctgctgt agtctagagc c                                          31

<210> SEQ ID NO 18
<211> LENGTH: 30
<212> TYPE: DNA
<213> ORGANISM: Homo sapiens

<400> SEQUENCE: 18
gccgaccacg agcgggccta gtctagagcc                                            30

<210> SEQ ID NO 19
<211> LENGTH: 147
<212> TYPE: PRT
<213> ORGANISM: Homo sapiens

<400> SEQUENCE: 19

Thr Cys Asp Lys Cys Pro Ala Gly Thr Tyr Val Ser Glu His Cys Thr
 1               5                  10                  15

Asn Thr Ser Leu Arg Val Cys Ser Ser Cys Pro Val Gly Thr Phe Thr
            20                  25                  30

Arg His Glu Asn Gly Ile Glu Lys Cys His Asp Cys Ser Gln Pro Cys
        35                  40                  45

Pro Trp Pro Met Ile Glu Lys Leu Pro Cys Ala Ala Leu Thr Asp Arg
    50                  55                  60

Glu Cys Thr Cys Pro Pro Gly Met Phe Gln Ser Asn Ala Thr Cys Ala
65                  70                  75                  80

Pro His Thr Val Cys Pro Val Gly Trp Gly Val Arg Lys Lys Gly Thr
                85                  90                  95

Glu Thr Glu Asp Val Arg Cys Lys Gln Cys Ala Arg Gly Thr Phe Ser
            100                 105                 110

Asp Val Pro Ser Ser Val Met Pro Cys Lys Ala Tyr Thr Asp Cys Leu
        115                 120                 125

Ser Gln Asn Leu Val Val Ile Lys Pro Gly Thr Lys Glu Thr Asp Asn
    130                 135                 140

Val Cys Gly
145

<210> SEQ ID NO 20
<211> LENGTH: 147
<212> TYPE: PRT
<213> ORGANISM: Homo sapiens -continued

```
<400> SEQUENCE: 20

Leu Cys Asp Lys Cys Pro Pro Gly Thr Tyr Leu Lys Gln His Cys Thr
 1               5                  10                  15

Ala Lys Trp Lys Thr Val Cys Ala Pro Cys Pro Asp His Tyr Tyr Thr
             20                  25                  30

Asp Ser Trp His Thr Ser Asp Glu Cys Leu Tyr Cys Ser Pro Val Cys
         35                  40                  45

Lys Glu Leu Gln Tyr Val Lys Gln Glu Cys Asn Arg Thr His Asn Arg
     50                  55                  60

Val Cys Glu Cys Lys Glu Gly Arg Tyr Leu Glu Ile Glu Phe Cys Leu
 65                  70                  75                  80

Lys His Arg Ser Cys Pro Pro Gly Phe Gly Val Val Gln Ala Gly Thr
                 85                  90                  95

Pro Glu Arg Asn Thr Val Cys Lys Arg Cys Pro Asp Gly Phe Phe Ser
            100                 105                 110

Asn Glu Thr Ser Ser Lys Ala Pro Cys Arg Lys His Thr Asn Cys Ser
        115                 120                 125

Val Phe Gly Leu Leu Leu Thr Gln Lys Gly Asn Ala Thr His Asp Asn
130                 135                 140

Ile Cys Ser
145

<210> SEQ ID NO 21
<211> LENGTH: 67
<212> TYPE: PRT
<213> ORGANISM: Homo sapiens

<400> SEQUENCE: 21

Gln Trp Lys Asp Ile Tyr Gln Phe Leu Cys Asn Ala Ser Glu Arg Glu
 1               5                  10                  15

Val Ala Ala Phe Ser Asn Gly Tyr Thr Ala Asp His Glu Arg Ala Tyr
             20                  25                  30

Ala Ala Leu Gln His Trp Thr Ile Arg Gly Pro Glu Ala Ser Leu Ala
         35                  40                  45

Gln Leu Ile Ser Ala Leu Arg Gln His Arg Arg Asn Asp Val Val Glu
     50                  55                  60

Lys Ile Arg
 65

<210> SEQ ID NO 22
<211> LENGTH: 68
<212> TYPE: PRT
<213> ORGANISM: Homo sapiens

<400> SEQUENCE: 22

Gln Val Lys Gly Phe Val Arg Lys Asn Gly Val Asn Glu Ala Lys Ile
 1               5                  10                  15

Asp Glu Ile Lys Asn Asp Asn Val Gln Asp Thr Ala Glu Gln Lys Val
             20                  25                  30

Gln Leu Leu Arg Asn Trp His Gln Leu His Gly Lys Lys Glu Ala Tyr
         35                  40                  45

Asp Thr Leu Ile Lys Asp Leu Lys Lys Ala Asn Leu Cys Thr Leu Ala
     50                  55                  60

Glu Lys Ile Gln
 65
```

<210> SEQ ID NO 23
<211> LENGTH: 68
<212> TYPE: PRT
<213> ORGANISM: Homo sapiens

<400> SEQUENCE: 23

Arg Trp Lys Glu Phe Val Arg Arg Leu Gly Leu Ser Asp His Glu Ile
1               5                   10                  15

Asp Arg Leu Glu Leu Gln Asn Gly Arg Cys Leu Arg Glu Ala Gln Tyr
            20                  25                  30

Ser Met Leu Ala Thr Trp Arg Arg Thr Arg Arg Glu Ala Thr Leu
        35                  40                  45

Glu Leu Leu Gly Arg Val Leu Arg Asp Met Asp Leu Leu Gly Cys Leu
    50                  55                  60

Glu Asp Ile Glu
65

<210> SEQ ID NO 24
<211> LENGTH: 65
<212> TYPE: PRT
<213> ORGANISM: Homo sapiens

<400> SEQUENCE: 24

Arg Trp Lys Glu Phe Val Arg Thr Leu Gly Leu Arg Glu Ala Glu Ile
1               5                   10                  15

Glu Ala Val Glu Val Glu Ile Gly Arg Phe Arg Asp Gln Gln Tyr Glu
            20                  25                  30

Met Leu Lys Arg Trp Arg Gln Gln Gln Pro Ala Gly Leu Gly Ala Val
        35                  40                  45

Tyr Ala Ala Leu Glu Arg Met Gly Leu Asp Gly Cys Val Glu Asp Leu
    50                  55                  60

Arg
65

<210> SEQ ID NO 25
<211> LENGTH: 67
<212> TYPE: PRT
<213> ORGANISM: Homo sapiens

<400> SEQUENCE: 25

Ser Trp Asp Gln Leu Met Arg Gln Leu Asp Leu Thr Lys Asn Glu Ile
1               5                   10                  15

Asp Val Val Arg Ala Gly Thr Ala Gly Pro Gly Asp Ala Leu Tyr Ala
            20                  25                  30

Met Leu Met Lys Trp Val Asn Lys Thr Gly Arg Asn Ala Ser Ile His
        35                  40                  45

Thr Leu Leu Asp Ala Leu Glu Arg Met Glu Glu Arg His Ala Lys Glu
    50                  55                  60

Lys Ile Gln
65

<210> SEQ ID NO 26
<211> LENGTH: 67
<212> TYPE: PRT
<213> ORGANISM: Homo sapiens

<400> SEQUENCE: 26

Ser Trp Glu Pro Leu Met Arg Lys Leu Gly Leu Met Asp Asn Glu Ile
1               5                   10                  15

```
Lys Val Ala Lys Ala Glu Ala Ala Gly His Arg Asp Thr Leu Tyr Thr
             20                  25                  30

Met Leu Ile Lys Trp Val Asn Lys Thr Gly Arg Asp Ala Ser Val His
         35                  40                  45

Thr Leu Leu Asp Ala Leu Glu Thr Leu Gly Glu Arg Leu Ala Lys Gln
     50                  55                  60

Lys Ile Glu
 65

<210> SEQ ID NO 27
<211> LENGTH: 733
<212> TYPE: DNA
<213> ORGANISM: Homo sapiens

<400> SEQUENCE: 27
gggatccgga gcccaaatct tctgacaaaa ctcacacatg cccaccgtgc ccagcacctg      60
aattcgaggg tgcaccgtca gtcttcctct tccccccaaa acccaaggac accctcatga     120
tctcccggac tcctgaggtc acatgcgtgg tggtggacgt aagccacgaa gaccctgagg     180
tcaagttcaa ctggtacgtg gacggcgtgg aggtgcataa tgccaagaca aagccgcggg     240
aggagcagta caacagcacg taccgtgtgg tcagcgtcct caccgtcctg caccaggact     300
ggctgaatgg caaggagtac aagtgcaagg tctccaacaa agcccteccca accccatcg     360 agaaaaccat ctccaaagcc aaagggcagc ccgagaacc acaggtgtac accctgcccc     420
catcccggga tgagctgacc aagaaccagg tcagcctgac ctgcctggtc aaaggcttct     480
atccaagcga catcgccgtg gagtgggaga gcaatgggca gccggagaac aactacaaga     540
ccacgcctcc cgtgctggac tccgacggct ccttcttcct ctacagcaag ctcaccgtgg     600
acaagagcag gtggcagcag gggaacgtct tctcatgctc cgtgatgcat gaggctctgc     660
acaaccacta cacgcagaag agcctctccc tgtctccggg taaatgagtg cgacggccgc     720
gactctagag gat                                                       733
```

HUMAN TUMOR NECROSIS FACTOR RECEPTOR TR9 ANTIBODY

This application is a continuation of U.S. patent application Ser. No. 10/834,966, filed Apr. 30, 2004, which is a divisional of U.S. patent application Ser. No. 10/041,574, filed Jan. 10, 2002 (now U.S. Pat. No. 6,919,078), which is a divisional of U.S. patent application Ser. No. 09/527,236, filed Mar. 16, 2000 (now U.S. Pat. No. 6,358,508), which is a continuation-in-part of U.S. application Ser. No. 09/095,094, filed Jun. 10, 1998, which claims benefit under 35 U.S.C. 119(e) of the filing date of U.S. Provisional Application Ser. No. 60/052,991, filed Jun. 11, 1997, and further claims benefit of priority under 35 U.S.C. §119(e) of the filing date of U.S. Provisional Application Ser. No. 60/126,019, filed on Mar. 24, 1999 and U.S. Provisional Application Ser. No. 60/134,220, filed on May 14, 1999; each of which is hereby incorporated by reference in its entirety.

STATEMENT UNDER 37 C.F.R. §1.77(b)(5)

This application refers to a "Sequence Listing" listed below, which is provided as a text document. The document is entitled "PF375P1D2C1_SeqListing.txt" (39,163 bytes, created Jul. 16, 2007), and is hereby incorporated by reference in its entirety herein.

FIELD OF THE INVENTION

The present invention relates to a novel member of the tumor necrosis factor family of receptors. More specifically, isolated nucleic acid molecules are provided encoding a novel human tumor necrosis factor receptor, TR9 (also known as Death Domain Containing Receptor 6, or simply DR6). TR9 polypeptides are also provided, as are vectors, host cells and recombinant methods for producing the same. The invention also relates to both the inhibition and enhancement of the activities of TR9 receptor polypeptides and diagnostic methods for detecting TR9 receptor gene expression. The invention further relates to screening methods for identifying agonists and antagonists of TR9 activity.

BACKGROUND OF THE INVENTION

Many biological actions, for instance, response to certain stimuli and natural biological processes, are controlled by factors, such as cytokines. Many cytokines act through receptors by engaging the receptor and producing an intra-cellular response.

For example, tumor necrosis factors (TNF) alpha and beta are cytokines, which act through TNF receptors to regulate numerous biological processes, including protection against infection and induction of shock and inflammatory disease. The TNF molecules belong to the "TNF-ligand" superfamily, and act together with their receptors or counter-ligands, the "TNF-receptor" superfamily. So far, nine members of the TNF ligand superfamily have been identified and ten members of the TNF-receptor superfamily have been characterized.

Among the ligands there are included TNF-alpha, lymphotoxin-alpha (LT-alpha, also known as TNF-beta), LT-beta (found in complex heterotrimer LT-alpha2-beta), FasL, CD40L, CD27L, CD30L, 4-IBBL, OX40L and nerve growth factor (NGF). The superfamily of TNF receptors includes the p55TNF receptor, p75TNF receptor, TNF receptor-related protein, FAS antigen or APO-1, CD40, CD27, CD30, 4-IBB, OX40, low affinity p75 and NGF-receptor (Meager, A., *Biologicals* 22:291-295 (1994)).

Many members of the TNF-ligand superfamily are expressed by activated T-cells, implying that they are necessary for T-cell interactions with other cell types which underlie cell ontogeny and functions. (Meager, A., supra).

Considerable insight into the essential functions of several members of the TNF receptor family has been gained from the identification and creation of mutants that abolish the expression of these proteins. For example, naturally occurring mutations in the FAS antigen and its ligand cause lymphoproliferative disease (Watanabe-Fukunaga. et al., *Nature* 356:314 (1992)), perhaps reflecting a failure of programmed cell death. Mutations of the CD40 ligand cause an X-linked immunodeficiency state characterized by high levels of immunoglobulin M and low levels of immunoglobulin G in plasma, indicating faulty T-cell-dependent B-cell activation (Allen et al., *Science* 259:990 (1993)). Targeted mutations of the low affinity nerve growth factor receptor cause a disorder characterized by faulty sensory innovation of peripheral structures (Lee et al., *Cell* 69:737 (1992)).

TNF and LT-alpha are capable of binding to two TNF receptors (the 55- and 75-kd TNF receptors). A large number of biological effects elicited by TNF and LT-alpha, acting through their receptors, include hemorrhagic necrosis of transplanted tumors, cytotoxicity, a role in endotoxic shock, inflammation, immunoregulation, proliferation and anti-viral responses, as well as protection against the deleterious effects of ionizing radiation. TNF and LT-alpha are involved in the pathogenesis of a wide range of diseases, including endotoxic shock, cerebral malaria, tumors, autoimmune disease, AIDS and graft-host rejection (Beutler et al., *Science* 264:667-668 (1994)). Mutations in the p55 receptor cause increased susceptibility to microbial infection.

Moreover, an about 80 amino acid domain near the C-terminus of TNFR1 (p55) and Fas was reported as the "death domain," which is responsible for transducing signals for programmed cell death (Tartaglia et al., *Cell* 74:845 (1993)).

Apoptosis, or programmed cell death, is a physiologic process essential to the normal development and homeostasis of multicellular organisms (Steller, *Science* 267:1445-1449 (1995)). Derangements of apoptosis contribute to the pathogenesis of several human diseases including cancer, neurodegenerative disorders, and acquired immune deficiency syndrome (Thompson C. B., *Science* 267:1456-1462 (1995)). Recently, much attention has focused on the signal transduction and biological function of two cell surface death receptors, Fas/APO-1 and TNFR-1 (Cleveland et al., *Cell* 81:479-482 (1995); Fraser et al., *Cell* 85:781-784 (1996); S. Nagata et al., *Science* 267:1449-56 (1995)). Both are members of the TNF receptor family, which also include TNFR-2, low affinity NGFR, CD40, and CD30, among others (Smith et al., *Science* 248:1019-23 (1990); Tewari et al., in *Modular Texts in Molecular and Cell Biology*; M. Purton, Heldin, Carl, Ed. (Chapman and Hall, London, 1995). While family members are defined by the presence of cysteine-rich repeats in their extracellular domains, Fas/APO-1 and TNFR-1 also share a region of intracellular homology, appropriately designated the "death domain," which is distantly related to the *Drosophila* suicide gene, reaper (Golstein et al., *Cell* 81:185-6 (1995); White et al., *Science* 264:677-83 (1994)). This shared death domain suggests that both receptors interact with a related set of signal transducing molecules that, until recently, remained unidentified. Activation of Fas/APO-1 recruits the death domain-containing adapter molecule FADD/MORT1 (Chinnaiyan et al., *Cell* 81:505-512 (1995); Boldin et al., *J. Biol. Chem.* 270:7795-8 (1995); Kischkel et al., *EMBO* 14:5579-5588 (1995)), which in turn binds and presumably activates FLICE/MACH1, a member of the ICE/CED-3 family of pro-apoptotic proteases (Muzio et al., *Cell* 85:817-827 (1996); Boldin et al., *Cell* 85:803-815 (1996)). While the central role of Fas/APO-1 is to trigger cell death, TNFR-1 can signal an array of diverse biological activities-many of which stem from its ability to activate NF-kappaB (Tartaglia et al., *Immunol Today* 13:151-153 (1992)). Accordingly, TNFR-1 recruits the multivalent adapter molecule TRADD, which like FADD, also contains a death domain (Hsu et al., *Cell* 81:495-504 (1995); Hsu et al., *Cell* 84:299-308 (1996)). Through its associations with a number of signaling molecules including FADD, TRAF2, and RIP, TRADD can signal both apoptosis and NF-kappaB activation (Hsu et al., *Cell* 84:299-308 (1996); Hsu et al., *Immunity* 4:387-396 (1996)).

The effects of TNF family ligands and receptors are varied and influence numerous functions, both normal and abnormal, in the biological processes of the mammalian system. There is a clear need, therefore, for identification and characterization of additional novel TNF receptors and ligands that influence biological activity, both normally and in disease states.

SUMMARY OF THE INVENTION

The present invention provides isolated nucleic acid molecules, or alternatively consisting of, a polynucleotide encoding the TR9 receptor having the amino acid sequence shown in FIGS. 1A-D (SEQ ID NO:2) or the amino acid sequence encoded by the cDNA clone deposited as ATCC Deposit Number 209037 on May 15, 1997.

The present invention also relates to recombinant vectors, which include the isolated nucleic acid molecules of the present invention, and to host cells containing the recombinant vectors, as well as to methods of making such vectors and host cells and for using them for production of TR9 receptor polypeptides or peptides by recombinant techniques.

The invention further provides an isolated TR9 polypeptide having an amino acid sequence encoded by a polynucleotide described herein.

In certain embodiments, TR9 polypeptides of the invention, or agonists thereof, are administered, to treat, prevent, prognose and/or diagnose an immunodeficiency (e.g., severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency) or conditions associated with an immunodeficiency.

In a specific embodiment, TR9 polypeptides or polynucleotides of the invention, or agonists thereof, is administered to treat, prevent, prognose and/or diagnose common variable immunodeficiency.

In a specific embodiment, TR9 polypeptides or polynucleotides of the invention, or agonists thereof, is administered to treat, prevent, prognose and/or diagnose X-linked agammaglobulinemia.

In another specific embodiment, TR9 polypeptides or polynucleotides of the invention, or agonists thereof, is administered to treat, prevent, prognose and/or diagnose severe combined immunodeficiency (SCID).

In another specific embodiment, TR9 polypeptides or polynucleotides of the invention, or agonists thereof, is administered to treat, prevent, prognose and/or diagnose Wiskott-Aldrich syndrome.

In another specific embodiment, TR9 polypeptides or polynucleotides of the invention, or agonists thereof, is administered to treat, prevent, prognose and/or diagnose X-linked Ig deficiency with hyper IgM.

In another embodiment, TR9 antagonists (e.g., an anti-TR9 antibody), are administered to treat, prevent, prognose and/or diagnose an autoimmune disease (e.g., rheumatoid arthritis, systemic lupus erythematosus, idiopathic thrombocytopenia purpura, autoimmune hemolytic anemia, autoimmune neonatal thrombocytopenia, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, scleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders) or conditions associated with an autoimmune disease. In a specific preferred embodiment, rheumatoid arthritis is treated, prevented, prognosed and/or diagnosed using anti-TR9 antibodies and/or other antagonist of the invention. In another specific preferred embodiment, systemic lupus erythemosus is treated, prevented, prognosed, and/or diagnosed using anti-TR9 antibodies and/or other antagonist of the invention. In another specific preferred embodiment, idiopathic thrombocytopenia purpura is treated, prevented, prognosed, and/or diagnosed using anti-TR9 antibodies and/or other antagonist of the invention. In another specific preferred embodiment IgA nephropathy is treated, prevented, prognosed and/or diagnosed using anti-TR9 antibodies and/or other antagonist of the invention. In a preferred embodiment, the autoimmune diseases and disorders and/or conditions associated with the diseases and disorders recited above are treated, prevented, prognosed and/or diagnosed using anti-TR9 antibodies.

The invention further provides compositions comprising a TR9 polynucleotide, a TR9 polypeptide, and/or an anti-TR9 antibody, for administration to cells in vitro, to cells ex vivo, and to cells in vivo, or to a multicellular organism. In preferred embodiments, the compositions of the invention comprise a TR9 polynucleotide for expression of a TR9 polypeptide in a host organism for treatment of disease. In a most preferred embodiment, the compositions of the invention comprise a TR9 polynucleotide for expression of a TR9 polypeptide in a host organism for treatment of an immunodeficiency and/or conditions associated with an immunodeficiency. Particularly preferred in this regard is expression in a human patient for treatment of a dysfunction associated with aberrant endogenous activity of a TR9 gene (e.g., expression to enhance the normal B-cell function by expanding B-cell numbers or increasing B cell lifespan; or expression to enhance the normal T cell function by expanding T cell numbers or increasing T cell lifespan).

The present invention also provides a screening method for identifying compounds capable of enhancing or inhibiting a cellular response induced by the TR9 receptor. The method involves contacting cells which express the TR9 receptor with the candidate compound, assaying a cellular response, and comparing the cellular response to a standard cellular response, the standard being assayed when contact is made in absence of the candidate compound; whereby, an increased cellular response over the standard indicates that the compound is an agonist and a decreased cellular response over the standard indicates that the compound is an antagonist.

In another aspect, a screening assay for agonists and antagonists is provided which involves determining the effect a candidate compound has on the binding of cellular ligands to TR9 receptors. In particular, the method involves contacting TR9 receptors with a ligand polypeptide and a candidate compound and determining whether ligand binding to the TR9 receptors is increased or decreased due to the presence of the candidate compound.

The invention further provides diagnostic assays such as quantitative and diagnostic assays for detecting levels of TR9 receptor protein. Thus, for instance, a diagnostic assay in accordance with the invention for detecting over-expression of TR9, or soluble form thereof, compared to normal control tissue samples, may be used to detect the presence of tumors.

Tumor Necrosis Factor (TNF) family ligands are known to be among the most pleiotropic cytokines, inducing a large number of cellular responses, including cytotoxicity, antiviral activity, immunoregulatory activities, and the transcriptional regulation of several genes. Cellular response to TNF-family ligands include not only normal physiological responses, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes. Diseases associated with increased cell survival, or the inhibition of apoptosis, include cancers, autoimmune disorders, viral infections, inflammation, graft vs. host disease, acute graft rejection, and chronic graft rejection. Diseases associated with increased apoptosis include AIDS, neurodegenerative disorders, myelodysplastic syndromes, ischemic injury, toxin-induced liver disease, septic shock, cachexia, and anorexia.

Thus, the invention further provides a method for enhancing apoptosis induced by a TNF-family ligand, which involves administering to a cell which expresses the TR9 polypeptide an effective amount of an agonist capable of increasing TR9 mediated signaling. Preferably, TR9 mediated signaling is increased to treat, prevent, diagnose, and/or detect a disease wherein decreased apoptosis is exhibited.

In a further aspect, the present invention is directed to a method for inhibiting apoptosis induced by a TNF-family ligand, which involves administering to a cell which expresses the TR9 polypeptide an effective amount of an antagonist capable of decreasing TR9 mediated signaling. Preferably, TR9 mediated signaling is decreased to treat, prevent, diagnose, and/or detect a disease wherein increased apoptosis is exhibited.

BRIEF DESCRIPTION OF THE FIGURES

FIGS. 1A-D show the nucleotide sequence (SEQ ID NO:1) and deduced amino acid sequence (SEQ ID NO:2) of the TR9 receptor. Analysis using the computer program PSORT reveals that the protein has a predicted leader sequence of about 40 amino acid residues (underlined) and a deduced molecular weight of about 72 kDa. It is further predicted that amino acid residues from about 41 to about 350 constitute the extracellular domain (amino acid residues from about 1 to about 310 in SEQ ID NO:2); from about 351 to about 367 the transmembrane domain (amino acid residues from about 311 to about 327 in SEQ ID NO:2); from about 368 to about 655 the intracellular domain (amino acid residues from about 328 to about 615 in SEQ ID NO:2); and from about 429 to about 495 the death domain (amino acid residues from about 389 to about 455 in SEQ ID NO:2).

FIG. 2 shows the regions of similarity between the amino acid sequences of the TR9 receptor (SEQ ID NO:2) and Fas (SEQ ID NO:3), NGFR p75 (SEQ ID NO:4), and TNFR 1 (SEQ ID NO:5). Residues that match the consensus are shaded.

FIGS. 4A-C. Highlight the predicted amino acid sequence of TR9.

FIG. 4A: The open reading frame for TR9 defines a type I transmembrane protein of 655 amino acids (SEQ ID NO:2). Application of a computer program other than PSORT has predicted the mature protein to start at amino acid 42 (Gln, indicated by a black triangle). The putative signal peptide and transmembrane domain are single and double underlined, respectively. Six potential N-glycosylation sites are indicated by black dots. The cytoplasmic death domain is boxed. An intracellular region containing a potential leucine-zipper motif overlapping with a proline rich sequence is underlined with a thick line. FIG. 4B: Sequence alignment of extracellular cysteine-rich domains of TR9 (SEQ ID NO:19) and osteoprotegerin (SEQ ID NO:20). Alignment was done with Megalign (DNASTAR) software. Shading represents identical residues. FIG. 4C: Sequence comparison of death domains of TR9 (SEQ ID NO:21), CD95 (SEQ ID NO:22), TNFR1 (SEQ ID NO:23), DR3 (SEQ ID NO:24), DR4 (SEQ ID NO:25), and DR5 (SEQ ID NO:26). Alignment was performed and represented in the same way as in FIG. 4B. OPG; osteoprotegerin.

DETAILED DESCRIPTION OF THE PREFERRED EMBODIMENTS

Figure 2:
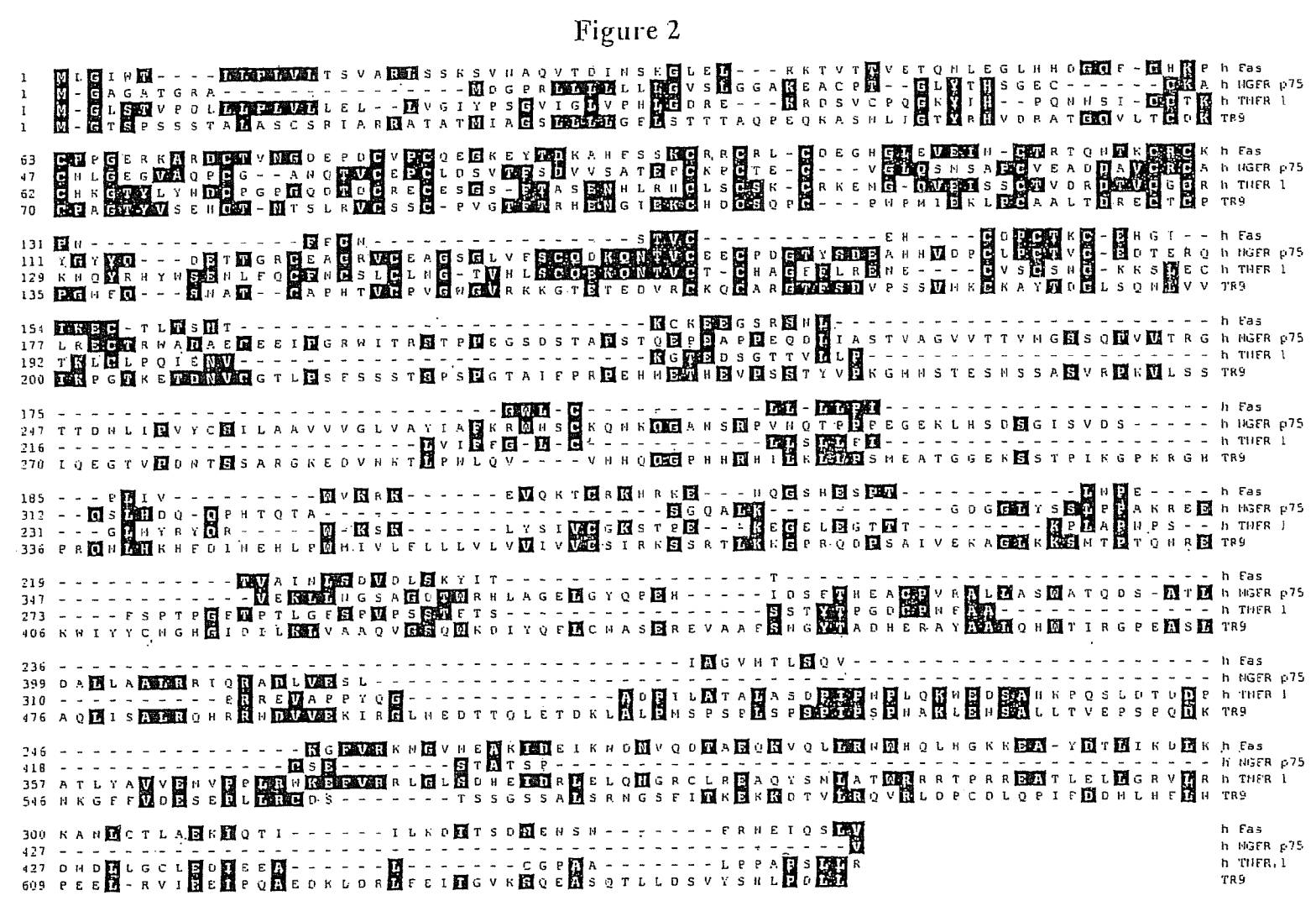
Figure 3:
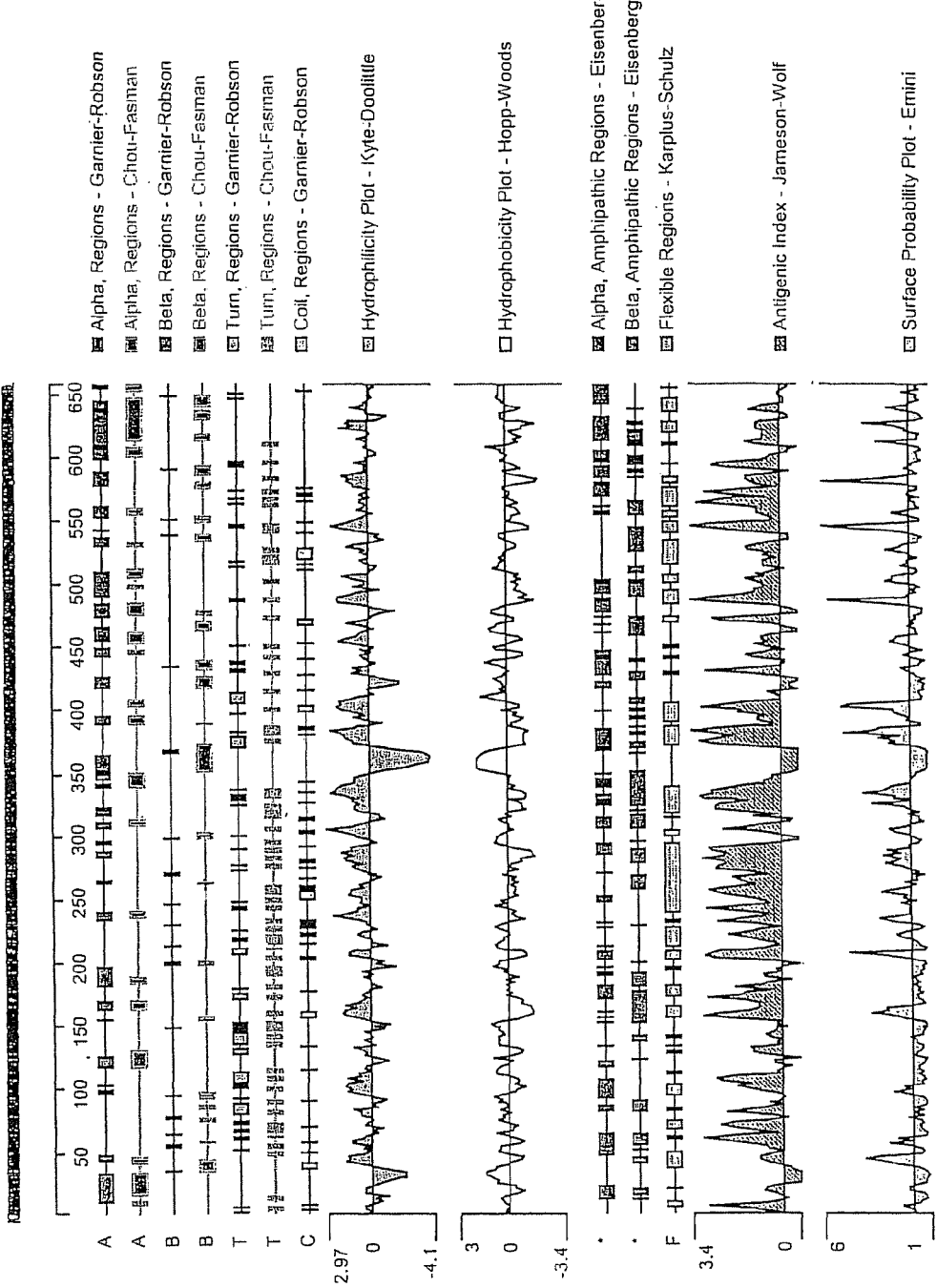
FIG. 3 shows an analysis of the TR9 amino acid sequence. Alpha, beta, turn and coil regions; hydrophilicity and hydrophobicity; amphipathic regions; flexible regions; antigenic index and surface probability are shown, as predicted for the amino acid sequence depicted in FIGS. 1A-D using the default parameters of the recited computer programs. In the "Antigenic Index—Jameson-Wolf" graph, amino acid residues about 44 to about 121, about 156 to about 311, about 323 to about 348, about 376 to about 412, about 433 to about 474, about 485 to about 599, and about 611 to about 628 in FIGS. 1A-D correspond to the shown highly antigenic regions of the TR9 protein. These highly antigenic fragments in FIGS. 1A-D correspond to the following fragments, respectively, in SEQ ID NO:2: amino acid residues about 4 to about 81, about 116 to about 271, about 283 to about 308, about 336 to about 372, about 393 to about 434, about 445 to about 559, and about 571 to about 588.

The present invention provides isolated nucleic acid molecules, or alternatively consisting of, a polynucleotide encoding a TR9 receptor polypeptide having the amino acid sequence shown in FIGS. 1A-C (SEQ ID NO:2), which was determined by sequencing a cloned cDNA. As shown in FIG. 2, the TR9 receptor protein of the present invention shares sequence homology with Fas (SEQ ID NO:3), NGFR p75 (SEQ ID NO:4), and TNFR 1 (SEQ ID NO:5). The nucleotide sequence shown in SEQ ID NO:1 was obtained by sequencing a cDNA clone, which was deposited on May 15, 1997 at the American Type Culture Collection, 10801 University Boulevard, Manassas, Va., 20110-2209, and given accession number 209037. The deposited clone is inserted in the pBluescript SK(–) plasmid (Stratagene, LaJolla, Calif.) using the EcoRI and XhoI restriction endonuclease cleavage sites.

Nucleic Acid Molecules

Unless otherwise indicated, all nucleotide sequences determined by sequencing a DNA molecule herein were determined using an automated DNA sequencer (such as the Model 373 from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

Using the information provided herein, such as the nucleotide sequence in FIGS. 1A-D (SEQ ID NO:1), a nucleic acid molecule of the present invention encoding a TR9 polypeptide may be obtained using standard cloning and screening procedures, such as those for cloning cDNAs using mRNA as starting material. Illustrative of the invention, the nucleic acid molecule described in FIGS. 1A-D (SEQ ID NO:1) was discovered in a cDNA library derived from human microvascular endothelial cells. The gene was also identified in cDNA libraries from the following tissues: human placenta, stromal cells, human amygdala, human umbilical vein endothelial cells, kidney cancer, human gall bladder, soares adult brain, normal human liver, hepatocellular tumor, keratinocytes, bone marrow, macrophage, human synovial sarcoma, human hippocampus, and human tonsils.

The determined nucleotide sequence of the TR9 cDNA of FIGS. 1A-D (SEQ ID NO:1) contains an open reading frame encoding a protein of about 615 amino acid residues, with a predicted leader sequence of about 40 amino acid residues, and a deduced molecular weight of about 72 kDa. The amino acid sequence of the predicted mature TR9 receptor is shown in FIGS. 1A-D (SEQ ID NO:2) from amino acid residue about 1 to residue about 615. The TR9 protein shown in FIGS. 1A-D (SEQ ID NO:2) is about 24% identical and about 43% similar to NGFR (FIG. 2).

Figure 4C:
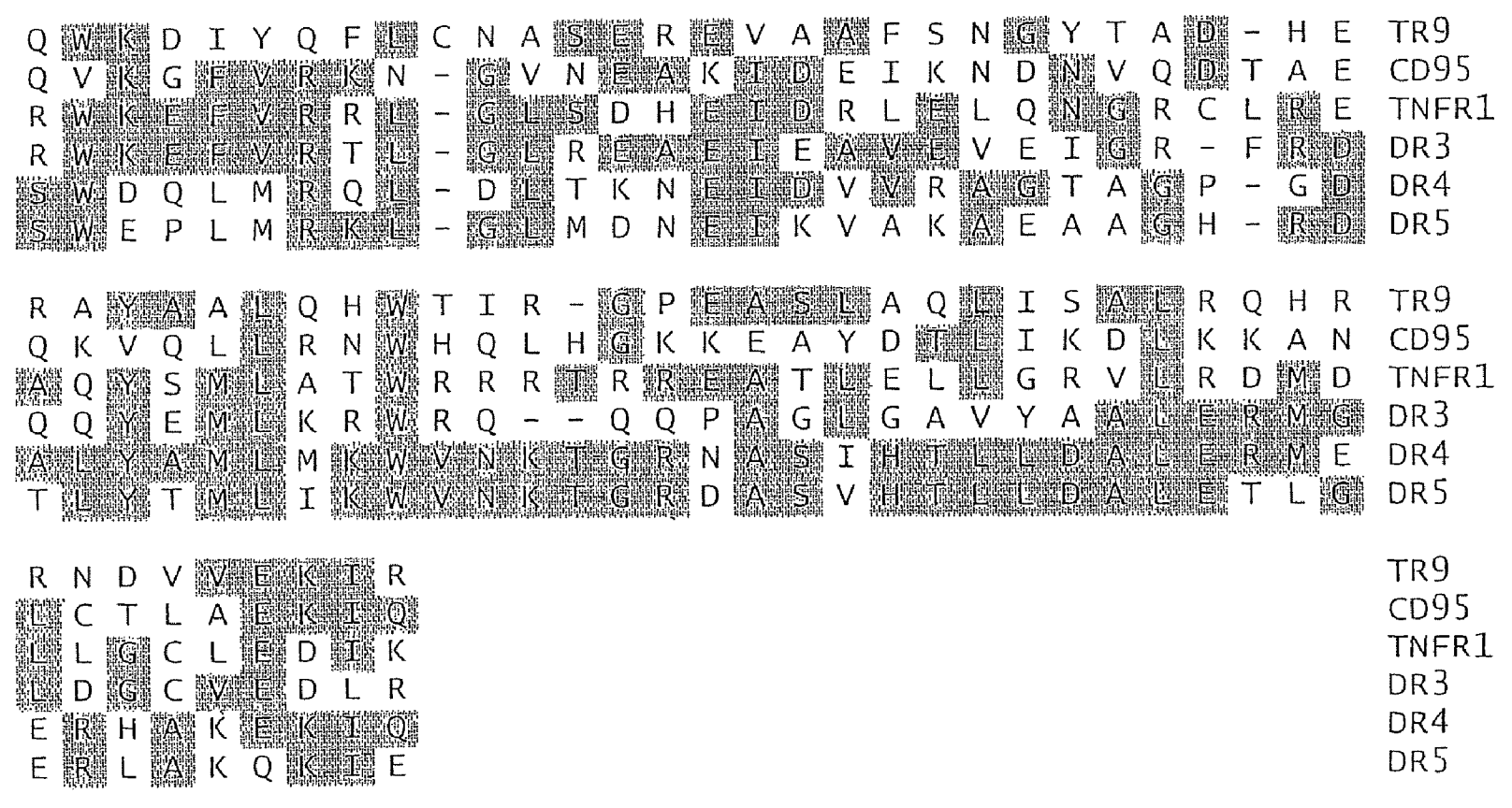
Figure 6:
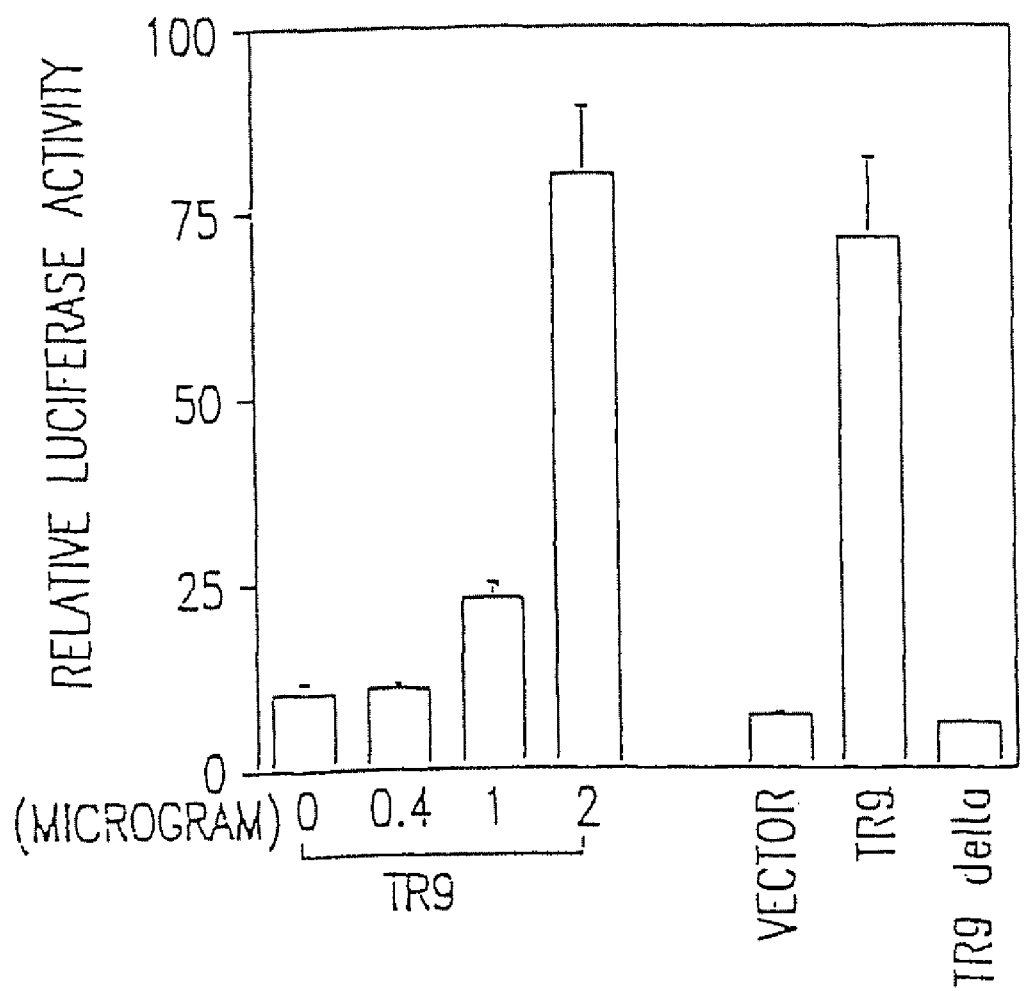
FIG. 6. TR9 mediates nuclear factor NF-kappaB activation. Cotransfection of 293 cells was performed with the indicated expression constructs and a NF-kappaB luciferase reporter construct. After transfection (at 36 hours), cell extracts were prepared and luciferase activities determined as previously described (Chinnaiyan et al., Science 274:990-992 (1996); and Pan et al., Science 276:111-113 (1997)). Transfection efficiency was monitored by beta-galactosidase activity. A portion of the transfected cells was used to monitor expression of TR9 or TR9 delta. Cell lysates were prepared and immunoprecipitated with FLAG M2 affinity gel and the presence of TR9 or TR9 delta detected by blotting with anti-FLAG.

As predicted by the sequence homology exhibited between TR9 and other death domain containing receptors (see FIG. 4C), TR9 induces apoptosis of mammalian cells (see FIG. 6). It is expected that TR9-induced apoptosis will be efficiently blocked by inhibitors of death proteases including z-VAD-fmk, an irreversible broad spectrum caspase inhibitor and CrmA, a cowpox virus encoded serpin that preferentially inhibits apical caspases such as FLICE/MACH-1 (caspase-8).

As indicated, the present invention also provides the mature form(s) of the TR9 receptor of the present invention. According to the signal hypothesis, proteins secreted by mammalian cells have a signal or secretory leader sequence which is cleaved from the mature protein once export of the growing protein chain across the rough endoplasmic reticulum has been initiated. Most mammalian cells and even insect cells cleave secreted proteins with the same specificity. However, in some cases, cleavage of a secreted protein is not entirely uniform, which results in two or more mature species on the protein. Further, it has long been known that the cleavage specificity of a secreted protein is ultimately determined by the primary structure of the complete protein, that is, it is inherent in the amino acid sequence of the polypeptide. Therefore, the present invention provides a nucleotide sequence encoding the mature TR9 receptor polypeptides having the amino acid sequence encoded by the cDNA clone contained in the host identified as ATCC Deposit No. 209037 and as shown in FIGS. 1A-D (SEQ ID NO:2). By the mature TR9 protein having the amino acid sequence encoded by the cDNA clone contained in the host identified as ATCC Deposit 209037 is meant the mature form(s) of the TR9 receptor produced by expression in a mammalian cell (e.g., COS cells, as described below) of the complete open reading frame encoded by the human DNA sequence of the clone contained in the vector in the deposited host. As indicated below, the mature TR9 receptor having the amino acid sequence encoded by the cDNA clone contained in ATCC Deposit No. 209037 may or may not differ from the predicted "mature" TR9 receptor protein shown in SEQ ID NO:2 (amino acids from about 1 to about 615) depending on the accuracy of the predicted cleavage site based on computer analysis.

Methods for predicting whether a protein has a secretory leader as well as the cleavage point for that leader sequence are available. For instance, the methods of McGeoch (*Virus Res.* 3:271-286 (1985)) and von Heinje (*Nucleic Acids Res.* 14:4683-4690 (1986)) can be used. The accuracy of predicting the cleavage points of known mammalian secretory proteins for each of these methods is in the range of 75-80%. von Heinje, supra. However, the two methods do not always produce the same predicted cleavage point(s) for a given protein.

In the present case, the predicted amino acid sequence of the complete TR9 polypeptides of the present invention were analyzed by a computer program ("PSORT") (K. Nakai and M. Kanehisa, *Genomics* 14:897-911 (1992)), which is an expert system for predicting the cellular location of a protein based on the amino acid sequence. As part of this computational prediction of localization, the methods of McGeoch and von Heinje are incorporated. The analysis by the PSORT program predicted the cleavage site between amino acid residues 40 and 41 in FIGS. 1A-D (amino acid residues −1 and 1 in SEQ ID NO:2). Thereafter, the complete amino acid sequences were further analyzed by visual inspection, applying a simple form of the (−1, −3) rule of von Heinje. von Heinje, supra. Thus, the leader sequence for the TR9 receptor protein is predicted to consist of amino acid residues from about 1 to 40 in FIGS. 1A-D (amino acid residues −40 to about −1 in SEQ ID NO:2), while the mature TR9 protein is predicted to consist of residues from about 41 to 655 in FIGS. 1A-D (about 1 to about 615 of SEQ ID NO:2). Analysis using a different computer program predicts that the mature protein of TR9 starts at amino acid 42 (Gln) as depicted in FIGS. 1A-D and 4A. The results of this analysis are presented in FIG. 4A and described in Example 6.

As one of ordinary skill would appreciate, due to the possibility of sequencing errors, as well as the variability of cleavage sites for leaders in different known proteins, the predicted TR9 receptor polypeptide encoded by the deposited cDNA comprises about 655 amino acids, but may be anywhere in the range of 645-665 amino acids; and the predicted leader sequence of this protein is about 40 amino acids, but may be anywhere in the range of about 30 to about 50 amino acids. It will further be appreciated that, the domains described herein have been predicted by computer analysis, and accordingly, that depending on the analytical criteria used for identifying various functional domains, the exact "address" of, for example, the extracellular domain, intracelluar domain, death domain, cystein-rich motifs, and transmembrane domain of TR9 may differ slightly. For example, the exact location of the TR9 extracellular domain in FIGS. 1A-D (SEQ ID NO:2) may vary slightly (e.g., the address may "shift" by about 1 to about 20 residues, more likely about 1 to about 5 residues) depending on the criteria used to define the domain. In any event, as discussed further below, the invention further provides polypeptides having various residues deleted from the N-terminus and/or C-terminus of the complete TR9, including polypeptides lacking one or more amino acids from the N-termini of the extracellular domain described herein, which constitute soluble forms of the extracellular domain of the TR9 polypeptides.

As indicated, nucleic acid molecules of the present invention may be in the form of RNA, such as mRNA, or in the form of DNA, including, for instance, cDNA and genomic DNA obtained by cloning or produced synthetically. The DNA may be double-stranded or single-stranded. Single-stranded DNA or RNA may be the coding strand, also known as the sense strand, or it may be the non-coding strand, also referred to as the anti-sense strand.

By "isolated" nucleic acid molecule(s) is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. However, a nucleic acid molecule contained in a clone that is a member of a mixed clone library (e.g., a genomic or cDNA library) and that has not been isolated from other clones of the library (e.g., in the form of a homogeneous solution containing the clone without other members of the library) or a chromosome isolated or removed from a cell or a cell lysate (e.g., a "chromosome spread", as in a karyotype), is not "isolated" for the purposes of this invention. Isolated RNA molecules include in vivo or in vitro RNA transcripts of the DNA molecules of the present invention. Isolated nucleic acid molecules according to the present invention further include such molecules produced synthetically.

Isolated nucleic acid molecules of the present invention include DNA molecules, or alternatively consisting of, an open reading frame (ORF) shown in FIGS. 1A-D (SEQ ID NO:1); DNA molecules, or alternatively consisting of, the coding sequence for the mature TR9 protein; and DNA molecules which comprise a sequence substantially different from those described above but which, due to the degeneracy of the genetic code, still encode the TR9 protein shown in FIGS. 1A-D (SEQ ID NO:2). Of course, the genetic code is well known in the art. Thus, it would be routine for one skilled in the art to generate such degenerate variants.

In addition, the invention provides nucleic acid molecules having nucleotide sequences related to extensive portions of the nucleotide sequence in FIGS. 1A-D of (SEQ ID NO:1), which have been determined from the following related cDNA clones: HIBEJ86R (SEQ ID NO:6), HL1AA79R (SEQ ID NO:7), HHFGD57R (SEQ ID NO: 8), HSABG38R (SEQ ID NO:9), and HHPDZ31R (SEQ ID NO:10).

Further, the invention includes a polynucleotide, or alternatively consisting of, any portion of at least about 30 nucleotides, preferably at least about 50 nucleotides, of the nucleotide sequence disclosed in FIGS. 1A-D from nucleotides 655 to 907 (nucleotides 615 to 867 of SEQ ID NO:1) and/or the nucleotide sequence disclosed in FIGS. 1A-D from nucleotides to 540 to 1020 (nucleotides 500 to 980 as depicted in SEQ ID NO:1).

In another aspect, the invention provides isolated nucleic acid molecules encoding the TR9 receptor polypeptide having an amino acid sequence as encoded by the cDNA clone contained in the plasmid deposited as ATCC Deposit No. 209037 on May 15, 1997. In a further embodiment, nucleic acid molecules are provided encoding the mature TR9 receptor polypeptide or the full-length TR9 receptor polypeptide lacking the N-terminal methionine. The invention also provides an isolated nucleic acid molecule having the nucleotide sequence shown in FIGS. 1A-D (SEQ ID NO:1) or the nucleotide sequence of the TR9 cDNA contained in the above-described deposited clone, or a nucleic acid molecule having a sequence complementary to one of the above sequences.

Such isolated molecules, particularly DNA molecules, have uses which include, but are not limited to, as probes for gene mapping, by in situ hybridization with chromosomes, and for detecting expression of the TR9 receptor gene in human tissue, for instance, by Northern blot analysis.

The present invention is further directed to fragments of the isolated nucleic acid molecules described herein. By a fragment of an isolated nucleic acid molecule having the nucleotide sequence of the deposited cDNA (the clone deposited as ATCC Deposit No. 209037), or the nucleotide sequence shown in FIGS. 1A-D (SEQ ID NO:1), or the complementary strand thereto, is intended fragments at least about 15 nt, and more preferably at least about 20 nt, still more preferably at least about 30 nt, and even more preferably, at least about 40, 50, 100, 150, 200, 250, 300, 400, or 500 nt in length. These fragments have numerous uses which include, but are not limited to, diagnostic probes and primers as discussed herein. Of course, larger fragments of 50-1500 nt or 501-1500 nt in length are also useful according to the present invention as are fragments corresponding to most, if not all, of the nucleotide sequence of the deposited cDNA or as shown in FIGS. 1A-D (SEQ ID NO:1). By a fragment at least about 20 nt in length, for example, is intended fragments which include 20 or more contiguous bases from the nucleotide sequence of the deposited cDNA or the nucleotide sequence as shown in FIGS. 1A-D (SEQ ID NO:1). In this context "about" includes the particularly recited size, larger or smaller by several (5, 4, 3, 2, or 1) nucleotides, at either terminus or at both termini.

Representative examples of TR9 polynucleotide fragments of the invention include, for example, fragments that comprise, or alternatively, consist of, a sequence from about nucleotide 1-50, 51-100, 101-150, 151-200, 201-250, 251-300, 301-350, 351-400, 401-450, 445-879, 451-500, 501-550, 551-600, 615-651, 651-700, 701-750, 751-800, 800-850, 850-867, 851-900, 901-950, 951-1000, 1001-1050, 1051-1100, 1101-1150, 1151-1200, 1201-1250, 1251-1300, 1301-1350, 1351-1400, 1401-1450, 1451-1500, 1501-1550, 1551-1600, 1601-1650, 1651-1700, 1701-1750, 1751-1800, 1801-1850, 1851-1900, 1901-1950, 1951-2000, 2001-2050, 2051-3000, or 3001 to the end of SEQ ID NO:1, or the complementary DNA strand thereto, or the cDNA contained in the deposited clone. In this context "about" includes the particularly recited ranges, larger or smaller by several (5, 4, 3, 2, or 1) nucleotides, at either terminus or at both termini.

In specific embodiments, the polynucleotide fragments of the invention encode a polypeptide which demonstrates a TR9 functional activity. By a polypeptide demonstrating a TR9 "functional activity" is meant, a polypeptide capable of displaying one or more known functional activities associated with a complete (full-length) or mature TR9 polypeptide. Such functional activities include, but are not limited to, biological activity (e.g., ability to induce apoptosis in cells expressing the polypeptide (see e.g., Example 5), the ability to activate monocytes (e.g., induce TNF-alpha and/or MCP-1 secretion from monocytes), and the ability to increase survival of monocytes (see, e.g., Example 8), antigenicity [ability to bind (or compete with a TR9 polypeptide for binding) to an anti-TR9 antibody], immunogenicity (ability to generate antibody which binds to a TR9 polypeptide), ability to form multimers, and ability to bind to a receptor or ligand for a TR9 polypeptide (e.g., AIM-II and TR9 ligands expressed on the surface of monocytes).

The functional activity of TR9 polypeptides, and fragments, variants derivatives, and analogs thereof, can be assayed by various methods.

For example, in one embodiment where one is assaying for the ability to bind or compete with full-length (complete) TR9 polypeptide for binding to anti-TR9 antibody, various immunoassays known in the art can be used, including but not limited to, competitive and non-competitive assay systems using techniques such as radioimmunoassays, ELISA (enzyme linked immunosorbent assay), "sandwich" immunoassays, immunoradiometric assays, gel diffusion precipitation reactions, immunodiffusion assays, in situ immunoassays (using colloidal gold, enzyme or radioisotope labels, for example), western blots, precipitation reactions, agglutination assays (e.g., gel agglutination assays, hemagglutination assays), complement fixation assays, immunofluorescence assays, protein A assays, and immunoelectrophoresis assays, etc. In one embodiment, antibody binding is detected by detecting a label on the primary antibody. In another embodiment, the primary antibody is detected by detecting binding of a secondary antibody or reagent to the primary antibody. In a further embodiment, the secondary antibody is labeled. Many means are known in the art for detecting binding in an immunoassay and are within the scope of the present invention.

In another embodiment, where a TR9 ligand is identified (e.g., AIM-II and TR9 ligands expressed on the surface of monocytes), or the ability of a polypeptide fragment, variant or derivative of the invention to multimerize is being evaluated, binding can be assayed, e.g., by means well-known in the art, such as, for example, reducing and non-reducing gel chromatography, protein affinity chromatography, and affinity blotting. See generally, Phizicky, et al., Microbiol. Rev. 59:94-123 (1995). In another embodiment, physiological correlates of TR9 binding to its substrates (signal transduction) can be assayed.

In addition, assays described herein (see Examples 5 and 8 and otherwise known in the art may routinely be applied to measure the ability of TR9 polypeptides and fragments, variants derivatives and analogs thereof to elicit TR9 related biological activity (e.g., ability to induce apoptosis in cells expressing the polypeptide (see e.g., Example 6), the ability to activate monocytes, and the ability to increase survival of monocytes (see, e.g., Examples 8 and 9) in vitro or in vivo. For example, biological activity can routinely be measured using the cell death assays performed essentially as previously described (Chinnaiyan et al., *Cell* 81:505-512 (1995); Boldin et al., *J. Biol. Chem.* 270:7795-8(1995); Kischkel et al., *EMBO* 14:5579-5588 (1995); Chinnaiyan et al., *J. Biol. Chem.* 271:4961-4965 (1996)) and as set forth in Example 5 below. In one embodiment involving MCF7 cells, plasmids encoding full-length TR9 or a candidate death domain containing receptor are co-transfected with the pLantern reporter construct encoding green fluorescent protein. Nuclei of cells transfected with TR9 will exhibit apoptotic morphology as assessed by DAPI staining.

Other methods will be known to the skilled artisan and are within the scope of the invention.

Preferred nucleic acid fragments of the present invention include a nucleic acid molecule encoding a member selected from the group: a polypeptide comprising or alternatively, consisting of, the TR9 receptor extracellular domain (predicted to constitute amino acid residues from about 1 to about 310 in SEQ ID NO:2); a polypeptide comprising or alternatively, consisting of, the four TNFR-like cysteine rich motifs of TR9 (amino acid residues 67 to 211 in FIGS. 1A-D; amino acid residues 27 to 171 in SEQ ID NO:2); a polypeptide comprising or alternatively, consisting of, the TR9 receptor transmembrane domain (predicted to constitute amino acid residues from about 311 to about 327 in SEQ ID NO:2); a polypeptide comprising, or alternatively, consisting of, a fragment of the predicted mature TR9 polypeptide, wherein the fragment has a TR9 functional activity (e.g., antigenic activity or biological activity); a polypeptide comprising or alternatively, consisting of, the TR9 receptor intracellular domain (predicted to constitute amino acid residues from about 328 to about 615 in SEQ ID NO:2); a polypeptide comprising or alternatively, consisting of, the TR9 receptor extracellular and intracellular domains with all or part of the transmembrane domain deleted; a polypeptide comprising, or alternatively, consisting of, the TR9 receptor death domain (predicted to constitute amino acid residues from about 389 to about 455 in SEQ ID NO:2); and a polypeptide comprising, or alternatively, consisting of, one, two, three, four or more, epitope bearing portions of the TR9 receptor protein. In additional embodiments, the polynucleotide fragments of the invention encode a polypeptide comprising, or alternatively, consisting of, any combination of 1, 2, 3, 4, 5, 6, 7, or all 8 of the above members. As above, with the leader sequence, the amino acid residues constituting the TR9 receptor extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain. Polypeptides encoded by these nucleic acid molecules are also encompassed by the invention.

It is believed one or more of the four extracellular cysteine rich motifs of TR9 disclosed in FIGS. 1A-D and FIG. 4B is important for interactions between TR9 and its (e.g., AIM-II and TR9 ligands expressed on the surface of monocytes). Accordingly, specific embodiments of the invention are directed to polynucleotides encoding polypeptides which comprise, or alternatively consist of, the amino acid sequence of amino acid residues 27 to 65, 66 to 105, 106 to 145, and/or 146 to 171 of SEQ ID NO:2, as disclosed in FIGS. 1A-D and FIG. 4B. Additional embodiments of the invention are directed to polynucleotides encoding TR9 polypeptides which comprise, or alternatively consist of, any combination of 1, 2, 3, or all 4, of the extracellular cysteine-rich motifs disclosed in FIGS. 1A-D and FIG. 4B. Polypeptides encoded by these polynucleotides are also encompassed by the invention.

In additional embodiments, the polynucleotides of the invention encode functional attributes of TR9. Preferred embodiments of the invention in this regard include fragments that comprise, or alternatively consist of, alpha-helix and alpha-helix forming regions ("alpha-regions"), beta-sheet and beta-sheet forming regions ("beta-regions"), turn and turn-forming regions ("turn-regions"), coil and coil-forming regions ("coil-regions"), hydrophilic regions, hydrophobic regions, alpha amphipathic regions, beta amphipathic regions, flexible regions, surface-forming regions and high antigenic index regions of TR9 polypeptides.

Certain preferred regions in this regard are set out in FIG. 3 (Table 1). The data presented in FIG. 3 and that presented in Table I, merely present a different format of the same results obtained when the amino acid sequence of TR9 as disclosed in FIGS. 1A-D, is analyzed using the default parameters of the DNA*STAR computer algorithm.

The above-mentioned preferred regions set out in FIG. 3 and in Table I include, but are not limited to, regions of the aforementioned types identified by analysis of the amino acid sequence set out in FIGS. 1A-D. As set out in FIG. 3 and in Table I, such preferred regions include Garnier-Robson alpha-regions, beta-regions, turn-regions, and coil-regions, Chou-Fasman alpha-regions, beta-regions, and coil-regions, Kyte-Doolittle hydrophilic regions and hydrophobic regions, Eisenberg alpha- and beta-amphipathic regions, Karplus-Schulz flexible regions, Emini surface-forming regions and Jameson-Wolf regions of high antigenic index. Among highly preferred polynucleotides in this regard are those that encode polypeptides comprise, or alternatively consist of, regions of TR9 that combine several structural features, such as several (e.g., 1, 2, 3, or 4) of the same or different region features set out above.

Additionally, the data presented in columns VIII, IX, XIII, and XIV of Table I can routinely be used to determine regions of TR9 which exhibit a high degree of potential for antigenicity. Regions of high antigenicity are determined from the data presented in columns VIII, IX, XIII, and/or IV by choosing values which represent regions of the polypeptide which are likely to be exposed on the surface of the polypeptide in an environment in which antigen recognition may occur in the process of initiation of an immune response.

Preferred nucleic acid fragments of the present invention also include nucleic acid molecules encoding polypeptides comprising, or alternatively consisting of, one, two, three, four, five, or more epitope-bearing portions of the TR9 receptor protein. In particular, such nucleic acid fragments of the present invention include nucleic acid molecules encoding: a polypeptide comprising or alternatively, consisting of, amino acid residues from about 4 to about 81 in SEQ ID NO:2; a polypeptide comprising or alternatively, consisting of, amino acid residues from about 116 to about 271 in SEQ ID NO:2; a polypeptide comprising or alternatively, consisting of, amino acid residues from about 283 to about 308 in SEQ ID NO:2; a polypeptide comprising or alternatively, consisting of, amino acid residues from about 336 to about 372 in SEQ ID NO:2; a polypeptide comprising or alternatively, consisting of, amino acid residues from about 393 to about 434 in SEQ ID NO:2; a polypeptide comprising or alternatively, consisting of, amino acid residues from about 445 to about 559 in SEQ ID NO:2; and a polypeptide comprising or alternatively, consisting of, amino acid residues from about 571 to about 588 in SEQ ID NO:2. In this context "about" includes the particularly recited range, larger or smaller by several (5, 4, 3, 2, or 1) nucleotides, at either terminus or at both termini. The inventors have determined that the above polypeptide fragments are antigenic regions of the TR9 receptor. Methods for determining other such epitope-bearing portions of the TR9 protein are described in detail below.

TABLE 1

| Res | Position | I | II | III | IV | V | VI | VII | VIII | IX | X | XI | XII | XIII | XIV |
|-----|----------|---|----|----|----|---|----|-----|------|----|---|----|-----|------|-----|
| Met | 1 | . | . | . | . | . | T | . | 0.18 | 0.2 | . | . | . | 0.3 | 0.71 |
| Gly | 2 | . | . | . | . | . | T | . | 0.27 | 0.2 | . | . | . | 0.58 | 0.86 |
| Thr | 3 | . | . | . | . | . | . | C | 0.36 | 0.16 | . | . | . | 0.66 | 0.9 |
| Ser | 4 | . | . | . | . | . | T | C | 0.44 | 0.11 | . | . | . | 1.29 | 1.22 |
| Pro | 5 | . | . | . | . | . | T | C | 0.52 | −0.11 | . | . | F | 2.32 | 1.65 |
| Ser | 6 | . | . | . | . | . | T | T | . | 0.53 | −0.06 | . | . | F | 2.8 | 1.65 |
| Ser | 7 | . | . | . | . | . | T | C | 0.07 | −0.04 | . | . | F | 2.32 | 1.24 |

TABLE 1-continued

| Res | Position | I | II | III | IV | V | VI | VII | VIII | IX | X | XI | XII | XIII | XIV |
|---|---|---|---|---|---|---|---|---|---|---|---|---|---|---|---|
| Ser | 8 | . | A | . | . | . | . | C | −0.21 | 0.26 | . | . | F | 0.89 | 0.66 |
| Thr | 9 | A | A | . | . | . | . | . | −0.21 | 0.33 | . | . | F | 0.41 | 0.5 |
| Ala | 10 | A | A | . | . | . | . | . | −0.67 | 0.33 | . | . | F | 0.13 | 0.5 |
| Leu | 11 | A | A | . | . | . | . | . | −0.67 | 0.51 | * | . | . | −0.6 | 0.2 |
| Ala | 12 | A | . | . | . | . | T | . | −0.26 | 0.51 | * | * | . | −0.2 | 0.19 |
| Ser | 13 | A | . | . | . | . | T | . | −0.84 | 0.03 | * | * | . | 0.1 | 0.36 |
| Cys | 14 | A | . | . | . | . | T | . | −1.12 | 0.21 | * | . | . | 0.1 | 0.31 |
| Ser | 15 | A | . | . | . | . | T | . | −0.42 | 0.03 | * | . | . | 0.1 | 0.31 |
| Arg | 16 | A | A | . | . | . | . | . | 0.5 | −0.47 | * | * | . | 0.3 | 0.45 |
| Ile | 17 | A | A | . | . | . | . | . | 0.5 | −0.86 | * | * | . | 0.75 | 1.63 |
| Ala | 18 | A | A | . | . | . | . | . | 0.49 | −0.93 | * | * | . | 0.75 | 1.23 |
| Arg | 19 | A | A | . | . | . | . | . | 0.57 | −0.83 | * | * | . | 0.6 | 0.91 |
| Arg | 20 | A | A | . | . | . | . | . | 0.56 | −0.33 | * | * | F | 0.6 | 1.31 |
| Ala | 21 | A | A | . | . | . | . | . | −0.16 | −0.53 | * | * | F | 0.9 | 1.87 |
| Thr | 22 | A | A | . | . | . | . | . | −0.16 | −0.41 | * | . | . | 0.3 | 0.94 |
| Ala | 23 | A | A | . | . | . | . | . | −0.16 | 0.27 | * | . | . | −0.3 | 0.34 |
| Thr | 24 | A | A | . | . | . | . | . | −0.61 | 0.77 | . | . | . | −0.6 | 0.34 |
| Met | 25 | A | A | . | . | . | . | . | −1.02 | 0.7 | . | * | . | −0.6 | 0.23 |
| Ile | 26 | A | A | . | . | . | . | . | −1.24 | 0.6 | . | . | . | −0.6 | 0.31 |
| Ala | 27 | A | A | . | . | . | . | . | −1.74 | 0.79 | . | . | . | −0.6 | 0.18 |
| Gly | 28 | A | A | . | . | . | . | . | −1.97 | 0.99 | . | . | . | −0.6 | 0.15 |
| Ser | 29 | A | A | . | . | . | . | . | −2.47 | 1.06 | . | . | . | −0.6 | 0.17 |
| Leu | 30 | A | A | . | . | . | . | . | −2.21 | 1.06 | . | . | . | −0.6 | 0.14 |
| Leu | 31 | A | A | . | . | . | . | . | −2.02 | 0.99 | . | . | . | −0.6 | 0.14 |
| Leu | 32 | A | A | . | . | . | . | . | −2.24 | 1.34 | . | . | . | −0.6 | 0.09 |
| Leu | 33 | A | A | . | . | . | . | . | −2.2 | 1.64 | . | . | . | −0.6 | 0.09 |
| Gly | 34 | A | . | . | B | . | . | . | −2.21 | 1.34 | . | . | . | −0.6 | 0.15 |
| Phe | 35 | . | . | B | B | . | . | . | −1.71 | 1.14 | . | . | . | −0.6 | 0.26 |
| Leu | 36 | . | . | . | B | . | . | C | −1.21 | 0.94 | . | . | . | −0.4 | 0.45 |
| Ser | 37 | . | . | . | B | . | . | C | −0.99 | 0.74 | . | . | F | −0.25 | 0.66 |
| Thr | 38 | . | . | . | B | . | . | C | −0.18 | 0.81 | . | . | F | −0.25 | 0.77 |
| Thr | 39 | . | . | . | B | . | . | C | −0.04 | 0.43 | . | . | F | −0.1 | 1.62 |
| Thr | 40 | . | . | . | B | . | . | C | 0.66 | 0.17 | . | . | F | 0.2 | 1.86 |
| Ala | 41 | . | A | . | B | . | . | C | 1.47 | −0.21 | . | * | F | 0.8 | 2.24 |
| Gln | 42 | A | A | . | B | . | . | . | 1.81 | −0.3 | . | * | F | 0.6 | 2.68 |
| Pro | 43 | A | A | . | B | . | . | . | 1.53 | −0.79 | . | * | F | 0.9 | 3.72 |
| Glu | 44 | A | A | . | . | . | . | . | 1.54 | −0.77 | . | * | F | 0.9 | 3.72 |
| Gln | 45 | A | A | . | . | . | . | . | 1.86 | −0.89 | . | * | F | 0.9 | 2.88 |
| Lys | 46 | A | A | . | . | . | . | . | 1.63 | −0.89 | * | * | F | 0.9 | 2.99 |
| Ala | 47 | A | . | . | . | . | T | . | 0.74 | −0.63 | * | . | F | 1.3 | 1.43 |
| Ser | 48 | . | . | . | . | . | T | C | 0.61 | 0.06 | * | . | F | 0.45 | 0.58 |
| Asn | 49 | . | . | . | . | . | T | C | 0.3 | 0.09 | * | . | F | 0.45 | 0.29 |
| Leu | 50 | . | . | . | . | . | T | C | 0.06 | 0.57 | * | * | . | 0 | 0.41 |
| Ile | 51 | . | . | . | . | T | . | . | 0.12 | 0.83 | * | * | . | 0.17 | 0.48 |
| Gly | 52 | . | . | . | . | T | T | . | 0.68 | 0.44 | * | . | . | 0.54 | 0.58 |
| Thr | 53 | . | . | B | . | . | T | . | 0.12 | 0.54 | * | . | . | 0.31 | 0.96 |
| Tyr | 54 | . | . | B | . | . | T | . | 0.12 | 0.5 | * | * | . | 0.63 | 1.01 |
| Arg | 55 | . | . | B | . | . | T | . | 1.04 | −0.19 | * | * | . | 1.7 | 1.71 |
| His | 56 | . | . | B | B | . | . | . | 1.34 | −0.61 | * | * | . | 1.43 | 2.32 |
| Val | 57 | . | . | . | B | . | . | C | 1.38 | −0.6 | * | * | . | 1.77 | 1.5 |
| Asp | 58 | . | . | . | B | T | . | . | 1.34 | −0.87 | * | * | F | 2.26 | 1.1 |
| Arg | 59 | . | . | . | . | T | . | . | 1.59 | −0.44 | * | * | F | 2.15 | 0.8 |
| Ala | 60 | . | . | . | . | T | T | . | 0.62 | −0.54 | * | * | F | 2.94 | 1.87 |
| Thr | 61 | . | . | . | . | T | T | . | −0.16 | −0.54 | * | * | F | 3.1 | 0.83 |
| Gly | 62 | . | . | . | . | T | T | . | 0.39 | 0.14 | * | * | F | 1.89 | 0.35 |
| Gln | 63 | . | . | . | . | T | T | . | −0.28 | 0.63 | * | * | F | 1.28 | 0.5 |
| Val | 64 | . | . | B | . | . | . | . | −0.39 | 0.7 | * | * | . | 0.22 | 0.19 |
| Leu | 65 | . | . | B | . | . | . | . | 0.24 | 0.21 | . | . | . | 0.21 | 0.31 |
| Thr | 66 | . | . | . | . | T | T | . | −0.11 | −0.21 | . | . | . | 1.1 | 0.36 |
| Cys | 67 | . | . | . | . | T | T | . | 0.02 | −0.04 | . | . | . | 1.41 | 0.26 |
| Asp | 68 | . | . | . | . | T | T | . | −0.57 | −0.26 | . | . | F | 1.87 | 0.49 |
| Lys | 69 | . | . | . | . | T | T | . | −0.06 | −0.44 | . | . | F | 2.18 | 0.34 |
| Cys | 70 | . | . | . | . | T | T | C | 0.44 | −0.5 | . | . | F | 2.59 | 0.63 |
| Pro | 71 | . | . | . | . | T | T | . | 0.51 | −0.59 | . | . | F | 3.1 | 0.55 |
| Ala | 72 | . | . | . | . | T | T | . | 0.32 | 0.17 | . | . | F | 1.89 | 0.43 |
| Gly | 73 | . | . | . | . | T | T | . | 0.02 | 0.81 | . | . | F | 1.28 | 0.59 |
| Thr | 74 | . | . | . | B | T | . | . | −0.02 | 0.63 | . | . | F | 0.57 | 0.52 |
| Tyr | 75 | . | . | B | B | . | . | . | 0.61 | 0.2 | . | . | . | 0.01 | 0.88 |
| Val | 76 | . | . | B | B | . | . | . | 0.16 | 0.2 | . | . | . | −0.15 | 1.22 |
| Ser | 77 | . | . | B | B | . | . | . | 0.43 | 0.34 | * | . | . | −0.05 | 0.45 |
| Glu | 78 | . | . | B | . | . | . | . | 0.78 | 0.34 | . | . | . | 0.4 | 0.42 |
| His | 79 | . | . | . | . | T | . | . | 0.78 | −0.01 | . | . | . | 1.65 | 0.9 |
| Cys | 80 | . | . | . | . | T | T | . | 0.72 | −0.17 | . | . | . | 2.1 | 0.97 |
| Thr | 81 | . | . | . | . | T | T | . | 0.77 | −0.17 | * | * | F | 2.5 | 0.75 |
| Asn | 82 | . | . | . | . | T | T | . | 1.18 | 0.51 | * | * | F | 1.35 | 0.45 |
| Thr | 83 | . | . | . | . | T | T | . | 0.32 | 0.01 | * | * | F | 1.55 | 1.66 |
| Ser | 84 | . | . | . | B | T | . | . | −0.31 | 0.09 | * | * | F | 0.75 | 0.85 |

TABLE 1-continued

| Res | Position | I | II | III | IV | V | VI | VII | VIII | IX | X | XI | XII | XIII | XIV |
|---|---|---|---|---|---|---|---|---|---|---|---|---|---|---|---|
| Leu | 85 | . | . | . | B | T | . | . | 0.06 | 0.17 | * | * | . | 0.35 | 0.28 |
| Arg | 86 | . | . | . | B | T | . | . | 0.07 | 0.16 | * | * | . | 0.1 | 0.26 |
| Val | 87 | . | . | . | B | T | . | . | −0.6 | 0.06 | * | * | . | 0.1 | 0.26 |
| Cys | 88 | . | . | . | . | T | T | . | −0.5 | 0.24 | . | * | . | 0.5 | 0.17 |
| Ser | 89 | . | . | . | . | T | T | . | −1.06 | −0.01 | . | * | . | 1.1 | 0.14 |
| Ser | 90 | . | . | . | . | T | T | . | −0.59 | 0.63 | . | * | . | 0.2 | 0.14 |
| Cys | 91 | . | . | . | . | . | T | C | −1.01 | 0.41 | . | * | . | 0 | 0.25 |
| Pro | 92 | . | . | . | B | T | . | . | −0.86 | 0.33 | . | . | . | 0.1 | 0.27 |
| Val | 93 | . | . | . | B | T | . | . | −0.5 | 0.73 | * | . | . | −0.2 | 0.17 |
| Gly | 94 | . | . | . | B | T | . | . | −0.09 | 0.83 | * | . | F | −0.05 | 0.47 |
| Thr | 95 | . | . | B | B | . | . | . | 0.18 | 0.26 | * | . | F | −0.15 | 0.59 |
| Phe | 96 | . | . | B | B | . | . | . | 0.84 | 0.33 | * | . | F | 0 | 1.09 |
| Thr | 97 | A | . | . | B | . | . | . | 1.06 | −0.31 | * | . | F | 0.6 | 1.91 |
| Arg | 98 | A | . | . | B | . | . | . | 1.57 | −0.34 | * | . | F | 0.6 | 2.13 |
| His | 99 | A | . | . | . | . | T | . | 1.02 | −0.4 | * | . | F | 1 | 2.43 |
| Glu | 100 | . | . | . | . | . | T | C | 1.33 | −0.5 | * | . | F | 1.2 | 1.18 |
| Asn | 101 | . | . | . | . | . | T | T | 2.08 | −0.99 | * | . | F | 1.7 | 1.04 |
| Gly | 102 | . | . | . | . | . | T | T | 1.72 | −0.99 | * | * | F | 1.7 | 1.53 |
| Ile | 103 | A | . | . | . | . | T | . | 1.58 | −0.91 | * | . | F | 1.63 | 0.47 |
| Glu | 104 | A | . | . | . | . | . | . | 1.61 | −0.41 | * | . | F | 1.21 | 0.4 |
| Lys | 105 | . | . | . | . | . | T | . | 0.94 | −0.81 | * | . | . | 2.04 | 0.68 |
| Cys | 106 | . | . | . | . | . | T | . | 0.64 | −0.67 | * | . | . | 2.32 | 0.52 |
| His | 107 | . | . | . | . | . | T | T | 0.99 | −0.97 | * | . | . | 2.8 | 0.4 |
| Asp | 108 | . | . | . | . | . | T | T | 1.67 | −0.57 | * | . | . | 2.52 | 0.35 |
| Cys | 109 | . | . | . | . | . | T | T | 1 | −0.14 | . | . | . | 2.09 | 1 |
| Ser | 110 | . | . | . | . | . | T | T | 0.74 | −0.14 | . | . | F | 1.81 | 0.39 |
| Gln | 111 | . | . | . | . | . | T | . | 1.12 | −0.21 | . | . | F | 1.33 | 0.37 |
| Pro | 112 | . | . | . | . | . | T | . | 0.94 | 0.7 | . | . | F | 0.15 | 0.72 |
| Cys | 113 | . | . | . | . | . | T | T | 0.34 | 0.56 | . | . | F | 0.35 | 0.83 |
| Pro | 114 | . | . | . | . | . | T | T | 0.12 | 0.79 | . | . | . | 0.2 | 0.47 |
| Trp | 115 | . | . | . | . | . | T | C | 0.42 | 1.07 | . | . | . | 0 | 0.21 |
| Pro | 116 | A | . | . | . | . | T | C | 0.47 | 0.64 | . | . | . | 0 | 0.69 |
| Met | 117 | A | A | . | . | . | . | . | −0.13 | 0.07 | * | . | . | −0.3 | 0.9 |
| Ile | 118 | A | A | . | . | . | . | . | 0.32 | 0.33 | * | . | . | −0.3 | 0.7 |
| Glu | 119 | A | A | . | . | . | . | . | −0.13 | −0.16 | * | . | . | 0.3 | 0.7 |
| Lys | 120 | A | A | . | . | . | . | . | −0.43 | −0.01 | * | . | . | 0.3 | 0.38 |
| Leu | 121 | A | A | . | . | . | . | . | −0.81 | −0.13 | * | . | . | 0.3 | 0.55 |
| Pro | 122 | A | A | . | . | . | . | . | −1.02 | −0.31 | * | . | . | 0.3 | 0.32 |
| Cys | 123 | A | A | . | . | . | . | . | −0.44 | 0.37 | * | . | . | −0.3 | 0.13 |
| Ala | 124 | A | A | . | . | . | . | . | −0.44 | 0.86 | . | * | . | −0.6 | 0.23 |
| Ala | 125 | A | A | . | . | . | . | . | −0.38 | 0.17 | . | * | . | −0.3 | 0.25 |
| Leu | 126 | A | A | . | . | . | . | . | 0.43 | −0.26 | . | . | . | 0.3 | 0.91 |
| Thr | 127 | A | A | . | . | . | . | . | −0.02 | −0.83 | . | . | . | 0.75 | 1.56 |
| Asp | 128 | . | A | . | . | T | . | . | 0.33 | −0.76 | . | . | F | 1.15 | 0.83 |
| Arg | 129 | . | A | . | . | T | . | . | 0.26 | −0.77 | . | . | F | 1.3 | 1.45 |
| Glu | 130 | . | A | . | . | T | . | . | 0.63 | −0.89 | . | . | F | 1.15 | 0.54 |
| Cys | 131 | . | A | . | . | T | . | . | 1.23 | −0.94 | . | . | . | 1 | 0.5 |
| Thr | 132 | . | . | . | . | T | . | . | 1.2 | −0.51 | . | . | . | 1.2 | 0.39 |
| Cys | 133 | . | . | . | . | . | . | C | 0.6 | −0.09 | * | . | F | 0.85 | 0.22 |
| Pro | 134 | . | . | . | . | . | T | C | −0.21 | 0.53 | * | . | F | 0.15 | 0.42 |
| Pro | 135 | . | . | . | . | . | T | T | −0.21 | 0.74 | . | . | F | 0.35 | 0.25 |
| Gly | 136 | . | . | . | . | . | T | T | 0.16 | 0.66 | . | . | . | 0.2 | 0.8 |
| Met | 137 | . | . | . | . | . | T | T | 0.47 | 0.47 | . | * | . | 0.2 | 0.7 |
| Phe | 138 | . | . | . | . | . | T | . | 0.54 | 0.44 | . | * | . | 0 | 0.73 |
| Gln | 139 | . | . | . | . | . | T | T | 0.44 | 0.51 | . | * | F | 0.35 | 0.74 |
| Ser | 140 | . | . | . | . | . | T | T | −0.01 | 0.57 | . | * | F | 0.5 | 1.08 |
| Asn | 141 | . | . | . | . | . | T | T | −0.26 | 0.53 | . | * | F | 0.35 | 0.67 |
| Ala | 142 | . | . | . | . | . | T | T | 0.13 | 0.24 | . | * | F | 0.65 | 0.39 |
| Thr | 143 | . | . | . | . | . | T | . | 0.8 | 0.27 | . | * | . | 0.3 | 0.45 |
| Cys | 144 | . | . | . | . | . | T | . | 0.49 | 0.39 | . | . | . | 0.3 | 0.38 |
| Ala | 145 | . | . | . | . | . | T | C | −0.07 | 0.47 | . | . | . | 0 | 0.54 |
| Pro | 146 | . | . | . | . | . | T | T | −0.73 | 0.61 | . | . | . | 0.2 | 0.28 |
| His | 147 | . | . | . | . | . | T | T | −0.36 | 0.7 | . | . | . | 0.2 | 0.28 |
| Thr | 148 | . | . | . | B | . | T | T | −0.9 | 0.56 | . | . | . | 0.2 | 0.43 |
| Val | 149 | . | . | . | B | . | . | . | −0.58 | 0.7 | . | . | . | −0.4 | 0.21 |
| Cys | 150 | . | . | . | B | . | . | T | −0.28 | 0.7 | . | . | . | −0.2 | 0.15 |
| Pro | 151 | . | . | . | . | . | T | T | −0.41 | 1.11 | . | . | . | 0.2 | 0.11 |
| Val | 152 | . | . | . | . | . | T | T | −1.23 | 1.06 | * | . | . | 0.2 | 0.15 |
| Gly | 153 | . | . | . | . | . | T | T | −0.81 | 1.06 | * | * | . | 0.2 | 0.2 |
| Trp | 154 | . | . | . | B | T | . | . | 0.09 | 0.49 | * | * | . | 0.1 | 0.25 |
| Gly | 155 | A | . | . | B | . | . | . | 0.8 | 0.06 | . | * | . | 0.3 | 0.69 |
| Val | 156 | . | . | . | B | . | . | C | 0.67 | −0.59 | * | . | . | 1.85 | 1.39 |
| Arg | 157 | . | . | . | B | . | . | C | 1.21 | −0.59 | * | * | F | 2.3 | 1.31 |
| Lys | 158 | . | . | . | . | . | T | C | 1.56 | −1.01 | . | * | F | 3 | 1.9 |
| Lys | 159 | . | . | . | . | . | T | C | 1.53 | −1.44 | . | * | F | 2.7 | 4.44 |
| Gly | 160 | . | . | . | . | . | T | C | 1.88 | −1.6 | * | * | F | 2.4 | 3.27 |
| Thr | 161 | . | . | . | . | . | T | C | 2.73 | −1.6 | * | * | F | 2.1 | 2.83 |

TABLE 1-continued

| Res | Position | I | II | III | IV | V | VI | VII | VIII | IX | X | XI | XII | XIII | XIV |
|---|---|---|---|---|---|---|---|---|---|---|---|---|---|---|---|
| Glu | 162 | A | A | . | . | . | . | . | 1.77 | −1.6 | . | * | F | 1.2 | 2.37 |
| Thr | 163 | A | A | . | . | . | . | . | 1.83 | −0.96 | . | * | F | 0.9 | 1.77 |
| Glu | 164 | A | A | . | . | . | . | . | 1.12 | −1.39 | . | * | F | 0.9 | 2.41 |
| Asp | 165 | A | A | . | . | . | . | . | 1.51 | −1.3 | . | * | F | 0.75 | 0.75 |
| Val | 166 | A | A | . | . | . | . | . | 1.82 | −1.3 | . | * | F | 0.9 | 1.03 |
| Arg | 167 | A | A | . | . | . | . | . | 1.16 | −1.39 | . | * | . | 0.75 | 1.03 |
| Cys | 168 | A | A | . | . | . | . | . | 0.88 | −0.81 | . | * | . | 0.88 | 0.33 |
| Lys | 169 | A | A | . | . | . | . | . | 0.99 | −0.31 | . | * | . | 0.86 | 0.45 |
| Gln | 170 | A | A | . | . | . | . | . | 0.64 | −0.96 | . | * | . | 1.44 | 0.45 |
| Cys | 171 | . | . | . | . | . | T | T | . | 1.19 | −0.53 | * | * | 2.52 | 0.83 |
| Ala | 172 | . | . | . | . | . | T | T | . | 0.38 | −0.61 | * | * | 2.8 | 0.6 |
| Arg | 173 | . | . | . | . | . | T | T | . | 0.74 | 0.17 | * | * | F | 1.77 | 0.3 |
| Gly | 174 | . | . | . | . | . | T | T | . | 0.7 | 0.16 | * | * | F | 1.49 | 0.75 |
| Thr | 175 | . | . | . | . | . | T | . | . | −0.16 | −0.41 | * | * | F | 1.76 | 1.24 |
| Phe | 176 | . | . | . | . | . | T | . | . | 0.3 | −0.27 | * | * | F | 1.33 | 0.47 |
| Ser | 177 | . | . | . | . | . | . | C | . | 0.59 | 0.16 | * | * | F | 0.38 | 0.74 |
| Asp | 178 | . | . | . | . | . | . | C | . | 0.18 | 0.11 | * | * | F | 0.51 | 0.68 |
| Val | 179 | . | . | . | . | . | . | C | . | −0.33 | 0.01 | * | . | F | 0.99 | 1.06 |
| Pro | 180 | . | . | . | . | . | T | T | . | −0.62 | −0.13 | * | . | F | 1.77 | 0.59 |
| Ser | 181 | . | . | . | . | . | T | T | . | 0.12 | 0.1 | * | . | F | 1.3 | 0.35 |
| Ser | 182 | A | . | . | . | . | T | . | . | −0.24 | 0.1 | * | * | F | 0.77 | 0.94 |
| Val | 183 | A | A | . | . | . | . | . | −0.2 | 0.03 | . | * | . | 0.09 | 0.32 |
| Met | 184 | A | A | . | . | . | . | . | 0.07 | −0.4 | . | * | . | 0.56 | 0.48 |
| Lys | 185 | A | A | . | . | . | . | . | 0.03 | −0.29 | . | * | . | 0.43 | 0.36 |
| Cys | 186 | A | A | . | . | . | . | . | 0.02 | 0.09 | . | * | . | −0.3 | 0.77 |
| Lys | 187 | A | A | . | . | . | . | . | 0.32 | −0.07 | . | * | . | 0.45 | 1.12 |
| Ala | 188 | A | A | . | . | . | . | . | 0.51 | −0.69 | . | * | . | 0.6 | 0.94 |
| Tyr | 189 | A | . | . | . | . | T | . | . | 0.3 | −0.11 | . | * | . | 0.7 | 0.94 |
| Thr | 190 | A | . | . | . | . | T | . | . | −0.04 | 0 | * | * | . | 0.7 | 0.39 |
| Asp | 191 | A | . | . | . | . | T | . | . | 0.62 | 0.39 | * | * | . | 0.1 | 0.51 |
| Cys | 192 | A | . | . | . | . | T | . | . | 0.58 | 0.29 | * | * | . | 0.1 | 0.57 |
| Leu | 193 | A | . | . | . | . | . | . | . | 0.36 | −0.07 | . | . | F | 0.65 | 0.63 |
| Ser | 194 | A | . | . | . | . | T | . | . | −0.26 | 0.13 | . | . | F | 0.25 | 0.31 |
| Gln | 195 | A | . | . | . | . | T | . | . | −0.8 | 0.77 | . | . | F | −0.05 | 0.43 |
| Asn | 196 | A | . | . | . | . | T | . | . | −1.69 | 0.84 | * | . | F | −0.05 | 0.39 |
| Leu | 197 | . | . | B | . | . | . | T | . | −0.98 | 0.84 | . | . | . | −0.2 | 0.2 |
| Val | 198 | . | . | B | B | . | . | . | . | −0.38 | 0.46 | . | . | . | −0.6 | 0.23 |
| Val | 199 | . | . | B | B | . | . | . | . | −0.42 | 0.49 | . | . | . | −0.26 | 0.23 |
| Ile | 200 | . | . | B | B | . | . | . | . | −0.73 | 0.51 | . | * | . | 0.08 | 0.27 |
| Lys | 201 | . | . | . | . | . | T | C | . | −0.69 | 0.31 | . | . | F | 1.47 | 0.53 |
| Pro | 202 | . | . | . | . | . | T | C | . | 0.12 | −0.33 | * | . | F | 2.56 | 1.42 |
| Gly | 203 | . | . | . | . | . | T | T | . | 0.67 | −0.97 | * | * | F | 3.4 | 3.51 |
| Thr | 204 | . | . | . | . | . | T | C | . | 1.52 | −1.17 | * | . | F | 2.86 | 2.53 |
| Lys | 205 | . | . | . | . | . | . | C | . | 2.41 | −1.17 | * | * | F | 2.54 | 2.73 |
| Glu | 206 | . | . | . | . | . | T | . | . | 1.51 | −1.2 | * | . | F | 2.62 | 4.44 |
| Thr | 207 | . | . | . | . | . | T | . | . | 1.06 | −0.99 | * | . | F | 2.5 | 2.28 |
| Asp | 208 | . | . | . | . | . | T | . | . | 1.06 | −0.9 | * | . | F | 2.23 | 0.61 |
| Asn | 209 | . | . | . | . | . | T | T | . | 1.06 | −0.47 | * | . | . | 2.2 | 0.35 |
| VAl | 210 | . | . | . | . | . | T | T | . | 0.2 | 0.01 | * | . | . | 1.38 | 0.35 |
| Cys | 211 | . | . | . | . | . | T | T | . | −0.01 | 0.21 | . | . | . | 1.16 | 0.17 |
| Gly | 212 | . | . | . | . | . | T | T | . | 0 | 0.64 | * | . | . | 0.64 | 0.17 |
| Thr | 213 | . | . | . | B | . | . | . | . | −0.7 | 0.63 | * | . | F | −0.03 | 0.3 |
| Leu | 214 | . | . | . | . | . | T | C | . | −1 | 0.77 | . | . | F | 0.15 | 0.48 |
| Pro | 215 | . | . | . | . | . | T | C | . | −0.44 | 0.59 | . | . | F | 0.15 | 0.66 |
| Ser | 216 | . | . | . | . | . | T | T | . | −0.08 | 0.54 | . | . | F | 0.35 | 0.61 |
| Phe | 217 | . | . | . | . | . | T | T | . | −0.04 | 0.44 | . | . | F | 0.35 | 0.99 |
| Ser | 218 | . | . | . | . | . | T | T | . | −0.03 | 0.24 | . | . | F | 0.85 | 0.92 |
| Ser | 219 | . | . | . | . | . | T | T | . | 0.57 | 0.2 | . | . | F | 1.05 | 0.92 |
| Ser | 220 | . | . | . | . | . | T | T | . | 0.48 | 0.24 | . | . | F | 1.4 | 1.65 |
| Thr | 221 | . | . | . | . | . | T | C | . | 0.57 | −0.16 | . | . | F | 2 | 1.65 |
| Ser | 222 | . | . | . | . | . | . | C | . | 0.92 | −0.11 | . | . | F | 2 | 1.9 |
| Pro | 223 | . | . | . | . | . | . | C | . | 0.91 | −0.07 | . | . | F | 1.8 | 1.41 |
| Ser | 224 | . | . | . | . | . | T | C | . | 0.62 | 0.03 | . | . | F | 1.2 | 1.41 |
| Pro | 225 | . | . | . | . | . | T | T | . | 0.03 | 0.04 | . | . | F | 1.2 | 1.06 |
| Gly | 226 | . | . | . | . | . | T | T | . | −0.36 | 0.34 | . | . | F | 0.85 | 0.48 |
| Thr | 227 | . | . | . | . | . | T | T | . | −0.27 | 0.7 | * | . | F | 0.15 | 0.31 |
| Ala | 228 | . | . | . | . | . | . | C | . | 0.06 | 0.74 | * | . | . | 0.04 | 0.31 |
| Ile | 229 | . | . | B | . | . | . | C | . | 0.14 | 0.31 | . | * | . | 0.58 | 0.61 |
| Phe | 230 | . | . | B | . | . | T | . | . | 0.36 | 0.31 | * | . | . | 0.82 | 0.66 |
| Pro | 231 | . | . | . | . | . | T | C | . | 0.67 | −0.17 | . | . | F | 2.16 | 1.13 |
| Arg | 232 | . | . | . | . | . | T | C | . | 0.38 | −0.17 | . | . | F | 2.4 | 2.19 |
| Pro | 233 | A | . | . | . | . | T | C | . | 0.97 | −0.24 | . | . | F | 2.16 | 2.5 |
| Glu | 234 | A | A | . | . | . | . | . | . | 1.54 | −1.03 | . | * | F | 1.62 | 2.8 |
| His | 235 | A | A | . | . | . | . | . | . | 2.21 | −0.97 | . | . | . | 1.23 | 2.07 |
| Met | 236 | A | A | . | . | . | . | . | . | 2.42 | −0.47 | . | . | . | 0.69 | 1.82 |
| Glu | 237 | A | A | . | . | . | . | . | . | 1.46 | −0.9 | . | . | . | 0.75 | 1.82 |
| Thr | 238 | A | A | . | . | . | . | . | . | 1.46 | −0.26 | . | . | . | 0.58 | 0.99 |

TABLE 1-continued

| Res | Position | I | II | III | IV | V | VI | VII | VIII | IX | X | XI | XII | XIII | XIV |
|---|---|---|---|---|---|---|---|---|---|---|---|---|---|---|---|
| His | 239 | A | A | . | . | . | . | . | 1.16 | −0.33 | . | . | . | 1.01 | 1.55 |
| Glu | 240 | A | A | . | . | . | . | . | 0.89 | −0.56 | . | . | F | 1.74 | 1.2 |
| Val | 241 | A | . | . | . | . | . | T | 1.18 | −0.17 | . | . | F | 2.12 | 1.11 |
| Pro | 242 | . | . | . | . | . | T | T | 0.93 | −0.17 | . | . | F | 2.8 | 1.18 |
| Ser | 243 | . | . | . | . | . | T | T | 0.39 | 0.09 | . | . | F | 1.92 | 1.07 |
| Ser | 244 | . | . | . | . | . | T | T | 0.21 | 0.73 | . | . | F | 1.34 | 1.07 |
| Thr | 245 | . | . | . | . | . | T | . | 0.26 | 0.51 | . | . | F | 0.86 | 1.07 |
| Tyr | 246 | . | . | B | . | . | . | . | 0.77 | 0.09 | . | . | F | 0.48 | 1.59 |
| Val | 247 | . | . | . | . | . | T | C | 0.38 | 0.13 | * | . | F | 0.6 | 1.18 |
| Pro | 248 | . | . | . | . | . | T | T | 0.68 | 0.36 | * | . | F | 0.65 | 0.81 |
| Lys | 249 | . | . | . | . | . | T | T | 0.68 | 0.27 | * | . | F | 0.65 | 0.83 |
| Gly | 250 | . | . | . | . | . | T | C | 0.68 | −0.1 | * | . | F | 1.2 | 1.5 |
| Met | 251 | . | . | . | . | . | . | C | 0.92 | −0.26 | * | . | F | 1.3 | 1.4 |
| Asn | 252 | . | . | . | . | . | . | C | 1.48 | −0.69 | * | . | F | 1.9 | 1.21 |
| Ser | 253 | . | . | . | . | . | T | C | 1.69 | −0.3 | . | . | F | 2.1 | 1.64 |
| Thr | 254 | . | . | . | . | . | T | C | 1.34 | −0.33 | . | . | F | 2.4 | 2.66 |
| Glu | 255 | . | . | . | . | . | T | C | 1.39 | −0.56 | . | . | F | 3 | 2.22 |
| Ser | 256 | . | . | . | . | . | T | C | 1.4 | −0.57 | . | . | F | 2.7 | 2.22 |
| Asn | 257 | . | . | . | . | . | T | T | 1.1 | −0.46 | . | * | F | 2.3 | 1.55 |
| Ser | 258 | . | . | . | . | . | T | C | 0.54 | −0.56 | . | * | F | 2.1 | 1.2 |
| Ser | 259 | . | . | . | . | . | T | C | 0.97 | 0.09 | . | * | F | 0.75 | 0.67 |
| Ala | 260 | . | . | . | . | . | T | C | 0.76 | −0.3 | . | * | F | 1.05 | 0.81 |
| Ser | 261 | . | . | . | B | . | . | C | 1.1 | −0.27 | . | * | F | 0.89 | 0.93 |
| Val | 262 | A | . | . | B | . | . | . | 0.24 | −0.66 | . | * | F | 1.38 | 1.4 |
| Arg | 263 | . | . | B | B | . | . | . | −0.27 | −0.4 | . | * | F | 1.32 | 1.03 |
| Pro | 264 | A | . | . | . | . | . | . | −0.27 | −0.21 | . | * | F | 1.61 | 0.63 |
| Lys | 265 | . | . | . | . | . | T | . | 0.02 | −0.21 | . | * | F | 2.4 | 1.14 |
| Val | 266 | . | . | . | . | . | . | C | −0.57 | −0.47 | . | * | F | 1.81 | 0.78 |
| Leu | 267 | . | . | . | . | . | . | C | 0.29 | 0.21 | . | * | F | 0.97 | 0.35 |
| Ser | 268 | . | . | B | . | . | . | . | 0.18 | 0.19 | . | * | F | 0.53 | 0.31 |
| Ser | 269 | . | . | B | . | . | . | . | 0.04 | 0.19 | * | * | F | 0.29 | 0.71 |
| Ile | 270 | . | . | B | . | . | . | . | −0.31 | −0.03 | * | * | F | 0.65 | 0.86 |
| Gln | 271 | . | . | B | . | . | . | . | −0.31 | −0.23 | * | . | F | 0.95 | 0.92 |
| Glu | 272 | . | . | . | . | T | . | . | 0.29 | 0.03 | . | . | F | 1.05 | 0.51 |
| Gly | 273 | . | . | . | . | T | . | . | 0.59 | 0.07 | . | . | F | 1.5 | 1.13 |
| Thr | 274 | . | . | . | . | . | . | C | 0.89 | −0.61 | . | . | F | 2.5 | 1.09 |
| Val | 275 | . | . | . | . | . | T | C | 1.47 | −0.61 | . | . | F | 3 | 1.01 |
| Pro | 276 | . | . | . | . | . | T | C | 1.17 | −0.13 | . | . | F | 2.4 | 1.47 |
| Asp | 277 | . | . | . | . | . | T | T | 0.87 | −0.17 | . | . | F | 2.3 | 1.37 |
| Asn | 278 | . | . | . | . | . | T | C | 0.62 | −0.27 | . | * | F | 2.1 | 2.47 |
| Thr | 279 | . | . | . | . | . | . | C | 1.04 | −0.41 | . | * | F | 1.9 | 1.61 |
| Ser | 280 | . | . | . | . | . | . | C | 1.56 | −0.84 | . | * | F | 2.2 | 1.89 |
| Ser | 281 | . | . | . | . | . | T | C | 1.81 | −0.41 | . | * | F | 2.4 | 1.16 |
| Ala | 282 | . | . | . | . | . | T | C | 1.81 | −0.81 | . | * | F | 3 | 1.61 |
| Arg | 283 | A | . | . | . | . | T | . | 1.81 | −1.3 | . | * | F | 2.5 | 2.08 |
| Gly | 284 | A | . | . | . | . | T | . | 1.27 | −1.69 | * | * | F | 2.2 | 2.6 |
| Lys | 285 | A | . | . | . | . | . | . | 1.57 | −1.43 | * | * | F | 2.04 | 1.91 |
| Glu | 286 | A | . | . | . | . | . | . | 1.91 | −1.53 | * | * | F | 2.08 | 1.57 |
| Asp | 287 | A | . | . | . | . | T | . | 2.19 | −1.53 | * | * | F | 2.32 | 3.16 |
| Val | 288 | A | . | . | . | . | T | . | 1.27 | −1.47 | * | * | F | 2.66 | 2.28 |
| Asn | 289 | . | . | . | . | T | T | . | 1.4 | −0.79 | * | * | F | 3.4 | 1.09 |
| Lys | 290 | . | . | . | . | T | T | . | 1.36 | −0.36 | * | * | F | 2.76 | 1.01 |
| Thr | 291 | . | . | . | . | . | . | C | 0.54 | 0.04 | * | . | F | 1.42 | 2.18 |
| Leu | 292 | . | . | . | . | . | T | C | 0.54 | 0.09 | * | * | F | 1.28 | 1.12 |
| Pro | 293 | A | . | . | . | . | T | . | 0.54 | 0.09 | * | . | F | 0.59 | 0.97 |
| Asn | 294 | A | . | . | . | . | T | . | −0.31 | 0.73 | . | . | . | 0.2 | 0.5 |
| Leu | 295 | A | . | . | . | . | T | . | −0.36 | 0.89 | . | * | . | −0.2 | 0.45 |
| Gln | 296 | . | . | B | B | . | . | . | −0.08 | 0.6 | . | . | . | −0.6 | 0.47 |
| Val | 297 | . | . | B | B | . | . | . | 0.73 | 0.67 | . | . | . | −0.6 | 0.39 |
| Val | 298 | . | . | B | B | . | . | . | 0.94 | 0.67 | . | . | . | −0.6 | 0.83 |
| Asn | 299 | . | . | . | B | . | . | C | 0.6 | 0.39 | . | . | . | −0.1 | 0.83 |
| His | 300 | . | . | . | B | T | . | . | 1.2 | 0.41 | . | . | F | 0.1 | 1.11 |
| Gln | 301 | . | . | . | B | T | . | . | 1.17 | 0.2 | . | . | F | 0.64 | 2.3 |
| Gln | 302 | . | . | . | B | . | . | C | 1.99 | 0.06 | . | . | F | 0.68 | 1.95 |
| Gly | 303 | . | . | . | . | . | T | C | 2.96 | 0.16 | . | . | F | 1.32 | 1.95 |
| Pro | 304 | . | . | . | . | . | T | C | 2.92 | −0.34 | . | . | F | 2.16 | 2.2 |
| His | 305 | . | . | . | . | . | T | C | 2.07 | −0.24 | . | . | F | 2.4 | 1.73 |
| His | 306 | A | . | . | . | . | T | . | 1.26 | 0.04 | * | * | . | 1.21 | 1.23 |
| Arg | 307 | A | A | . | . | . | . | . | 1.3 | 0.3 | * | * | . | 0.42 | 0.65 |
| His | 308 | A | A | . | . | . | . | . | 0.83 | −0.13 | * | * | . | 0.78 | 0.96 |
| Ile | 309 | A | A | . | . | . | . | . | 0.23 | 0.06 | * | * | . | −0.06 | 0.58 |
| Leu | 310 | A | A | . | . | . | . | . | 0.06 | 0.24 | * | * | . | −0.3 | 0.25 |
| Lys | 311 | A | A | . | . | . | . | . | −0.21 | 0.67 | * | * | . | −0.6 | 0.28 |
| Leu | 312 | . | A | . | . | . | . | C | −0.92 | 0.56 | * | * | . | −0.4 | 0.53 |
| Leu | 313 | . | . | . | . | . | T | C | −0.89 | 0.49 | * | * | F | 0.15 | 0.64 |
| Pro | 314 | . | . | . | . | . | T | C | −0.59 | −0.2 | * | * | F | 1.05 | 0.55 |
| Ser | 315 | A | . | . | . | . | T | . | −0.09 | 0.3 | . | * | F | 0.25 | 0.68 |

TABLE 1-continued

| Res | Position | I | II | III | IV | V | VI | VII | VIII | IX | X | XI | XII | XIII | XIV |
|---|---|---|---|---|---|---|---|---|---|---|---|---|---|---|---|
| Met | 316 | A | . | . | . | . | T | . | −0.48 | 0.1 | . | * | . | 0.25 | 1.19 |
| Glu | 317 | A | . | . | . | . | . | . | −0.01 | −0.16 | . | . | F | 0.95 | 0.76 |
| Ala | 318 | A | . | . | . | . | T | . | 0.8 | −0.16 | . | . | F | 1.45 | 0.56 |
| Thr | 319 | A | . | . | . | . | T | . | 1.06 | −0.54 | . | * | F | 2.05 | 0.98 |
| Gly | 320 | A | . | . | . | . | T | . | 1.06 | −1.16 | . | * | F | 2.5 | 1.13 |
| Gly | 321 | . | . | . | . | . | T | C | 1.36 | −0.77 | . | . | F | 3 | 1.5 |
| Glu | 322 | A | . | . | . | . | T | . | 1.04 | −0.89 | . | . | F | 2.5 | 1.4 |
| Lys | 323 | . | . | . | . | . | T | C | 1.42 | −0.89 | * | . | F | 2.4 | 2.04 |
| Ser | 324 | . | . | . | . | T | T | . | 0.84 | −0.89 | * | * | F | 2.3 | 3.18 |
| Ser | 325 | . | . | . | . | T | T | C | 1.23 | −0.63 | * | * | F | 1.8 | 1.29 |
| Thr | 326 | . | . | . | . | . | . | C | 1.23 | −0.63 | * | * | F | 1.3 | 1.29 |
| Pro | 327 | . | . | . | . | . | . | C | 1.02 | −0.2 | . | * | F | 1.19 | 0.95 |
| Ile | 328 | . | . | . | . | T | . | . | 1.02 | −0.16 | * | * | F | 1.88 | 1.1 |
| Lys | 329 | . | . | . | . | T | . | . | 1.43 | −0.54 | * | * | F | 2.52 | 1.52 |
| Gly | 330 | . | . | . | . | . | T | C | 1.39 | −1.03 | * | * | F | 2.86 | 1.93 |
| Pro | 331 | . | . | . | . | T | T | . | 1.67 | −1.03 | * | * | F | 3.4 | 2.72 |
| Lys | 332 | . | . | . | . | T | T | . | 1.67 | −1.21 | * | * | F | 3.06 | 1.85 |
| Arg | 333 | . | . | . | . | T | T | . | 2.67 | −0.79 | * | * | F | 3 | 2.89 |
| Gly | 334 | . | . | . | . | . | . | C | 2.62 | −1.21 | * | * | F | 2.54 | 3.66 |
| His | 335 | . | . | . | . | . | T | C | 2.97 | −1.24 | . | * | F | 2.68 | 3.17 |
| Pro | 336 | . | . | . | . | . | T | C | 2.37 | −0.84 | . | * | F | 2.62 | 2.6 |
| Arg | 337 | . | . | . | . | T | T | . | 2.29 | −0.16 | * | * | F | 2.8 | 2.17 |
| Gln | 338 | A | . | . | . | . | T | . | 2.22 | −0.09 | * | * | F | 2.12 | 2.17 |
| Asn | 339 | A | A | . | . | . | . | . | 2.53 | −0.59 | * | * | F | 1.74 | 2.81 |
| Leu | 340 | A | A | . | . | . | . | . | 1.87 | −0.51 | * | * | F | 1.46 | 1.95 |
| His | 341 | A | A | . | . | . | . | . | 2.08 | 0.27 | * | * | . | −0.02 | 0.97 |
| Lys | 342 | . | A | . | . | . | . | C | 1.08 | −0.13 | * | * | . | 0.65 | 1.01 |
| His | 343 | . | A | . | . | . | . | C | 1.08 | 0.16 | * | * | . | −0.1 | 0.86 |
| Phe | 344 | . | A | . | . | . | . | C | 1.08 | −0.13 | . | * | . | 0.65 | 1.02 |
| Asp | 345 | A | A | . | . | . | . | . | 1.86 | −0.63 | * | * | . | 0.6 | 0.88 |
| Ile | 346 | A | A | . | . | . | . | . | 1.08 | −0.13 | . | * | . | 0.3 | 0.88 |
| Asn | 347 | A | A | . | . | . | . | . | 0.82 | 0.06 | . | * | . | −0.3 | 0.84 |
| Glu | 348 | A | A | . | . | . | . | . | 0.57 | −0.3 | . | * | . | 0.3 | 0.78 |
| His | 349 | A | A | . | . | . | . | . | 0.67 | 0.61 | * | * | . | −0.45 | 1.16 |
| Leu | 350 | . | . | . | B | . | . | C | −0.22 | 0.54 | . | * | . | −0.4 | 0.72 |
| Pro | 351 | A | . | . | B | . | . | . | −0.19 | 0.83 | . | * | . | −0.6 | 0.29 |
| Trp | 352 | A | . | . | B | . | . | . | −1 | 1.47 | . | . | . | −0.6 | 0.16 |
| Met | 353 | A | . | . | B | . | . | . | −1.7 | 1.66 | . | . | . | −0.6 | 0.16 |
| Ile | 354 | A | . | . | B | . | . | . | −2.48 | 1.76 | . | . | . | −0.6 | 0.09 |
| Val | 355 | A | . | . | B | . | . | . | −2.48 | 2.01 | . | . | . | −0.6 | 0.07 |
| Leu | 356 | A | . | . | B | . | . | . | −3.08 | 1.79 | . | . | . | −0.6 | 0.06 |
| Phe | 357 | A | . | . | B | . | . | . | −3.64 | 1.86 | . | . | . | −0.6 | 0.07 |
| Leu | 358 | A | . | . | B | . | . | . | −3.86 | 1.81 | . | . | . | −0.6 | 0.07 |
| Leu | 359 | A | . | . | B | . | . | . | −3.82 | 1.86 | . | . | . | −0.6 | 0.07 |
| Leu | 360 | A | . | . | B | . | . | . | −3.82 | 1.81 | . | . | . | −0.6 | 0.06 |
| Val | 361 | A | . | . | B | . | . | . | −3.9 | 1.67 | . | . | . | −0.6 | 0.05 |
| Leu | 362 | A | . | . | B | . | . | . | −4.06 | 1.67 | . | . | . | −0.6 | 0.04 |
| Val | 363 | A | . | . | B | . | . | . | −4.1 | 1.63 | . | . | . | −0.6 | 0.04 |
| Val | 364 | A | . | . | B | . | . | . | −3.96 | 1.59 | . | . | . | −0.6 | 0.04 |
| Ile | 365 | A | . | . | B | . | . | . | −3.44 | 1.51 | . | . | . | −0.6 | 0.03 |
| Val | 366 | . | . | B | B | . | . | . | −3.48 | 1.21 | . | * | . | −0.6 | 0.05 |
| Val | 367 | . | . | B | B | . | . | . | −2.56 | 1.26 | * | . | . | −0.6 | 0.04 |
| Cys | 368 | . | . | B | B | . | . | . | −1.66 | 0.61 | * | . | . | −0.6 | 0.12 |
| Ser | 369 | A | . | . | B | . | . | . | −1.1 | −0.07 | . | . | . | 0.64 | 0.34 |
| Ile | 370 | . | . | . | B | T | . | . | −0.51 | −0.33 | * | * | . | 1.38 | 0.61 |
| Arg | 371 | . | . | . | B | T | . | . | 0.46 | −0.59 | * | * | F | 2.32 | 1.51 |
| Lys | 372 | . | . | . | B | T | . | . | 1 | −1.16 | * | * | F | 2.66 | 2.21 |
| Ser | 373 | . | . | . | . | T | T | . | 0.86 | −1.06 | * | * | F | 3.4 | 4.56 |
| Ser | 374 | . | . | . | . | T | T | . | 1.2 | −1.06 | * | * | F | 3.06 | 1.92 |
| Arg | 375 | . | . | . | . | T | T | . | 2.13 | −1.06 | * | * | F | 2.72 | 1.92 |
| Thr | 376 | . | . | . | . | T | T | . | 1.68 | −1.06 | * | . | F | 2.38 | 2.86 |
| Leu | 377 | . | . | . | . | . | T | . | 1.42 | −1.01 | * | . | F | 1.84 | 2.12 |
| Lys | 378 | . | . | . | . | . | T | . | 1.83 | −0.97 | * | . | F | 1.84 | 1.67 |
| Lys | 379 | . | . | . | . | . | T | . | 2.13 | −0.97 | * | . | F | 2.18 | 2.27 |
| Gly | 380 | . | . | . | . | . | T | C | 2.02 | −1.06 | * | * | F | 2.52 | 4.76 |
| Pro | 381 | . | . | . | . | . | T | C | 2.12 | −1.74 | * | * | F | 2.86 | 3.97 |
| Arg | 382 | . | . | . | . | T | T | . | 2.63 | −1.31 | * | * | F | 3.4 | 3.07 |
| Gln | 383 | . | . | . | . | . | T | C | 2 | −0.93 | * | . | F | 2.86 | 4.16 |
| Asp | 384 | . | . | . | . | . | T | C | 1.07 | −0.86 | * | . | F | 2.52 | 2.72 |
| Pro | 385 | . | . | . | . | . | T | C | 0.56 | −0.6 | * | * | F | 2.03 | 0.97 |
| Ser | 386 | . | . | . | . | . | T | C | 0.77 | 0.04 | . | * | F | 0.79 | 0.42 |
| Ala | 387 | A | . | . | . | . | T | . | 0.7 | −0.36 | * | * | . | 0.7 | 0.43 |
| Ile | 388 | A | A | . | B | . | . | . | 0.11 | −0.36 | * | . | . | 0.3 | 0.56 |
| Val | 389 | A | A | . | B | . | . | . | −0.23 | −0.29 | . | . | . | 0.3 | 0.42 |
| Glu | 390 | A | A | . | B | . | . | . | −0.83 | −0.24 | . | * | . | 0.3 | 0.41 |
| Lys | 391 | A | A | . | . | . | . | . | −0.49 | −0.06 | . | . | F | 0.45 | 0.49 |
| Ala | 392 | A | A | . | . | . | . | . | 0.14 | −0.74 | . | . | F | 0.9 | 1.31 |

TABLE 1-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 393 | A | A | . | . | . | . | . | 0.73 | −1.39 | . | * | F | 0.9 | 1.51 |
| Leu | 394 | A | A | . | . | . | . | . | 0.99 | −1 | . | . | F | 0.9 | 1.01 |
| Lys | 395 | A | A | . | . | . | . | . | 0.68 | −0.39 | . | * | F | 0.45 | 0.99 |
| Lys | 396 | A | A | . | . | . | . | . | 0.42 | −0.4 | . | * | F | 0.6 | 1.45 |
| Ser | 397 | . | . | . | . | T | . | . | 0.7 | −0.4 | . | . | F | 1.2 | 2.71 |
| Met | 398 | . | . | . | . | . | . | C | 1.04 | −0.6 | * | . | F | 1.6 | 1.96 |
| Thr | 399 | . | . | . | . | . | T | C | 1.86 | −0.2 | * | * | F | 1.8 | 1.7 |
| Pro | 400 | . | . | . | . | . | T | C | 1.92 | 0.2 | . | . | F | 1.5 | 2.03 |
| Thr | 401 | . | . | . | . | . | T | C | 1.88 | −0.19 | . | * | F | 2.4 | 4.03 |
| Gln | 402 | . | . | . | . | . | T | C | 2.22 | −0.8 | . | * | F | 3 | 4.83 |
| Asn | 403 | . | A | . | . | . | . | C | 2.53 | −1.29 | . | . | F | 2.3 | 6.25 |
| Arg | 404 | . | A | . | . | T | . | . | 1.96 | −0.8 | . | * | F | 2.2 | 4.55 |
| Glu | 405 | . | A | . | . | T | . | . | 1.92 | −0.6 | . | * | F | 1.9 | 1.84 |
| Lys | 406 | . | A | . | . | T | . | . | 1.99 | −0.24 | . | * | F | 1.3 | 1.8 |
| Trp | 407 | . | A | . | . | T | . | . | 1.32 | 0.11 | . | * | . | 0.25 | 1.44 |
| Ile | 408 | . | . | . | . | T | . | . | 1.32 | 0.69 | . | * | . | 0 | 0.44 |
| Tyr | 409 | . | . | . | . | T | . | . | 0.87 | 1.09 | . | * | . | 0 | 0.36 |
| Tyr | 410 | . | . | . | . | T | . | . | 0.83 | 1.51 | . | . | . | 0 | 0.34 |
| Cys | 411 | . | . | . | . | T | . | . | 0.44 | 1.1 | . | . | . | 0 | 0.65 |
| Asn | 412 | . | . | . | . | T | T | . | −0.16 | 0.84 | . | . | . | 0.2 | 0.41 |
| Gly | 413 | . | . | . | . | T | T | . | 0.73 | 0.77 | . | . | . | 0.2 | 0.18 |
| His | 414 | . | . | . | . | T | T | . | 0.09 | 0.01 | . | . | . | 0.5 | 0.58 |
| Gly | 415 | . | . | . | . | . | T | C | −0.48 | 0.13 | . | . | . | 0.3 | 0.25 |
| Ile | 416 | A | . | . | B | . | . | . | 0.23 | 0.41 | . | . | . | −0.6 | 0.21 |
| Asp | 417 | A | . | . | B | . | . | . | −0.58 | −0.01 | * | . | . | 0.3 | 0.31 |
| Ile | 418 | A | . | . | B | . | . | . | −1.09 | 0.17 | * | . | . | −0.3 | 0.26 |
| Leu | 419 | A | . | . | B | . | . | . | −1.64 | 0.39 | * | . | . | −0.3 | 0.27 |
| Lys | 420 | A | . | . | B | . | . | . | −1.89 | 0.2 | * | . | . | −0.3 | 0.16 |
| Leu | 421 | A | . | . | B | . | . | . | −1 | 0.7 | * | . | . | −0.6 | 0.24 |
| Val | 422 | A | . | . | B | . | . | . | −1.86 | 0.41 | * | . | . | −0.6 | 0.5 |
| Ala | 423 | A | . | . | B | . | . | . | −1.31 | 0.37 | * | . | . | −0.3 | 0.18 |
| Ala | 424 | A | . | . | B | . | . | . | −0.8 | 0.8 | . | * | . | −0.6 | 0.22 |
| Gln | 425 | A | . | . | B | . | . | . | −0.84 | 0.5 | . | * | . | −0.6 | 0.4 |
| Val | 426 | A | . | . | B | . | . | . | −0.32 | 0.26 | . | * | . | −0.02 | 0.68 |
| Gly | 427 | A | . | . | . | . | T | . | 0.58 | 0.67 | * | * | F | 0.51 | 0.71 |
| Ser | 428 | . | . | . | . | . | T | C | 1.17 | 0.17 | * | * | F | 1.29 | 0.82 |
| Gln | 429 | . | . | . | . | T | T | . | 0.87 | −0.23 | * | * | F | 2.52 | 1.85 |
| Trp | 430 | . | . | . | . | T | T | . | 0.62 | −0.19 | * | * | F | 2.8 | 1.31 |
| Lys | 431 | . | . | . | B | T | . | . | 1.48 | 0.14 | * | * | F | 1.52 | 1.53 |
| Asp | 432 | . | . | . | B | T | . | . | 1.12 | 0.16 | * | . | . | 1.09 | 1.53 |
| Ile | 433 | . | . | B | B | . | . | . | 0.61 | 0.54 | * | . | . | 0.11 | 1.26 |
| Tyr | 434 | . | . | B | B | . | . | . | −0.06 | 0.31 | * | . | . | −0.02 | 0.52 |
| Gln | 435 | . | . | B | B | . | . | . | 0.23 | 0.89 | * | . | . | −0.6 | 0.17 |
| Phe | 436 | . | . | . | B | T | . | . | −0.4 | 1.29 | * | . | . | −0.2 | 0.38 |
| Leu | 437 | . | . | . | B | . | . | C | −0.7 | 1.1 | * | . | . | −0.4 | 0.25 |
| Cys | 438 | . | . | . | B | T | . | . | 0.19 | 0.73 | * | * | . | −0.2 | 0.19 |
| Asn | 439 | . | . | . | . | . | T | C | 0.54 | 0.33 | * | * | . | 0.3 | 0.38 |
| Ala | 440 | . | . | . | . | . | T | C | 0.54 | −0.46 | * | * | F | 1.05 | 0.91 |
| Ser | 441 | A | . | . | . | . | T | . | 0.39 | −1.14 | . | . | F | 1.3 | 2.93 |
| Glu | 442 | A | . | . | . | . | T | . | 0.61 | −1.07 | * | . | F | 1.3 | 1.35 |
| Arg | 443 | A | A | . | . | . | . | . | 0.69 | −0.97 | * | . | F | 0.9 | 1.35 |
| Glu | 444 | A | A | . | . | . | . | . | −0.01 | −0.97 | * | . | . | 0.75 | 1.02 |
| Val | 445 | A | A | . | . | . | . | . | 0.28 | −0.57 | * | . | . | 0.6 | 0.51 |
| Ala | 446 | A | A | . | . | . | . | . | 0.58 | −0.19 | * | . | . | 0.3 | 0.35 |
| Ala | 447 | A | A | . | . | . | . | . | 0.23 | 0.21 | * | . | . | −0.3 | 0.32 |
| Phe | 448 | A | . | . | . | . | T | . | −0.12 | 0.64 | * | . | . | −0.2 | 0.43 |
| Ser | 449 | A | . | . | . | . | T | . | −0.43 | 0.76 | . | . | F | −0.2 | 0.67 |
| Asn | 450 | . | . | . | . | T | T | . | −0.17 | 0.74 | . | . | F | 0.35 | 0.96 |
| Gly | 451 | . | . | . | . | T | T | . | 0.42 | 0.74 | . | . | F | 0.5 | 1.12 |
| Tyr | 452 | . | . | . | . | . | . | C | 0.98 | −0.04 | . | . | F | 1 | 1.39 |
| Thr | 453 | . | A | . | . | . | . | C | 1.68 | 0.07 | . | . | . | 0.05 | 1.18 |
| Ala | 454 | A | A | . | . | . | . | . | 2.09 | −0.33 | . | . | . | 0.45 | 2.06 |
| Asp | 455 | A | A | . | . | . | . | . | 1.5 | −0.76 | . | . | . | 0.75 | 2.58 |
| His | 456 | A | A | . | . | . | . | . | 1.6 | −1.01 | . | . | . | 0.75 | 1.8 |
| Glu | 457 | A | A | . | . | . | . | . | 1.26 | −0.74 | . | . | . | 0.75 | 2.8 |
| Arg | 458 | A | A | . | . | . | . | . | 0.98 | −0.74 | . | * | . | 0.75 | 1.69 |
| Ala | 459 | A | A | . | . | . | . | . | 0.76 | −0.24 | . | * | . | 0.45 | 1.26 |
| Tyr | 460 | A | A | . | . | . | . | . | 0.76 | −0.06 | * | * | . | 0.3 | 0.6 |
| Ala | 461 | A | A | . | . | . | . | . | 0.76 | 0.34 | * | * | . | −0.3 | 0.53 |
| Ala | 462 | A | A | . | . | . | . | . | 0.47 | 0.84 | * | * | . | −0.6 | 0.71 |
| Leu | 463 | A | . | . | B | . | . | . | 0.04 | 1.26 | . | * | . | −0.6 | 0.48 |
| Gln | 464 | A | . | . | B | . | . | . | −0.26 | 0.99 | . | * | . | −0.6 | 0.68 |
| His | 465 | A | . | . | B | . | . | . | 0.1 | 1.17 | . | * | . | −0.6 | 0.47 |
| Trp | 466 | . | . | . | B | T | . | . | 0.34 | 0.67 | . | * | . | −0.05 | 1.13 |
| Thr | 467 | . | . | . | B | . | . | C | 0.72 | 0.41 | * | * | . | −0.1 | 0.64 |
| Ile | 468 | . | . | . | B | . | . | C | 1.53 | 0.44 | * | * | F | 0.35 | 0.73 |
| Arg | 469 | . | . | . | B | . | . | C | 0.94 | −0.06 | . | * | F | 1.7 | 1.2 |

TABLE 1-continued

| Res | Position | I | II | III | IV | V | VI | VII | VIII | IX | X | XI | XII | XIII | XIV |
|---|---|---|---|---|---|---|---|---|---|---|---|---|---|---|---|
| Gly | 470 | . | . | . | . | . | T | C | 0.68 | −0.47 | . | * | F | 2.25 | 0.84 |
| Pro | 471 | . | . | . | . | . | T | C | 0.16 | −0.57 | . | * | F | 3 | 1.61 |
| Glu | 472 | . | . | . | . | . | T | C | −0.12 | −0.57 | * | * | F | 2.55 | 0.68 |
| Ala | 473 | A | . | . | . | . | T | . | 0.77 | −0.07 | * | * | F | 1.75 | 0.69 |
| Ser | 474 | A | A | . | . | . | . | . | −0.16 | −0.1 | * | . | . | 0.9 | 0.78 |
| Leu | 475 | . | . | . | B | . | . | . | −0.7 | 0.16 | . | . | . | 0 | 0.37 |
| Ala | 476 | A | A | . | B | . | . | . | −0.79 | 0.84 | . | . | . | −0.6 | 0.26 |
| Gln | 477 | A | A | . | B | . | . | . | −1.38 | 0.73 | * | . | . | −0.6 | 0.26 |
| Leu | 478 | A | A | . | B | . | . | . | −1.6 | 0.84 | * | * | . | −0.6 | 0.31 |
| Ile | 479 | A | A | . | B | . | . | . | −1.19 | 0.84 | * | . | . | −0.6 | 0.26 |
| Ser | 480 | A | A | . | . | . | . | . | −0.38 | 0.34 | * | . | . | −0.3 | 0.29 |
| Ala | 481 | A | A | . | . | . | . | . | 0.18 | 0.34 | * | . | . | −0.3 | 0.61 |
| Leu | 482 | A | A | . | . | . | . | . | 0.29 | 0.16 | * | . | . | 0.19 | 1.18 |
| Arg | 483 | A | A | . | . | . | . | . | 1.21 | −0.53 | * | . | . | 1.43 | 1.73 |
| Gln | 484 | A | A | . | . | . | . | . | 2.1 | −0.91 | * | . | F | 1.92 | 3.35 |
| His | 485 | . | . | . | . | T | T | . | 2.4 | −1.01 | * | * | F | 3.06 | 6.53 |
| Arg | 486 | . | . | . | . | T | T | . | 2.13 | −1.7 | * | . | F | 3.4 | 5.57 |
| Arg | 487 | . | . | . | . | T | T | . | 2.09 | −1.06 | . | * | F | 3.06 | 2.39 |
| Asn | 488 | . | . | . | . | T | T | . | 1.98 | −0.81 | * | . | F | 2.72 | 1.3 |
| Asp | 489 | . | . | . | . | T | . | . | 2.02 | −1.31 | * | * | F | 2.18 | 1.15 |
| Val | 490 | A | . | . | . | . | . | . | 1.17 | −1.31 | . | * | F | 1.44 | 1.17 |
| Val | 491 | A | . | . | . | . | . | . | 1.17 | −0.63 | . | * | F | 0.95 | 0.51 |
| Glu | 492 | A | . | . | . | . | . | . | 0.71 | −1.03 | * | * | F | 0.95 | 0.6 |
| Lys | 493 | A | . | . | . | . | . | . | −0.1 | −0.6 | * | * | F | 0.95 | 0.8 |
| Ile | 494 | A | . | . | . | . | . | . | −0.7 | −0.56 | * | * | F | 0.95 | 0.89 |
| Arg | 495 | A | A | . | . | . | . | . | 0.16 | −0.59 | * | * | F | 0.75 | 0.51 |
| Gly | 496 | A | A | . | . | . | . | . | 1.01 | −0.59 | * | * | . | 0.6 | 0.44 |
| Leu | 497 | A | A | . | . | . | . | . | 0.7 | −0.59 | * | * | . | 0.75 | 1.05 |
| Met | 498 | A | A | . | . | . | . | . | 0.34 | −0.79 | * | * | . | 0.6 | 0.77 |
| Glu | 499 | A | A | . | . | . | . | . | 1.23 | −0.3 | * | * | F | 0.6 | 1.13 |
| Asp | 500 | A | . | . | . | . | T | . | 0.31 | −0.33 | * | * | F | 1 | 2.37 |
| Thr | 501 | A | . | . | . | . | T | . | 0.66 | −0.33 | . | . | F | 1 | 1.97 |
| Thr | 502 | A | . | . | . | . | T | . | 1.16 | −0.94 | * | * | F | 1.3 | 1.97 |
| Gln | 503 | A | . | . | . | . | T | . | 1.76 | −0.46 | . | * | F | 1 | 1.7 |
| Leu | 504 | A | A | . | . | . | . | . | 1.8 | −0.46 | . | . | F | 0.6 | 1.97 |
| Glu | 505 | A | A | . | . | . | . | . | 0.99 | −0.94 | . | . | F | 0.9 | 2.73 |
| Thr | 506 | A | A | . | . | . | . | . | 0.71 | −0.74 | . | . | F | 0.9 | 1.3 |
| Asp | 507 | A | A | . | . | . | . | . | 0.21 | −0.64 | . | . | F | 0.9 | 1.59 |
| Lys | 508 | A | A | . | . | . | . | . | 0 | −0.64 | . | * | F | 0.75 | 0.76 |
| Leu | 509 | A | A | . | . | . | . | . | 0.21 | −0.21 | . | * | . | 0.3 | 0.81 |
| Ala | 510 | A | A | . | . | . | . | . | −0.09 | −0.09 | . | * | . | 0.3 | 0.48 |
| Leu | 511 | . | A | . | . | . | . | C | 0.01 | 0.3 | . | * | . | −0.1 | 0.32 |
| Pro | 512 | . | A | . | . | T | . | . | −0.29 | 0.73 | . | * | . | −0.2 | 0.61 |
| Met | 513 | . | . | . | . | T | . | . | −0.54 | 0.43 | . | * | . | 0 | 0.8 |
| Ser | 514 | . | . | . | . | . | T | C | −0.54 | 0.36 | . | . | F | 0.6 | 1.51 |
| Pro | 515 | . | . | . | . | . | T | C | −0.26 | 0.36 | . | . | F | 0.45 | 0.8 |
| Ser | 516 | . | . | . | . | . | T | C | 0.34 | 0.31 | . | . | F | 0.6 | 1.09 |
| Pro | 517 | . | . | . | . | T | T | . | 0.26 | 0.13 | . | . | F | 0.8 | 1.26 |
| Leu | 518 | . | . | . | . | T | . | . | 0.64 | 0.13 | . | . | F | 0.6 | 1.09 |
| Ser | 519 | . | . | . | . | . | T | C | 0.06 | 0.13 | . | . | F | 0.6 | 1.26 |
| Pro | 520 | . | . | . | . | . | T | C | 0.06 | 0.43 | . | . | F | 0.15 | 0.57 |
| Ser | 521 | . | . | . | . | . | T | C | 0.06 | 0.43 | . | . | F | 0.3 | 1.07 |
| Pro | 522 | . | . | . | . | . | T | C | 0.06 | 0.13 | . | . | F | 0.6 | 1.07 |
| Ile | 523 | . | . | . | . | . | . | C | 0.87 | 0.17 | . | . | F | 0.4 | 1.07 |
| Pro | 524 | . | . | . | . | . | . | C | 0.58 | 0.14 | . | . | F | 0.4 | 1.28 |
| Ser | 525 | . | . | . | . | . | T | C | 0.83 | 0.26 | . | . | F | 0.45 | 0.84 |
| Pro | 526 | . | . | . | . | . | T | C | 0.32 | −0.17 | . | * | F | 1.2 | 2.39 |
| Asn | 527 | . | . | . | . | . | T | C | 0.53 | −0.17 | . | * | F | 1.2 | 1.27 |
| Ala | 528 | A | . | . | . | . | T | . | 1.42 | −0.6 | . | * | F | 1.3 | 1.64 |
| Lys | 529 | A | A | . | . | . | . | . | 1.33 | −0.59 | . | * | F | 0.9 | 1.71 |
| Leu | 530 | A | A | . | . | . | . | . | 1.04 | −0.63 | . | * | F | 0.9 | 1.43 |
| Glu | 531 | A | A | . | . | . | . | . | 0.44 | −0.53 | . | * | F | 0.9 | 1.43 |
| Asn | 532 | A | A | . | . | . | . | . | −0.37 | −0.34 | . | * | F | 0.45 | 0.59 |
| Ser | 533 | A | . | . | B | . | . | . | −0.09 | 0.34 | . | * | F | −0.15 | 0.59 |
| Ala | 534 | A | . | . | B | . | . | . | −0.99 | 0.14 | * | * | . | −0.3 | 0.49 |
| Leu | 535 | A | . | . | B | . | . | . | −0.18 | 0.79 | . | * | . | −0.6 | 0.23 |
| Leu | 536 | A | . | . | B | . | . | . | −0.39 | 0.39 | . | * | . | −0.3 | 0.29 |
| Thr | 537 | A | . | . | B | . | . | . | −0.69 | 0.43 | . | * | . | −0.6 | 0.45 |
| Val | 538 | . | . | B | B | . | . | . | −0.6 | 0.31 | . | * | . | −0.3 | 0.73 |
| Glu | 539 | . | . | B | . | . | T | . | −0.01 | 0.06 | . | * | F | 0.4 | 1.36 |
| Pro | 540 | . | . | . | . | . | T | C | 0.8 | −0.23 | . | * | F | 1.54 | 1.64 |
| Ser | 541 | . | . | . | . | . | T | C | 1.66 | −0.71 | . | * | F | 2.18 | 3.68 |
| Pro | 542 | A | . | . | . | . | T | . | 1.97 | −1.36 | . | * | F | 2.32 | 4.25 |
| Gln | 543 | . | . | . | . | T | . | . | 2.87 | −0.96 | . | . | F | 2.86 | 4.42 |
| Asp | 544 | . | . | . | . | T | T | . | 2.52 | −1.39 | . | . | F | 3.4 | 6.59 |
| Lys | 545 | . | . | . | . | T | T | . | 2.03 | −1.34 | . | . | F | 3.06 | 4.22 |
| Asn | 546 | . | . | . | . | T | T | . | 1.63 | −0.99 | . | . | F | 2.72 | 2.11 |

TABLE 1-continued

| Res | Position | I | II | III | IV | V | VI | VII | VIII | IX | X | XI | XII | XIII | XIV |
|---|---|---|---|---|---|---|---|---|---|---|---|---|---|---|---|
| Lys | 547 | . | . | . | . | T | T | . | 0.99 | −0.6 | . | . | F | 2.38 | 1.09 |
| Gly | 548 | . | . | . | B | . | . | C | 0.99 | 0.04 | . | . | F | 0.39 | 0.41 |
| Phe | 549 | . | . | B | B | . | . | . | 0.99 | 0.04 | . | . | . | −0.3 | 0.42 |
| Phe | 550 | . | . | B | B | . | . | . | 0.64 | −0.36 | . | . | . | 0.3 | 0.37 |
| Val | 551 | A | . | . | B | . | . | . | 0.64 | 0.03 | . | . | . | −0.3 | 0.49 |
| Asp | 552 | A | . | . | B | . | . | . | 0.39 | −0.4 | . | . | F | 0.45 | 0.99 |
| Glu | 553 | A | A | . | . | . | . | . | −0.08 | −0.76 | . | . | F | 0.9 | 1.77 |
| Ser | 554 | A | A | . | . | . | . | . | −0.19 | −0.86 | * | * | F | 0.9 | 1.96 |
| Glu | 555 | A | A | . | . | . | . | . | 0.62 | −0.81 | * | * | F | 0.75 | 0.97 |
| Pro | 556 | A | A | . | . | . | . | . | 0.81 | −0.81 | * | * | F | 0.9 | 1.1 |
| Leu | 557 | A | A | . | . | . | . | . | 0.81 | −0.24 | * | * | F | 0.45 | 0.44 |
| Leu | 558 | A | A | . | . | . | . | . | 0.51 | −0.63 | . | * | . | 0.91 | 0.42 |
| Arg | 559 | A | A | . | . | . | . | . | 0.5 | −0.24 | * | * | . | 0.92 | 0.37 |
| Cys | 560 | A | . | . | . | . | . | T | 0.2 | −0.19 | * | * | F | 1.78 | 0.64 |
| Asp | 561 | . | . | . | . | T | T | . | 0.11 | −0.49 | . | * | F | 2.64 | 1.04 |
| Ser | 562 | . | . | . | . | T | T | . | 0.58 | −0.79 | . | * | F | 3.1 | 0.71 |
| Thr | 563 | . | . | . | . | T | T | . | 1.09 | −0.36 | . | * | F | 2.64 | 1.32 |
| Ser | 564 | . | . | . | . | T | T | C | 0.68 | −0.54 | . | * | F | 2.43 | 1.06 |
| Ser | 565 | . | . | . | . | T | T | C | 0.76 | −0.16 | . | . | F | 1.82 | 1.06 |
| Gly | 566 | . | . | . | . | T | T | . | −0.06 | −0.04 | . | . | F | 1.56 | 0.74 |
| Ser | 567 | . | . | . | . | . | T | C | −0.06 | 0.16 | * | . | F | 0.45 | 0.45 |
| Ser | 568 | . | . | . | . | . | . | C | 0.37 | 0.16 | * | . | F | 0.53 | 0.45 |
| Ala | 569 | . | . | . | . | . | . | C | 0.67 | −0.23 | * | . | F | 1.41 | 0.9 |
| Leu | 570 | . | . | . | . | . | . | C | 0.62 | −0.26 | * | . | F | 1.84 | 1.08 |
| Ser | 571 | . | . | . | . | . | T | C | 0.67 | −0.21 | * | . | F | 2.17 | 0.8 |
| Arg | 572 | . | . | . | . | T | T | . | 0.27 | −0.21 | * | . | F | 2.8 | 1.06 |
| Asn | 573 | . | . | . | . | T | T | . | −0.32 | 0.07 | * | . | F | 1.92 | 1.11 |
| Gly | 574 | . | . | . | . | T | T | . | −0.04 | 0.07 | * | . | F | 1.49 | 0.58 |
| Ser | 575 | . | . | . | B | . | . | C | 0.81 | 0.17 | * | . | F | 0.61 | 0.43 |
| Phe | 576 | A | . | . | B | . | . | . | 1.11 | 0.17 | * | . | F | 0.13 | 0.53 |
| Ile | 577 | A | . | . | B | . | . | . | 1.04 | −0.23 | * | . | . | 0.3 | 0.93 |
| Thr | 578 | A | . | . | B | . | . | . | 1.09 | −0.66 | . | . | F | 0.9 | 1.39 |
| Lys | 579 | A | . | . | B | . | . | . | 1.43 | −1.04 | * | . | F | 0.9 | 3.21 |
| Glu | 580 | A | . | . | . | . | . | . | 1.42 | −1.83 | . | . | F | 1.1 | 7.65 |
| Lys | 581 | A | . | . | . | . | T | . | 1.27 | −2.03 | . | . | F | 1.3 | 7.65 |
| Lys | 582 | A | . | . | . | . | T | . | 1.34 | −1.87 | * | * | F | 1.3 | 2.84 |
| Asp | 583 | A | . | . | . | . | T | . | 1.77 | −1.19 | * | * | F | 1.3 | 1.35 |
| Thr | 584 | A | . | . | . | . | T | . | 1.72 | −1.19 | * | . | F | 1.3 | 1.32 |
| Val | 585 | A | . | . | B | . | . | . | 0.87 | −0.79 | * | . | . | 0.75 | 1.15 |
| Leu | 586 | A | . | . | B | . | . | . | 0.93 | −0.14 | * | * | . | 0.3 | 0.51 |
| Arg | 587 | A | . | . | B | . | . | . | 0.08 | −0.14 | * | * | . | 0.3 | 0.69 |
| Gln | 588 | . | . | B | B | . | . | . | 0.08 | 0.06 | * | * | . | −0.3 | 0.77 |
| Val | 589 | . | . | B | B | . | . | . | 0.18 | −0.59 | * | * | . | 1.06 | 1.56 |
| Arg | 590 | . | . | . | B | T | . | . | 0.37 | −0.84 | * | * | . | 1.77 | 1.23 |
| Leu | 591 | . | . | . | B | T | . | . | 1.18 | −0.27 | * | . | . | 1.63 | 0.38 |
| Asp | 592 | . | . | . | . | T | T | C | 0.26 | −0.67 | * | * | F | 2.59 | 0.86 |
| Pro | 593 | . | . | . | . | T | T | . | 0.26 | −0.63 | . | * | F | 3.1 | 0.36 |
| Cys | 594 | . | . | . | . | T | T | . | 0.9 | −0.23 | * | * | . | 2.34 | 0.76 |
| Asp | 595 | . | . | . | . | T | T | . | −0.1 | −0.49 | * | * | . | 2.03 | 0.7 |
| Leu | 596 | . | . | . | . | . | . | C | 0.01 | 0.2 | . | * | . | 0.72 | 0.32 |
| Gln | 597 | . | . | B | . | . | . | . | 0.01 | 0.56 | * | . | . | −0.09 | 0.51 |
| Pro | 598 | A | . | . | . | . | . | . | 0.22 | −0.01 | * | * | . | 0.5 | 0.51 |
| Ile | 599 | A | A | . | . | . | . | . | 0.29 | −0.01 | * | * | . | 0.45 | 1.04 |
| Phe | 600 | A | A | . | . | . | . | . | −0.52 | −0.09 | * | * | . | 0.3 | 0.59 |
| Asp | 601 | A | A | . | . | . | . | . | 0.26 | 0.2 | * | * | . | −0.3 | 0.32 |
| Asp | 602 | A | A | . | . | . | . | . | −0.44 | 0.27 | * | . | . | −0.3 | 0.61 |
| Met | 603 | A | A | . | . | . | . | . | −1.04 | 0.37 | * | . | . | −0.3 | 0.61 |
| Leu | 604 | A | A | . | . | . | . | . | −0.16 | 0.27 | * | . | . | −0.3 | 0.3 |
| His | 605 | A | A | . | . | . | . | . | 0.33 | 0.67 | * | . | . | −0.6 | 0.29 |
| Phe | 606 | A | A | . | . | . | . | . | 0.33 | 1.1 | . | . | . | −0.6 | 0.46 |
| Leu | 607 | . | A | . | . | . | . | C | 0.33 | 0.49 | . | . | . | −0.4 | 0.96 |
| Asn | 608 | A | . | . | . | . | T | . | 0.12 | −0.2 | . | * | F | 1 | 1.22 |
| Pro | 609 | A | . | . | . | . | T | . | 1.04 | −0.01 | . | * | F | 1 | 1.16 |
| Glu | 610 | A | . | . | . | . | T | . | 0.22 | −0.8 | . | * | F | 1.3 | 2.76 |
| Glu | 611 | A | . | . | . | . | T | . | 0.03 | −0.84 | * | * | F | 1.3 | 1.27 |
| Leu | 612 | A | A | . | B | . | . | . | 0.84 | −0.56 | * | * | . | 0.6 | 0.58 |
| Arg | 613 | A | A | . | B | . | . | . | 0.84 | −0.99 | * | * | . | 0.6 | 0.58 |
| Val | 614 | A | A | . | B | . | . | . | 0.17 | −0.99 | * | * | . | 0.6 | 0.58 |
| Ile | 615 | A | A | . | B | . | . | . | −0.04 | −0.3 | * | * | . | 0.3 | 0.49 |
| Glu | 616 | A | A | . | B | . | . | . | −0.04 | −0.56 | * | * | . | 0.6 | 0.39 |
| Glu | 617 | A | A | . | . | . | . | . | 0.18 | −0.16 | * | * | F | 0.45 | 0.9 |
| Ile | 618 | A | A | . | . | . | . | . | 0.07 | −0.3 | * | * | F | 0.6 | 1.3 |
| Pro | 619 | A | A | . | . | . | . | . | 0.92 | −0.99 | * | . | F | 0.9 | 1.3 |
| Gln | 620 | A | A | . | . | . | . | . | 1.86 | −0.99 | * | * | F | 0.9 | 1.26 |
| Ala | 621 | A | A | . | . | . | . | . | 1.04 | −0.99 | * | * | F | 0.9 | 3.59 |
| Glu | 622 | A | A | . | . | . | . | . | 1.04 | −0.99 | * | . | F | 0.9 | 1.91 |
| Asp | 623 | A | A | . | . | . | . | . | 2.04 | −1.41 | * | . | F | 0.9 | 1.84 |

TABLE 1-continued

| Res | Position | I | II | III | IV | V | VI | VII | VIII | IX | X | XI | XII | XIII | XIV |
|-----|----------|---|----|----|----|---|----|-----|------|-----|---|----|-----|------|-----|
| Lys | 624 | A | A | . | . | . | . | . | 1.44 | −1.81 | * | * | F | 0.9 | 3.58 |
| Leu | 625 | A | A | . | . | . | . | . | 0.74 | −1.63 | * | * | F | 0.9 | 1.7 |
| Asp | 626 | A | A | . | . | . | . | . | 1.33 | −0.84 | * | * | F | 0.75 | 0.88 |
| Arg | 627 | A | A | . | . | . | . | . | 0.44 | −0.84 | * | . | F | 0.75 | 0.76 |
| Leu | 628 | A | A | . | B | . | . | . | −0.44 | −0.16 | * | . | . | 0.3 | 0.65 |
| Phe | 629 | A | A | . | B | . | . | . | −0.83 | −0.16 | * | . | . | 0.3 | 0.27 |
| Glu | 630 | A | A | . | B | . | . | . | −0.88 | 0.27 | * | . | . | −0.3 | 0.14 |
| Ile | 631 | A | A | . | B | . | . | . | −0.83 | 0.91 | * | . | . | −0.6 | 0.12 |
| Ile | 632 | A | A | . | B | . | . | . | −1.24 | 0.23 | * | * | . | −0.3 | 0.29 |
| Gly | 633 | A | A | . | B | . | . | . | −0.43 | −0.17 | . | . | . | 0.3 | 0.22 |
| Val | 634 | A | A | . | B | . | . | . | 0.27 | 0.23 | . | . | F | −0.15 | 0.55 |
| Lys | 635 | A | A | . | B | . | . | . | −0.32 | −0.46 | . | . | F | 0.6 | 1.35 |
| Ser | 636 | . | A | . | . | . | . | C | 0.27 | −0.64 | . | . | F | 1.1 | 1.38 |
| Gln | 637 | A | A | . | . | . | . | . | 1.16 | −0.69 | . | * | F | 0.9 | 2.49 |
| Glu | 638 | A | A | . | . | . | . | . | 1.19 | −0.93 | . | . | F | 0.9 | 2.16 |
| Ala | 639 | A | A | . | B | . | . | . | 1.23 | −0.44 | . | . | F | 0.6 | 2.33 |
| Ser | 640 | A | A | . | B | . | . | . | 0.38 | −0.14 | * | . | F | 0.6 | 1.11 |
| Gln | 641 | A | A | . | B | . | . | . | 0.68 | 0.14 | * | . | F | −0.15 | 0.53 |
| Thr | 642 | A | A | . | B | . | . | . | 0.38 | 0.14 | * | . | F | −0.15 | 0.87 |
| Leu | 643 | A | A | . | B | . | . | . | −0.48 | 0.03 | * | . | F | −0.15 | 0.87 |
| Leu | 644 | A | A | . | B | . | . | . | −0.13 | 0.29 | * | . | F | −0.15 | 0.37 |
| Asp | 645 | . | A | . | B | T | . | . | −0.13 | 0.64 | * | . | F | −0.05 | 0.41 |
| Ser | 646 | . | A | . | B | T | . | . | −0.17 | 0.54 | * | . | . | −0.2 | 0.66 |
| Val | 647 | . | . | B | B | . | . | . | −0.67 | 0.36 | * | . | . | −0.15 | 1.09 |
| Tyr | 648 | . | . | . | B | T | . | . | −0.07 | 0.36 | * | . | . | 0.1 | 0.54 |
| Ser | 649 | . | . | . | . | T | . | . | 0.74 | 0.79 | * | . | . | 0 | 0.62 |
| His | 650 | . | A | . | . | . | . | C | −0.07 | 0.4 | * | . | . | 0.05 | 1.39 |
| Leu | 651 | . | A | . | . | . | . | C | −0.58 | 0.44 | * | . | . | −0.4 | 0.73 |
| Pro | 652 | A | A | . | . | . | . | . | −0.11 | 0.37 | * | . | F | −0.15 | 0.45 |
| Asp | 653 | A | A | . | . | . | . | . | −0.26 | 0.41 | * | . | . | −0.6 | 0.42 |
| Leu | 654 | A | A | . | . | . | . | . | −0.34 | 0.34 | * | . | . | −0.3 | 0.66 |
| Leu | 655 | A | A | . | . | . | . | . | −0.7 | 0.09 | * | . | . | −0.3 | 0.54 |

In specific embodiments, the polynucleotides of the invention are less than 100000 kb, 50000 kb, 10000 kb, 1000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise, or alternatively consist of, at least 15, at least 30, at least 50, at least 100, or at least 250, at least 500, or at least 1000 contiguous nucleotides of TR9 coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide set forth in FIGS. 1A-D (SEQ ID NO:1). In further embodiments, polynucleotides of the invention comprise, or alternatively consist of, at least 15, at least 30, at least 50, at least 100, or at least 250, at least 500, or at least 1000 contiguous nucleotides of TR9 coding sequence, but do not comprise all or a portion of any TR9 intron. In another embodiment, the nucleic acid comprising, or alternatively consisting of, TR9 coding sequence does not contain coding sequences of a genomic flanking gene (i.e., 5' or 3' to the TR9 gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

In another embodiment, the invention provides an isolated nucleic acid molecule comprising, or alternatively consisting of, a polynucleotide which hybridizes, preferably under stringent hybridization conditions, to a portion of the polynucleotide sequence of a polynucleotide of the invention such as, for instance, the sequence complementary to the coding and/or noncoding (i.e., transcribed, untranslated) sequence depicted in FIGS. 1A-D, the sequence of the cDNA clone contained in ATCC Deposit 209037 and the sequence encoding a TR9 domain or a polynucleotide fragment as described herein. By "stringent hybridization conditions" is intended overnight incubation at 42° C. in a solution comprising: 50% formamide, 5×SSC (750 mM NaCl, 75 mM trisodium citrate), 50 mM sodium phosphate (pH 7.6), 5×Denhardt's solution, 10% dextran sulfate, and 20 g/ml denatured, sheared salmon sperm DNA, followed by washing the filters in 0.1× SSC at about 65° C.

By a polynucleotide which hybridizes to a "portion" of a polynucleotide is intended a polynucleotide (either DNA or RNA) hybridizing to at least about 15 nucleotides (nt), and more preferably at least about 20 nt, still more preferably at least about 30 nt, and even more preferably about 30-70, or 80-150 nt, or the entire length of the reference polynucleotide. By a portion of a polynucleotide of "at least about 20 nt in length," for example, is intended 20 or more contiguous nucleotides from the nucleotide sequence of the reference polynucleotide (e.g., the deposited cDNA or the nucleotide sequence as shown in FIGS. 1A-D (SEQ ID NO:1). In this context "about" includes the particularly recited size, larger or smaller by several (5, 4, 3, 2, or 1) nucleotides, at either terminus or at both termini. These have uses, which include, but are not limited to, as diagnostic probes and primers as discussed above and in more detail below.

In specific embodiments, polynucleotides of the invention hybridize to a complementary strand of a polynucleotide encoding amino acid residues 40-152, 40-48, 40-51, 51-66, 66-73, 73-83, 83-104, 104-110, 110-128, 128-146, and/or 146-152 as depicted in SEQ ID NO:2.

Of course, a polynucleotide which hybridizes only to a poly A sequence (such as the 3' terminal poly tract of the TR9 receptor cDNA shown in SEQ ID NO:1), or to a complementary stretch of T (or U) residues, would not be included in a polynucleotide of the invention used to hybridize to a portion of a nucleic acid of the invention, since such a polynucleotide would hybridize to any nucleic acid molecule containing a poly (A) stretch or the complement thereof (e.g., practically any double-stranded cDNA clone generated using oligo dT as a primer).

As indicated, nucleic acid molecules of the present invention which encode a TR9 receptor polypeptide may include, but are not limited to, those encoding the amino acid sequence of the mature polypeptide, by itself; the coding sequence for the mature polypeptide and additional sequences, such as those encoding the about amino acid leader or secretory sequence, such as a pre-, or pro- or prepro-protein sequence; the coding sequence of the mature polypeptide, with or without the aforementioned additional coding sequences, together with additional, non-coding sequences, including for example, but not limited to introns and non-coding 5' and 3' sequences, such as the transcribed, non-translated sequences that play a role in transcription, mRNA processing, including splicing and polyadenylation signals, for example—ribosome binding and stability of mRNA; an additional coding sequence which codes for additional amino acids, such as those which provide additional functionalities. Thus, the sequence encoding the polypeptide may be fused to a marker sequence, such as a sequence encoding a peptide which facilitates purification of the fused polypeptide. In certain preferred embodiments of this aspect of the invention, the marker amino acid sequence is a hexa-histidine peptide, such as the tag provided in a pQE vector (Qiagen, Inc.), among others, many of which are commercially available. As described in Gentz et al., *Proc. Natl. Acad. Sci. USA* 86:821-824 (1989), for instance, hexa-histidine provides for convenient purification of the fusion protein. The "HA" tag is another peptide useful for purification which corresponds to an epitope derived from the influenza hemagglutinin protein, which has been described by Wilson et al., *Cell* 37:767-778 (1984). As discussed below, other such fusion proteins include the TR9 receptor fused to Fc at the N- or C-terminus.

The present invention further relates to variants of the nucleic acid molecules of the present invention, which encode portions, analogs or derivatives of the TR9 receptor. Variants may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., Nucl. Acids Res. 13:4331 (1986); and Zoller et al., Nucl. Acids Res. 10:6487 (1982)), cassette mutagenesis (see e.g., Wells et al., Gene 34:315 (1985)), restriction selection mutagenesis (see e.g., Wells er al., Philos. Trans. R. Soc. London SerA 317:415 (1986)).

Such variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions. Especially preferred among these are silent substitutions, additions and deletions, which do not alter the properties and functional activities of the TR9 receptor or portions thereof. Also especially preferred in this regard are conservative substitutions.

Further embodiments of the invention include isolated nucleic acid molecules comprising, or alternatively consisting of, a polynucleotide having a nucleotide sequence at least 90% identical, and more preferably at least 80%, 85%, 95%, 96%, 97%, 98% or 99% identical to (a) a nucleotide sequence encoding the polypeptide having the amino acid sequence shown in FIGS. 1A-D (SEQ ID NO:2); (b) a nucleotide sequence encoding the polypeptide having the amino acid sequence shown in FIGS. 1A-D (SEQ ID NO:2), but lacking the N-terminal methionine; (c) a nucleotide sequence encoding the predicted mature TR9 polypeptide (full-length polypeptide with any attending leader sequence removed) comprising, or alternatively consisting of, the amino acid sequence at positions from about 1 to about 615 in SEQ ID NO:2; (d) a nucleotide sequence encoding the TR9 polypeptide having the amino acid sequence encoded by the cDNA clone contained in ATCC Deposit No. 209037; (e) a nucleotide sequence encoding the mature TR9 polypeptide having the amino acid sequence encoded by the cDNA clone contained in ATCC Deposit No. 209037; (f) a nucleotide sequence encoding the TR9 receptor extracellular domain; (g) a nucleotide sequence encoding one, two, three or all four TNFR-like cysteine rich motifs of TR9 (amino acid residues 67 to 211 in FIGS. 1A-D; amino acid residues 27 to 171 in SEQ ID NO:2); (h) a nucleotide sequence encoding the TR9 receptor transmembrane domain; (i) a nucleotide sequence encoding the TR9 receptor intracellular domain; (j) a nucleotide sequence encoding the TR9 receptor extracellular and intracellular domains with all or part of the transmembrane domain deleted; (k) a nucleotide sequence encoding the TR9 receptor death domain; (l) a nucleotide sequence encoding the TR9 leucine zipper; (m) a fragment of the polypeptide of (c) having TR9 functional activity (e.g., antigenic or biological activity); and (n) a nucleotide sequence complementary to any of the nucleotide sequences in (a), (b), (c), (d), (e), (f), (g), (h), (i), (j), (k), (l), or (m). Polypeptides encoded by these polynucleotides are also encompassed by the invention.

By a polynucleotide having a nucleotide sequence at least, for example, 95% "identical" to a reference nucleotide sequence encoding a TR9 receptor polypeptide is intended that the nucleotide sequence of the polynucleotide is identical to the reference sequence except that the polynucleotide sequence may include up to five mismatches per each 100 nucleotides of the reference nucleotide sequence encoding the TR9 receptor. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These mismatches of the reference sequence may occur at the 5' or 3' terminal positions of the reference nucleotide sequence or anywhere between those terminal positions, interspersed either individually among nucleotides in the reference sequence or in one or more contiguous groups within the reference sequence. The reference (query) sequence may be the entire TR9 nucleotide sequence shown in FIGS. 1A-D (SEQ ID NO:1) or any fragment (e.g., a polynucleotide encoding the amino acid sequence of a TR9 N and/or C terminal deletion described herein) as described herein.

As a practical matter, whether any particular nucleic acid molecule is at least 80%, 85%, 90%, 95%, 96%, 97%, 98% or 99% identical to, for instance, the nucleotide sequence shown in FIGS. 1A-D (SEQ ID NO:1) or to the nucleotides sequence of the deposited cDNA clone can be determined conventionally using known computer programs such as the Bestfit program (Wisconsin Sequence Analysis Package, Version 8 for Unix, Genetics Computer Group, University Research Park, 575 Science Drive, Madison, Wis. 53711). Bestfit uses the local homology algorithm of Smith and Waterman, *Advances in Applied Mathematics* 2:482-489 (1981), to find the best segment of homology between two sequences. When using Bestfit or any other sequence alignment program to determine whether a particular sequence is, for instance, 95% identical to a reference sequence according to the present invention, the parameters are set, of course, such that the percentage of identity is calculated over the full length of the reference nucleotide sequence and that gaps in homology of up to 5% of the total number of nucleotides in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB alignment of DNA sequences to calculate percent identity are: Matrix=Unitary, k-tuple=4, Mismatch Penalty=1, Joining Penalty=30, Randomization Group Length=0, Cutoff Score=1, Gap Penalty=5, Gap Size Penalty=0.05, Window Size=500 or the length of the subject nucleotide sequence, whichever is shorter. According to this embodiment, if the subject sequence is shorter than the query sequence because of 5' or 3' deletions, not because of internal deletions, a manual correction is made to the results to take into consideration the fact that the FASTDB program does not account for 5' and 3' truncations of the subject sequence when calculating percent identity. For subject sequences truncated at the 5' or 3' ends, relative to the query sequence, the percent identity is corrected by calculating the number of bases of the query sequence that are 5' and 3' of the subject sequence, which are not matched/aligned, as a percent of the total bases of the query sequence. A determination of whether a nucleotide is matched/aligned is determined by results of the FASTDB sequence alignment. This percentage is then subtracted from the percent identity, calculated by the above FASTDB program using the specified parameters, to arrive at a final percent identity score. This corrected score is what is used for the purposes of this embodiment. Only bases outside the 5' and 3' bases of the subject sequence, as displayed by the FASTDB alignment, which are not matched/aligned with the query sequence, are calculated for the purposes of manually adjusting the percent identity score. For example, a 90 base subject sequence is aligned to a 100 base query sequence to determine percent identity. The deletions occur at the 5' end of the subject sequence and therefore, the FASTDB alignment does not show a matched/alignment of the first 10 bases at 5' end. The 10 unpaired bases represent 10% of the sequence (number of bases at the 5' and 3' ends not matched/total number of bases in the query sequence) so 10% is subtracted from the percent identity score calculated by the FASTDB program. If the remaining 90 bases were perfectly matched the final percent identity would be 90%. In another example, a 90 base subject sequence is compared with a 100 base query sequence. This time the deletions are internal deletions so that there are no bases on the 5' or 3' of the subject sequence which are not matched/aligned with the query. In this case the percent identity calculated by FASTDB is not manually corrected. Once again, only bases 5' and 3' of the subject sequence which are not matched/aligned with the query sequence are manually corrected for. No other manual corrections are made for the purposes of this embodiment.

The present application is directed to nucleic acid molecules at least 80%, 85%, 90%, 95%, 96%, 97%, 98% or 99% identical to the nucleic acid sequence shown in FIGS. 1A-D (SEQ ID NO:1) or to the nucleic acid sequence of the deposited cDNA, irrespective of whether they encode a polypeptide having TR9 receptor functional activity. Polypeptides encoded by these polynucleotides are also encompassed by the invention. This is because even where a particular nucleic acid molecule does not encode a polypeptide having TR9 receptor functional activity, one of skill in the art would still know how to use the nucleic acid molecule, for instance, as a hybridization probe or a polymerase chain reaction (PCR) primer. Uses of the nucleic acid molecules of the present invention that do not encode a polypeptide having TR9 receptor functional activity include, inter alia, (1) isolating the TR9 receptor gene or allelic variants thereof in a cDNA library; (2) in situ hybridization (e.g., "FISH") to metaphase chromosomal spreads to provide precise chromosomal location of the TR9 receptor gene, as described in Verma et al., *Human Chromosomes: A Manual of Basic Techniques*, Pergamon Press, N.Y. (1988); and (3) Northern Blot analysis for detecting TR9 receptor mRNA expression in specific tissues.

Preferred, however, are nucleic acid molecules having sequences at least 80%, 85%, 90%, 95%, 96%, 97%, 98% or 99% identical to the nucleic acid sequence shown in FIGS. 1A-D (SEQ ID NO:1), the nucleic acid sequence of the deposited cDNA, or fragments thereof, which do, in fact, encode a polypeptide having TR9 receptor functional activity. Polypeptides encoded by these polynucleotides are also encompassed by the invention. By "a polypeptide having TR9 receptor functional activity" is intended polypeptides exhibiting activity similar, but not necessarily identical, to a functional activity of the TR9 receptor of the invention (e.g., the full-length (i.e., complete) protein or, preferably, the mature protein), as measured in a particular functional assay (e.g., immunoassay and/or biological assay). For example, TR9 polypeptide functional activity can be measured by the ability of a polypeptide sequence described herein to form multimers (e.g., homodimers and homotrimers) with complete TR9, and to bind a TR9 ligand (e.g., TR9 ligand expressed on the surface of monocytes). TR9 polypeptide functional activity can be also be measured, for example, by determining the ability of a polypeptide of the invention to activate monocytes, increase cell survival of monocytes or to induce apoptosis in cells expressing the polypeptide. These functional assays can be routinely performed using techniques described herein and otherwise known in the art.

For example, TR9 receptor functional activity (e.g., biological activity) can routinely be measured using the cell death assays performed essentially as previously described (Chinnaiyan et al., *Cell* 81:505-512 (1995); Boldin et al., *J. Biol. Chem.* 270:7795-8(1995); Kischkel et al., *EMBO* 14:5579-5588 (1995); Chinnaiyan et al., *J. Biol. Chem.* 271: 4961-4965 (1996)) and as set forth in Example 5 below. In MCF7 cells, plasmids encoding full-length TR9 or a candidate death domain containing receptor are co-transfected with the pLantern reporter construct encoding green fluorescent protein. Nuclei of cells transfected with TR9 will exhibit apoptotic morphology as assessed by DAPI staining. It is expected that like TNFR-1 and Fas/APO-1 (Muzio et al., *Cell* 85:817-827 (1996); Boldin et al., *Cell* 85:803-815 (1996); Tewari et al., *J. Biol. Chem.* 270:3255-60 (1995)), TR9-induced apoptosis will be blocked by the inhibitors of ICE-like proteases, CrmA and z-VAD-fmk. In addition, it is expected that apoptosis induced by TR9 will be blocked by dominant negative versions of FADD (FADD-DN) or FLICE (FLICE-DN/MACHa1C360S).

Of course, due to the degeneracy of the genetic code, one of ordinary skill in the art will immediately recognize that a large number of the nucleic acid molecules having a sequence at least 80%, 85%, 90%, 95%, 96%, 97%, 98%, or 99% identical to, for example, the nucleic acid sequence of the deposited cDNA or the nucleic acid sequence shown in FIGS. 1A-D (SEQ ID NO:1), or fragments thereof, will encode a polypeptide "having TR9 receptor functional activity." In fact, since degenerate variants of these nucleotide sequences all encode the same polypeptide, in many instances, this will be clear to the skilled artisan even without performing the above described assay. It will be further recognized in the art that, for such nucleic acid molecules that are not degenerate variants, a reasonable number will also encode a polypeptide having TR9 receptor functional activity. This is because the skilled artisan is fully aware of amino acid substitutions that are either less likely or not likely to significantly effect protein function (e.g., replacing one aliphatic amino acid with a second aliphatic amino acid), as further described below.

For example, guidance concerning how to make phenotypically silent amino acid substitutions is provided in J. U. Bowie et al., "Deciphering the Message in Protein Sequences: Tolerance to Amino Acid Substitutions," *Science* 247:1306-1310 (1990), wherein the authors indicate that proteins are surprisingly tolerant of amino acid substitutions.

Polynucleotide Assays

This invention is also related to the use of TR9 polynucleotides to detect complementary polynucleotides such as, for example, as a diagnostic reagent. Detection of a mutated form of TR9 associated with a dysfunction will provide a diagnostic tool that can add or define a diagnosis of a disease or susceptibility to a disease which results from under-expression, over-expression, or altered expression of TR9 or a soluble form thereof, such as, for example, tumors or autoimmune diseases.

Individuals carrying mutations in the TR9 gene may be detected at the DNA level by a variety of techniques. Nucleic acids for diagnosis may be obtained from a patient's cells, such as from blood, urine, saliva, tissue biopsy and autopsy material. The genomic DNA may be used directly for detection or may be amplified enzymatically by using PCR prior to analysis. (Saiki et al., *Nature* 324:163-166 (1986)). RNA or cDNA may also be used in the same ways. As an example, PCR primers complementary to the nucleic acid encoding TR9 can be used to identify and analyze TR9 expression and mutations. For example, deletions and insertions can be detected by a change in size of the amplified product in comparison to the normal genotype. Point mutations can be identified by hybridizing amplified DNA to radiolabeled TR9 RNA or alternatively, radiolabeled TR9 antisense DNA sequences. Perfectly matched sequences can be distinguished from mismatched duplexes by RNase A digestion or by differences in melting temperatures.

Sequence differences between a reference gene and genes having mutations also may be revealed by direct DNA sequencing. In addition, cloned DNA segments may be employed as probes to detect specific DNA segments. The sensitivity of such methods can be greatly enhanced by appropriate use of PCR or another amplification method. For example, a sequencing primer is used with double-stranded PCR product or a single-stranded template molecule generated by a modified PCR. The sequence determination is performed by conventional procedures with radiolabeled nucleotide or by automatic sequencing procedures with fluorescent-tags.

Genetic testing based on DNA sequence differences may be achieved by detection of alteration in electrophoretic mobility of DNA fragments in gels, with or without denaturing agents. Small sequence deletions and insertions can be visualized by high resolution gel electrophoresis. DNA fragments of different sequences may be distinguished on denaturing formamide gradient gels in which the mobilities of different DNA fragments are retarded in the gel at different positions according to their specific melting or partial melting temperatures (see, e.g., Myers et al., *Science* 230:1242 (1985)).

Sequence changes at specific locations also may be revealed by nuclease protection assays, such as RNase and S1 protection or the chemical cleavage method (e.g., Cotton et al., *Proc. Natl. Acad. Sci. USA* 85:4397-4401 (1985)).

Thus, the detection of a specific DNA sequence may be achieved by methods such as hybridization, RNase protection, chemical cleavage, direct DNA sequencing or the use of restriction enzymes, (e.g., restriction fragment length polymorphisms ("RFLP") and Southern blotting of genomic DNA.

In addition to more conventional gel-electrophoresis and DNA sequencing, mutations also can be detected by in situ analysis.

Vectors and Host Cells

The present invention also relates to vectors which include the isolated DNA molecules of the present invention, host cells which are genetically engineered with the recombinant vectors, or which are otherwise engineered to produce the polypeptides of the invention, and the production of TR9 receptor polypeptides, or fragments thereof, by recombinant or synthetic techniques.

The polynucleotides may be joined to a vector containing a selectable marker for propagation in a host. Generally, a plasmid vector is introduced in a precipitate, such as a calcium phosphate precipitate, or in a complex with a charged lipid. If the vector is a virus, it may be packaged in vitro using an appropriate packaging cell line and then transduced into host cells.

In one embodiment, the DNA of the invention is operatively associated with an appropriate heterologous regulatory element (e.g., promoter or enhancer), such as, the phage lambda PL promoter, the *E. coli* lac, trp, and tac promoters, the SV40 early and late promoters and promoters of retroviral LTRs, to name a few. Other suitable promoters will be known to the skilled artisan.

In embodiments in which vectors contain expression constructs, these constructs will further contain sites for transcription initiation, termination and, in the transcribed region, a ribosome binding site for translation. The coding portion of the mature transcripts expressed by the constructs will preferably include a translation initiating at the beginning and a termination codon (UAA, UGA or UAG) appropriately positioned at the end of the polypeptide to be translated.

As indicated, the expression vectors will preferably include at least one selectable marker. Such markers include dihydrofolate reductase or neomycin resistance for eukaryotic cell culture and tetracycline or ampicillin resistance genes for culturing in *E. coli* and other bacteria. Representative examples of appropriate hosts include, but are not limited to, bacterial cells, such as *E. coli, Streptomyces* and *Salmonella typhimurium* cells; fungal cells, such as yeast cells (e.g., *Saccharomyces cerevisiae* or *Pichia pastoris* (ATCC Accession No. 201178)); insect cells such as *Drosophila* S2 and *Spodoptera* Sf9 cells; animal cells such as CHO, COS and Bowes melanoma cells; and plant cells. Appropriate culture mediums and conditions for the above-described host cells are known in the art.

Among vectors preferred for use in bacteria include pHE4 (ATCC Accession Number 209645, deposited Feb. 25, 1998), pQE70, pQE60 and pQE-9, available from Qiagen; pBS vectors, Phagescript vectors, Bluescript vectors, pNH8A, pNH16a, pNH18A, pNH46A, available from Stratagene; and ptrc99a, pKK223-3, pKK233-3, pDR540, pRIT5 available from Pharmacia. Among preferred eukaryotic vectors are pWLNEO, pSV2CAT, pOG44, pXT1 and pSG available from Stratagene; and pSVK3, pBPV, pMSG and pSVL available from Pharmacia. Preferred expression vectors for use in yeast systems include, but are not limited to, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, pPIC9K, and PAO815 (all available from Invitrogen, Carlsbad, Calif.). Other suitable vectors will be readily apparent to the skilled artisan.

Selection of appropriate vectors and promoters for expression in a host cell is a well known procedure and the requisite techniques for expression vector construction, introduction of the vector into the host and expression in the host are routine skills in the art.

The present invention also relates to host cells containing the vector constructs discussed herein, and additionally encompasses host cells containing nucleotide sequences of the invention that are operably associated with one or more heterologous control regions (e.g., promoter and/or enhancer) using techniques known of in the art. The host cell can be a higher eukaryotic cell, such as a mammalian cell (e.g., a human derived cell), or a lower eukaryotic cell, such as a yeast cell, or the host cell can be a prokaryotic cell, such as a bacterial cell. The host strain may be chosen which modulates the expression of the inserted gene sequences, or modifies and processes the gene product in the specific fashion desired. Expression from certain promoters can be elevated in the presence of certain inducers; thus expression of the genetically engineered polypeptide may be controlled. Furthermore, different host cells have characteristics and specific mechanisms for the translational and post-translational processing and modification (e.g., phosphorylation, cleavage) of proteins. Appropriate cell lines can be chosen to ensure the desired modifications and processing of the foreign protein expressed.

Introduction of the construct into the host cell can be effected by calcium phosphate transfection, DEAE-dextran mediated transfection, cationic lipid-mediated transfection, electroporation, transduction, infection or other methods. Such methods are described in many standard laboratory manuals, such as Davis et al., *Basic* Methods In Molecular Biology (1986).

TR9 polypeptides can be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

TR9 polypeptides, and preferably the secreted form, can also be recovered from: products purified from natural sources, including bodily fluids, tissues and cells, whether directly isolated or cultured; products of chemical synthetic procedures; and products produced by recombinant techniques from a prokaryotic or eukaryotic host, including, for example, bacterial, yeast, higher plant, insect, and mammalian cells.

In one embodiment, the yeast *Pichia pastoris* is used to express TR9 protein in a eukaryotic system. *Pichia pastoris* is a methylotrophic yeast which can metabolize methanol as its sole carbon source. A main step in the methanol metabolization pathway is the oxidation of methanol to formaldehyde using $O_2$. This reaction is catalyzed by the enzyme alcohol oxidase. In order to metabolize methanol as its sole carbon source, *Pichia pastoris* must generate high levels of alcohol oxidase due, in part, to the relatively low affinity of alcohol oxidase for $O_2$. Consequently, in a growth medium depending on methanol as a main carbon source, the promoter region of one of the two alcohol oxidase genes (AOX1) is highly active. In the presence of methanol, alcohol oxidase produced from the AOX1 gene comprises up to approximately 300% of the total soluble protein in *Pichia pastoris*. See, Ellis, S. B., et al., *Mol. Cell. Biol.* 5:1111-21 (1985); Koutz, P. J, et al., *Yeast* 5:167-77 (1989); Tschopp, J. F., et al., Nucl Acids Res. 15:3859-76 (1987). Thus, a heterologous coding sequence, such as, for example, a TR9 polynucleotide of the present invention, under the transcriptional regulation of all or part of the AOX1 regulatory sequence is expressed at exceptionally high levels in *Pichia* yeast grown in the presence of methanol.

In one example, the plasmid vector pPIC9K is used to express DNA encoding a TR9 polypeptide of the invention, as set forth herein, in a *Pichea* yeast system essentially as described in "*Pichia* Protocols: Methods in Molecular Biology," D. R. Higgins and J. Cregg, eds. The Humana Press, Totowa, N.J., 1998. This expression vector allows expression and secretion of a TR9 protein of the invention by virtue of the strong AOX1 promoter linked to the *Pichia pastoris* alkaline phosphatase (PHO) secretory signal peptide (i.e., leader) located upstream of a multiple cloning site.

Many other yeast vectors could be used in place of pPIC9K, such as, pYES2, pYD1, pTEF1/Zeo, pYES2/GS, pPICZ, pGAPZ, pGAPZalpha, pPIC9, pPIC3.5, pHIL-D2, pHIL-S1, pPIC3.5K, and PAO815, as one skilled in the art would readily appreciate, as long as the proposed expression construct provides appropriately located signals for transcription, translation, secretion (if desired), and the like, including an in-frame AUG as required.

In another embodiment, high-level expression of a heterologous coding sequence, such as, for example, a TR9 polynucleotide of the present invention, may be achieved by cloning the heterologous polynucleotide of the invention into an expression vector such as, for example, pGAPZ or pGAPZalpha, and growing the yeast culture in the absence of methanol.

Depending upon the host employed in a recombinant production procedure, the TR9 polypeptides may be glycosylated or may be non-glycosylated. In addition, TR9 polypeptides may also include an initial modified methionine residue, in some cases as a result of host-mediated processes. Thus, it is well known in the art that the N-terminal methionine encoded by the translation initiation codon generally is removed with high efficiency from any protein after translation in all eukaryotic cells. While the N-terminal methionine on most proteins also is efficiently removed in most prokaryotes, for some proteins, this prokaryotic removal process is inefficient, depending on the nature of the amino acid to which the N-terminal methionine is covalently linked.

In addition to encompassing host cells containing the vector constructs discussed herein, the invention also encompasses primary, secondary, and immortalized host cells of vertebrate origin, particularly mammalian origin, that have been engineered to delete or replace endogenous genetic material (e.g., TR9 coding sequence), and/or to include genetic material (e.g., heterologous polynucleotide sequences) that is operably associated with TR9 polynucleotides of the invention, and which activates, alters, and/or amplifies endogenous TR9 polynucleotides. For example, techniques known in the art may be used to operably associate heterologous control regions (e.g., promoter and/or enhancer) and endogenous TR9 polynucleotide sequences via homologous recombination (see, e.g., U.S. Pat. No. 5,641, 670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932-8935 (1989); and Zijlstra et al., Nature 342:435-438 (1989), the disclosures of each of which are incorporated by reference in their entireties).

The polypeptide may be expressed or synthesized in a modified form, such as a fusion protein (comprising, or alternatively consisting of, the polypeptide joined via a peptide bond to a heterologous protein sequence (of a different protein)), and may include not only secretion signals, but also additional heterologous functional regions. Such a fusion protein can be made by ligating polynucleotides of the invention and the desired nucleic acid sequence encoding the desired amino acid sequence to each other, by methods known in the art, in the proper reading frame, and expressing the fusion protein product by methods known in the art. Alternatively, such a fusion protein can be made by protein synthetic techniques, e.g., by use of a peptide synthesizer. Thus, for instance, a region of additional amino acids, particularly charged amino acids, may be added to the N-terminus of the polypeptide to improve stability and persistence in the host cell, during purification, or during subsequent handling and storage. Additionally, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art. For example, in one embodiment, polynucleotides encoding TR9 polypeptides of the invention may be fused to the pelB pectate lyase signal sequence to increase the efficiency to expression and purification of such polypeptides in Gram-negative bacteria. See, U.S. Pat. Nos. 5,576, 195 and 5,846,818, the contents of which are herein incorporated by reference in their entireties.

A preferred fusion protein comprises a heterologous region from immunoglobulin that is useful to solubilize proteins. For example, EP-A-O 464 533 (Canadian counterpart 2045869) discloses fusion proteins comprising various portions of constant region of immunoglobin molecules together with another human protein or part thereof. In many cases, the Fc part in a fusion protein is thoroughly advantageous for use in therapy and diagnosis and thus results, for example, in improved pharmacokinetic properties (EPA 0 232 262). Thus, in a specific embodiment, fusion proteins of the invention comprise, or alternatively, consist of, amino acid residues 1 to 310 of SEQ ID NO:2 fused to an Fc polypeptide sequence. On the other hand, for some uses it would be desirable to be able to delete the Fc part after the fusion protein has been expressed, detected and purified in the advantageous manner described. This is the case when the Fc portion proves to be a hindrance to use in therapy and diagnosis, for example when the fusion protein is to be used as an antigen for immunizations. In drug discovery, for example, human proteins, such as the hIL5-receptor, have been fused with Fc portions for the purpose of high-throughput screening assays to identify antagonists of hIL-5. See, Bennett et al., *J. of Molec. Recognition* 8:52-58 (1995) and Johanson et al., *J. Biol. Chem.* 270:9459-9471 (1995).

TR9 polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue or alternatively, may be missing the N-terminal methionine, in some cases as a result of host-mediated processes.

In addition, polypeptides of the invention can be chemically synthesized using techniques known in the art (e.g., see Creighton, 1983, Proteins: Structures and Molecular Principles, W.H. Freeman & Co., N.Y., and Hunkapiller, M., et al., Nature 310:105-111 (1984)). For example, a peptide corresponding to a fragment of the TR9 polypeptides of the invention can be synthesized by use of a peptide synthesizer. Furthermore, if desired, nonclassical amino acids or chemical amino acid analogs can be introduced as a substitution or addition into the TR9 polypeptide sequence. Non-classical amino acids include, but are not limited to, to the D-isomers of the common amino acids, 2,4-diaminobutyric acid, a-amino isobutyric acid, 4-aminobutyric acid, Abu, 2-amino butyric acid, g-Abu, e-Ahx, 6-amino hexanoic acid, Aib, 2-amino isobutyric acid, 3-amino propionic acid, ornithine, norleucine, norvaline, hydroxyproline, sarcosine, citrulline, homocitrulline, cysteic acid, t-butylglycine, t-butylalanine, phenylglycine, cyclohexylalanine, b-alanine, fluoro-amino acids, designer amino acids such as b-methyl amino acids, Ca-methyl amino acids, Na-methyl amino acids, and amino acid analogs in general. Furthermore, the amino acid can be D (dextrorotary) or L (levorotary).

Non-naturally occurring variants may be produced using art-known mutagenesis techniques, which include, but are not limited to oligonucleotide mediated mutagenesis, alanine scanning, PCR mutagenesis, site directed mutagenesis (see, e.g., Carter et al., *Nucl. Acids Res.* 13:4331 (1986); and Zoller et al., *Nucl. Acids Res.* 10:6487 (1982)), cassette mutagenesis (see, e.g., Wells et al., *Gene* 34:315 (1985)), restriction selection mutagenesis (see, e.g., Wells et al., *Philos. Trans. R. Soc. London SerA* 317:415 (1986)).

The invention additionally, encompasses TR9 proteins which are differentially modified during or after translation, e.g., by glycosylation, acetylation, phosphorylation, amidation, derivatization by known protecting/blocking groups, proteolytic cleavage, linkage to an antibody molecule or other cellular ligand, etc. Any of numerous chemical modifications may be carried out by known techniques, including but not limited to, specific chemical cleavage by cyanogen bromide, trypsin, chymotrypsin, papain, V8 protease, NaBH$_4$, acetylation, formylation, oxidation, reduction, metabolic synthesis in the presence of tunicamycin; etc.

Additional post-translational modifications encompassed by the invention include, for example, e.g., N-linked or O-linked carbohydrate chains, processing of N-terminal or C-terminal ends), attachment of chemical moieties to the amino acid backbone, chemical modifications of N-linked or O-linked carbohydrate chains, and addition or deletion of an N-terminal methionine residue as a result of procaryotic host cell expression. The polypeptides may also be modified with a detectable label, such as an enzymatic, fluorescent, isotopic or affinity label to allow for detection and isolation of the protein.

Also provided by the invention are chemically modified derivatives of TR9 which may provide additional advantages such as increased solubility, stability and circulating time of the polypeptide, or decreased immunogenicity (see U.S. Pat. No. 4,179,337). The chemical moieties for derivitization may be selected from water soluble polymers such as polyethylene glycol, ethylene glycol/propylene glycol copolymers, carboxymethylcellulose, dextran, polyvinyl alcohol and the like. The polypeptides may be modified at random positions within the molecule, or at predetermined positions within the molecule and may include one, two, three or more attached chemical moieties.

The polymer may be of any molecular weight, and may be branched or unbranched. For polyethylene glycol, the preferred molecular weight is between about 1 kDa and about 100 kDa (the term "about" indicating that in preparations of polyethylene glycol, some molecules will weigh more, some less, than the stated molecular weight) for ease in handling and manufacturing. Other sizes may be used, depending on the desired therapeutic profile (e.g., the duration of sustained release desired, the effects, if any on biological activity, the ease in handling, the degree or lack of antigenicity and other known effects of the polyethylene glycol to a therapeutic protein or analog). For example, the polyethylene glycol may have an average molecular weight of about 200, 500, 1000, 1500, 2000, 2500, 3000, 3500, 4000, 4500, 5000, 5500, 6000, 6500, 7000, 7500, 8000, 8500, 9000, 9500, 10,000, 10,500, 11,000, 11,500, 12,000, 12,500, 13,000, 13,500, 14,000, 14,500, 15,000, 15,500, 16,000, 16,500, 17,000, 17,500, 18,000, 18,500, 19,000, 19,500, 20,000, 25,000, 30,000, 35,000, 40,000, 50,000, 55,000, 60,000, 65,000, 70,000, 75,000, 80,000, 85,000, 90,000, 95,000, or 100,000 kDa.

As noted above, the polyethylene glycol may have a branched structure. Branched polyethylene glycols are described, for example, in U.S. Pat. No. 5,643,575; Morpurgo et al., *Appl. Biochem. Biotechnol.* 56:59-72 (1996); Vorobjev et al., *Nucleosides Nucleotides* 18:2745-2750 (1999); and Caliceti et al., *Bioconjug. Chem.* 10: 638-646 (1999), the disclosures of each of which are incorporated herein by reference.

The polyethylene glycol molecules (or other chemical moieties) should be attached to the protein with consideration of effects on functional or antigenic domains of the protein. There are a number of attachment methods available to those skilled in the art, e.g., EP 0 401 384, herein incorporated by reference (coupling PEG to G-CSF), see also Malik et al., Exp. Hematol. 20:1028-1035 (1992) (reporting pegylation of GM-CSF using tresyl chloride). For example, polyethylene glycol may be covalently bound through amino acid residues via a reactive group, such as, a free amino or carboxyl group. Reactive groups are those to which an activated polyethylene glycol molecule may be bound. The amino acid residues having a free amino group may include lysine residues and the N-terminal amino acid residues; those having a free carboxyl group may include aspartic acid residues glutamic acid residues and the C-terminal amino acid residue. Sulfhydryl groups may also be used as a reactive group for attaching the polyethylene glycol molecules. Preferred for therapeutic purposes is attachment at an amino group, such as attachment at the N-terminus or lysine group.

As suggested above, polyethylene glycol may be attached to proteins via linkage to any of a number of amino acid residues. For example, polyethylene glycol can be linked to a proteins via covalent bonds to lysine, histidine, aspartic acid, glutamic acid, or cysteine residues. One or more reaction chemistries may be employed to attach polyethylene glycol to specific amino acid residues (e.g., lysine, histidine, aspartic acid, glutamic acid, or cysteine) of the protein or to more than one type of amino acid residue (e.g., lysine, histidine, aspartic acid, glutamic acid, cysteine and combinations thereof) of the protein.

One may specifically desire polypeptides chemically modified at the N-terminus. Using polyethylene glycol as an illustration of the present composition, one may select from a variety of polyethylene glycol molecules (by molecular weight, branching, etc.), the proportion of polyethylene glycol molecules to protein (or peptide) molecules in the reaction mix, the type of pegylation reaction to be performed, and the method of obtaining the selected N-terminally pegylated protein. The method of obtaining the N-terminally pegylated preparation (i.e., separating this moiety from other monopegylated moieties if necessary) may be by purification of the N-terminally pegylated material from a population of pegylated protein molecules. Selective polypeptides chemically modified at the N-terminus modification may be accomplished by reductive alkylation which exploits differential reactivity of different types of primary amino groups (lysine versus the N-terminal) available for derivatization in a particular protein. Under the appropriate reaction conditions, substantially selective derivatization of the protein at the N-terminus with a carbonyl group containing polymer is achieved.

As indicated above, pegylation of the proteins of the invention may be accomplished by any number of means. For example, polyethylene glycol may be attached to the protein either directly or by an intervening linker. Linkerless systems for attaching polyethylene glycol to proteins are described in Delgado et al., *Crit. Rev. Thera. Drug Carrier Sys.* 9:249-304 (1992); Francis et al., *Intern. J. of Hematol.* 68:1-18 (1998); U.S. Pat. Nos. 4,002,531; 5,349,052; WO 95/06058; and WO 98/32466, the disclosures of each of which are incorporated herein by reference.

One system for attaching polyethylene glycol directly to amino acid residues of proteins without an intervening linker employs tresylated MPEG, which is produced by the modification of monomethoxy polyethylene glycol (MPEG) using tresylchloride ($ClSO_2CH_2CF_3$). Upon reaction of protein with tresylated MPEG, polyethylene glycol is directly attached to amine groups of the protein. Thus, the invention includes protein-polyethylene glycol conjugates produced by reacting proteins of the invention with a polyethylene glycol molecule having a 2,2,2-trifluoroethane sulphonyl group.

Polyethylene glycol can also be attached to proteins using a number of different intervening linkers. For example, U.S. Pat. No. 5,612,460, the entire disclosure of which is incorporated herein by reference, discloses urethane linkers for connecting polyethylene glycol to proteins. Protein-polyethylene glycol conjugates wherein the polyethylene glycol is attached to the protein by a linker can also be produced by reaction of proteins with compounds such as MPEG-succinimidylsuccinate, MPEG activated with 1,1'-carbonyldiimidazole, MPEG-2,4,5-trichloropenylcarbonate, MPEG-p-nitrophenolcarbonate, and various MPEG-succinate derivatives. A number additional polyethylene glycol derivatives and reaction chemistries for attaching polyethylene glycol to proteins are described in WO 98/32466, the entire disclosure of which is incorporated herein by reference. Pegylated protein products produced using the reaction chemistries set out herein are included within the scope of the invention.

The number of polyethylene glycol moieties attached to each protein of the invention (i.e., the degree of substitution) may also vary. For example, the pegylated proteins of the invention may be linked, on average, to 1, 2, 3, 4, 5, 6, 7, 8, 9, 10, 12, 15, 17, 20, or more polyethylene glycol molecules. Similarly, the average degree of substitution within ranges such as 1-3, 2-4, 3-5, 4-6, 5-7, 6-8, 7-9, 8-10, 9-11, 10-12, 11-13, 12-14, 13-15, 14-16, 15-17, 16-18, 17-19, or 18-20 polyethylene glycol moieties per protein molecule. Methods for determining the degree of substitution are discussed, for example, in Delgado et al., *Crit. Rev. Thera. Drug Carrier Sys.* 9:249-304 (1992).

The TR9 can be recovered and purified by standard methods which include, but are not limited to, ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

TR9 receptor polynucleotides and polypeptides may be used in accordance with the present invention for a variety of applications, particularly those that make use of the chemical and biological properties of TR9. Among these are applications in treatment, prevention, diagnosis, and/or detection of tumors, resistance to parasites, bacteria and viruses, to induce proliferation of T-cells, endothelial cells and certain hematopoietic cells, to treat, prevent, diagnose, and/or detect restenosis, graft vs. host disease, to regulate anti-viral responses and to prevent certain autoimmune diseases after stimulation of TR9 by an agonist. Additional applications relate to diagnosis and to treatment, prevention, diagnosis, and/or detection of disorders of cells, tissues and organisms. These aspects of the invention are discussed further below.

Transgenics and "Knock-Outs"

The TR9 polypeptides of the invention can also be expressed in transgenic animals. Animals of any species, including, but not limited to, mice, rats, rabbits, hamsters, guinea pigs, pigs, micro-pigs, goats, sheep, cows and non-human primates, e.g., baboons, monkeys, and chimpanzees may be used to generate transgenic animals. In a specific embodiment, techniques described herein or otherwise known in the art, are used to express polypeptides of the invention in humans, as part of a gene therapy protocol.

Any technique known in the art may be used to introduce the transgene (i.e., nucleic acids of the invention) into animals to produce the founder lines of transgenic animals. Such techniques include, but are not limited to, pronuclear microinjection (Paterson et al., Appl. Microbiol. Biotechnol. 40:691-698 (1994); Carver et al., Biotechnology (NY) 11:1263-1270 (1993); Wright et al., Biotechnology (NY) 9:830-834 (1991); and Hoppe et al., U.S. Pat. No. 4,873,191 (1989)); retrovirus mediated gene transfer into germ lines (Van der Putten et al., Proc. Natl. Acad. Sci., USA 82:6148-6152 (1985)), blastocysts or embryos; gene targeting in embryonic stem cells (Thompson et al., Cell 56:313-321 (1989)); electroporation of cells or embryos (Lo, Mol. Cell. Biol. 3:1803-1814 (1983)); introduction of the polynucleotides of the invention using a gene gun (see, e.g., Ulmer et al., Science 259:1745 (1993); introducing nucleic acid constructs into embryonic pleuripotent stem cells and transferring the stem cells back into the blastocyst; and sperm-mediated gene transfer (Lavitrano et al., Cell 57:717-723 (1989); etc. For a review of such techniques, see Gordon, "Transgenic Animals," Intl. Rev. Cytol. 115:171-229 (1989), which is incorporated by reference herein in its entirety. Further, the contents of each of the documents recited in this paragraph is herein incorporated by reference in its entirety.

Any technique known in the art may be used to produce transgenic clones containing polynucleotides of the invention, for example, nuclear transfer into enucleated oocytes of nuclei from cultured embryonic, fetal, or adult cells induced to quiescence (Campell et al., Nature 380:64-66 (1996); Wilmut et al., Nature 385:810-813 (1997)), each of which is herein incorporated by reference in its entirety).

The present invention provides for transgenic animals that carry the transgene in all their cells, as well as animals which carry the transgene in some, but not all their cells, i.e., mosaic animals or chimeric animals. The transgene may be integrated as a single transgene or as multiple copies such as in concatamers, e.g., head-to-head tandems or head-to-tail tandems. The transgene may also be selectively introduced into and activated in a particular cell type by following, for example, the teaching of Lasko et al. (Proc. Natl. Acad. Sci. USA 89:6232-6236 (1992)). The regulatory sequences required for such a cell-type specific activation will depend upon the particular cell type of interest, and will be apparent to those of skill in the art. When it is desired that the polynucleotide transgene be integrated into the chromosomal site of the endogenous gene, gene targeting is preferred. Briefly, when such a technique is to be utilized, vectors containing some nucleotide sequences homologous to the endogenous gene are designed for the purpose of integrating, via homologous recombination with chromosomal sequences, into and disrupting the function of the nucleotide sequence of the endogenous gene. The transgene may also be selectively introduced into a particular cell type, thus inactivating the endogenous gene in only that cell type, by following, for example, the teaching of Gu et al. (Science 265:103-106 (1994)). The regulatory sequences required for such a cell-type specific inactivation will depend upon the particular cell type of interest, and will be apparent to those of skill in the art. The contents of each of the documents recited in this paragraph is herein incorporated by reference in its entirety.

Once transgenic animals have been generated, the expression of the recombinant gene may be assayed utilizing standard techniques. Initial screening may be accomplished by Southern blot analysis or PCR techniques to analyze animal tissues to verify that integration of the transgene has taken place. The level of mRNA expression of the transgene in the tissues of the transgenic animals may also be assessed using techniques which include, but are not limited to, Northern blot analysis of tissue samples obtained from the animal, in situ hybridization analysis, and reverse transcriptase-PCR (rt-PCR). Samples of transgenic gene-expressing tissue may also be evaluated immunocytochemically or immunohistochemically using antibodies specific for the transgene product.

Once the founder animals are produced, they may be bred, inbred, outbred, or crossbred to produce colonies of the particular animal. Examples of such breeding strategies include, but are not limited to: outbreeding of founder animals with more than one integration site in order to establish separate lines; inbreeding of separate lines in order to produce compound transgenics that express the transgene at higher levels because of the effects of additive expression of each transgene; crossing of heterozygous transgenic animals to produce animals homozygous for a given integration site in order to both augment expression and eliminate the need for screening of animals by DNA analysis; crossing of separate homozygous lines to produce compound heterozygous or homozygous lines; and breeding to place the transgene on a distinct background that is appropriate for an experimental model of interest.

Transgenic and "knock-out" animals of the invention have uses which include, but are not limited to, animal model systems useful in elaborating the biological function of TR9 polypeptides, studying conditions and/or disorders associated with aberrant TR9 expression, and in screening for compounds effective in ameliorating such conditions and/or disorders.

In further embodiments of the invention, cells that are genetically engineered to express the proteins of the invention, or alternatively, that are genetically engineered not to express the proteins of the invention (e.g., knockouts) are administered to a patient in vivo. Such cells may be obtained from the patient (i.e., animal, including human) or an MHC compatible donor and can include, but are not limited to fibroblasts, bone marrow cells, blood cells (e.g., lymphocytes), adipocytes, muscle cells, endothelial cells, etc. The cells are genetically engineered in vitro using recombinant DNA techniques to introduce the coding sequence of polypeptides of the invention into the cells, or alternatively, to disrupt the coding sequence and/or endogenous regulatory sequence associated with the polypeptides of the invention, e.g., by transduction (using viral vectors, and preferably vectors that integrate the transgene into the cell genome) or transfection procedures, including, but not limited to, the use of plasmids, cosmids, YACs, naked DNA, electroporation, liposomes, etc. The coding sequence of the polypeptides of the invention can be placed under the control of a strong constitutive or inducible promoter or promoter/enhancer to achieve expression, and preferably secretion, of the polypeptides of the invention. The engineered cells which express and preferably secrete the polypeptides of the invention can be introduced into the patient systemically, e.g., in the circulation, or intraperitoneally. Alternatively, the cells can be incorporated into a matrix and implanted in the body, e.g., genetically engineered fibroblasts can be implanted as part of a skin graft; genetically engineered endothelial cells can be implanted as part of a lymphatic or vascular graft. (See, for example, Anderson et al., U.S. Pat. No. 5,399,349; and Mulligan & Wilson, U.S. Pat. No. 5,460,959, each of which is incorporated by reference herein in its entirety).

When the cells to be administered are non-autologous or non-MHC compatible cells, they can be administered using well known techniques which prevent the development of a host immune response against the introduced cells. For example, the cells may be introduced in an encapsulated form which, while allowing for an exchange of components with the immediate extracellular environment, does not allow the introduced cells to be recognized by the host immune system.

TR9 Receptor Proteins and Fragments

The invention further provides for proteins containing polypeptide sequences encoded by polynucleotides of the invention.

The TR9 proteins of the invention may be in monomers or multimers (i.e., dimers, trimers, tetramers, and higher multimers). Accordingly, the present invention relates to monomers and multimers of the TR9 proteins of the invention, their preparation, and compositions (preferably, pharmaceutical compositions) containing them. In specific embodiments, the polypeptides of the invention are monomers, dimers, trimers or tetramers. In additional embodiments, the multimers of the invention are at least dimers, at least trimers, or at least tetramers.

Multimers encompassed by the invention may be homomers or heteromers. As used herein, the term homomer, refers to a multimer containing only TR9 proteins of the invention (including TR9 fragments, variants, and fusion proteins, as described herein). These homomers may contain TR9 proteins having identical or different polypeptide sequences. In a specific embodiment, a homomer of the invention is a multimer containing only TR9 proteins having an identical polypeptide sequence. In another specific embodiment, a homomer of the invention is a multimer containing TR9 proteins having different polypeptide sequences.

In specific embodiments, the multimer of the invention is a homodimer (e.g., containing TR9 proteins having identical or different polypeptide sequences) or a homotrimer (e.g., containing TR9 proteins having identical or different polypeptide sequences). In additional embodiments, the homomeric multimer of the invention is at least a homodimer, at least a homotrimer, or at least a homotetramer.

As used herein, the term heteromer refers to a multimer containing heterologous proteins (i.e., proteins containing only polypeptide sequences that do not correspond to a polypeptide sequences encoded by the TR9 gene) in addition to the TR9 proteins of the invention. In a specific embodiment, the multimer of the invention is a heterodimer, a heterotrimer, or a heterotetramer. In additional embodiments, the homomeric multimer of the invention is at least a homodimer, at least a homotrimer, or at least a homotetramer.

Multimers of the invention may be the result of hydrophobic, hydrophilic, ionic and/or covalent associations and/or may be indirectly linked, by for example, liposome formation. Thus, in one embodiment, multimers of the invention, such as, for example, homodimers or homotrimers, are formed when proteins of the invention contact one another in solution. In another embodiment, heteromultimers of the invention, such as, for example, heterotrimers or heterotetramers, are formed when proteins of the invention contact antibodies to the polypeptides of the invention (including antibodies to the heterologous polypeptide sequence in a fusion protein of the invention) in solution. In other embodiments, multimers of the invention are formed by covalent associations with and/or between the TR9 proteins of the invention. Such covalent associations may involve one or more amino acid residues contained in the polypeptide sequence of the protein (e.g., the polypeptide sequence recited in SEQ ID NO:2 or contained in the polypeptide encoded by the deposited cDNA clone. In one instance, the covalent associations are cross-linking between cysteine residues located within the polypeptide sequences of the proteins which interact in the native (i.e., naturally occurring) polypeptide. In another instance, the covalent associations are the consequence of chemical or recombinant manipulation. Alternatively, such covalent associations may involve one or more amino acid residues contained in the heterologous polypeptide sequence in a TR9 fusion protein. In one example, covalent associations are between the heterologous sequence contained in a fusion protein of the invention (see, e.g., U.S. Pat. No. 5,478,925). In a specific example, the covalent associations are between the heterologous sequence contained in a TR9-Fc fusion protein of the invention (as described herein). In another specific example, covalent associations of fusion proteins of the invention are between heterologous polypeptide sequences from another TNF family ligand/receptor member that is capable of forming covalently associated multimers, such as for example, osteoprotegerin (see, e.g., International Publication No. WO 98/49305, the contents of which are herein incorporated by reference in its entirety).

The multimers of the invention may be generated using chemical techniques known in the art. For example, proteins desired to be contained in the multimers of the invention may be chemically cross-linked using linker molecules and linker molecule length optimization techniques known in the art (see, e.g., U.S. Pat. No. 5,478,925, which is herein incorporated by reference in its entirety). Additionally, multimers of the invention may be generated using techniques known in the art to form one or more inter-molecule cross-links between the cysteine residues located within the polypeptide sequence of the proteins desired to be contained in the multimer (see, e.g., U.S. Pat. No. 5,478,925, which is herein incorporated by reference in its entirety). Further, proteins of the invention may be routinely modified by the addition of cysteine or biotin to the C terminus or N-terminus of the polypeptide sequence of the protein and techniques known in the art may be applied to generate multimers containing one or more of these modified proteins (see, e.g., U.S. Pat. No. 5,478,925, which is herein incorporated by reference in its entirety). Additionally, techniques known in the art may be applied to generate liposomes containing the protein components desired to be contained in the multimer of the invention (see, e.g., U.S. Pat. No. 5,478,925, which is herein incorporated by reference in its entirety).

Alternatively, multimers of the invention may be generated using genetic engineering techniques known in the art. In one embodiment, proteins contained in multimers of the invention are produced recombinantly using fusion protein technology described herein or otherwise known in the art (see, e.g., U.S. Pat. No. 5,478,925, which is herein incorporated by reference in its entirety). In a specific embodiment, polynucleotides coding for a homodimer of the invention are generated by ligating a polynucleotide sequence encoding a polypeptide of the invention to a sequence encoding a linker polypeptide and then further to a synthetic polynucleotide encoding the translated product of the polypeptide in the reverse orientation from the original C-terminus to the N-terminus (lacking the leader sequence) (see, e.g., U.S. Pat. No. 5,478,925, which is herein incorporated by reference in its entirety). In another embodiment, recombinant techniques described herein or otherwise known in the art are applied to generate recombinant polypeptides of the invention which contain a transmembrane domain and which can be incorporated by membrane reconstitution techniques into liposomes (see, e.g., U.S. Pat. No. 5,478,925, which is herein incorporated by reference in its entirety).

In one embodiment, the invention provides an isolated TR9 protein having the amino acid sequence encoded by the deposited cDNA, or the amino acid sequence in FIGS. 1A-D (SEQ ID NO:2), or a polypeptide comprising, or alternatively consisting of, a portion (i.e., fragment) of the above polypeptides.

Polypeptide fragments of the present invention include polypeptides comprising, or alternatively, consisting of, an amino acid sequence contained in SEQ ID NO:2, encoded by the cDNA contained in the deposited clone, or encoded by nucleic acids which hybridize (e.g., under stringent hybridization conditions) to the nucleotide sequence contained in the deposited clone, or shown in FIGS. 1A-D (SEQ ID NO:1) or the complementary strand thereto. Protein fragments may be "free-standing," or comprised within a larger polypeptide of which the fragment forms a part or region, most preferably as a single continuous region. Representative examples of polypeptide fragments of the invention, include, for example, fragments that comprise or alternatively, consist of, from about amino acid residues –40 to 1, 1 to 20, 21 to 40, 41 to 60, 61 to 83, 84 to 100, 101 to 120, 121 to 140, 141 to 160, 160-167, 161 to 180, 181 to 200, 201 to 220, 221 to 240, 241 to 260, 261 to 280, 281 to 310, 311 to 350, 351 to 400, 401 to 450, 451 to 500, 551 to 600, or 601 to the end of the coding region of SEQ ID NO:2. Polynucleotides encoding these polypeptides are also encompassed by the invention. In this context "about" includes the particularly recited ranges, larger or smaller by several (5, 4, 3, 2, or 1) amino acids, at either extreme or at both extremes. Moreover, polypeptide fragments can be at least about 20, 30, 40, 50, 60, 70, 80, 90, 100, 110, 120, 130, 140, or 150 amino acids in length. In this context "about" includes the particularly recited value, larger or smaller by several (5, 4, 3, 2, or 1) amino acids, at either extreme or at both extremes.

In specific embodiments, polypeptide fragments of the invention comprise, or alternatively, consist of, amino acid residues: 40 to 48, 40 to 51, 51 to 66, 66 to 73, 73 to 83, 83 to 104, 104 to 110, 110 to 128, 128 to 146, 146 to 152, 40 to 152, and/or 28 to 171 in SEQ ID NO:2. Polynucleotides encoding these polypeptides are also encompassed by the invention.

Preferred polypeptide fragments of the present invention include a member selected from the group: a polypeptide comprising or alternatively, consisting of, the TR9 receptor extracellular domain (predicted to constitute amino acid residues from about 1 to about 310 in SEQ ID NO:2); a polypeptide comprising or alternatively, consisting of, the four TNFR-like cysteine rich motifs of TR9 (amino acid residues 67 to 211 in FIGS. 1A-D; amino acid residues 27 to 171 in SEQ ID NO:2); a polypeptide comprising or alternatively, consisting of, the TR9 receptor transmembrane domain (predicted to constitute amino acid residues from about 311 to about 327 in SEQ ID NO:2); a polypeptide comprising or alternatively, consisting of, fragment of the predicted mature TR9 polypeptide, wherein the fragment has a TR9 functional activity (e.g., antigenic activity or biological activity); a polypeptide comprising or alternatively, consisting of, the TR9 receptor intracellular domain (predicted to constitute amino acid residues from about 328 to about 615 in SEQ ID NO:2); a polypeptide comprising or alternatively, consisting of, the TR9 receptor extracellular and intracellular domains with all or part of the transmembrane domain deleted; a polypeptide comprising, or alternatively consisting of, the TR9 receptor death domain (predicted to constitute amino acid residues from about 389 to about 455 in SEQ ID NO:2); and a polypeptide comprising, or alternatively, consisting of, one, two, three, four or more, epitope bearing portions of the TR9 receptor protein. In additional embodiments, the polypeptide fragments of the invention comprise, or alternatively, consist of, any combination of 1, 2, 3, 4, 5, 6, 7, or all 8 of the above members. As above, with the leader sequence, the amino acid residues constituting the TR9 receptor extracellular, transmembrane and intracellular domains have been predicted by computer analysis. Thus, as one of ordinary skill would appreciate, the amino acid residues constituting these domains may vary slightly (e.g., by about 1 to about 15 amino acid residues) depending on the criteria used to define each domain. Polynucleotides encoding these polypeptides are also encompassed by the invention.

As discussed above, it is believed that one or more of the four extracellular cysteine-rich motifs of TR9 is important for interactions between TR9 and its ligands. Accordingly, in preferred embodiments, polypeptide fragments of the invention comprise, or alternatively consist of amino acid residues 27 to 65, 66 to 105, 106 to 145, and/or 146 to 171 of SEQ ID NO:2. Polynucleotides encoding these polypeptides are also encompassed by the invention. Additional embodiments of the invention are directed to polypeptides which comprise, or alternatively consist of, any combination of 1, 2, 3, or all 4 of the extracellular cysteine-rich motifs disclosed in FIGS. 1A-D and FIG. 4B.

Among the especially preferred fragments of the invention are fragments comprising, or alternatively, consisting of structural or functional attributes of TR9. Such fragments include amino acid residues that comprise alpha-helix and alpha-helix forming regions ("alpha-regions"), beta-sheet and beta-sheet-forming regions ("beta-regions"), turn and turn-forming regions ("turn-regions"), coil and coil-forming regions ("coil-regions"), hydrophillic regions, hydrophobic regions, alpha amphipathic regions, beta amphipathic regions, surface forming regions, and high antigenic index regions (i.e., regions of polypeptides consisting of amino acid residues having an antigenic index of or equal to greater than 1.5, as identified using the default parameters of the Jameson-Wolf program) of TR9. Certain preferred regions are those disclosed in FIG. 3 and Table I and include, but are not limited to, regions of the aforementioned types identified by analysis of the amino acid sequence depicted in FIGS. 1A-D, such preferred regions include; Garnier-Robson predicted alpha-regions, beta-regions, turn-regions, and coil-regions; Chou-Fasman predicted alpha-regions, beta-regions, turn-regions, and coil-regions; Kyte-Doolittle predicted hydrophilic and hydrophobic regions; Eisenberg alpha and beta amphipathic regions; Emini surface-forming regions; and Jameson-Wolf high antigenic index regions, as predicted using the default parameters of these computer programs. Polynucleotides encoding these polypeptides are also encompassed by the invention.

In another aspect, the invention provides a peptide or polypeptide comprising, or alternatively, consisting of, one, two, three, four, five or more, epitope-bearing portions of a polypeptide of the invention. The epitope of this polypeptide portion is an immunogenic or antigenic epitope of a polypeptide described herein. An "immunogenic epitope" is defined as a part of a protein that elicits an antibody response when the whole protein is the immunogen. On the other hand, a region of a protein molecule to which an antibody can bind is defined as an "antigenic epitope." The number of immunogenic epitopes of a protein generally is less than the number of antigenic epitopes. See, for instance, Geysen et al., *Proc. Natl. Acad. Sci. USA* 81:3998-4002 (1983).

As to the selection of peptides or polypeptides bearing an antigenic epitope (i.e., that contain a region of a protein molecule to which an antibody can bind), it is well known in that art that relatively short synthetic peptides that mimic part of a protein sequence are routinely capable of eliciting an antiserum that reacts with the partially mimicked protein. See, for instance, J. G. Sutcliffe et al., "Antibodies That React With Predetermined Sites on Proteins," *Science* 219:660-666 (1983). Peptides capable of eliciting protein-reactive sera are frequently represented in the primary sequence of a protein, can be characterized by a set of simple chemical rules, and are confined neither to immunodominant regions of intact proteins (i.e., immunogenic epitopes) nor to the amino or carboxyl terminals.

Antigenic epitope-bearing peptides and polypeptides of the invention are therefore useful to raise antibodies, including monoclonal antibodies, that bind specifically to a polypeptide of the invention. See, for instance, Wilson et al., *Cell* 37:767-778 (1984) at 777. Antigenic epitope-bearing peptides and polypeptides of the invention preferably contain a sequence of at least seven, more preferably at least nine and most preferably between at least about 15 to about 30 amino acids contained within the amino acid sequence of a polypeptide of the invention.

Non-limiting examples of antigenic polypeptides or peptides that can be used to generate TR9 receptor-specific antibodies include: a polypeptide comprising, or alternatively consisting of, amino acid residues from about 4 to about 81 in SEQ ID NO:2, about 116 to about 271 in SEQ ID NO:2, about 283 to about 308 in SEQ ID NO:2, about 336 to about 372 in SEQ ID NO:2, about 393 to about 434 in SEQ ID NO:2, about 445 to about 559 in SEQ ID NO:2, and about 571 to about 588 in SEQ ID NO:2. In this context "about" includes the particularly recited ranges, larger or smaller by several (5, 4, 3, 2, or 1) nucleotides, at either terminus or at both termini. As indicated above, the inventors have determined that the above polypeptide fragments are antigenic regions of the TR9 receptor protein. Polynucleotides encoding these polypeptides are also encompassed by the invention.

The epitope-bearing peptides and polypeptides of the invention may be produced by any conventional means. R. A. Houghten, "General Method for the Rapid Solid-Phase Synthesis of Large Numbers of Peptides: Specificity of Antigen-Antibody Interaction at the Level of Individual Amino Acids," *Proc. Natl. Acad. Sci. USA* 82:5131-5135 (1985). This "Simultaneous Multiple Peptide Synthesis (SMPS)" process is further described in U.S. Pat. No. 4,631,211 to Houghten et al. (1986).

As one of skill in the art will appreciate, TR9 receptor polypeptides of the present invention and the epitope-bearing fragments thereof described above can be combined with parts of the constant domain of immunoglobulins (IgG), resulting in chimeric polypeptides. These fusion proteins facilitate purification and show an increased half-life in vivo. This has been shown, e.g., for chimeric proteins consisting of the first two domains of the human CD4-polypeptide and various domains of the constant regions of the heavy or light chains of mammalian immunoglobulins (EPA 394,827; Traunecker et al., *Nature* 331:84-86 (1988)). Fusion proteins that have a disulfide-linked dimeric structure due to the IgG part can also be more efficient in binding and neutralizing other molecules than the monomeric TR9 protein or protein fragment alone (Fountoulakis et al., *J. Biochem.* 270:3958-3964 (1995)).

To improve or alter the characteristics of TR9 polypeptides, protein engineering may be employed. Recombinant DNA technology known to those skilled in the art can be used to create novel mutant proteins or "muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions. For many proteins, including the extracellular domain of a membrane associated protein or the mature form(s) of a secreted protein, it is known in the art that one or more amino acids may be deleted from the N-terminus or C-terminus without substantial loss of biological function. However, even if deletion of one or more amino acids from the N-terminus or C-terminus of a protein results in modification or loss of one or more biological functions of the protein, other TR9 functional activities may still be retained. For example, in many instances, the ability of the shortened protein to induce and/or bind to antibodies which recognize TR9 (preferably antibodies that bind specifically to TR9) will retained irrespective of the size or location of the deletion. In fact, polypeptides composed of as few as six TR9 amino acid residues may often evoke an immune response. Whether a particular polypeptide lacking N-terminal and/or C-terminal residues of a complete protein retains such immunologic activities can readily be determined by routine methods described herein and otherwise known in the art.

As mentioned above, even if deletion of one or more amino acids from the N-terminus of a protein results in modification or loss of one or more biological functions of the protein, other functional activities (e.g., biological activities, ability to multimerize, ability to bind TR9 ligand) may still be retained. For example, the ability of shortened TR9 muteins to induce and/or bind to antibodies which recognize the complete or mature forms of the polypeptides generally will be retained when less than the majority of the residues of the complete or mature polypeptide are removed from the N-terminus. Whether a particular polypeptide lacking N-terminal residues of a complete polypeptide retains such immunologic activities can readily be determined by routine methods described herein and otherwise known in the art. It is not unlikely that an TR9 mutein with a large number of deleted N-terminal amino acid residues may retain some biological or immunogenic activities. In fact, peptides composed of as few as six TR9 amino acid residues may often evoke an immune response.

Accordingly, in one embodiment, the present invention further provides polypeptides having one or more residues deleted from the amino terminus of the amino acid sequence of the TR9 polypeptide depicted in FIGS. 1A-D (SEQ ID NO:2) or encoded by the cDNA of the deposited clone. Particularly, in one embodiment, N-terminal deletions of the TR9 polypeptide can be described by the general formula m to 615, where m is a number from −39 to 614 corresponding to the position of amino acid identified in SEQ ID NO:2 and preferably, corresponds to one of the N-terminal amino acid residues identified in the N-terminal deletions specified herein. In specific embodiments, N-terminal deletions of the TR9 polypeptide of the invention comprise, or alternatively consist of, amino acid residues: Q-2 to L-615; P-3 to L-615; E-4 to L-615; Q-5 to L-615; K-6 to L-615; A-7 to L-615; S-8 to L-615; N-9 to L-615; L-10 to L-615; I-11 to L-615; G-12 to L-615; T-13 to L-615; Y-14 to L-615; R-15 to L-615; H-16 to L-615; V-17 to L-615; D-18 to L-615; R-19 to L-615; A-20 to L-615; T-21 to L-615; G-22 to L-615; Q-23 to L-615; V-24 to L-615; L-25 to L-615; T-26 to L-615; C-27 to L-615; D-28 to L-615; K-29 to L-615; C-30 to L-615; P-31 to L-615; A-32 to L-615; G-33 to L-615; T-34 to L-615; Y-35 to L-615; V-36 to L-615; S-37 to L-615; E-38 to L-615; H-39 to L-615; C-40 to L-615; T-41 to L-615; N-42 to L-615; T-43 to L-615; S-44 to L-615; L-45 to L-615; R-46 to L-615; V-47 to L-615; C-48 to L-615; S-49 to L-615; S-50 to L-615; C-51 to L-615; P-52 to L-615; V-53 to L-615; G-54 to L-615; T-55 to L-615; F-56 to L-615; T-57 to L-615; R-58 to L-615; H-59 to L-615; E-60 to L-615; N-61 to L-615; G-62 to L-615; I-63 to L-615; E-64 to L-615; K-65 to L-615; C-66 to L-615; H-67 to L-615; D-68 to L-615; C-69 to L-615; S-70 to L-615; Q-71 to L-615; P-72 to L-615; C-73 to L-615; P-74 to L-615; W-75 to L-615; P-76 to L-615; M-77 to L-615; I-78 to L-615; E-79 to L-615; K-80 to L-615; L-81 to L-615; P-82 to L-615; C-83 to L-615; A-84 to L-615; A-85 to L-615; L-86 to L-615; T-87 to L-615; D-88 to L-615; R-89 to L-615; E-90 to L-615; C-91 to L-615; T-92 to L-615; C-93 to L-615; P-94 to L-615; P-95 to L-615; G-96 to L-615; M-97 to L-615; F-98 to L-615; Q-99 to L-615; S-100 to L-615; N-101 to L-615; A-102 to L-615; T-103 to L-615; C-104 to L-615; A-105 to L-615; P-106 to L-615; H-107 to L-615; T-108 to L-615; V-109 to L-615; C-110 to L-615; P-111 to L-615; V-112 to L-615; G-113 to L-615; W-114 to L-615; G-115 to L-615; V-116 to L-615; R-117 to L-615; K-118 to L-615; K-119 to L-615; G-120 to L-615; T-121 to L-615; E-122 to L-615; T-123 to L-615; E-124 to L-615; D-125 to L-615; V-126 to L-615; R-127 to L-615; C-128 to L-615; K-129 to L-615; Q-130 to L-615; C-131 to L-615; A-132 to L-615; R-133 to L-615; G-134 to L-615; T-135 to L-615; F-136 to L-615; S-137 to L-615; D-138 to L-615; V-139 to L-615; P-140 to L-615; S-141 to L-615; S-142 to L-615; V-143 to L-615; M-144 to L-615; K-145 to L-615; C-146 to L-615; K-147 to L-615; A-148 to L-615; Y-149 to L-615; T-150 to L-615; D-151 to L-615; C-152 to L-615; L-153 to L-615; S-154 to L-615; Q-155 to L-615; N-156 to L-615; L-157 to L-615; V-158 to L-615; V-159 to L-615; I-160 to L-615; K-161 to L-615; P-162 to L-615; G-163 to L-615; T-164 to L-615; K-165 to L-615; E-166 to L-615; T-167 to L-615; D-168 to L-615; N-169 to L-615; V-170 to L-615; C-171 to L-615; G-172 to L-615; T-173 to L-615; L-174 to L-615; P-175 to L-615; S-176 to L-615; F-177 to L-615; S-178 to L-615; S-179 to L-615; S-180 to L-615; T-181 to L-615; S-182 to L-615; P-183 to L-615; S-184 to L-615; P-185 to L-615; G-186 to L-615; T-187 to L-615; A-188 to L-615; I-189 to L-615; F-190 to L-615; P-191 to L-615; R-192 to L-615; P-193 to L-615; E-194 to L-615; H-195 to L-615; M-196 to L-615; E-197 to L-615; T-198 to L-615; H-199 to L-615; E-200 to L-615; V-201 to L-615; P-202 to L-615; S-203 to L-615; S-204 to L-615; T-205 to L-615; Y-206 to L-615; V-207 to L-615; P-208 to L-615; K-209 to L-615; G-210 to L-615; M-211 to L-615; N-212 to L-615; S-213 to L-615; T-214 to L-615; E-215 to L-615; S-216 to L-615; N-217 to L-615; S-218 to L-615; S-219 to L-615; A-220 to L-615; S-221 to L-615; V-222 to L-615; R-223 to L-615; P-224 to L-615; K-225 to L-615; V-226 to L-615; L-227 to L-615; S-228 to L-615; S-229 to L-615; I-230 to L-615; Q-231 to L-615; E-232 to L-615; G-233 to L-615; T-234 to L-615; V-235 to L-615; P-236 to L-615; D-237 to L-615; N-238 to L-615; T-239 to L-615; S-240 to L-615; S-241 to L-615; A-242 to L-615; R-243 to L-615; G-244 to L-615; K-245 to L-615; E-246 to L-615; D-247 to L-615; V-248 to L-615; N-249 to L-615; K-250 to L-615; T-251 to L-615; L-252 to L-615; P-253 to L-615; N-254 to L-615; L-255 to L-615; Q-256 to L-615; V-257 to L-615; V-258 to L-615; N-259 to L-615; H-260 to L-615; Q-261 to L-615; Q-262 to L-615; G-263 to L-615; P-264 to L-615; H-265 to L-615; H-266 to L-615; R-267 to L-615; H-268 to L-615; I-269 to L-615; L-270 to L-615; K-271 to L-615; L-272 to L-615; L-273 to L-615; P-274 to L-615; S-275 to L-615; M-276 to L-615; E-277 to L-615; A-278 to L-615; T-279 to L-615; G-280 to L-615; G-281 to L-615; E-282 to L-615; K-283 to L-615; S-284 to L-615; S-285 to L-615; T-286 to L-615; P-287 to L-615; I-288 to L-615; K-289 to L-615; G-290 to L-615; P-291 to L-615; K-292 to L-615; R-293 to L-615; G-294 to L-615; H-295 to L-615; P-296 to L-615; R-297 to L-615; Q-298 to L-615; N-299 to L-615; L-300 to L-615; H-301 to L-615; K-302 to L-615; H-303 to L-615; F-304 to L-615; D-305 to L-615; I-306 to L-615; N-307 to L-615; E-308 to L-615; H-309 to L-615; L-310 to L-615; P-311 to L-615; W-312 to L-615; M-313 to L-615; I-314 to L-615; V-315 to L-615; L-316 to L-615; F-317 to L-615; L-318 to L-615; L-319 to L-615; L-320 to L-615; V-321 to L-615; L-322 to L-615; V-323 to L-615; V-324 to L-615; I-325 to L-615; V-326 to L-615; V-327 to L-615; C-328 to L-615; S-329 to L-615; I-330 to L-615; R-331 to L-615; K-332 to L-615; S-333 to L-615; S-334 to L-615; R-335 to L-615; T-336 to L-615; L-337 to L-615; K-338 to L-615; K-339 to L-615; G-340 to L-615; P-341 to L-615; R-342 to L-615; Q-343 to L-615; D-344 to L-615; P-345 to L-615; S-346 to L-615; A-347 to L-615; I-348 to L-615; V-349 to L-615; E-350 to L-615; K-351 to L-615; A-352 to L-615; G-353 to L-615; L-354 to L-615; K-355 to L-615; K-356 to L-615; S-357 to L-615; M-358 to L-615; T-359 to L-615; P-360 to L-615; T-361 to L-615; Q-362 to L-615; N-363 to L-615; R-364 to L-615; E-365 to L-615; K-366 to L-615; W-367 to L-615; I-368 to L-615; Y-369 to L-615; Y-370 to L-615; C-371 to L-615; N-372 to L-615; G-373 to L-615; H-374 to L-615; G-375 to L-615; I-376 to L-615; D-377 to L-615; I-378 to L-615; L-379 to L-615; K-380 to L-615; L-381 to L-615; V-382 to L-615; A-383 to L-615; A-384 to L-615; Q-385 to L-615; V-386 to L-615; G-387 to L-615; S-388 to L-615; Q-389 to L-615; W-390 to L-615; K-391 to L-615; D-392 to L-615; I-393 to L-615; Y-394 to L-615; Q-395 to L-615; F-396 to L-615; L-397 to L-615; C-398 to L-615; N-399 to L-615; A-400 to L-615; S-401 to L-615; E-402 to L-615; R-403 to L-615; E-404 to L-615;

V-405 to L-615; A-406 to L-615; A-407 to L-615; F-408 to L-615; S-409 to L-615; N-410 to L-615; G-411 to L-615; Y-412 to L-615; T-413 to L-615; A-414 to L-615; D-415 to L-615; H-416 to L-615; E-417 to L-615; R-418 to L-615; A-419 to L-615; Y-420 to L-615; A-421 to L-615; A-422 to L-615; L-423 to L-615; Q-424 to L-615; H-425 to L-615; W-426 to L-615; T-427 to L-615; I-428 to L-615; R-429 to L-615; G-430 to L-615; P-431 to L-615; E-432 to L-615; A-433 to L-615; S-434 to L-615; L-435 to L-615; A-436 to L-615; Q-437 to L-615; L-438 to L-615; I-439 to L-615; S-440 to L-615; A-441 to L-615; L-442 to L-615; R-443 to L-615; Q-444 to L-615; H-445 to L-615; R-446 to L-615; R-447 to L-615; N-448 to L-615; D-449 to L-615; V-450 to L-615; V-451 to L-615; E-452 to L-615; K-453 to L-615; I-454 to L-615; R-455 to L-615; G-456 to L-615; L-457 to L-615; M-458 to L-615; E-459 to L-615; D-460 to L-615; T-461 to L-615; T-462 to L-615; Q-463 to L-615; L-464 to L-615; E-465 to L-615; T-466 to L-615; D-467 to L-615; K-468 to L-615; L-469 to L-615; A-470 to L-615; L-471 to L-615; P-472 to L-615; M-473 to L-615; S-474 to L-615; P-475 to L-615; S-476 to L-615; P-477 to L-615; L-478 to L-615; S-479 to L-615; P-480 to L-615; S-481 to L-615; P-482 to L-615; I-483 to L-615; P-484 to L-615; S-485 to L-615; P-486 to L-615; N-487 to L-615; A-488 to L-615; K-489 to L-615; L-490 to L-615; E-491 to L-615; N-492 to L-615; S-493 to L-615; A-494 to L-615; L-495 to L-615; L-496 to L-615; T-497 to L-615; V-498 to L-615; E-499 to L-615; P-500 to L-615; S-501 to L-615; P-502 to L-615; Q-503 to L-615; D-504 to L-615; K-505 to L-615; N-506 to L-615; K-507 to L-615; G-508 to L-615; F-509 to L-615; F-510 to L-615; V-511 to L-615; D-512 to L-615; E-513 to L-615; S-514 to L-615; E-515 to L-615; P-516 to L-615; L-517 to L-615; L-518 to L-615; R-519 to L-615; C-520 to L-615; D-521 to L-615; S-522 to L-615; T-523 to L-615; S-524 to L-615; S-525 to L-615; G-526 to L-615; S-527 to L-615; S-528 to L-615; A-529 to L-615; L-530 to L-615; S-531 to L-615; R-532 to L-615; N-533 to L-615; G-534 to L-615; S-535 to L-615; F-536 to L-615; I-537 to L-615; T-538 to L-615; K-539 to L-615; E-540 to L-615; K-541 to L-615; K-542 to L-615; D-543 to L-615; T-544 to L-615; V-545 to L-615; L-546 to L-615; R-547 to L-615; Q-548 to L-615; V-549 to L-615; R-550 to L-615; L-551 to L-615; D-552 to L-615; P-553 to L-615; C-554 to L-615; D-555 to L-615; L-556 to L-615; Q-557 to L-615; P-558 to L-615; I-559 to L-615; F-560 to L-615; D-561 to L-615; D-562 to L-615; M-563 to L-615; L-564 to L-615; H-565 to L-615; F-566 to L-615; L-567 to L-615; N-568 to L-615; P-569 to L-615; E-570 to L-615; E-571 to L-615; L-572 to L-615; R-573 to L-615; V-574 to L-615; I-575 to L-615; E-576 to L-615; E-577 to L-615; I-578 to L-615; P-579 to L-615; Q-580 to L-615; A-581 to L-615; E-582 to L-615; D-583 to L-615; K-584 to L-615; L-585 to L-615; D-586 to L-615; R-587 to L-615; L-588 to L-615; F-589 to L-615; E-590 to L-615; I-591 to L-615; I-592 to L-615; G-593 to L-615; V-594 to L-615; K-595 to L-615; S-596 to L-615; Q-597 to L-615; E-598 to L-615; A-599 to L-615; S-600 to L-615; Q-601 to L-615; T-602 to L-615; L-603 to L-615; L-604 to L-615; D-605 to L-615; S-606 to L-615; V-607 to L-615; Y-608 to L-615; S-609 to L-615; and/or H-610 to L-615 of SEQ ID NO:2. Polynucleotides encoding these polypeptides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR9 polypeptides described above, and the polypeptides encoded thereby. The present invention also encompasses the above polynucleotide sequences fused to a heterologous polynucleotide sequence, and the polypeptides encoded thereby.

In another embodiment, N-terminal deletions of the TR9 polypeptide can be described by the general formula m to 310 where m is a number from −40 to 309 corresponding to the amino acid sequence identified in SEQ ID NO:2. In specific embodiments, N terminal deletions of the TR9 of the invention comprise, or alternatively, consist of, amino acid residues: Q-2 to L-310; P-3 to L-310; E-4 to L-310; Q-5 to L-310; K-6 to L-310; A-7 to L-310; S-8 to L-310; N-9 to L-310; L-10 to L-310; I-11 to L-310; G-12 to L-310; T-13 to L-310; Y-14 to L-310; R-15 to L-310; H-16 to L-310; V-17 to L-310; D-18 to L-310; R-19 to L-310; A-20 to L-310; T-21 to L-310; G-22 to L-310; Q-23 to L-310; V-24 to L-310; L-25 to L-310; T-26 to L-310; C-27 to L-310; D-28 to L-310; K-29 to L-310; C-30 to L-310; P-31 to L-310; A-32 to L-310; G-33 to L-310; T-34 to L-310; Y-35 to L-310; V-36 to L-310; S-37 to L-310; E-38 to L-310; H-39 to L-310; C-40 to L-310; T-41 to L-310; N-42 to L-310; T-43 to L-310; S-44 to L-310; L-45 to L-310; R-46 to L-310; V-47 to L-310; C-48 to L-310; S-49 to L-310; S-50 to L-310; C-51 to L-310; P-52 to L-310; V-53 to L-310; G-54 to L-310; T-55 to L-310; F-56 to L-310; T-57 to L-310; R-58 to L-310; H-59 to L-310; E-60 to L-310; N-61 to L-310; G-62 to L-310; I-63 to L-310; E-64 to L-310; K-65 to L-310; C-66 to L-310; H-67 to L-310; D-68 to L-310; C-69 to L-310; S-70 to L-310; Q-71 to L-310; P-72 to L-310; C-73 to L-310; P-74 to L-310; W-75 to L-310; P-76 to L-310; M-77 to L-310; I-78 to L-310; E-79 to L-310; K-80 to L-310; L-81 to L-310; P-82 to L-310; C-83 to L-310; A-84 to L-310; A-85 to L-310; L-86 to L-310; T-87 to L-310; D-88 to L-310; R-89 to L-310; E-90 to L-310; C-91 to L-310; T-92 to L-310; C-93 to L-310; P-94 to L-310; P-95 to L-310; G-96 to L-310; M-97 to L-310; F-98 to L-310; Q-99 to L-310; S-100 to L-310; N-101 to L-310; A-102 to L-310; T-103 to L-310; C-104 to L-310; A-105 to L-310; P-106 to L-310; H-107 to L-310; T-108 to L-310; V-109 to L-310; C-110 to L-310; P-111 to L-310; V-112 to L-310; G-113 to L-310; W-114 to L-310; G-115 to L-310; V-116 to L-310; R-117 to L-310; K-118 to L-310; K-119 to L-310; G-120 to L-310; T-121 to L-310; E-122 to L-310; T-123 to L-310; E-124 to L-310; D-125 to L-310; V-126 to L-310; R-127 to L-310; C-128 to L-310; K-129 to L-310; Q-130 to L-310; C-131 to L-310; A-132 to L-310; R-133 to L-310; G-134 to L-310; T-135 to L-310; F-136 to L-310; S-137 to L-310; D-138 to L-310; V-139 to L-310; P-140 to L-310; S-141 to L-310; S-142 to L-310; V-143 to L-310; M-144 to L-310; K-145 to L-310; C-146 to L-310; K-147 to L-310; A-148 to L-310; Y-149 to L-310; T-150 to L-310; D-151 to L-310; C-152 to L-310; L-153 to L-310; S-154 to L-310; Q-155 to L-310; N-156 to L-310; L-157 to L-310; V-158 to L-310; V-159 to L-310; I-160 to L-310; K-161 to L-310; P-162 to L-310; G-163 to L-310; T-164 to L-310; K-165 to L-310; E-166 to L-310; T-167 to L-310; D-168 to L-310; N-169 to L-310; V-170 to L-310; C-171 to L-310; G-172 to L-310; T-173 to L-310; L-174 to L-310; P-175 to L-310; S-176 to L-310; F-177 to L-310; S-178 to L-310; S-179 to L-310; S-180 to L-310; T-181 to L-310; S-182 to L-310; P-183 to L-310; S-184 to L-310; P-185 to L-310; G-186 to L-310; T-187 to L-310; A-188 to L-310; I-189 to L-310; F-190 to L-310; P-191 to L-310; R-192 to L-310; P-193 to L-310; E-194 to L-310; H-195 to L-310; M-196 to L-310; E-197 to L-310; T-198 to L-310; H-199 to L-310; E-200 to L-310; V-201 to L-310; P-202 to L-310; S-203 to L-310; S-204 to L-310; T-205 to L-310; Y-206 to L-310; V-207 to L-310; P-208 to L-310; K-209 to L-310; G-210 to L-310; M-211 to L-310; N-212 to L-310; S-213 to L-310; T-214 to L-310; E-215 to L-310; S-216 to L-310; N-217 to L-310; S-218 to L-310; S-219 to L-310; A-220 to L-310;

S-221 to L-310; V-222 to L-310; R-223 to L-310; P-224 to L-310; K-225 to L-310; V-226 to L-310; L-227 to L-310; S-228 to L-310; S-229 to L-310; I-230 to L-310; Q-231 to L-310; E-232 to L-310; G-233 to L-310; T-234 to L-310; V-235 to L-310; P-236 to L-310; D-237 to L-310; N-238 to L-310; T-239 to L-310; S-240 to L-310; S-241 to L-310; A-242 to L-310; R-243 to L-310; G-244 to L-310; K-245 to L-310; E-246 to L-310; D-247 to L-310; V-248 to L-310; N-249 to L-310; K-250 to L-310; T-251 to L-310; L-252 to L-310; P-253 to L-310; N-254 to L-310; L-255 to L-310; Q-256 to L-310; V-257 to L-310; V-258 to L-310; N-259 to L-310; H-260 to L-310; Q-261 to L-310; Q-262 to L-310; G-263 to L-310; P-264 to L-310; H-265 to L-310; H-266 to L-310; R-267 to L-310; H-268 to L-310; I-269 to L-310; L-270 to L-310; K-271 to L-310; L-272 to L-310; L-273 to L-310; P-274 to L-310; S-275 to L-310; M-276 to L-310; E-277 to L-310; A-278 to L-310; T-279 to L-310; G-280 to L-310; G-281 to L-310; E-282 to L-310; K-283 to L-310; S-284 to L-310; S-285 to L-310; T-286 to L-310; P-287 to L-310; I-288 to L-310; K-289 to L-310; G-290 to L-310; P-291 to L-310; K-292 to L-310; R-293 to L-310; G-294 to L-310; H-295 to L-310; P-296 to L-310; R-297 to L-310; Q-298 to L-310; N-299 to L-310; L-300 to L-310; H-301 to L-310; K-302 to L-310; H-303 to L-310; F-304 to L-310; and/or D-305 to L-310 of SEQ ID NO:2. Polynucleotides encoding these polypeptides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR9 polypeptides described above, and the polypeptides encoded thereby. The present invention also encompasses the above polynucleotide sequences fused to a heterologous polynucleotide sequence, and the polypeptides encoded thereby.

Also as mentioned above, even if deletion of one or more amino acids from the C-terminus of a protein results in modification of loss of one or more biological functions of the protein, other functional activities (e.g., biological activities, ability to multimerize, ability to bind TR9 ligand) may still be retained. For example the ability of the shortened TR9 mutein to induce and/or bind to antibodies which recognize the complete or mature forms of the polypeptide generally will be retained when less than the majority of the residues of the complete or mature polypeptide are removed from the C-terminus. Whether a particular polypeptide lacking C-terminal residues of a complete polypeptide retains such immunologic activities can readily be determined by routine methods described herein and otherwise known in the art. It is not unlikely that an TR9 mutein with a large number of deleted C-terminal amino acid residues may retain some biological or immunogenic activities. In fact, as discussed above, peptides composed of as few as six TR9 amino acid residues may often evoke an immune response.

Accordingly, further embodiments of the invention are directed to C-terminal deletions of the TR9 polypeptide described by the general formula 1 to n, where n is a number from 2 to 614 corresponding to the position of amino acid residue identified in SEQ ID NO:2 and preferably, corresponds to one of the C-terminal amino acid residues identified in the C-terminal deletions specified herein. In specific embodiments, C terminal deletions of the TR9 polypeptide of the invention comprise, or alternatively, consist of, amino acid residues: A-1 to L-614; A-1 to D-613; A-1 to P-612; A-1 to L-611; A-1 to H-610; A-1 to S-609; A-1 to Y-608; A-1 to V-607; A-1 to S-606; A-1 to D-605; A-1 to L-604; A-1 to L-603; A-1 to T-602; A-1 to Q-601; A-1 to S-600; A-1 to A-599; A-1 to E-598; A-1 to Q-597; A-1 to S-596; A-1 to K-595; A-1 to V-594; A-1 to G-593; A-1 to I-592; A-1 to I-591; A-1 to E-590; A-1 to F-589; A-1 to L-588; A-1 to R-587; A-1 to D-586; A-1 to L-585; A-1 to K-584; A-1 to D-583; A-1 to E-582; A-1 to A-581; A-1 to Q-580; A-1 to P-579; A-1 to I-578; A-1 to E-577; A-1 to E-576; A-1 to I-575; A-1 to V-574; A-1 to R-573; A-1 to L-572; A-1 to E-571; A-1 to E-570; A-1 to P-569; A-1 to N-568; A-1 to L-567; A-1 to F-566; A-1 to H-565; A-1 to L-564; A-1 to M-563; A-1 to D-562; A-1 to D-561; A-1 to F-560; A-1 to I-559; A-1 to P-558; A-1 to Q-557; A-1 to L-556; A-1 to D-555; A-1 to C-554; A-1 to P-553; A-1 to D-552; A-1 to L-551; A-1 to R-550; A-1 to V-549; A-1 to Q-548; A-1 to R-547; A-1 to L-546; A-1 to V-545; A-1 to T-544; A-1 to D-543; A-1 to K-542; A-1 to K-541; A-1 to E-540; A-1 to K-539; A-1 to T-538; A-1 to I-537; A-1 to F-536; A-1 to S-535; A-1 to G-534; A-1 to N-533; A-1 to R-532; A-1 to S-531; A-1 to L-530; A-1 to A-529; A-1 to S-528; A-1 to S-527; A-1 to G-526; A-1 to S-525; A-1 to S-524; A-1 to T-523; A-1 to S-522; A-1 to D-521; A-1 to C-520; A-1 to R-519; A-1 to L-518; A-1 to L-517; A-1 to P-516; A-1 to E-515; A-1 to S-514; A-1 to E-513; A-1 to D-512; A-1 to V-511; A-1 to F-510; A-1 to F-509; A-1 to G-508; A-1 to K-507; A-1 to N-506; A-1 to K-505; A-1 to D-504; A-1 to Q-503; A-1 to P-502; A-1 to S-501; A-1 to P-500; A-1 to E-499; A-1 to V-498; A-1 to T-497; A-1 to L-496; A-1 to L-495; A-1 to A-494; A-1 to S-493; A-1 to N-492; A-1 to E-491; A-1 to L-490; A-1 to K-489; A-1 to A-488; A-1 to N-487; A-1 to P-486; A-1 to S-485; A-1 to P-484; A-1 to I-483; A-1 to P-482; A-1 to S-481; A-1 to P-480; A-1 to S-479; A-1 to L-478; A-1 to P-477; A-1 to S-476; A-1 to P-475; A-1 to S-474; A-1 to M-473; A-1 to P-472; A-1 to L-471; A-1 to A-470; A-1 to L-469; A-1 to K-468; A-1 to D-467; A-1 to T-466; A-1 to E-465; A-1 to L-464; A-1 to Q-463; A-1 to T-462; A-1 to T-461; A-1 to D-460; A-1 to E-459; A-1 to M-458; A-1 to L-457; A-1 to G-456; A-1 to R-455; A-1 to I-454; A-1 to K-453; A-1 to E-452; A-1 to V-451; A-1 to V-450; A-1 to D-449; A-1 to N-448; A-1 to R-447; A-1 to R-446; A-1 to H-445; A-1 to Q-444; A-1 to R-443; A-1 to L-442; A-1 to A-441; A-1 to S-440; A-1 to I-439; A-1 to L-438; A-1 to Q-437; A-1 to A-436; A-1 to L-435; A-1 to S-434; A-1 to A-433; A-1 to E-432; A-1 to P-431; A-1 to G-430; A-1 to R-429; A-1 to I-428; A-1 to T-427; A-1 to W-426; A-1 to H-425; A-1 to Q-424; A-1 to L-423; A-1 to A-422; A-1 to A-421; A-1 to Y-420; A-1 to A-419; A-1 to R-418; A-1 to E-417; A-1 to H-416; A-1 to D-415; A-1 to A-414; A-1 to T-413; A-1 to Y-412; A-1 to G-411; A-1 to N-410; A-1 to S-409; A-1 to F-408; A-1 to A-407; A-1 to A-406; A-1 to V-405; A-1 to E-404; A-1 to R-403; A-1 to E-402; A-1 to S-401; A-1 to A-400; A-1 to N-399; A-1 to C-398; A-1 to L-397; A-1 to F-396; A-1 to Q-395; A-1 to Y-394; A-1 to I-393; A-1 to D-392; A-1 to K-391; A-1 to W-390; A-1 to Q-389; A-1 to S-388; A-1 to G-387; A-1 to V-386; A-1 to Q-385; A-1 to A-384; A-1 to A-383; A-1 to V-382; A-1 to L-381; A-1 to K-380; A-1 to L-379; A-1 to I-378; A-1 to D-377; A-1 to I-376; A-1 to G-375; A-1 to H-374; A-1 to G-373; A-1 to N-372; A-1 to C-371; A-1 to Y-370; A-1 to Y-369; A-1 to I-368; A-1 to W-367; A-1 to K-366; A-1 to E-365; A-1 to R-364; A-1 to N-363; A-1 to Q-362; A-1 to T-361; A-1 to P-360; A-1 to T-359; A-1 to M-358; A-1 to S-357; A-1 to K-356; A-1 to K-355; A-1 to L-354; A-1 to G-353; A-1 to A-352; A-1 to K-351; A-1 to E-350; A-1 to V-349; A-1 to I-348; A-1 to A-347; A-1 to S-346; A-1 to P-345; A-1 to D-344; A-1 to Q-343; A-1 to R-342; A-1 to P-341; A-1 to G-340; A-1 to K-339; A-1 to K-338; A-1 to L-337; A-1 to T-336; A-1 to R-335; A-1 to S-334; A-1 to S-333; A-1 to K-332; A-1 to R-331; A-1 to I-330; A-1 to S-329; A-1 to C-328; A-1 to V-327; A-1 to V-326; A-1 to I-325; A-1 to V-324; A-1 to V-323; A-1 to L-322; A-1 to V-321; A-1 to L-320; A-1 to L-319; A-1 to L-318; A-1 to F-317; A-1 to L-316; A-1 to V-315; A-1 to I-314; A-1 to M-313; A-1 to W-312; A-1 to P-311; A-1 to L-310; A-1 to H-309; A-1 to E-308; A-1 to N-307; A-1 to I-306; A-1 to D-305; A-1 to F-304; A-1 to H-303; A-1 to K-302; A-1 to H-301; A-1 to L-300; A-1 to N-299; A-1 to Q-298; A-1 to R-297; A-1 to P-296; A-1 to H-295; A-1 to G-294; A-1 to R-293; A-1 to K-292; A-1 to P-291; A-1 to G-290; A-1 to K-289; A-1 to I-288; A-1 to P-287; A-1 to T-286; A-1 to S-285; A-1 to S-284; A-1 to K-283; A-1 to E-282; A-1 to G-281; A-1 to G-280; A-1 to T-279; A-1 to A-278; A-1 to E-277; A-1 to M-276; A-1 to S-275; A-1 to P-274; A-1 to L-273; A-1 to L-272; A-1 to K-271; A-1 to L-270; A-1 to I-269; A-1 to H-268; A-1 to R-267; A-1 to H-266; A-1 to H-265; A-1 to P-264; A-1 to G-263; A-1 to Q-262; A-1 to Q-261; A-1 to H-260; A-1 to N-259; A-1 to V-258; A-1 to V-257; A-1 to Q-256; A-1 to L-255; A-1 to N-254; A-1 to P-253; A-1 to L-252; A-1 to T-251; A-1 to K-250; A-1 to N-249; A-1 to V-248; A-1 to D-247; A-1 to E-246; A-1 to K-245; A-1 to G-244; A-1 to R-243; A-1 to A-242; A-1 to S-241; A-1 to S-240; A-1 to T-239; A-1 to N-238; A-1 to D-237; A-1 to P-236; A-1 to V-235; A-1 to T-234; A-1 to G-233; A-1 to E-232; A-1 to Q-231; A-1 to I-230; A-1 to S-229; A-1 to S-228; A-1 to L-227; A-1 to V-226; A-1 to K-225; A-1 to P-224; A-1 to R-223; A-1 to V-222; A-1 to S-221; A-1 to A-220; A-1 to S-219; A-1 to S-218; A-1 to N-217; A-1 to S-216; A-1 to E-215; A-1 to T-214; A-1 to S-213; A-1 to N-212; A-1 to M-211; A-1 to G-210; A-1 to K-209; A-1 to P-208; A-1 to V-207; A-1 to Y-206; A-1 to T-205; A-1 to S-204; A-1 to S-203; A-1 to P-202; A-1 to V-201; A-1 to E-200; A-1 to H-199; A-1 to T-198; A-1 to E-197; A-1 to M-196; A-1 to H-195; A-1 to E-194; A-1 to P-193; A-1 to R-192; A-1 to P-191; A-1 to F-190; A-1 to I-189; A-1 to A-188; A-1 to T-187; A-1 to G-186; A-1 to P-185; A-1 to S-184; A-1 to P-183; A-1 to S-182; A-1 to T-181; A-1 to S-180; A-1 to S-179; A-1 to S-178; A-1 to F-177; A-1 to S-176; A-1 to P-175; A-1 to L-174; A-1 to T-173; A-1 to G-172; A-1 to C-171; A-1 to V-170; A-1 to N-169; A-1 to D-168; A-1 to T-167; A-1 to E-166; A-1 to K-165; A-1 to T-164; A-1 to G-163; A-1 to P-162; A-1 to K-161; A-1 to I-160; A-1 to V-159; A-1 to V-158; A-1 to L-157; A-1 to N-156; A-1 to Q-155; A-1 to S-154; A-1 to L-153; A-1 to C-152; A-1 to D-151; A-1 to T-150; A-1 to Y-149; A-1 to A-148; A-1 to K-147; A-1 to C-146; A-1 to K-145; A-1 to M-144; A-1 to V-143; A-1 to S-142; A-1 to S-141; A-1 to P-140; A-1 to V-139; A-1 to D-138; A-1 to S-137; A-1 to F-136; A-1 to T-135; A-1 to G-134; A-1 to R-133; A-1 to A-132; A-1 to C-131; A-1 to Q-130; A-1 to K-129; A-1 to C-128; A-1 to R-127; A-1 to V-126; A-1 to D-125; A-1 to E-124; A-1 to T-123; A-1 to E-122; A-1 to T-121; A-1 to G-120; A-1 to K-119; A-1 to K-118; A-1 to R-117; A-1 to V-116; A-1 to G-115; A-1 to W-114; A-1 to G-113; A-1 to V-112; A-1 to P-111; A-1 to C-110; A-1 to V-109; A-1 to T-108; A-1 to H-107; A-1 to P-106; A-1 to A-105; A-1 to C-104; A-1 to T-103; A-1 to A-102; A-1 to N-101; A-1 to S-100; A-1 to Q-99; A-1 to F-98; A-1 to M-97; A-1 to G-96; A-1 to P-95; A-1 to P-94; A-1 to C-93; A-1 to T-92; A-1 to C-91; A-1 to –90; A-1 to R-89; A-1 to D-88; A-1 to T-87; A-1 to L-86; A-1 to A-85; A-1 to A-84; A-1 to C-83; A-1 to P-82; A-1 to L-81; A-1 to K-80; A-1 to E-79; A-1 to I-78; A-1 to M-77; A-1 to P-76; A-1 to W-75; A-1 to P-74; A-1 to C-73; A-1 to A-71; A-1 to Q-71; A-1 to S-70; A-1 to C-69; A-1 to D-68; A-1 to H-67; A-1 to C-66; A-1 to K-65; A-1 to E-64; A-1 to I-63; A-1 to G-62; A-1 to N-61; A-1 to E-60; A-1 to H-59; A-1 to R-58; A-1 to T-57; A-1 to F-56; A-1 to T-55; A-1 to G-54; A-1 to V-53; A-1 to P-52; A-1 to C-51; A-1 to S-50; A-1 to S-49; A-1 to C-48; A-1 to V-47; A-1 to R-46; A-1 to L-45; A-1 to S-44; A-1 to T-43; A-1 to N-42; A-1 to T-41; A-1 to C-40; A-1 to H-39; A-1 to E-38; A-1 to S-37; A-1 to V-36; A-1 to Y-35; A-1 to T-34; A-1 to G-33; A-1 to A-32; A-1 to P-31; A-1 to C-30; A-1 to K-29; A-1 to D-28; A-1 to C-27; A-1 to T-26; A-1 to L-25; A-1 to V-24; A-1 to Q-23; A-1 to G-22; A-1 to T-21; A-1 to A-20; A-1 to R-19; A-1 to D-18; A-1 to V-17; A-1 to H-16; A-1 to R-15; A-1 to Y-14; A-1 to T-13; A-1 to G-12; A-1 to I-11; A-1 to L-10; A-1 to N-9; A-1 to S-8; A-1 to A-7; and/or A-1 to K-6 of SEQ ID NO:2. Polynucleotides encoding these polypeptides are also encompassed by the invention. The present invention is also directed to nucleic acid molecules comprising, or alternatively, consisting of, a polynucleotide sequence at least 80%, 85%, 90%, 92%, 95%, 96%, 97%, 98% or 99% identical to the polynucleotide sequences encoding the TR9 polypeptides described above, and the polypeptides encoded thereby. The present invention also encompasses the above polynucleotide sequences fused to a heterologous polynucleotide sequence, and the polypeptides encoded thereby.

Further embodiments of the invention are directed to polypeptide fragments comprising, or alternatively, consisting of, amino acids described by the general formula m to n, where m and n correspond to any one of the amino acid residues specified above for these symbols, respectively. Polynucleotides encoding these polypeptides are also encompassed by the invention.

However, many polynucleotide sequences, such as EST sequences, are publicly available and accessible through sequence databases. Some of these sequences are related to SEQ ID NO:1 and may have been publicly available prior to conception of the present invention. Preferably, such related polynucleotides are specifically excluded from the scope of the present invention. To list every related sequence would be cumbersome. Similarly, preferably excluded from the present invention are one or more polynucleotides comprising a nucleotide sequence described by the general formula of $a^1$–$b^1$, where $a^1$ is any integer between 1 to 3437 of SEQ ID NO:1, $b^1$ is an integer of 15 to 3452, where both $a^1$ and $b^1$ correspond to the positions of nucleotide residues shown in SEQ ID NO: 1, and where the $b^1$ is greater than or equal to $a^1+14$.

In specific embodiments, the polynucleotides of the invention are less than 300 kb, 200 kb, 100 kb, 50 kb, 15 kb, 10 kb, or 7.5 kb in length. In a further embodiment, polynucleotides of the invention comprise at least 15 contiguous nucleotides of TR9 coding sequence, but do not comprise all or a portion of any TR9 intron. In another embodiment, the nucleic acid comprising TR9 coding sequence does not contain coding sequences of a genomic flanking gene (i.e., 5' or 3' to the TR9 gene in the genome).

In specific embodiments, the polynucleotides of the invention are less than 100,000 kb, 50,000 kb, 10,000 kb, 1,000 kb, 500 kb, 400 kb, 350 kb, 300 kb, 250 kb, 200 kb, 175 kb, 150 kb, 125 kb, 100 kb, 75 kb, 50 kb, 40 kb, 30 kb, 25 kb, 20 kb, 15 kb, 10 kb, 7.5 kb, or 5 kb in length.

In further embodiments, polynucleotides of the invention comprise at least 15, at least 30, at least 50, at least 100, or at least 250, at least 500, or at least 1000 contiguous nucleotides of TR9 coding sequence, but consist of less than or equal to 1000 kb, 500 kb, 250 kb, 200 kb, 150 kb, 100 kb, 75 kb, 50 kb, 30 kb, 25 kb, 20 kb, 15 kb, 10 kb, or 5 kb of genomic DNA that flanks the 5' or 3' coding nucleotide sequences set forth in FIGS. 1A-D (SEQ ID NO:1). In further embodiments, polynucleotides of the invention comprise at least 15, at least 30, at least 50, at least 100, or at least 250, at least 500, or at least 1000 contiguous nucleotides of TR9 coding sequence, but do not comprise all or a portion of any TR9 intron. In another embodiment, the nucleic acid comprising TR9 coding sequence does not contain coding sequences of a genomic flanking gene (i.e., 5' or 3' to the TR9 gene in the genome). In other embodiments, the polynucleotides of the invention do not contain the coding sequence of more than 1000, 500, 250, 100, 50, 25, 20, 15, 10, 5, 4, 3, 2, or 1 genomic flanking gene(s).

The invention further provides isolated TR9 polypeptides having the amino acid sequence encoded by the deposited cDNAs, or the amino acid sequences in FIGS. 1A-D (SEQ ID NO:2) or a peptide or polypeptide comprising a portion of the above polypeptides.

The polypeptides of the invention may be membrane bound or may be in a soluble circulating form. Soluble peptides are defined by amino acid sequence wherein the sequence comprises, or alternatively consists of, the polypeptide sequence lacking the transmembrane domain.

The polypeptides of the present invention may exist as a membrane bound receptor having a transmembrane region and an intra- and extracellular region or they may exist in soluble form wherein the transmembrane domain is lacking. One example of such a form of the TR9 receptor is the TR9 receptor shown in FIGS. 1A-D (SEQ ID NO:2) which contains, in addition to a leader sequence, transmembrane, intracellular and extracellular domains. Thus, this form of the TR9 receptor appears to be localized in the cytoplasmic membrane of cells which express this protein.

In specific embodiments, the polypeptide fragments of the invention (i.e., those described herein) are not larger than 610, 600, 580, 570, 550, 525, 500, 475, 450, 400, 425, 390, 380, 375, 350, 336, 334, 331, 305, 300, 295, 290, 285, 280, 275, 260, 250, 225, 200, 185, 175, 170, 165, 160, 155, 150, 145, 140, 135, 130, 125, 120, 115, 110, 105, 100, 90, 80, 75, 60, 50, 40, 30, or 25 amino acid residues in length.

It will be recognized in the art that some amino acid sequences of the TR9 receptor can be varied without significant effect on the structure or function of the protein. If such differences in sequence are contemplated, it should be remembered that there will be critical areas on the protein which determine activity. Thus, the invention further includes variations of the TR9 receptor which show substantial TR9 receptor functional activity (e.g., biological activity) or which include regions of TR9 receptor polypeptide such as the protein portions discussed herein. Such mutants include deletions, insertions, inversions, repeats, and type substitutions. As indicated above, guidance concerning which amino acid changes are likely to be phenotypically silent can be found in Bowie et al., "Deciphering the Message in Protein Sequences: Tolerance to Amino Acid Substitutions," *Science* 247:1306-1310 (1990).

Of special interest are substitutions of charged amino acids with other charged or neutral amino acids which may produce proteins with highly desirable improved characteristics, such as less aggregation. Aggregation may not only reduce activity but also be problematic when preparing pharmaceutical formulations, because aggregates can be immunogenic (Pinckard et al., *Clin. Exp. Immunol.* 2:331-340 (1967); Robbins et al., Diabetes 36: 838-845 (1987); Cleland et al., *Crit. Rev. Therapeutic Drug Carrier Systems* 10:307-377 (1993).

Thus, the fragment, derivative or analog of the polypeptide of FIGS. 1A-D (SEQ ID NO:2), or that encoded by the deposited cDNA, may be: (i) one in which one or more of the amino acid residues are substituted with a conserved or non-conserved amino acid residue (preferably a conserved amino acid residue(s), and more preferably at least one but less than ten conserved amino acid residues), and such substituted amino acid residue(s) may or may not be one encoded by the genetic code; or (ii) one in which one or more of the amino acid residues includes a substituent group; or (iii) one in which the mature polypeptide is fused with another compound, such as a compound to increase the half-life of the polypeptide (for example, polyethylene glycol); or (iv) one in which the additional amino acids are fused to the mature polypeptide, such as an IgG Fc fusion region peptide or leader or secretory sequence or a sequence which is employed for purification of the mature polypeptide or a proprotein sequence. Such fragments, derivatives and analogs are deemed to be within the scope of those skilled in the art from the teachings herein.

Of particular interest are substitutions of charged amino acids with another charged amino acid and with neutral or negatively charged amino acids. The latter results in proteins with reduced positive charge to improve the characteristics of the TR9 receptor. The prevention of aggregation is highly desirable. Aggregation of proteins not only results in a loss of activity but can also be problematic when preparing pharmaceutical formulations, because they can be immunogenic. (Pinckard et al., *Clin. Exp. Immunol* 2:331-340 (1967); Robbins et al., *Diabetes* 36:838-845 (1987); Cleland et al., *Crit. Rev. Therapeutic Drug Carrier Systems* 10:307-377 (1993)).

The replacement of amino acids can also change the selectivity of binding to cell surface receptors. Ostade et al., *Nature* 361:266-268 (1993), describes certain mutations resulting in selective binding of TNF-alpha to only one of the two known types of TNF receptors. Thus, the TR9 receptor of the present invention may include one or more amino acid substitutions, deletions, or additions, either from natural mutations or human manipulation.

As indicated, changes are preferably of a minor nature, such as conservative amino acid substitutions that do not significantly affect the folding or activity of the protein (see Table II).

TABLE II

| Conservative Amino Acid Substitutions | |
|---|---|
| Aromatic | Phenylalanine |
|  | Tryptophan |
|  | Tyrosine |
| Hydrophobic | Leucine |
|  | Isoleucine |
|  | Valine |
| Polar | Glutamine |
|  | Asparagine |
| Basic | Arginine |
|  | Lysine |
|  | Histidine |
| Acidic | Aspartic Acid |
|  | Glutamic Acid |
| Small | Alanine |
|  | Serine |
|  | Threonine |
|  | Methionine |
|  | Glycine |

In specific embodiments, the number of substitutions, additions or deletions in the amino acid sequence of FIGS. 1A-D and/or any of the polypeptide fragments described herein (e.g., the extracellular domain or intracellular domain) is 75, 70, 60, 50, 40, 35, 30, 25, 20, 15, 10, 9, 8, 7, 6, 5, 4, 3, 2, 1 or 30-20, 20-15, 20-10, 15-10, 10-1, 5-10, 1-5, 1-3 or 1-2.

Amino acids in the TR9 protein of the present invention that are essential for function can be identified by methods known in the art, such as site-directed mutagenesis or alanine-scanning mutagenesis (Cunningham and Wells, *Science* 244:

1081-1085 (1989)). The latter procedure introduces single alanine mutations at every residue in the molecule. The resulting mutant molecules are then tested for biological activity such as, receptor/ligand binding or in vitro proliferative, and/or activation activity upon monocytes. Sites that are critical for ligand-receptor binding can also be determined by structural analysis such as crystallization, nuclear magnetic resonance or photoaffinity labeling (Smith et al., *J. Mol. Biol.* 224:899-904 (1992) and de Vos et al. *Science* 255:306-312 (1992)).

Additionally, protein engineering may be employed to improve or alter the characteristics of TR9 polypeptides. Recombinant DNA technology known to those skilled in the art can be used to create novel mutant proteins or muteins including single or multiple amino acid substitutions, deletions, additions or fusion proteins. Such modified polypeptides can show, e.g., enhanced activity or increased stability. In addition, they may be purified in higher yields and show better solubility than the corresponding natural polypeptide, at least under certain purification and storage conditions.

Non-naturally occurring variants may be produced using art-known mutagenesis techniques, which include, but are not limited to oligonucleotide mediated mutagenesis, alanine scanning, PCR mutagenesis, site directed mutagenesis (see e.g., Carter et al., *Nucl. Acids Res.* 13:4331 (1986); and Zoller et al., *Nucl. Acids Res.* 10:6487 (1982)), cassette mutagenesis (see e.g., Wells et al., *Gene* 34:315 (1985)), restriction selection mutagenesis (see e.g., Wells et al., *Philos. Trans. R. Soc. London SerA* 317:415 (1986)).

Thus, the invention also encompasses TR9 derivatives and analogs that have one or more amino acid residues deleted, added, or substituted to generate TR9 polypeptides that are better suited for expression, scale up, etc., in the host cells chosen. For example, cysteine residues can be deleted or substituted with another amino acid residue in order to eliminate disulfide bridges; N-linked glycosylation sites can be altered or eliminated to achieve, for example, expression of a homogeneous product that is more easily recovered and purified from yeast hosts which are known to hyperglycosylate N-linked sites. To this end, a variety of amino acid substitutions at one or both of the first or third amino acid positions on any one or more of the glycosylation recognitions sequences in the TR9 polypeptides of the invention, and/or an amino acid deletion at the second position of any one or more such recognition sequences will prevent glycosylation of the TR9 at the modified tripeptide sequence (see, e.g., Miyajimo et al., *EMBO J* 5(6):1193-1197).

Additionally, the techniques of gene-shuffling, motif-shuffling, exon-shuffling, and/or codon-shuffling (collectively referred to as "DNA shuffling") may be employed to modulate the activities of TR9 thereby effectively generating agonists and antagonists of TR9. See generally, U.S. Pat. Nos. 5,605,793, 5,811,238, 5,830,721, 5,834,252, and 5,837,458, and Patten, P. A., et al., *Curr. Opinion Biotechnol.* 8:724-33 (1997); Harayama, S. *Trends Biotechnol.* 16(2):76-82 (1998); Hansson, L. O., et al., *J. Mol. Biol.* 287:265-76 (1999); and Lorenzo, M. M. and Blasco, R. *Biotechniques* 24(2):308-13 (1998) (each of these patents and publications are hereby incorporated by reference). In one embodiment, alteration of TR9 polynucleotides and corresponding polypeptides may be achieved by DNA shuffling. DNA shuffling involves the assembly of two or more DNA segments into a desired TR9 molecule by homologous, or site-specific, recombination. In another embodiment, TR9 polynucleotides and corresponding polypeptides may be altered by being subjected to random mutagenesis by error-prone PCR, random nucleotide insertion or other methods prior to recombination. In another embodiment, one or more components, motifs, sections, parts, domains, fragments, etc., of TR9 may be recombined with one or more components, motifs, sections, parts, domains, fragments, etc. of one or more heterologous molecules. In preferred embodiments, the heterologous molecules are, for example, TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II (International Publication No. WO 97/34911), APRIL (J. Exp. Med. 188(6):1185-1190), endokine-alpha (International Publication No. WO 98/07880), Neutrokine-alpha (International Publication No. WO 98/18921), OPG, OX40, and nerve growth factor (NGF), and soluble forms of Fas, CD30, CD27, CD40 and 4-IBB, DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR10 (International Publication No. WO 98/54202), 312C2 (International Publication No. WO 98/06842), TR11, TR11SV1, TR11SV2, TR12, and TNF-R1, TRAMP/DR3/APO-3/WSL/LARD, TRAIL-R1/DR4/APO-2, TRAIL-R2/DR5, DcR1/TRAIL-R3/TRID/LIT, DcR2/TRAIL-R4, CAD, TRAIL, TRAMP, v-FLIP.

In further preferred embodiments, the heterologous molecules are any member of the TNF family.

The polypeptides of the present invention are preferably provided in an isolated form. By "isolated polypeptide" is intended a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell. For example, a recombinantly produced version of the TR9 receptor can be substantially purified by the one-step method described in Smith and Johnson, *Gene* 67:31-40 (1988).

The polypeptides of the present invention include a polypeptide comprising, or alternatively, consisting of, the polypeptide encoded by the deposited cDNA including the leader; a polypeptide comprising, or alternatively, consisting of, the mature polypeptide encoded by the deposited cDNA minus the leader (i.e., the mature protein); a polypeptide comprising, or alternatively, consisting of, amino acids about −40 to about 615 in SEQ ID NO:2; a polypeptide comprising, or alternatively, consisting of, amino acids about −39 to about 615 in SEQ ID NO:2; a polypeptide comprising, or alternatively, consisting of, amino acids about 1 to about 615 in SEQ ID NO:2; a polypeptide comprising, or alternatively, consisting of, the extracellular domain; a polypeptide comprising, or alternatively, consisting of, the four TNFR-like cysteine rich motifs of TR9 (amino acid residues 67 to 211 in FIGS. 1A-D; amino acid residues 27-171 in SEQ ID NO:2); a polypeptide comprising, or alternatively, consisting of, the transmembrane domain; a polypeptide comprising, or alternatively, consisting of, the intracellular domain; a polypeptide comprising, or alternatively, consisting of, the extracellular and intracellular domains with all or part of the transmembrane domain deleted; a polypeptide comprising, or alternatively, consisting of, the death domain (amino acid residues 429-495 as depicted in FIGS. 1A-D; amino acid residues 389-455 in SEQ ID NO:2); and/or a polypeptide comprising, or alternatively, consisting of, the TR9 leucine zipper (amino acid residues 497-518 of FIGS. 1A-D; amino acid residues 457-478 of SEQ ID NO:2); as well as polypeptides which are at least 80% identical, more preferably at least 85%, 90% or 95% identical, still more preferably at least 96%, 97%, 98% or 99% identical to the polypeptides described above, and also include portions of such polypeptides with at least 30 amino acids and more preferably at least 50 amino acids. Polynucleotides encoding these polypeptides are also encompassed by the invention.

By a polypeptide having an amino acid sequence at least, for example, 95% "identical" to a reference amino acid sequence of a TR9 receptor polypeptide is intended that the amino acid sequence of the polypeptide is identical to the reference sequence except that the polypeptide sequence may include up to five amino acid alterations per each 100 amino acids of the reference amino acid of the TR9 receptor. In other words, to obtain a polypeptide having an amino acid sequence at least 95% identical to a reference amino acid sequence, up to 5% of the amino acid residues in the reference sequence may be deleted or substituted with another amino acid, or a number of amino acids up to 5% of the total amino acid residues in the reference sequence may be inserted into the reference sequence. These alterations of the reference sequence may occur at the amino or carboxy terminal positions of the reference amino acid sequence or anywhere between those terminal positions, interspersed either individually among residues in the reference sequence or in one or more contiguous groups within the reference sequence.

As a practical matter, whether any particular polypeptide is at least 80%, 85%, 90%, 95%, 96%, 97%, 98% or 99% identical to, for instance, the amino acid sequence shown in FIGS. 1A-D (SEQ ID NO:2), the amino acid sequence encoded by deposited cDNA clone, or fragments thereof, can be determined conventionally using known computer programs such the Bestfit program (Wisconsin Sequence Analysis Package, Version 8 for Unix, Genetics Computer Group, University Research Park, 575 Science Drive, Madison, Wis. 53711). When using Bestfit or any other sequence alignment program to determine whether a particular sequence is, for instance, 95% identical to a reference sequence according to the present invention, the parameters are set, of course, such that the percentage of identity is calculated over the full length of the reference amino acid sequence and that gaps in homology of up to 5% of the total number of amino acid residues in the reference sequence are allowed.

In a specific embodiment, the identity between a reference (query) sequence (a sequence of the present invention) and a subject sequence, also referred to as a global sequence alignment, is determined using the FASTDB computer program based on the algorithm of Brutlag et al. (Comp. App. Biosci. 6:237-245 (1990)). Preferred parameters used in a FASTDB amino acid alignment are: Matrix=PAM 0, k-tuple=2, Mismatch Penalty=1, Joining Penalty=20, Randomization Group Length=0, Cutoff Score=1, Window Size=sequence length, Gap Penalty=5, Gap Size Penalty=0.05, Window Size=500 or the length of the subject amino acid sequence, whichever is shorter. According to this embodiment, if the subject sequence is shorter than the query sequence due to N- or C-terminal deletions, not because of internal deletions, a manual correction is made to the results to take into consideration the fact that the FASTDB program does not account for N- and C-terminal truncations of the subject sequence when calculating global percent identity. For subject sequences truncated at the N- and C-termini, relative to the query sequence, the percent identity is corrected by calculating the number of residues of the query sequence that are N- and C-terminal of the subject sequence, which are not matched/aligned with a corresponding subject residue, as a percent of the total bases of the query sequence. A determination of whether a residue is matched/aligned is determined by results of the FASTDB sequence alignment. This percentage is then subtracted from the percent identity, calculated by the above FASTDB program using the specified parameters, to arrive at a final percent identity score. This final percent identity score is what is used for the purposes of this embodiment. Only residues to the N- and C-termini of the subject sequence, which are not matched/aligned with the query sequence, are considered for the purposes of manually adjusting the percent identity score. That is, only query residue positions outside the farthest N- and C-terminal residues of the subject sequence. For example, a 90 amino acid residue subject sequence is aligned with a 100 residue query sequence to determine percent identity. The deletion occurs at the N-terminus of the subject sequence and therefore, the FASTDB alignment does not show a matching/alignment of the first 10 residues at the N-terminus. The 10 unpaired residues represent 10% of the sequence (number of residues at the N- and C-termini not matched/total number of residues in the query sequence) so 10% is subtracted from the percent identity score calculated by the FASTDB program. If the remaining 90 residues were perfectly matched the final percent identity would be 90%. In another example, a 90 residue subject sequence is compared with a 100 residue query sequence. This time the deletions are internal deletions so there are no residues at the N- or C-termini of the subject sequence which are not matched/aligned with the query. In this case the percent identity calculated by FASTDB is not manually corrected. Once again, only residue positions outside the N- and C-terminal ends of the subject sequence, as displayed in the FASTDB alignment, which are not matched/aligned with the query sequence are manually corrected for. No other manual corrections are made for the purposes of this embodiment.

The polypeptides of the present invention have uses which include, but are not limited to, molecular weight marker on SDS-PAGE gels or on molecular sieve gel filtration columns and as a source for generating antibodies that bind the polypeptides of the invention, using methods well known to those of skill in the art.

The present application is also directed to proteins containing polypeptides at least 80%, 85%, 90%, 95%, 96%, 97%, 98% or 99% identical to the TR9 polypeptide sequences set forth herein as m-n. In preferred embodiments, the application is directed to proteins containing polypeptides at least 80%, 85%, 90%, 95%, 96%, 97%, 98% or 99% identical to polypeptides having the amino acid sequence of the a specific TR9 N- and/or C-terminal deletion recited herein. Polynucleotides encoding these polypeptides are also encompassed by the invention.

In certain preferred embodiments, TR9 proteins of the invention comprise, or alternatively consist of, fusion proteins, as described above, wherein the TR9 polypeptide component of the fusion protein is one of the polypeptide sequences set forth herein as m-n. In preferred embodiments, the polypeptide sequence component of the fusion protein that is homologous to the TR9 polypeptides of the invention is at least 80%, 85%, 90%, 95%, 96%, 97%, 98% or 99% identical to the polypeptide acid sequence of a specific N- and/or C-terminal deletion recited herein. Polynucleotides encoding these polypeptides are also encompassed by the invention.

The present invention encompasses polypeptides comprising, or alternatively consisting of, an epitope of the polypeptide having an amino acid sequence of SEQ ID NO:2, or an epitope of the polypeptide sequence encoded by a polynucleotide sequence contained in ATCC deposit No. 209037 or encoded by a polynucleotide that hybridizes to the complement of the sequence of SEQ ID NO:1 or contained in ATCC deposit No. 209037 under stringent hybridization conditions or lower stringency hybridization conditions as defined supra. The present invention further encompasses polynucleotide sequences encoding an epitope of a polypeptide sequence of the invention (such as, for example, the sequence disclosed in SEQ ID NO:1), polynucleotide sequences of the complementary strand of a polynucleotide sequence encoding an epitope of the invention, and polynucleotide sequences which hybridize to the complementary strand under stringent hybridization conditions or lower stringency hybridization conditions defined supra.

The term "epitopes," as used herein, refers to portions of a polypeptide having antigenic or immunogenic activity in an animal, preferably a mammal, and most preferably in a human. In a preferred embodiment, the present invention encompasses a polypeptide comprising an epitope, as well as the polynucleotide encoding this polypeptide. An "immunogenic epitope," as used herein, is defined as a portion of a protein that elicits an antibody response in an animal, as determined by any method known in the art, for example, by the methods for generating antibodies described infra. (See, for example, Geysen et al., Proc. Natl. Acad. Sci. USA 81:3998-4002 (1983)). The term "antigenic epitope," as used herein, is defined as a portion of a protein to which an antibody can immunospecifically bind its antigen as determined by any method well known in the art, for example, by the immunoassays described herein. Immunospecific binding excludes non-specific binding but does not necessarily exclude cross-reactivity with other antigens. Antigenic epitopes need not necessarily be immunogenic.

Fragments which function as epitopes may be produced by any conventional means. (See, e.g., Houghten, Proc. Natl. Acad. Sci. USA 82:5131-5135 (1985), further described in U.S. Pat. No. 4,631,211).

In the present invention, antigenic epitopes preferably contain a sequence of at least 4, at least 5, at least 6, at least 7, more preferably at least 8, at least 9, at least 10, at least 11, at least 12, at least 13, at least 14, at least 15, at least 20, at least 25, at least 30, at least 40, at least 50, and, most preferably, between about 15 to about 30 amino acids. Preferred polypeptides comprising immunogenic or antigenic epitopes are at least 10, 15, 20, 25, 30, 35, 40, 45, 50, 55, 60, 65, 70, 75, 80, 85, 90, 95, or 100 amino acid residues in length. Additional non-exclusive preferred antigenic epitopes include the antigenic epitopes disclosed herein, as well as portions thereof. Antigenic epitopes are useful, for example, to raise antibodies, including monoclonal antibodies, that specifically bind the epitope. Preferred antigenic epitopes include the antigenic epitopes disclosed herein, as well as any combination of two, three, four, five or more of these antigenic epitopes. Antigenic epitopes can be used as the target molecules in immunoassays. (See, for instance, Wilson et al., Cell 37:767-778 (1984); Sutcliffe et al., Science 219:660-666 (1983)).

Similarly, immunogenic epitopes can be used, for example, to induce antibodies according to methods well known in the art. (See, for instance, Sutcliffe et al., supra; Wilson et al., supra; Chow et al., Proc. Natl. Acad. Sci. USA 82:910-914; and Bittle et al., J. Gen. Virol. 66:2347-2354 (1985). Preferred immunogenic epitopes include the immunogenic epitopes disclosed herein, as well as any combination of two, three, four, five or more of these immunogenic epitopes. The polypeptides comprising one or more immunogenic epitopes may be presented for eliciting an antibody response together with a carrier protein, such as an albumin, to an animal system (such as rabbit or mouse), or, if the polypeptide is of sufficient length (at least about 25 amino acids), the polypeptide may be presented without a carrier. However, immunogenic epitopes comprising as few as 8 to 10 amino acids have been shown to be sufficient to raise antibodies capable of binding to, at the very least, linear epitopes in a denatured polypeptide (e.g., in Western blotting).

Epitope-bearing polypeptides of the present invention may be used to induce antibodies according to methods well known in the art including, but not limited to, in vivo immunization, in vitro immunization, and phage display methods. See, e.g., Sutcliffe et al., supra; Wilson et al., supra, and Bittle et al., J. Gen. Virol., 66:2347-2354 (1985). If in vivo immunization is used, animals may be immunized with free peptide; however, anti-peptide antibody titer may be boosted by coupling the peptide to a macromolecular carrier, such as keyhole limpet hemacyanin (KLH) or tetanus toxoid. For instance, peptides containing cysteine residues may be coupled to a carrier using a linker such as maleimidobenzoyl-N-hydroxysuccinimide ester (MBS), while other peptides may be coupled to carriers using a more general linking agent such as glutaraldehyde. Animals such as rabbits, rats and mice are immunized with either free or carrier-coupled peptides, for instance, by intraperitoneal and/or intradermal injection of emulsions containing about 100 µg of peptide or carrier protein and Freund's adjuvant or any other adjuvant known for stimulating an immune response. Several booster injections may be needed, for instance, at intervals of about two weeks, to provide a useful titer of anti-peptide antibody which can be detected, for example, by ELISA assay using free peptide adsorbed to a solid surface. The titer of anti-peptide antibodies in serum from an immunized animal may be increased by selection of anti-peptide antibodies, for instance, by adsorption to the peptide on a solid support and elution of the selected antibodies according to methods well known in the art.

As one of skill in the art will appreciate, and as discussed above, the polypeptides of the present invention comprising an immunogenic or antigenic epitope can be fused to other polypeptide sequences. For example, the polypeptides of the present invention may be fused with the constant domain of immunoglobulins (IgA, IgE, IgG, IgM), or portions thereof (CH1, CH2, CH3, or any combination thereof and portions thereof) resulting in chimeric polypeptides. Such fusion proteins may facilitate purification and may increase half-life in vivo. This has been shown for chimeric proteins consisting of the first two domains of the human CD4-polypeptide and various domains of the constant regions of the heavy or light chains of mammalian immunoglobulins. See, e.g., EP 394, 827; Traunecker et al., Nature, 331:84-86 (1988). Enhanced delivery of an antigen across the epithelial barrier to the immune system has been demonstrated for antigens (e.g., insulin) conjugated to an FcRn binding partner such as IgG or Fc fragments (see, e.g., PCT Publications WO 96/22024 and WO 99/04813). IgG Fusion proteins that have a disulfide-linked dimeric structure due to the IgG portion desulfide bonds have also been found to be more efficient in binding and neutralizing other molecules than monomeric polypeptides or fragments thereof alone. See, e.g., Fountoulakis et al., J. Biochem., 270:3958-3964 (1995). Nucleic acids encoding the above epitopes can also be recombined with a gene of interest as an epitope tag (e.g., the hemagglutinin ("HA") tag or flag tag) to aid in detection and purification of the expressed polypeptide. For example, a system described by Janknecht et al. allows for the ready purification of non-denatured fusion proteins expressed in human cell lines (Janknecht et al., 1991, Proc. Natl. Acad. Sci. USA 88:8972-897). In this system, the gene of interest is subcloned into a vaccinia recombination plasmid such that the open reading frame of the gene is translationally fused to an amino-terminal tag consisting of six histidine residues. The tag serves as a matrix-binding domain for the fusion protein. Extracts from cells infected with the recombinant vaccinia virus are loaded onto $Ni^{2+}$ nitriloacetic acid-agarose column and histidine-tagged proteins can be selectively eluted with imidazole-containing buffers.

In another embodiment, the TR9 polypeptides of the present invention and the epitope-bearing fragments thereof are fused with a heterologous antigen (e.g., polypeptide, carbohydrate, phospholipid, or nucleic acid). In specific embodiments, the heterologous antigen is an immunogen.

In a more specific embodiment, the heterologous antigen is the gp120 protein of HIV, or a fragment thereof. Polynucleotides encoding these polypeptides are also encompassed by the invention.

In another embodiment, the TR9 polypeptides of the present invention and the epitope-bearing fragments thereof are fused with polypeptide sequences of another TNF family member (or biologically active fragments or variants thereof). In a specific embodiment, the TR9 polypeptides of the present invention are fused with a CD40L polypeptide sequence. In a preferred embodiment, the CD40L polypeptide sequence is soluble.

Additional fusion proteins of the invention may be generated through the techniques of gene-shuffling, motif-shuffling, exon-shuffling, and/or codon-shuffling (collectively referred to as "DNA shuffling"). DNA shuffling may be employed to modulate the activities of polypeptides of the invention, such methods can be used to generate polypeptides with altered activity, as well as agonists and antagonists of the polypeptides. See generally, U.S. Pat. Nos. 5,605,793; 5,811,238; 5,830,721; 5,834,252; and 5,837,458, and Patten et al., Curr. Opinion Biotechnol. 8:724-33 (1997); Harayama, Trends Biotechnol. 16(2):76-82 (1998); Hansson, et al., J. Mol. Biol. 287:265-76 (1999); and Lorenzo and Blasco, Biotechniques 24(2):308-13 (1998) (each of these patents and publications are hereby incorporated by reference in its entirety). In one embodiment, alteration of polynucleotides corresponding to SEQ ID NO:1, and the polypeptides encoded by these polynucleotides, may be achieved by DNA shuffling. DNA shuffling involves the assembly of two or more DNA segments by homologous or site-specific recombination to generate variation in the polynucleotide sequence. In another embodiment, polynucleotides of the invention, or the encoded polypeptides, may be altered by being subjected to random mutagenesis by error-prone PCR, random nucleotide insertion or other methods prior to recombination. In another embodiment, one or more components, motifs, sections, parts, domains, fragments, etc., of a polynucleotide encoding a polypeptide of the invention may be recombined with one or more components, motifs, sections, parts, domains, fragments, etc. of one or more heterologous molecules.

In a preferred embodiments, TR9 polypeptides of the invention (including biologically active fragments or variants thereof), are fused with soluble CD40L polypeptides, or biologically active fragments or variants thereof.

Antibodies

Further polypeptides of the invention relate to antibodies and T-cell antigen receptors (TCR) which immunospecifically bind a polypeptide, polypeptide fragment, or variant of SEQ ID NO:2, and/or an epitope, of the present invention (as determined by immunoassays well known in the art for assaying specific antibody-antigen binding). Antibodies of the invention include, but are not limited to, polyclonal, monoclonal, multispecific, human, humanized or chimeric antibodies, single chain antibodies, Fab fragments, F(ab') fragments, fragments produced by a Fab expression library, anti-idiotypic (anti-Id) antibodies (including, e.g., anti-Id antibodies to antibodies of the invention), and epitope-binding fragments of any of the above. The term "antibody," as used herein, refers to immunoglobulin molecules and immunologically active portions of immunoglobulin molecules, i.e., molecules that contain an antigen binding site that immunospecifically binds an antigen. The immunoglobulin molecules of the invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins may have both a heavy and light chain. An array of IgG, IgE, IgM, IgD, IgA, and IgY heavy chains may be paired with a light chain of the kappa or lambda forms.

Most preferably the antibodies are human antigen-binding antibody fragments of the present invention and include, but are not limited to, Fab, Fab' and F(ab')2, Fd, single-chain Fvs (scFv), single-chain antibodies, disulfide-linked Fvs (sdFv) and fragments comprising either a VL or VH domain. Antigen-binding antibody fragments, including single-chain antibodies, may comprise the variable region(s) alone or in combination with the entirety or a portion of the following: hinge region, CH1, CH2, and CH3 domains. Also included in the invention are antigen-binding fragments also comprising any combination of variable region(s) with a hinge region, CH1, CH2, and CH3 domains. The antibodies of the invention may be from any animal origin including birds and mammals. Preferably, the antibodies are human, murine (e.g., mouse and rat), donkey, ship rabbit, goat, guinea pig, camel, horse, or chicken. As used herein, "human" antibodies include antibodies having the amino acid sequence of a human immunoglobulin and include antibodies isolated from human immunoglobulin libraries or from animals transgenic for one or more human immunoglobulin and that do not express endogenous immunoglobulins, as described infra and, for example in, U.S. Pat. No. 5,939,598 by Kucherlapati et al.

The antibodies of the present invention may be monospecific, bispecific, trispecific or of greater multispecificity. Multispecific antibodies may be specific for different epitopes of a polypeptide of the present invention or may be specific for both a polypeptide of the present invention as well as for a heterologous epitope, such as a heterologous polypeptide or solid support material. See, e.g., PCT publications WO 93/17715; WO 92/08802; WO 91/00360; WO 92/05793; Tutt, et al., J. Immunol. 147:60-69 (1991); U.S. Pat. Nos. 4,474,893; 4,714,681; 4,925,648; 5,573,920; 5,601,819; Kostelny et al., J. Immunol. 148:1547-1553 (1992).

Antibodies of the present invention may be described or specified in terms of the epitope(s) or portion(s) of a polypeptide of the present invention which they recognize or specifically bind. The epitope(s) or polypeptide portion(s) may be specified as described herein, e.g., by N-terminal and C-terminal positions, by size in contiguous amino acid residues, or listed in the Tables and Figures. Antibodies which specifically bind any epitope or polypeptide of the present invention may also be excluded. Therefore, the present invention includes antibodies that specifically bind polypeptides of the present invention, and allows for the exclusion of the same.

Antibodies of the present invention may also be described or specified in terms of their cross-reactivity. Antibodies that do not bind any other analog, ortholog, or homolog of a polypeptide of the present invention are included. Antibodies that bind polypeptides with at least 95%, at least 90%, at least 85%, at least 80%, at least 75%, at least 70%, at least 65%, at least 60%, at least 55%, and at least 50% identity (as calculated using methods known in the art and described herein) to a polypeptide of the present invention are also included in the present invention. In specific embodiments, antibodies of the present invention cross-react with murine, rat and/or rabbit homologs of human proteins and the corresponding epitopes thereof. Antibodies that do not bind polypeptides with less than 95%, less than 90%, less than 85%, less than 80%, less than 75%, less than 70%, less than 65%, less than 60%, less than 55%, and less than 50% identity (as calculated using methods known in the art and described herein) to a polypeptide of the present invention are also included in the present invention. In a specific embodiment, the above-described cross-reactivity is with respect to any single specific antigenic or immunogenic polypeptide, or combination(s) of 2, 3, 4, 5, or more of the specific antigenic and/or immunogenic polypeptides disclosed herein. Further included in the present invention are antibodies which bind polypeptides encoded by polynucleotides which hybridize to a polynucleotide of the present invention under stringent hybridization conditions (as described herein). Antibodies of the present invention may also be described or specified in terms of their binding affinity to a polypeptide of the invention. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$M, $5 \times 10^{-7}$ M, $10^{7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, or $10^{-15}$ M.

The invention also provides antibodies that competitively inhibit binding of an antibody to an epitope of the invention as determined by any method known in the art for determining competitive binding, for example, the immunoassays described herein. In preferred embodiments, the antibody competitively inhibits binding to the epitope by at least 95%, at least 90%, at least 85%, at least 80%, at least 75%, at least 70%, at least 60%, or at least 50%.

Antibodies of the present invention may act as agonists or antagonists of the polypeptides of the present invention. For example, the present invention includes antibodies which disrupt the receptor/ligand interactions with the polypeptides of the invention either partially or fully. Preferrably, antibodies of the present invention bind an antigenic epitope disclosed herein, or a portion thereof. The invention features both receptor-specific antibodies and ligand-specific antibodies. The invention also features receptor-specific antibodies which do not prevent ligand binding but prevent receptor activation. Receptor activation (i.e., signaling) may be determined by techniques described herein or otherwise known in the art. For example, receptor activation can be determined by detecting the phosphorylation (e.g., tyrosine or serine/threonine) of the receptor or its substrate by immunoprecipitation followed by western blot analysis (for example, as described supra). In specific embodiments, antibodies are provided that inhibit ligand activity or receptor activity by at least 95%, at least 90%, at least 85%, at least 80%, at least 75%, at least 70%, at least 60%, or at least 50% of the activity in absence of the antibody.

The invention also features receptor-specific antibodies which both prevent ligand binding and receptor activation as well as antibodies that recognize the receptor-ligand complex, and, preferably, do not specifically recognize the unbound receptor or the unbound ligand. Likewise, included in the invention are neutralizing antibodies which bind the ligand and prevent binding of the ligand to the receptor, as well as antibodies which bind the ligand, thereby preventing receptor activation, but do not prevent the ligand from binding the receptor. Further included in the invention are antibodies which activate the receptor. These antibodies may act as receptor agonists, i.e., potentiate or activate either all or a subset of the biological activities of the ligand-mediated receptor activation, for example, by inducing dimerization of the receptor. The antibodies may be specified as agonists, antagonists or inverse agonists for biological activities comprising the specific biological activities of the peptides of the invention disclosed herein. The above antibody agonists can be made using methods known in the art. See, e.g., PCT publication WO 96/40281; U.S. Pat. No. 5,811,097; Deng et al., Blood 92(6):1981-1988 (1998); Chen et al., Cancer Res. 58(16):3668-3678 (1998); Harrop et al., J. Immunol. 161(4): 1786-1794 (1998); Zhu et al., Cancer Res. 58(15):3209-3214 (1998); Yoon et al., J. Immunol. 160(7):3170-3179 (1998); Prat et al., J. Cell. Sci. 111(Pt2):237-247 (1998); Pitard et al., J. Immunol. Methods 205(2):177-190 (1997); Liautard et al., Cytokine 9(4):233-241 (1997); Carlson et al., J. Biol. Chem. 272(17): 11295-11301 (1997); Taryman et al., Neuron 14(4): 755-762 (1995); Muller et al., Structure 6(9):1153-1167 (1998); Bartunek et al., Cytokine 8(1):14-20 (1996) (which are all incorporated by reference herein in their entireties).

Antibodies of the present invention may be used, for example, but not limited to, to purify, detect, and target the polypeptides of the present invention, including both in vitro and in vivo diagnostic and therapeutic methods. For example, the antibodies have use in immunoassays for qualitatively and quantitatively measuring levels of the polypeptides of the present invention in biological samples. See, e.g., Harlow et al., Antibodies: A Laboratory Manual, (Cold Spring Harbor Laboratory Press, 2nd ed. 1988) (incorporated by reference herein in its entirety).

As discussed in more detail below, the antibodies of the present invention may be used either alone or in combination with other compositions. The antibodies may further be recombinantly fused to a heterologous polypeptide at the N- or C-terminus or chemically conjugated (including covalently and non-covalently conjugations) to polypeptides or other compositions. For example, antibodies of the present invention may be recombinantly fused or conjugated to molecules useful as labels in detection assays and effector molecules such as heterologous polypeptides, drugs, radionuclides, or toxins. See, e.g., PCT publications WO 92/08495; WO 91/14438; WO 89/12624; U.S. Pat. No. 5,314,995; and EP 396,387.

The antibodies of the invention include derivatives that are modified, i.e., by the covalent attachment of any type of molecule to the antibody such that covalent attachment does not prevent the antibody from generating an anti-idiotypic response. For example, but not by way of limitation, the antibody derivatives include antibodies that have been modified, e.g., by glycosylation, acetylation, pegylation, phosphylation, amidation, derivatization by known protecting/blocking groups, proteolytic cleavage, linkage to a cellular ligand or other protein, etc. Any of numerous chemical modifications may be carried out by known techniques, including, but not limited to specific chemical cleavage, acetylation, formylation, metabolic synthesis of tunicamycin, etc. Additionally, the derivative may contain one or more non-classical amino acids.

The antibodies of the present invention may be generated by any suitable method known in the art. Polyclonal antibodies to an antigen-of-interest can be produced by various procedures well known in the art. For example, a polypeptide of the invention can be administered to various host animals including, but not limited to, rabbits, mice, rats, etc. to induce the production of sera containing polyclonal antibodies specific for the antigen. Various adjuvants may be used to increase the immunological response, depending on the host species, and include but are not limited to, Freund's (complete and incomplete), mineral gels such as aluminum hydroxide, surface active substances such as lysolecithin, pluronic polyols, polyanions, peptides, oil emulsions, keyhole limpet hemocyanins, dinitrophenol, and potentially useful human adjuvants such as BCG (bacille Calmette-Guerin) and *corynebacterium parvum*. Such adjuvants are also well known in the art.

Monoclonal antibodies can be prepared using a wide variety of techniques known in the art including the use of hybridoma, recombinant, and phage display technologies, or a combination thereof. For example, monoclonal antibodies can be produced using hybridoma techniques including those known in the art and taught, for example, in Harlow et al., Antibodies: A Laboratory Manual, (Cold Spring Harbor Laboratory Press, 2nd ed. 1988); Hammerling, et al., in: Monoclonal Antibodies and T-Cell Hybridomas 563-681 (Elsevier, N.Y., 1981) (said references incorporated by reference in their entireties). The term "monoclonal antibody" as used herein is not limited to antibodies produced through hybridoma technology. The term "monoclonal antibody" refers to an antibody that is derived from a single clone, including any eukaryotic, prokaryotic, or phage clone, and not the method by which it is produced.

A "monoclonal antibody" may comprise, or alternatively consist of, two proteins, i.e., a heavy and a light chain.

Methods for producing and screening for specific antibodies using hybridoma technology are routine and well known in the art and are discussed in detail in the Examples (e.g., Example 11). In a non-limiting example, mice can be immunized with a polypeptide of the invention or a cell expressing such peptide. Once an immune response is detected, e.g., antibodies specific for the antigen are detected in the mouse serum, the mouse spleen is harvested and splenocytes isolated. The splenocytes are then fused by well-known techniques to any suitable myeloma cells, for example cells from cell line SP20 available from the ATCC. Hybridomas are selected and cloned by limited dilution. The hybridoma clones are then assayed by methods known in the art for cells that secrete antibodies capable of binding a polypeptide of the invention. Ascites fluid, which generally contains high levels of antibodies, can be generated by immunizing mice with positive hybridoma clones.

Accordingly, the present invention provides methods of generating monoclonal antibodies as well as antibodies produced by the method comprising culturing a hybridoma cell secreting an antibody of the invention wherein, preferably, the hybridoma is generated by fusing splenocytes solated from a mouse immunized with an antigen of the invention with myeloma cells and then screening the hybridomas resulting from the fusion for hybridoma clones that secrete an antibody able to bind a polypeptide of the invention.

Antibody fragments which recognize specific epitopes may be generated by known techniques. For example, Fab and F(ab')2 fragments of the invention may be produced by proteolytic cleavage of immunoglobulin molecules, using enzymes such as papain (to produce Fab fragments) or pepsin (to produce F(ab')2 fragments). F(ab')2 fragments contain the variable region, the light chain constant region and the CH1 domain of the heavy chain.

For example, the antibodies of the present invention can also be generated using various phage display methods known in the art. In phage display methods, functional antibody domains are displayed on the surface of phage particles which carry the polynucleotide sequences encoding them. In a particular embodiment, such phage can be utilized to display antigen binding domains expressed from a repertoire or combinatorial antibody library (e.g., human or murine). Phage expressing an antigen binding domain that binds the antigen of interest can be selected or identified with antigen, e.g., using labeled antigen or antigen bound or captured to a solid surface or bead. Phage used in these methods are typically filamentous phage including fd and M13 binding domains expressed from phage with Fab, Fv or disulfide stabilized Fv antibody domains recombinantly fused to either the phage gene III or gene VIII protein. Examples of phage display methods that can be used to make the antibodies of the present invention include those disclosed in Brinkman et al., J. Immunol. Methods 182:41-50 (1995); Ames et al., J. Immunol. Methods 184:177-186 (1995); Kettleborough et al., Eur. J. Immunol. 24:952-958 (1994); Persic et al., Gene 187 9-18 (1997); Burton et al., Advances in Immunology 57:191-280 (1994); PCT application No. PCT/GB91/01134; PCT publications WO 90/02809; WO 91/10737; WO 92/01047; WO 92/18619; WO 93/11236; WO 95/15982; WO 95/20401; and U.S. Pat. Nos. 5,698,426; 5,223,409; 5,403,484; 5,580,717; 5,427,908; 5,750,753; 5,821,047; 5,571,698; 5,427,908; 5,516,637; 5,780,225; 5,658,727; 5,733,743 and 5,969,108; each of which is incorporated herein by reference in its entirety.

As described in the above references, after phage selection, the antibody coding regions from the phage can be isolated and used to generate whole antibodies, including human antibodies, or any other desired antigen binding fragment, and expressed in any desired host, including mammalian cells, insect cells, plant cells, yeast, and bacteria, e.g., as described in detail below. For example, techniques to recombinantly produce Fab, Fab' and F(ab')2 fragments can also be employed using methods known in the art such as those disclosed in PCT publication WO 92/22324; Mullinax et al., BioTechniques 12(6):864-869 (1992); and Sawai et al., AJRI 34:26-34 (1995); and Better et al., Science 240:1041-1043 (1988) (said references incorporated by reference in their entireties).

Examples of techniques which can be used to produce single-chain Fvs and antibodies include those described in U.S. Pat. Nos. 4,946,778 and 5,258,498; Huston et al., Methods in Enzymology 203:46-88 (1991); Shu et al., PNAS 90:7995-7999 (1993); and Skerra et al., Science 240:1038-1040 (1988). For some uses, including in vivo use of antibodies in humans and in vitro detection assays, it may be preferable to use chimeric, humanized, or human antibodies. A chimeric antibody is a molecule in which different portions of the antibody are derived from different animal species, such as antibodies having a variable region derived from a murine monoclonal antibody and a human immunoglobulin constant region. Methods for producing chimeric antibodies are known in the art. See e.g., Morrison, Science 229:1202 (1985); Oi et al., BioTechniques 4:214 (1986); Gillies et al., (1989) J. Immunol. Methods 125:191-202; U.S. Pat. Nos. 5,807,715; 4,816,567; and 4,816,397, which are incorporated herein by reference in their entirety. Humanized antibodies are antibody molecules from non-human species antibody that binds the desired antigen having one or more complementarity determining regions (CDRs) from the non-human species and framework regions from a human immunoglobulin molecule. Often, framework residues in the human framework regions will be substituted with the corresponding residue from the CDR donor antibody to alter, preferably improve, antigen binding. These framework substitutions are identified by methods well known in the art, e.g., by modeling of the interactions of the CDR and framework residues to identify framework residues important for antigen binding and sequence comparison to identify unusual framework residues at particular positions. (See, e.g., Queen et al., U.S. Pat. No. 5,585,089; Riechmann et al., Nature 332:323 (1988), which are incorporated herein by reference in their entireties.) Antibodies can be humanized using a variety of techniques known in the art including, for example, CDR-grafting (EP 239,400; PCT publication WO 91/09967; U.S. Pat. Nos. 5,225,539; 5,530,101; and 5,585,089), veneering or resurfacing (EP 592,106; EP 519,596; Padlan, Molecular Immunology 28(4/5):489-498 (1991); Studnicka et al., Protein Engineering 7(6):805-814 (1994); Roguska. et al., PNAS 91:969-973 (1994)), and chain shuffling (U.S. Pat. No. 5,565,332).

Completely human antibodies are particularly desirable for therapeutic treatment, detection, and/or prevention in human patients. Human antibodies can be made by a variety of methods known in the art including phage display methods described above using antibody libraries derived from human immunoglobulin sequences. See also, U.S. Pat. Nos. 4,444,887 and 4,716,111; and PCT publications WO 98/46645, WO 98/50433, WO 98/24893, WO 98/16654, WO 96/34096, WO 96/33735, and WO 91/10741; each of which is incorporated herein by reference in its entirety.

Human antibodies can also be produced using transgenic mice which are incapable of expressing functional endogenous immunoglobulins, but which can express human immunoglobulin genes. For example, the human heavy and light chain immunoglobulin gene complexes may be introduced randomly or by homologous recombination into mouse embryonic stem cells. Alternatively, the human variable region, constant region, and diversity region may be introduced into mouse embryonic stem cells in addition to the human heavy and light chain genes. The mouse heavy and light chain immunoglobulin genes may be rendered non-functional separately or simultaneously with the introduction of human immunoglobulin loci by homologous recombination. In particular, homozygous deletion of the JH region prevents endogenous antibody production. The modified embryonic stem cells are expanded and microinjected into blastocysts to produce chimeric mice. The chimeric mice are then bred to produce homozygous offspring which express human antibodies. The transgenic mice are immunized in the normal fashion with a selected antigen, e.g., all or a portion of a polypeptide of the invention. Monoclonal antibodies directed against the antigen can be obtained from the immunized, transgenic mice using conventional hybridoma technology. The human immunoglobulin transgenes harbored by the transgenic mice rearrange during B cell differentiation, and subsequently undergo class switching and somatic mutation. Thus, using such a technique, it is possible to produce therapeutically useful IgG, IgA, IgM and IgE antibodies. For an overview of this technology for producing human antibodies, see Lonberg and Huszar, Int. Rev. Immunol. 13:65-93 (1995). For a detailed discussion of this technology for producing human antibodies and human monoclonal antibodies and protocols for producing such antibodies, see, e.g., PCT publications WO 98/24893; WO 92/01047; WO 96/34096; WO 96/33735; European Patent No. 0 598 877; U.S. Pat. Nos. 5,413,923; 5,625,126; 5,633,425; 5,569,825; 5,661,016; 5,545,806; 5,814,318; 5,885,793; 5,916,771; and 5,939,598, which are incorporated by reference herein in their entirety. In addition, companies such as Abgenix, Inc. (Freemont, Calif.) and Genpharm (San Jose, Calif.) can be engaged to provide human antibodies directed against a selected antigen using technology similar to that described above.

Completely human antibodies which recognize a selected epitope can be generated using a technique referred to as "guided selection." In this approach a selected non-human monoclonal antibody, e.g., a mouse antibody, is used to guide the selection of a completely human antibody recognizing the same epitope. (Jespers et al., Bio/technology 12:899-903 (1988)).

Further, antibodies to the polypeptides of the invention can, in turn, be utilized to generate anti-idiotype antibodies that "mimic" polypeptides of the invention using techniques well known to those skilled in the art. (See, e.g., Greenspan & Bona, FASEB J. 7(5):437-444; (1989) and Nissinoff, J. Immunol. 147(8):2429-2438 (1991)). For example, antibodies which bind to and competitively inhibit polypeptide multimerization and/or binding of a polypeptide of the invention to a ligand can be used to generate anti-idiotypes that "mimic" the polypeptide multimerization and/or binding domain and, as a consequence, bind to and neutralize polypeptide and/or its ligand. Such neutralizing anti-idiotypes or Fab fragments of such anti-idiotypes can be used in therapeutic regimens to neutralize polypeptide ligand. For example, such anti-idiotypic antibodies can be used to bind a polypeptide of the invention and/or to bind its ligands/receptors, and thereby block its biological activity.

Polynucleotides Encoding Antibodies

The invention further provides polynucleotides comprising a nucleotide sequence encoding an antibody of the invention and fragments thereof. The invention also encompasses polynucleotides that hybridize under stringent or lower stringency hybridization conditions, e.g., as defined supra, to polynucleotides that encode an antibody, preferably, that specifically binds to a polypeptide of the invention, preferably, an antibody that binds to a polypeptide having the amino acid sequence of SEQ ID NO:2.

The polynucleotides may be obtained, and the nucleotide sequence of the polynucleotides determined, by any method known in the art. For example, if the nucleotide sequence of the antibody is known, a polynucleotide encoding the antibody may be assembled from chemically synthesized oligonucleotides (e.g., as described in Kutmeier et al., BioTechniques 17:242 (1994)), which, briefly, involves the synthesis of overlapping oligonucleotides containing portions of the sequence encoding the antibody, annealing and ligating of those oligonucleotides, and then amplification of the ligated oligonucleotides by PCR.

Alternatively, a polynucleotide encoding an antibody may be generated from nucleic acid from a suitable source. If a clone containing a nucleic acid encoding a particular antibody is not available, but the sequence of the antibody molecule is known, a nucleic acid encoding the immunoglobulin may be chemically synthesized or obtained from a suitable source (e.g., an antibody cDNA library, or a cDNA library generated from, or nucleic acid, preferably poly A+ RNA, isolated from, any tissue or cells expressing the antibody, such as hybridoma cells selected to express an antibody of the invention) by PCR amplification using synthetic primers hybridizable to the 3' and 5' ends of the sequence or by cloning using an oligonucleotide probe specific for the particular gene sequence to identify, e.g., a cDNA clone from a cDNA library that encodes the antibody. Amplified nucleic acids generated by PCR may then be cloned into replicable cloning vectors using any method well known in the art.

Once the nucleotide sequence and corresponding amino acid sequence of the antibody is determined, the nucleotide sequence of the antibody may be manipulated using methods well known in the art for the manipulation of nucleotide sequences, e.g., recombinant DNA techniques, site directed mutagenesis, PCR, etc. (see, for example, the techniques described in Sambrook et al., 1990, Molecular Cloning, A Laboratory Manual, 2d Ed., Cold Spring Harbor Laboratory, Cold Spring Harbor, N.Y. and Ausubel et al., eds., 1998, Current Protocols in Molecular Biology, John Wiley & Sons, NY, which are both incorporated by reference herein in their entireties), to generate antibodies having a different amino acid sequence, for example to create amino acid substitutions, deletions, and/or insertions.

In a specific embodiment, the amino acid sequence of the heavy and/or light chain variable domains may be inspected to identify the sequences of the complementarity determining regions (CDRs) by methods that are well know in the art, e.g., by comparison to known amino acid sequences of other heavy and light chain variable regions to determine the regions of sequence hypervariability. Using routine recombinant DNA techniques, one or more of the CDRs may be inserted within framework regions, e.g., into human framework regions to humanize a non-human antibody, as described supra. The framework regions may be naturally occurring or consensus framework regions, and preferably human framework regions (see, e.g., Chothia et al., J. Mol. Biol. 278: 457-479 (1998) for a listing of human framework regions). Preferably, the polynucleotide generated by the combination of the framework regions and CDRs encodes an antibody that specifically binds a polypeptide of the invention. Preferably, as discussed supra, one or more amino acid substitutions may be made within the framework regions, and, preferably, the amino acid substitutions improve binding of the antibody to its antigen. Additionally, such methods may be used to make amino acid substitutions or deletions of one or more variable region cysteine residues participating in an intrachain disulfide bond to generate antibody molecules lacking one or more intrachain disulfide bonds. Other alterations to the polynucleotide are encompassed by the present invention and within the skill of the art.

In addition, techniques developed for the production of "chimeric antibodies" (Morrison et al., Proc. Natl. Acad. Sci. 81:851-855 (1984); Neuberger et al., Nature 312:604-608 (1984); Takeda et al., Nature 314:452-454 (1985)) by splicing genes from a mouse antibody molecule of appropriate antigen specificity together with genes from a human antibody molecule of appropriate biological activity can be used. As described supra, a chimeric antibody is a molecule in which different portions are derived from different animal species, such as those having a variable region derived from a murine mAb and a human immunoglobulin constant region, e.g., humanized antibodies.

Alternatively, techniques described for the production of single chain antibodies (U.S. Pat. No. 4,946,778; Bird, Science 242:423-42 (1988); Huston et al., Proc. Natl. Acad. Sci. USA 85:5879-5883 (1988); and Ward et al., Nature 334:544-54 (1989)) can be adapted to produce single chain antibodies. Single chain antibodies are formed by linking the heavy and light chain fragments of the Fv region via an amino acid bridge, resulting in a single chain polypeptide. Techniques for the assembly of functional Fv fragments in *E. coli* may also be used (Skerra et al., Science 242:1038-1041 (1988)).

Methods of Producing Antibodies

The antibodies of the invention can be produced by any method known in the art for the synthesis of antibodies, in particular, by chemical synthesis or preferably, by recombinant expression techniques.

Recombinant expression of an antibody of the invention, or fragment, derivative or analog thereof, (e.g., a heavy or light chain of an antibody of the invention or a single chain antibody of the invention), requires construction of an expression vector containing a polynucleotide that encodes the antibody. Once a polynucleotide encoding an antibody molecule or a heavy or light chain of an antibody, or portion thereof (preferably containing the heavy or light chain variable domain), of the invention has been obtained, the vector for the production of the antibody molecule may be produced by recombinant DNA technology using techniques well known in the art. Thus, methods for preparing a protein by expressing a polynucleotide containing an antibody encoding nucleotide sequence are described herein. Methods which are well known to those skilled in the art can be used to construct expression vectors containing antibody coding sequences and appropriate transcriptional and translational control signals. These methods include, for example, in vitro recombinant DNA techniques, synthetic techniques, and in vivo genetic recombination. The invention, thus, provides replicable vectors comprising a nucleotide sequence encoding an antibody molecule of the invention, or a heavy or light chain thereof, or a heavy or light chain variable domain, operably linked to a promoter. Such vectors may include the nucleotide sequence encoding the constant region of the antibody molecule (see, e.g., PCT Publication WO 86/05807; PCT Publication WO 89/01036; and U.S. Pat. No. 5,122,464) and the variable domain of the antibody may be cloned into such a vector for expression of the entire heavy or light chain.

The expression vector is transferred to a host cell by conventional techniques and the transfected cells are then cultured by conventional techniques to produce an antibody of the invention. Thus, the invention includes host cells containing a polynucleotide encoding an antibody of the invention, or a heavy or light chain thereof, or a single chain antibody of the invention, operably linked to a heterologous promoter. In preferred embodiments for the expression of double-chained antibodies, vectors encoding both the heavy and light chains may be co-expressed in the host cell for expression of the entire immunoglobulin molecule, as detailed below.

A variety of host-expression vector systems may be utilized to express the antibody molecules of the invention. Such host-expression systems represent vehicles by which the coding sequences of interest may be produced and subsequently purified, but also represent cells which may, when transformed or transfected with the appropriate nucleotide coding sequences, express an antibody molecule of the invention in situ. These include but are not limited to microorganisms such as bacteria (e.g., *E. coli, B. subtilis*) transformed with recombinant bacteriophage DNA, plasmid DNA or cosmid DNA expression vectors containing antibody coding sequences; yeast (e.g., *Saccharomyces, Pichia*) transformed with recombinant yeast expression vectors containing antibody coding sequences; insect cell systems infected with recombinant virus expression vectors (e.g., baculovirus) containing antibody coding sequences; plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing antibody coding sequences; or mammalian cell systems (e.g., COS, CHO, BHK, 293, 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter). Preferably, bacterial cells such as *Escherichia coli*, and more preferably, eukaryotic cells, especially for the expression of whole recombinant antibody molecule, are used for the expression of a recombinant antibody molecule. For example, mammalian cells such as Chinese hamster ovary cells (CHO), in conjunction with a vector such as the major intermediate early gene promoter element from human cytomegalovirus is an effective expression system for antibodies (Foecking et al., Gene 45:101 (1986); Cockett et al., Bio/Technology 8:2 (1990)).

In bacterial systems, a number of expression vectors may be advantageously selected depending upon the use intended for the antibody molecule being expressed. For example, when a large quantity of such a protein is to be produced, for the generation of pharmaceutical compositions of an antibody molecule, vectors which direct the expression of high levels of fusion protein products that are readily purified may be desirable. Such vectors include, but are not limited, to the *E. coli* expression vector pUR278 (Ruther et al., EMBO J. 2:1791 (1983)), in which the antibody coding sequence may be ligated individually into the vector in frame with the lac Z coding region so that a fusion protein is produced; pIN vectors (Inouye & Inouye, Nucleic Acids Res. 13:3101-3109 (1985); Van Heeke & Schuster, J. Biol. Chem. 24:5503-5509 (1989)); and the like. pGEX vectors may also be used to express foreign polypeptides as fusion proteins with glutathione S-transferase (GST). In general, such fusion proteins are soluble and can easily be purified from lysed cells by adsorption and binding to matrix glutathione-agarose beads followed by elution in the presence of free glutathione. The pGEX vectors are designed to include thrombin or factor Xa protease cleavage sites so that the cloned target gene product can be released from the GST moiety.

In an insect system, *Autographa californica* nuclear polyhedrosis virus (AcNPV) is used as a vector to express foreign genes. The virus grows in *Spodoptera frugiperda* cells. The antibody coding sequence may be cloned individually into non-essential regions (for example the polyhedrin gene) of the virus and placed under control of an AcNPV promoter (for example the polyhedrin promoter).

In mammalian host cells, a number of viral-based expression systems may be utilized. In cases where an adenovirus is used as an expression vector, the antibody coding sequence of interest may be ligated to an adenovirus transcription/translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing the antibody molecule in infected hosts. (e.g., see Logan & Shenk, Proc. Natl. Acad. Sci. USA 81:355-359 (1984)). Specific initiation signals may also be required for efficient translation of inserted antibody coding sequences. These signals include the ATG initiation codon and adjacent sequences. Furthermore, the initiation codon must be in phase with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators, etc. (see Bittner et al., Methods in Enzymol. 153:51-544 (1987)).

In addition, a host cell strain may be chosen which modulates the expression of the inserted sequences, or modifies and processes the gene product in the specific fashion desired. Such modifications (e.g., glycosylation) and processing (e.g., cleavage) of protein products may be important for the function of the protein. Different host cells have characteristic and specific mechanisms for the post-translational processing and modification of proteins and gene products. Appropriate cell lines or host systems can be chosen to ensure the correct modification and processing of the foreign protein expressed. To this end, eukaryotic host cells which possess the cellular machinery for proper processing of the primary transcript, glycosylation, and phosphorylation of the gene product may be used. Such mammalian host cells include but are not limited to CHO, VERY, BHK, Hela, COS, MDCK, 293, 3T3, WI38, and in particular, breast cancer cell lines such as, for example, BT483, Hs578T, HTB2, BT20 and T47D, and normal mammary gland cell line such as, for example, CRL7030 and Hs578Bst.

For long-term, high-yield production of recombinant proteins, stable expression is preferred. For example, cell lines which stably express the antibody molecule may be engineered. Rather than using expression vectors which contain viral origins of replication, host cells can be transformed with DNA controlled by appropriate expression control elements (e.g., promoter, enhancer, sequences, transcription terminators, polyadenylation sites, etc.), and a selectable marker. Following the introduction of the foreign DNA, engineered cells may be allowed to grow for 1-2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines. This method may advantageously be used to engineer cell lines which express the antibody molecule. Such engineered cell lines may be particularly useful in screening and evaluation of compounds that interact directly or indirectly with the antibody molecule.

A number of selection systems may be used, including but not limited to the herpes simplex virus thymidine kinase (Wigler et al., Cell 11:223 (1977)), hypoxanthine-guanine phosphoribosyltransferase (Szybalska & Szybalski, Proc. Natl. Acad. Sci. USA 48:202 (1992)), and adenine phosphoribosyltransferase (Lowy et al., Cell 22:817 (1980)) genes can be employed in tk–, hgprt– or aprt– cells, respectively. Also, antimetabolite resistance can be used as the basis of selection for the following genes: dhfr, which confers resistance to methotrexate (Wigler et al., Natl. Acad. Sci. USA 77:357 (1980); O'Hare et al., Proc. Natl. Acad. Sci. USA 78:1527 (1981)); gpt, which confers resistance to mycophenolic acid (Mulligan & Berg, Proc. Natl. Acad. Sci. USA 78:2072 (1981)); neo, which confers resistance to the aminoglycoside G-418 Clinical Pharmacy 12:488-505; Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, 1993, TIB TECH 11(5):155-215); and hygro, which confers resistance to hygromycin (Santerre et al., Gene 30:147 (1984)). Methods commonly known in the art of recombinant DNA technology may be routinely applied to select the desired recombinant clone, and such methods are described, for example, in Ausubel et al. (eds.), Current Protocols in Molecular Biology, John Wiley & Sons, NY (1993); Kriegler, Gene Transfer and Expression, A Laboratory Manual, Stockton Press, NY (1990); and in Chapters 12 and 13, Dracopoli et al. (eds), Current Protocols in Human Genetics, John Wiley & Sons, NY (1994); Colberre-Garapin et al., J. Mol. Biol. 150:1 (1981), which are incorporated by reference herein in their entireties.

The expression levels of an antibody molecule can be increased by vector amplification (for a review, see Bebbington and Hentschel, The use of vectors based on gene amplification for the expression of cloned genes in mammalian cells in DNA cloning, Vol. 3. (Academic Press, New York, 1987)). When a marker in the vector system expressing antibody is amplifiable, increase in the level of inhibitor present in culture of host cell will increase the number of copies of the marker gene. Since the amplified region is associated with the antibody gene, production of the antibody will also increase (Crouse et al., Mol. Cell. Biol. 3:257 (1983)).

The host cell may be co-transfected with two expression vectors of the invention, the first vector encoding a heavy chain derived polypeptide and the second vector encoding a light chain derived polypeptide. The two vectors may contain identical selectable markers which enable equal expression of heavy and light chain polypeptides. Alternatively, a single vector may be used which encodes, and is capable of expressing, both heavy and light chain polypeptides. In such situations, the light chain should be placed before the heavy chain to avoid an excess of toxic free heavy chain (Proudfoot, Nature 322:52 (1986); Kohler, Proc. Natl. Acad. Sci. USA 77:2197 (1980)). The coding sequences for the heavy and light chains may comprise cDNA or genomic DNA.

Once an antibody molecule of the invention has been produced by an animal, chemically synthesized, or recombinantly expressed, it may be purified by any method known in the art for purification of an immunoglobulin molecule, for example, by chromatography (e.g., ion exchange, affinity, particularly by affinity for the specific antigen after Protein A, and sizing column chromatography), centrifugation, differential solubility, or by any other standard technique for the purification of proteins. In addition, the antibodies of the present invention or fragments thereof can be fused to heterologous polypeptide sequences described herein or otherwise known in the art, to facilitate purification.

The present invention encompasses antibodies recombinantly fused or chemically conjugated (including both covalently and non-covalently conjugations) to a polypeptide (or portion thereof, preferably at least 10, 20, 30, 40, 50, 60, 70, 80, 90 or 100 amino acids of the polypeptide) of the present invention to generate fusion proteins. The fusion does not necessarily need to be direct, but may occur through linker sequences. The antibodies may be specific for antigens other than polypeptides (or portion thereof, preferably at least 10, 20, 30, 40, 50, 60, 70, 80, 90 or 100 amino acids of the polypeptide) of the present invention. For example, antibodies may be used to target the polypeptides of the present invention to particular cell types, either in vitro or in vivo, by fusing or conjugating the polypeptides of the present invention to antibodies specific for particular cell surface receptors. Antibodies fused or conjugated to the polypeptides of the present invention may also be used in in vitro immunoassays and purification methods using methods known in the art. See e.g., Harbor et al., supra, and PCT publication WO 93/21232; EP 439,095; Naramura et al., Immunol. Lett. 39:91-99 (1994); U.S. Pat. No. 5,474,981; Gillies et al., PNAS 89:1428-1432 (1992); Fell et al., J. Immunol. 146:2446-2452 (1991), which are incorporated by reference in their entireties.

The present invention further includes compositions comprising the polypeptides of the present invention fused or conjugated to antibody domains other than the variable regions. For example, the polypeptides of the present invention may be fused or conjugated to an antibody Fc region, or portion thereof. The antibody portion fused to a polypeptide of the present invention may comprise the constant region, hinge region, CH1 domain, CH2 domain, and CH3 domain or any combination of whole domains or portions thereof. The polypeptides may also be fused or conjugated to the above antibody portions to form multimers. For example, Fc portions fused to the polypeptides of the present invention can form dimers through disulfide bonding between the Fc portions. Higher multimeric forms can be made by fusing the polypeptides to portions of IgA and IgM. Methods for fusing or conjugating the polypeptides of the present invention to antibody portions are known in the art. See, e.g., U.S. Pat. Nos. 5,336,603; 5,622,929; 5,359,046; 5,349,053; 5,447,851; 5,112,946; EP 307,434; EP 367,166; PCT publications WO 96/04388; WO 91/06570; Ashkenazi et al., Proc. Natl. Acad. Sci. USA 88:10535-10539 (1991); Zheng et al., J. Immunol. 154:5590-5600 (1995); and Vil et al., Proc. Natl. Acad. Sci. USA 89:11337-11341(1992) (said references incorporated by reference in their entireties).

As discussed, supra, the polypeptides corresponding to a polypeptide, polypeptide fragment, or a variant of SEQ ID NO:2, may be fused or conjugated to the above antibody portions to increase the in vivo half life of the polypeptides or for use in immunoassays using methods known in the art. Further, the polypeptides corresponding to SEQ ID NO:2 may be fused or conjugated to the above antibody portions to facilitate purification. One reported example describes chimeric proteins consisting of the first two domains of the human CD4-polypeptide and various domains of the constant regions of the heavy or light chains of mammalian immunoglobulins. (EP 394,827; Traunecker et al., Nature 331:84-86 (1988). The polypeptides of the present invention fused or conjugated to an antibody having disulfide-linked dimeric structures (due to the IgG) may also be more efficient in binding and neutralizing other molecules, than the monomeric secreted protein or protein fragment alone. (Fountoulakis et al., J. Biochem. 270:3958-3964 (1995)). In many cases, the Fc part in a fusion protein is beneficial in therapy and diagnosis, and thus can result in, for example, improved pharmacokinetic properties. (EP A 232,262). Alternatively, deleting the Fc part after the fusion protein has been expressed, detected, and purified, would be desired. For example, the Fc portion may hinder therapy and diagnosis if the fusion protein is used as an antigen for immunizations. In drug discovery, for example, human proteins, such as hIL-5, have been fused with Fc portions for the purpose of high-throughput screening assays to identify antagonists of hIL-5. (See, Bennett et al., J. Molecular Recognition 8:52-58 (1995); Johanson et al., J. Biol. Chem. 270:9459-9471 (1995).

Moreover, the antibodies or fragments thereof of the present invention can be fused to marker sequences, such as a peptide to facilitate purification. In preferred embodiments, the marker amino acid sequence is a hexa-histidine peptide, such as the tag provided in a pQE vector (QIAGEN, Inc., 9259 Eton Avenue, Chatsworth, Calif., 91311), among others, many of which are commercially available. As described in Gentz et al., Proc. Natl. Acad. Sci. USA 86:821-824 (1989), for instance, hexa-histidine provides for convenient purification of the fusion protein. Other peptide tags useful for purification include, but are not limited to, the "HA" tag, which corresponds to an epitope derived from the influenza hemagglutinin protein (Wilson et al., Cell 37:767 (1984)) and the "flag" tag.

The present invention further encompasses antibodies or fragments thereof conjugated to a diagnostic or therapeutic agent. The antibodies can be used diagnostically to, for example, monitor the development or progression of a tumor as part of a clinical testing procedure to, e.g., determine the efficacy of a given treatment regimen. Detection can be facilitated by coupling the antibody to a detectable substance. Examples of detectable substances include various enzymes, prosthetic groups, fluorescent materials, luminescent materials, bioluminescent materials, radioactive materials, positron emitting metals using various positron emission tomographies, and nonradioactive paramagnetic metal ions. The detectable substance may be coupled or conjugated either directly to the antibody (or fragment thereof) or indirectly, through an intermediate (such as, for example, a linker known in the art) using techniques known in the art. See, for example, U.S. Pat. No. 4,741,900 for metal ions which can be conjugated to antibodies for use as diagnostics according to the present invention. Examples of suitable enzymes include horseradish peroxidase, alkaline phosphatase, beta-galactosidase, or acetylcholinesterase; examples of suitable prosthetic group complexes include streptavidin/biotin and avidin/biotin; examples of suitable fluorescent materials include umbelliferone, fluorescein, fluorescein isothiocyanate, rhodamine, dichlorotriazinylamine fluorescein, dansyl chloride or phycoerythrin; an example of a luminescent material includes luminol; examples of bioluminescent materials include luciferase, luciferin, and acquorin; and examples of suitable radioactive material include $^{125}$I, $^{131}$I, $^{111}$In or $^{99}$Tc.

Further, an antibody or fragment thereof may be conjugated to a therapeutic moiety such as a cytotoxin, e.g., a cytostatic or cytocidal agent, a therapeutic agent or a radioactive metal ion, e.g., alpha-emitters such as, for example, 213Bi. A cytotoxin or cytotoxic agent includes any agent that is detrimental to cells. Examples include paclitaxol, cytochalasin B, gramicidin D, ethidium bromide, emetine, mitomycin, etoposide, tenoposide, vincristine, vinblastine, colchicin, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. Therapeutic agents include, but are not limited to, antimetabolites (e.g., methotrexate, 6-mercaptopurine, 6-thioguanine, cytarabine, 5-fluorouracil decarbazine), alkylating agents (e.g., mechlorethamine, thioepa chlorambucil, melphalan, carmustine (BSNU) and lomustine (CCNU), cyclothosphamide, busulfan, dibromomannitol, streptozotocin, mitomycin C, and cis-dichlorodiamine platinum(II) (DDP) cisplatin), anthracyclines (e.g., daunorubicin (formerly daunomycin) and doxorubicin), antibiotics (e.g., dactinomycin (formerly actinomycin), bleomycin, mithramycin, and anthramycin (AMC)), and anti-mitotic agents (e.g., vincristine and vinblastine).

The conjugates of the invention can be used for modifying a given biological response, the therapeutic agent or drug moiety is not to be construed as limited to classical chemical therapeutic agents. For example, the drug moiety may be a protein or polypeptide possessing a desired biological activity. Such proteins may include, for example, a toxin such as abrin, ricin A, pseudomonas exotoxin, or diphtheria toxin; a protein such as tumor necrosis factor, alpha-interferon, beta-interferon, nerve growth factor, platelet derived growth factor, tissue plasminogen activator, an apoptotic agent, e.g., TNF-alpha, TNF-beta, AIM I (See, International Publication No. WO 97/33899), AIM II (See, International Publication No. WO 97/34911), Fas Ligand (Takahashi et al., *Int. Immunol.*, 6:1567-1574 (1994)), VEGI (See, International Publication No. WO 99/23105), CD40 Ligand, a thrombotic agent or an anti-angiogenic agent, e.g., angiostatin or endostatin; or, biological response modifiers such as, for example, lymphokines, interleukin-1 ("IL-1"), interleukin-2 ("IL-2"), interleukin-6 ("IL-6"), granulocyte macrophage colony stimulating factor ("GM-CSF"), granulocyte colony stimulating factor ("G-CSF"), or other growth factors.

Antibodies may also be attached to solid supports, which are particularly useful for immunoassays or purification of the target antigen. Such solid supports include, but are not limited to, glass, cellulose, polyacrylamide, nylon, polystyrene, polyvinyl chloride or polypropylene.

Techniques for conjugating such therapeutic moiety to antibodies are well known, see, e.g., Arnon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985); "Analysis, Results, And Future Prospective Of The Therapeutic Use Of Radiolabeled Antibody In Cancer Therapy", in Monoclonal Antibodies For Cancer Detection And Therapy, Baldwin et al. (eds.), pp. 303-16 (Academic Press 1985), and Thorpe et al., "The Preparation And Cytotoxic Properties Of Antibody-Toxin Conjugates", Immunol. Rev. 62:119-58 (1982).

Alternatively, an antibody can be conjugated to a second antibody to form an antibody heteroconjugate as described by Segal in U.S. Pat. No. 4,676,980, which is incorporated herein by reference in its entirety.

An antibody, with or without a therapeutic moiety conjugated to it, administered alone or in combination with cytotoxic factor(s) and/or cytokine(s) can be used as a therapeutic.

Immunophenotyping

The antibodies of the invention may be utilized for immunophenotyping of cell lines and biological samples. The translation product of the gene of the present invention may be useful as a cell specific marker, or more specifically as a cellular marker that is differentially expressed at various stages of differentiation and/or maturation of particular cell types. Monoclonal antibodies directed against a specific epitope, or combination of epitopes, will allow for the screening of cellular populations expressing the marker. Various techniques can be utilized using monoclonal antibodies to screen for cellular populations expressing the marker(s), and include magnetic separation using antibody-coated magnetic beads, "panning" with antibody attached to a solid matrix (i.e., plate), and flow cytometry (See, e.g., U.S. Pat. No. 5,985,660; and Morrison et al., *Cell*, 96:737-49 (1999)).

These techniques allow for the screening of particular populations of cells, such as might be found with hematological malignancies (i.e. minimal residual disease (MRD) in acute leukemic patients) and "non-self" cells in transplantations to prevent Graft-versus-Host Disease (GVHD). Alternatively, these techniques allow for the screening of hematopoietic stem and progenitor cells capable of undergoing proliferation and/or differentiation, as might be found in human umbilical cord blood.

Assays for Antibody Binding

The antibodies of the invention may be assayed for immunospecific binding by any method known in the art. The immunoassays which can be used include but are not limited to competitive and non-competitive assay systems using techniques such as western blots, radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art (see, e.g., Ausubel et al, eds, 1994, Current Protocols in Molecular Biology, Vol. 1, John Wiley & Sons, Inc., New York, which is incorporated by reference herein in its entirety). Exemplary immunoassays are described briefly below (but are not intended by way of limitation).

Immunoprecipitation protocols generally comprise lysing a population of cells in a lysis buffer such as RIPA buffer (1% NP-40 or Triton X-100, 1% sodium deoxycholate, 0.1% SDS, 0.15 M NaCl, 0.01 M sodium phosphate at pH 7.2, 1% Trasylol) supplemented with protein phosphatase and/or protease inhibitors (e.g., EDTA, PMSF, aprotinin, sodium vanadate), adding the antibody of interest to the cell lysate, incubating for a period of time (e.g., 1-4 hours) at 4° C., adding protein A and/or protein G sepharose beads to the cell lysate, incubating for about an hour or more at 4° C., washing the beads in lysis buffer and resuspending the beads in SDS/sample buffer. The ability of the antibody of interest to immunoprecipitate a particular antigen can be assessed by, e.g., western blot analysis. One of skill in the art would be knowledgeable as to the parameters that can be modified to increase the binding of the antibody to an antigen and decrease the background (e.g., pre-clearing the cell lysate with sepharose beads). For further discussion regarding immunoprecipitation protocols see, e.g., Ausubel et al, eds, 1994, Current Protocols in Molecular Biology, Vol. 1, John Wiley & Sons, Inc., New York at 10.16.1.

Western blot analysis generally comprises preparing protein samples, electrophoresis of the protein samples in a polyacrylamide gel (e.g., 8%-20% SDS-PAGE depending on the molecular weight of the antigen), transferring the protein sample from the polyacrylamide gel to a membrane such as nitrocellulose, PVDF or nylon, blocking the membrane in blocking solution (e.g., PBS with 3% BSA or non-fat milk), washing the membrane in washing buffer (e.g., PBS-Tween 20), blocking the membrane with primary antibody (the antibody of interest) diluted in blocking buffer, washing the membrane in washing buffer, blocking the membrane with a secondary antibody (which recognizes the primary antibody, e.g., an anti-human antibody) conjugated to an enzymatic substrate (e.g., horseradish peroxidase or alkaline phosphatase) or radioactive molecule (e.g., $^{32}P$ or $^{125}I$) diluted in blocking buffer, washing the membrane in wash buffer, and detecting the presence of the antigen. One of skill in the art would be knowledgeable as to the parameters that can be modified to increase the signal detected and to reduce the background noise. For further discussion regarding western blot protocols see, e.g., Ausubel et al, eds, 1994, Current Protocols in Molecular Biology, Vol. 1, John Wiley & Sons, Inc., New York at 10.8.1.

ELISAs comprise preparing antigen, coating the well of a 96 well microtiter plate with the antigen, adding the antibody of interest conjugated to a detectable compound such as an enzymatic substrate (e.g., horseradish peroxidase or alkaline phosphatase) to the well and incubating for a period of time, and detecting the presence of the antigen. In ELISAs the antibody of interest does not have to be conjugated to a detectable compound; instead, a second antibody (which recognizes the antibody of interest) conjugated to a detectable compound may be added to the well. Further, instead of coating the well with the antigen, the antibody may be coated to the well. In this case, a second antibody conjugated to a detectable compound may be added following the addition of the antigen of interest to the coated well. One of skill in the art would be knowledgeable as to the parameters that can be modified to increase the signal detected as well as other variations of ELISAs known in the art. For further discussion regarding ELISAs see, e.g., Ausubel et al, eds, 1994, Current Protocols in Molecular Biology, Vol. 1, John Wiley & Sons, Inc., New York at 11.2.1.

The binding affinity of an antibody to an antigen and the off-rate of an antibody-antigen interaction can be determined by competitive binding assays. One example of a competitive binding assay is a radioimmunoassay comprising the incubation of labeled antigen (e.g., 3H or 125I) with the antibody of interest in the presence of increasing amounts of unlabeled antigen, and the detection of the antibody bound to the labeled antigen. The affinity of the antibody of interest for a particular antigen and the binding off-rates can be determined from the data by scatchard plot analysis. Competition with a second antibody can also be determined using radioimmunoassays. In this case, the antigen is incubated with antibody of interest conjugated to a labeled compound (e.g., $^3H$ or $^{125}I$) in the presence of increasing amounts of an unlabeled second antibody.

Therapeutic Uses

The present invention is further directed to antibody-based therapies which involve administering antibodies of the invention to an animal, preferably a mammal, and most preferably a human, patient for treating, detecting, and/or preventing one or more of the disclosed diseases, disorders, or conditions. Therapeutic compounds of the invention include, but are not limited to, antibodies of the invention (including fragments, analogs and derivatives thereof as described herein) and nucleic acids encoding antibodies of the invention (including fragments, analogs and derivatives thereof and anti-idiotypic antibodies as described herein). The antibodies of the invention can be used to treat, diagnose, inhibit or prevent diseases, disorders or conditions associated with aberrant expression and/or activity of a polypeptide of the invention, including, but not limited to, any one or more of the diseases, disorders, or conditions described herein (e.g., autoimmune diseases, disorders, or conditions associated with such diseases or disorders, including, but not limited to, autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis, systemic lupus erythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders).

In a specific embodiment, antibodies of the invention are be used to treat, inhibit, prognose, diagnose or prevent rheumatoid arthritis.

In another specific embodiment, antibodies of the invention are used to treat, inhibit, prognose, diagnose or prevent systemic lupus erythematosis. The treatment, detection, and/or prevention of diseases, disorders, or conditions associated with aberrant expression and/or activity of a polypeptide of the invention includes, but is not limited to, alleviating symptoms associated with those diseases, disorders or conditions.

Antibodies of the invention may be provided in pharmaceutically acceptable compositions as known in the art or as described herein.

A summary of the ways in which the antibodies of the present invention may be used therapeutically includes binding polynucleotides or polypeptides of the present invention locally or systemically in the body or by direct cytotoxicity of the antibody, e.g. as mediated by complement (CDC) or by effector cells (ADCC). Some of these approaches are described in more detail below. Armed with the teachings provided herein, one of ordinary skill in the art will know how to use the antibodies of the present invention for diagnostic, monitoring or therapeutic purposes without undue experimentation.

The antibodies of this invention may be advantageously utilized in combination with other monoclonal or chimeric antibodies, or with lymphokines or hematopoietic growth factors (such as, e.g., IL-2, IL-3 and IL-7), for example, which serve to increase the number or activity of effector cells which interact with the antibodies.

The antibodies of the invention may be administered alone or in combination with other types of treatments (e.g., radiation therapy, chemotherapy, hormonal therapy, immunotherapy and anti-tumor agents, antibiotics, and immunoglobulin). Generally, administration of products of a species origin or species reactivity (in the case of antibodies) that is the same species as that of the patient is preferred. Thus, in a preferred embodiment, human antibodies, fragments derivatives, analogs, or nucleic acids, are administered to a human patient for therapy or prophylaxis.

It is preferred to use high affinity and/or potent in vivo inhibiting and/or neutralizing antibodies against polypeptides or polynucleotides of the present invention, fragments or regions thereof, for both immunoassays directed to and therapy of disorders related to polynucleotides or polypeptides, including fragments thereof, of the present invention. Such antibodies, fragments, or regions, will preferably have an affinity for polynucleotides or polypeptides of the invention, including fragments thereof. Preferred binding affinities include those with a dissociation constant or Kd less than $5 \times 10^{-2}$ M, $10^{-2}$ M, $5 \times 10^{-3}$ M, $10^{-3}$ M, $5 \times 10^{-4}$ M, $10^{-4}$ M, $5 \times 10^{-5}$ M, $10^{-5}$ M, $5 \times 10^{-6}$ M, $10^{-6}$ M, $5 \times 10^{-7}$ M, $10^{-7}$ M, $5 \times 10^{-8}$ M, $10^{-8}$ M, $5 \times 10^{-9}$ M, $10^{-9}$ M, $5 \times 10^{-10}$ M, $10^{-10}$ M, $5 \times 10^{-11}$ M, $10^{-11}$ M, $5 \times 10^{-12}$ M, $10^{-12}$ M, $5 \times 10^{-13}$ M, $10^{-13}$ M, $5 \times 10^{-14}$ M, $10^{-14}$ M, $5 \times 10^{-15}$ M, and $10^{-15}$ M.

Gene Therapy

In a specific embodiment, nucleic acids comprising sequences encoding antibodies or functional derivatives thereof, are administered to treat, inhibit or prevent a disease or disorder associated with aberrant expression and/or activity of a polypeptide of the invention, by way of gene therapy. Gene therapy refers to therapy performed by the administration to a subject of an expressed or expressible nucleic acid. In this embodiment of the invention, the nucleic acids produce their encoded protein that mediates a therapeutic effect.

Any of the methods for gene therapy available in the art can be used according to the present invention. Exemplary methods are described below.

For general reviews of the methods of gene therapy, see Goldspiel et al., Clinical Pharmacy 12:488-505 (1993); Wu and Wu, Biotherapy 3:87-95 (1991); Tolstoshev, Ann. Rev. Pharmacol. Toxicol. 32:573-596 (1993); Mulligan, Science 260:926-932 (1993); and Morgan and Anderson, Ann. Rev. Biochem. 62:191-217 (1993); May, TIBTECH 11(5):155-215 (1993). Methods commonly known in the art of recombinant DNA technology which can be used are described in Ausubel et al. (eds.), Current Protocols in Molecular Biology, John Wiley & Sons, NY (1993); and Kriegler, Gene Transfer and Expression, A Laboratory Manual, Stockton Press, NY (1990).

In a preferred aspect, the compound comprises nucleic acid sequences encoding an antibody, said nucleic acid sequences being part of expression vectors that express the antibody or fragments or chimeric proteins or heavy or light chains thereof in a suitable host. In particular, such nucleic acid sequences have promoters operably linked to the antibody coding region, said promoter being inducible or constitutive, and, optionally, tissue-specific. In another particular embodiment, nucleic acid molecules are used in which the antibody coding sequences and any other desired sequences are flanked by regions that promote homologous recombination at a desired site in the genome, thus providing for intrachromosomal expression of the antibody encoding nucleic acids (Koller and Smithies, Proc. Natl. Acad. Sci. USA 86:8932-8935 (1989); Zijlstra et al., Nature 342:435-438 (1989). In specific embodiments, the expressed antibody molecule is a single chain antibody; alternatively, the nucleic acid sequences include sequences encoding both the heavy and light chains, or fragments thereof, of the antibody.

Delivery of the nucleic acids into a patient may be either direct, in which case the patient is directly exposed to the nucleic acid or nucleic acid-carrying vectors, or indirect, in which case, cells are first transformed with the nucleic acids in vitro, then transplanted into the patient. These two approaches are known, respectively, as in vivo or ex vivo gene therapy.

In a specific embodiment, the nucleic acid sequences are directly administered in vivo, where it is expressed to produce the encoded product. This can be accomplished by any of numerous methods known in the art, e.g., by constructing them as part of an appropriate nucleic acid expression vector and administering it so that they become intracellular, e.g., by infection using defective or attenuated retrovirals or other viral vectors (see U.S. Pat. No. 4,980,286), or by direct injection of naked DNA, or by use of microparticle bombardment (e.g., a gene gun; Biolistic, Dupont), or coating with lipids or cell-surface receptors or transfecting agents, encapsulation in liposomes, microparticles, or microcapsules, or by administering them in linkage to a peptide which is known to enter the nucleus, by administering it in linkage to a ligand subject to receptor-mediated endocytosis (see, e.g., Wu and Wu, J. Biol. Chem. 262:4429-4432 (1987)) (which can be used to target cell types specifically expressing the receptors), etc. In another embodiment, nucleic acid-ligand complexes can be formed in which the ligand comprises a fusogenic viral peptide to disrupt endosomes, allowing the nucleic acid to avoid lysosomal degradation. In yet another embodiment, the nucleic acid can be targeted in vivo for cell specific uptake and expression, by targeting a specific receptor (see, e.g., PCT Publications WO 92/06180; WO 92/22635; WO92/20316; WO93/14188, WO 93/20221). Alternatively, the nucleic acid can be introduced intracellularly and incorporated within host cell DNA for expression, by homologous recombination (Koller and Smithies, Proc. Natl. Acad. Sci. USA 86:8932-8935 (1989); Zijlstra et al., Nature 342:435-438 (1989)).

In a specific embodiment, viral vectors that contains nucleic acid sequences encoding an antibody of the invention are used. For example, a retroviral vector can be used (see Miller et al., Meth. Enzymol. 217:581-599 (1993)). These retroviral vectors contain the components necessary for the correct packaging of the viral genome and integration into the host cell DNA. The nucleic acid sequences encoding the antibody to be used in gene therapy are cloned into one or more vectors, which facilitates delivery of the gene into a patient. More detail about retroviral vectors can be found in Boesen et al., Biotherapy 6:291-302 (1994), which describes the use of a retroviral vector to deliver the mdr1 gene to hematopoietic stem cells in order to make the stem cells more resistant to chemotherapy. Other references illustrating the use of retroviral vectors in gene therapy are: Clowes et al., J. Clin. Invest. 93:644-651 (1994); Kiem et al., Blood 83:1467-1473 (1994); Salmons and Gunzberg, Human Gene Therapy 4:129-141 (1993); and Grossman and Wilson, Curr. Opin. in Genetics and Devel. 3:110-114 (1993).

Adenoviruses are other viral vectors that can be used in gene therapy. Adenoviruses are especially attractive vehicles for delivering genes to respiratory epithelia. Adenoviruses naturally infect respiratory epithelia where they cause a mild disease. Other targets for adenovirus-based delivery systems are liver, the central nervous system, endothelial cells, and muscle. Adenoviruses have the advantage of being capable of infecting non-dividing cells. Kozarsky and Wilson, Current Opinion in Genetics and Development 3:499-503 (1993) present a review of adenovirus-based gene therapy. Bout et al., Human Gene Therapy 5:3-10 (1994) demonstrated the use of adenovirus vectors to transfer genes to the respiratory epithelia of rhesus monkeys. Other instances of the use of adenoviruses in gene therapy can be found in Rosenfeld et al., Science 252:431-434 (1991); Rosenfeld et al., Cell 68:143-155 (1992); Mastrangeli et al., J. Clin. Invest. 91:225-234 (1993); PCT Publication WO94/12649; and Wang, et al., Gene Therapy 2:775-783 (1995). In a preferred embodiment, adenovirus vectors are used.

Adeno-associated virus (AAV) has also been proposed for use in gene therapy (Walsh et al., Proc. Soc. Exp. Biol. Med. 204:289-300 (1993); U.S. Pat. No. 5,436,146).

Another approach to gene therapy involves transferring a gene to cells in tissue culture by such methods as electroporation, lipofection, calcium phosphate mediated transfection, or viral infection. Usually, the method of transfer includes the transfer of a selectable marker to the cells. The cells are then placed under selection to isolate those cells that have taken up and are expressing the transferred gene. Those cells are then delivered to a patient.

In this embodiment, the nucleic acid is introduced into a cell prior to administration in vivo of the resulting recombinant cell. Such introduction can be carried out by any method known in the art, including but not limited to transfection, electroporation, microinjection, infection with a viral or bacteriophage vector containing the nucleic acid sequences, cell fusion, chromosome-mediated gene transfer, microcell-mediated gene transfer, spheroplast fusion, etc. Numerous techniques are known in the art for the introduction of foreign genes into cells (see, e.g., Loeffler and Behr, Meth. Enzymol. 217:599-618 (1993); Cohen et al., Meth. Enzymol. 217:618-644 (1993); Cline, Pharmac. Ther. 29:69-92m (1985) and may be used in accordance with the present invention, provided that the necessary developmental and physiological functions of the recipient cells are not disrupted. The technique should provide for the stable transfer of the nucleic acid to the cell, so that the nucleic acid is expressible by the cell and preferably heritable and expressible by its cell progeny.

The resulting recombinant cells can be delivered to a patient by various methods known in the art. Recombinant blood cells (e.g., hematopoietic stem or progenitor cells) are preferably administered intravenously. The amount of cells envisioned for use depends on the desired effect, patient state, etc., and can be determined by one skilled in the art.

Cells into which a nucleic acid can be introduced for purposes of gene therapy encompass any desired, available cell type, and include but are not limited to epithelial cells, endothelial cells, keratinocytes, fibroblasts, muscle cells, hepatocytes; blood cells such as T lymphocytes, B lymphocytes, monocytes, macrophages, neutrophils, eosinophils, megakaryocytes, granulocytes; various stem or progenitor cells, in particular hematopoietic stem or progenitor cells, e.g., as obtained from bone marrow, umbilical cord blood, peripheral blood, fetal liver, etc.

In a preferred embodiment, the cell used for gene therapy is autologous to the patient.

In an embodiment in which recombinant cells are used in gene therapy, nucleic acid sequences encoding an antibody are introduced into the cells such that they are expressible by the cells or their progeny, and the recombinant cells are then administered in vivo for therapeutic effect. In a specific embodiment, stem or progenitor cells are used. Any stem and/or progenitor cells which can be isolated and maintained in vitro can potentially be used in accordance with this embodiment of the present invention (see e.g. PCT Publication WO 94/08598; Stemple and Anderson, Cell 71:973-985 (1992); Rheinwald, Meth. Cell Bio. 21A:229 (1980); and Pittelkow and Scott, Mayo Clinic Proc. 61:771 (1986)).

In a specific embodiment, the nucleic acid to be introduced for purposes of gene therapy comprises an inducible promoter operably linked to the coding region, such that expression of the nucleic acid is controllable by controlling the presence or absence of the appropriate inducer of transcription.

Demonstration of Therapeutic or Prophylactic Activity

The compounds or pharmaceutical compositions of the invention are preferably tested in vitro, and then in vivo for the desired therapeutic or prophylactic activity, prior to use in humans. For example, in vitro assays to demonstrate the therapeutic or prophylactic utility of a compound or pharmaceutical composition include, the effect of a compound on a cell line or a patient tissue sample. The effect of the compound or composition on the cell line and/or tissue sample can be determined utilizing techniques known to those of skill in the art including, but not limited to, rosette formation assays and cell lysis assays. In accordance with the invention, in vitro assays which can be used to determine whether administration of a specific compound is indicated, include in vitro cell culture assays in which a patient tissue sample is grown in culture, and exposed to or otherwise administered a compound, and the effect of such compound upon the tissue sample is observed.

Therapeutic/Prophylactic Administration and Composition

The invention provides methods of treatment, inhibition and prophylaxis by administration to a subject of an effective amount of a compound or pharmaceutical composition of the invention, preferably an antibody of the invention. In a preferred aspect, the compound is substantially purified (e.g., substantially free from substances that limit its effect or produce undesired side-effects). The subject is preferably an animal, including but not limited to animals such as cows, pigs, horses, chickens, cats, dogs, etc., and is preferably a mammal, and most preferably human.

Formulations and methods of administration that can be employed when the compound comprises a nucleic acid or an immunoglobulin are described above; additional appropriate formulations and routes of administration can be selected from among those described herein below.

Various delivery systems are known and can be used to administer a compound of the invention, e.g., encapsulation in liposomes, microparticles, microcapsules, recombinant cells capable of expressing the compound, receptor-mediated endocytosis (see, e.g., Wu and Wu, J. Biol. Chem. 262:4429-

4432 (1987)), construction of a nucleic acid as part of a retroviral or other vector, etc. Methods of introduction include but are not limited to intradermal, intramuscular, intraperitoneal, intravenous, subcutaneous, intranasal, epidural, and oral routes. The compounds or compositions may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local. In addition, it may be desirable to introduce the pharmaceutical compounds or compositions of the invention into the central nervous system by any suitable route, including intraventricular and intrathecal injection; intraventricular injection may be facilitated by an intraventricular catheter, for example, attached to a reservoir, such as an Ommaya reservoir. Pulmonary administration can also be employed, e.g., by use of an inhaler or nebulizer, and formulation with an aerosolizing agent.

In a specific embodiment, it may be desirable to administer the pharmaceutical compounds or compositions of the invention locally to the area in need of treatment; this may be achieved by, for example, and not by way of limitation, local infusion during surgery, topical application, e.g., in conjunction with a wound dressing after surgery, by injection, by means of a catheter, by means of a suppository, or by means of an implant, said implant being of a porous, non-porous, or gelatinous material, including membranes, such as silastic membranes, or fibers. Preferably, when administering a protein, including an antibody, of the invention, care must be taken to use materials to which the protein does not absorb.

In another embodiment, the compound or composition can be delivered in a vesicle, in particular a liposome (see Langer, Science 249:1527-1533 (1990); Treat et al., in Liposomes in the Therapy of Infectious Disease and Cancer, Lopez-Berestein and Fidler (eds.), Liss, New York, pp. 353-365 (1989); Lopez-Berestein, ibid., pp. 317-327; see generally ibid.)

In yet another embodiment, the compound or composition can be delivered in a controlled release system. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321: 574 (1989)). In another embodiment, polymeric materials can be used (see Medical Applications of Controlled Release, Langer and Wise (eds.), CRC Pres., Boca Raton, Fla. (1974); Controlled Drug Bioavailability, Drug Product Design and Performance, Smolen and Ball (eds.), Wiley, New York (1984); Ranger and Peppas, J., Macromol. Sci. Rev. Macromol. Chem. 23:61 (1983); see also Levy et al., Science 228: 190 (1985); During et al., Ann. Neurol. 25:351 (1989); Howard et al., J. Neurosurg. 71:105 (1989)). In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115-138 (1984)).

Other controlled release systems are discussed in the review by Langer (Science 249:1527-1533 (1990)).

In a specific embodiment where the compound of the invention is a nucleic acid encoding a protein, the nucleic acid can be administered in vivo to promote expression of its encoded protein, by constructing it as part of an appropriate nucleic acid expression vector and administering it so that it becomes intracellular, e.g., by use of a retroviral vector (see U.S. Pat. No. 4,980,286), or by direct injection, or by use of microparticle bombardment (e.g., a gene gun; Biolistic, Dupont), or coating with lipids or cell-surface receptors or transfecting agents, or by administering it in linkage to a homeobox-like peptide which is known to enter the nucleus (see e.g., Joliot et al., Proc. Natl. Acad. Sci. USA 88:1864-1868 (1991)), etc. Alternatively, a nucleic acid can be introduced intracellularly and incorporated within host cell DNA for expression, by homologous recombination.

The present invention also provides pharmaceutical compositions. Such compositions comprise a therapeutically effective amount of a compound, and a pharmaceutically acceptable carrier. In a specific embodiment, the term "pharmaceutically acceptable" means approved by a regulatory agency of the Federal or a state government or listed in the U.S. Pharmacopeia or other generally recognized pharmacopeia for use in animals, and more particularly in humans. The term "carrier" refers to a diluent, adjuvant, excipient, or vehicle with which the therapeutic is administered. Such pharmaceutical carriers can be sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The composition, if desired, can also contain minor amounts of wetting or emulsifying agents, or pH buffering agents. These compositions can take the form of solutions, suspensions, emulsion, tablets, pills, capsules, powders, sustained-release formulations and the like. The composition can be formulated as a suppository, with traditional binders and carriers such as triglycerides. Oral formulation can include standard carriers such as pharmaceutical grades of mannitol, lactose, starch, magnesium stearate, sodium saccharine, cellulose, magnesium carbonate, etc. Examples of suitable pharmaceutical carriers are described in "Remington's Pharmaceutical Sciences" by E. W. Martin. Such compositions will contain a therapeutically effective amount of the compound, preferably in purified form, together with a suitable amount of carrier so as to provide the form for proper administration to the patient. The formulation should suit the mode of administration.

In a preferred embodiment, the composition is formulated in accordance with routine procedures as a pharmaceutical composition adapted for intravenous administration to human beings. Typically, compositions for intravenous administration are solutions in sterile isotonic aqueous buffer. Where necessary, the composition may also include a solubilizing agent and a local anesthetic such as lignocaine to ease pain at the site of the injection. Generally, the ingredients are supplied either separately or mixed together in unit dosage form, for example, as a dry lyophilized powder or water free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients may be mixed prior to administration.

The compounds of the invention can be formulated as neutral or salt forms. Pharmaceutically acceptable salts include those formed with anions such as those derived from hydrochloric, phosphoric, acetic, oxalic, tartaric acids, etc., and those formed with cations such as those derived from sodium, potassium, ammonium, calcium, ferric hydroxides, isopropylamine, triethylamine, 2-ethylamino ethanol, histidine, procaine, etc.

The amount of the compound of the invention which will be effective in the treatment, inhibition and prevention of a disease or disorder associated with aberrant expression and/or activity of a polypeptide of the invention can be determined by standard clinical techniques. In addition, in vitro assays may optionally be employed to help identify optimal dosage ranges. The precise dose to be employed in the formulation will also depend on the route of administration, and the seriousness of the disease or disorder, and should be decided according to the judgment of the practitioner and each patient's circumstances. Effective doses may be extrapolated from dose-response curves derived from in vitro or animal model test systems.

For antibodies, the dosage administered to a patient is typically 0.1 mg/kg to 100 mg/kg of the patient's body weight. Preferably, the dosage administered to a patient is between 0.1 mg/kg and 20 mg/kg of the patient's body weight, more preferably 1 mg/kg to 10 mg/kg of the patient's body weight. Generally, human antibodies have a longer half-life within the human body than antibodies from other species due to the immune response to the foreign polypeptides. Thus, lower dosages of human antibodies and less frequent administration is often possible. Further, the dosage and frequency of administration of antibodies of the invention may be reduced by enhancing uptake and tissue penetration (e.g., into the brain) of the antibodies by modifications such as, for example, lipidation.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

Diagnosis and Imaging

Labeled antibodies, and derivatives and analogs thereof, which specifically bind to a polypeptide of interest can be used for diagnostic purposes to detect, diagnose, or monitor diseases and/or disorders associated with the aberrant expression and/or activity of a polypeptide of the invention. The invention provides for the detection of aberrant expression of a polypeptide of interest, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of aberrant expression.

The invention provides a diagnostic assay for diagnosing a disorder, comprising (a) assaying the expression of the polypeptide of interest in cells or body fluid of an individual using one or more antibodies specific to the polypeptide interest and (b) comparing the level of gene expression with a standard gene expression level, whereby an increase or decrease in the assayed polypeptide gene expression level compared to the standard expression level is indicative of a particular disorder. With respect to cancer, the presence of a relatively high amount of transcript in biopsied tissue from an individual may indicate a predisposition for the development of the disease, or may provide a means for detecting the disease prior to the appearance of actual clinical symptoms. A more definitive diagnosis of this type may allow health professionals to employ preventative measures or aggressive treatment earlier thereby preventing the development or further progression of the cancer.

Antibodies of the invention can be used to assay protein levels in a biological sample using classical immunohistological methods known to those of skill in the art (e.g., see Jalkanen, et al., J. Cell. Biol. 101:976-985 (1985); Jalkanen, et al., J. Cell. Biol. 105:3087-3096 (1987)). Other antibody-based methods useful for detecting protein gene expression include immunoassays, such as the enzyme linked immunosorbent assay (ELISA) and the radioimmunoassay (RIA). Suitable antibody assay labels are known in the art and include enzyme labels, such as, glucose oxidase; radioisotopes, such as iodine ($^{131}$I, $^{125}$I, $^{123}$I, $^{121}$I), carbon ($^{14}$C), sulfur ($^{35}$S), tritium ($^{3}$H), indium ($^{115m}$In, $^{113m}$In, $^{112}$In, $^{111}$In), and technetium ($^{99}$Tc, $^{99m}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$Sm, $^{177}$Lu, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru; luminescent labels, such as luminol; and fluorescent labels, such as fluorescein and rhodamine, and biotin.

Techniques known in the art may be applied to label antibodies of the invention. Such techniques include, but are not limited to, the use of bifunctional conjugating agents (see e.g., U.S. Pat. Nos. 5,756,065; 5,714,631; 5,696,239; 5,652,361; 5,505,931; 5,489,425; 5,435,990; 5,428,139; 5,342,604; 5,274,119; 4,994,560; and 5,808,003; the contents of each of which are hereby incorporated by reference in its entirety).

One aspect of the invention is the detection and diagnosis of a disease or disorder associated with aberrant expression of a polypeptide of interest in an animal, preferably a mammal and most preferably a human. In one embodiment, diagnosis comprises: a) administering (for example, parenterally, subcutaneously, or intraperitoneally) to a subject an effective amount of a labeled molecule which specifically binds to the polypeptide of interest; b) waiting for a time interval following the administering for permitting the labeled molecule to preferentially concentrate at sites in the subject where the polypeptide is expressed (and for unbound labeled molecule to be cleared to background level); c) determining background level; and d) detecting the labeled molecule in the subject, such that detection of labeled molecule above the background level indicates that the subject has a particular disease or disorder associated with aberrant expression of the polypeptide of interest. Background level can be determined by various methods including, comparing the amount of labeled molecule detected to a standard value previously determined for a particular system.

As described herein, specific embodiments of the invention are directed to the use of the antibodies of the invention to quantitate or qualitate concentrations of cells of B cell lineage or cells of monocytic lineage.

Also as described herein, antibodies of the invention may be used to treat, diagnose, or prognose an individual having an immunodeficiency. In a specific embodiment, antibodies of the invention are used to treat, diagnose, and/or prognose an individual having common variable immunodeficiency disease (CVID) or a subset of this disease. In another embodiment, antibodies of the invention are used to diagnose, prognose, treat or prevent a disorder characterized by deficient serum immunoglobulin production, recurrent infections, and/or immune system dysfunction.

Also as described herein, antibodies of the invention may be used to treat, diagnose, or prognose an individual having an autoimmune disease or disorder. In a specific embodiment, antibodies of the invention are used to treat, diagnose, and/or prognose an individual having systemic lupus erythematosus, or a subset of the disease. In another specific embodiment, antibodies of the invention are used to treat, diagnose and/or prognose an individual having rheumatoid arthritis, or a subset of this disease.

It will be understood in the art that the size of the subject and the imaging system used will determine the quantity of imaging moiety needed to produce diagnostic images. In the case of a radioisotope moiety, for a human subject, the quantity of radioactivity injected will normally range from about 5 to 20 millicuries of $^{99m}$Tc. The labeled antibody or antibody fragment will then preferentially accumulate at the location of cells which contain the specific protein. In vivo tumor imaging is described in S. W. Burchiel et al., "Immunopharmacokinetics of Radiolabeled Antibodies and Their Fragments." (Chapter 13 in Tumor Imaging: The Radiochemical Detection of Cancer, S. W. Burchiel and B. A. Rhodes, eds., Masson Publishing Inc. (1982).

Depending on several variables, including the type of label used and the mode of administration, the time interval following the administration for permitting the labeled molecule to preferentially concentrate at sites in the subject and for unbound labeled molecule to be cleared to background level is 6 to 48 hours or 6 to 24 hours or 6 to 12 hours. In another embodiment the time interval following administration is 5 to 20 days or 5 to 10 days.

In an embodiment, monitoring of the disease or disorder is carried out by repeating the method for diagnosing the disease or disease, for example, one month after initial diagnosis, six months after initial diagnosis, one year after initial diagnosis, etc.

Presence of the labeled molecule can be detected in the patient using methods known in the art for in vivo scanning. These methods depend upon the type of label used. Skilled artisans will be able to determine the appropriate method for detecting a particular label. Methods and devices that may be used in the diagnostic methods of the invention include, but are not limited to, computed tomography (CT), whole body scan such as position emission tomography (PET), magnetic resonance imaging (MRI), and sonography.

In a specific embodiment, the molecule is labeled with a radioisotope and is detected in the patient using a radiation responsive surgical instrument (Thurston et al., U.S. Pat. No. 5,441,050). In another embodiment, the molecule is labeled with a fluorescent compound and is detected in the patient using a fluorescence responsive scanning instrument. In another embodiment, the molecule is labeled with a positron emitting metal and is detected in the patent using positron emission-tomography. In yet another embodiment, the molecule is labeled with a paramagnetic label and is detected in a patient using magnetic resonance imaging (MRI).

Kits

The present invention provides kits that can be used in the above methods. In one embodiment, a kit comprises an antibody of the invention, preferably a purified antibody, in one or more containers. In a specific embodiment, the kits of the present invention contain a substantially isolated polypeptide comprising an epitope which is specifically immunoreactive with an antibody included in the kit. Preferably, the kits of the present invention further comprise a control antibody which does not react with the polypeptide of interest. In another specific embodiment, the kits of the present invention comprise two or more antibodies (monoclonal and/or polyclonal) that recognize the same and/or different sequences or regions of the polypeptide of the invention. In another specific embodiment, the kits of the present invention contain a means for detecting the binding of an antibody to a polypeptide of interest (e.g., the antibody may be conjugated to a detectable substrate such as a fluorescent compound, an enzymatic substrate, a radioactive compound or a luminescent compound, or a second antibody which recognizes the first antibody may be conjugated to a detectable substrate).

In another specific embodiment of the present invention, the kit is a diagnostic kit for use in screening serum containing antibodies specific against proliferative and/or cancerous polynucleotides and polypeptides. Such a kit may include a control antibody that does not react with the polypeptide of interest. Such a kit may include a substantially isolated polypeptide antigen comprising an epitope which is specifically immunoreactive with at least one anti-polypeptide antigen antibody. Further, such a kit includes means for detecting the binding of said antibody to the antigen (e.g., the antibody may be conjugated to a fluorescent compound such as fluorescein or rhodamine which can be detected by flow cytometry). In specific embodiments, the kit may include a recombinantly produced or chemically synthesized polypeptide antigen. The polypeptide antigen of the kit may also be attached to a solid support.

In a more specific embodiment the detecting means of the above-described kit includes a solid support to which said polypeptide antigen is attached. Such a kit may also include a non-attached reporter-labeled anti-human antibody. In this embodiment, binding of the antibody to the polypeptide antigen can be detected by binding of the said reporter-labeled antibody.

In an additional embodiment, the invention includes a diagnostic kit for use in screening serum containing antigens of the polypeptide of the invention. The diagnostic kit includes a substantially isolated antibody specifically immunoreactive with polypeptide or polynucleotide antigens, and means for detecting the binding of the polynucleotide or polypeptide antigen to the antibody. In one embodiment, the antibody is attached to a solid support. In a specific embodiment, the antibody may be a monoclonal antibody. The detecting means of the kit may include a second, labeled monoclonal antibody. Alternatively, or in addition, the detecting means may include a labeled, competing antigen.

In one diagnostic configuration, test serum is reacted with a solid phase reagent having a surface-bound antigen obtained by the methods of the present invention. After binding with specific antigen antibody to the reagent and removing unbound serum components by washing, the reagent is reacted with reporter-labeled anti-human antibody to bind reporter to the reagent in proportion to the amount of bound anti-antigen antibody on the solid support. The reagent is again washed to remove unbound labeled antibody, and the amount of reporter associated with the reagent is determined. Typically, the reporter is an enzyme which is detected by incubating the solid phase in the presence of a suitable fluorometric, luminescent or calorimetric substrate (Sigma, St. Louis, Mo.).

The solid surface reagent in the above assay is prepared by known techniques for attaching protein material to solid support material, such as polymeric beads, dip sticks, 96-well plate or filter material. These attachment methods generally include non-specific adsorption of the protein to the support or covalent attachment of the protein, typically through a free amine group, to a chemically reactive group on the solid support, such as an activated carboxyl, hydroxyl, or aldehyde group. Alternatively, streptavidin coated plates can be used in conjunction with biotinylated antigen(s).

Thus, the invention provides an assay system or kit for carrying out this diagnostic method. The kit generally includes a support with surface-bound recombinant antigens, and a reporter-labeled anti-human antibody for detecting surface-bound anti-antigen antibody.

The invention further relates to antibodies that act as agonists or antagonists of the polypeptides of the present invention. For example, the present invention includes antibodies that disrupt the receptor/ligand interactions with the polypeptides of the invention either partially or fully. Included are both receptor-specific antibodies and ligand-specific antibodies. Included are receptor-specific antibodies that do not prevent ligand binding but prevent receptor activation. Receptor activation (i.e., signaling) may be determined by techniques described herein or otherwise known in the art. Also included are receptor-specific antibodies which both prevent ligand binding and receptor activation. Likewise, included are neutralizing antibodies which bind the ligand and prevent binding of the ligand to the receptor, as well as antibodies which bind the ligand, thereby preventing receptor activation, but do not prevent the ligand from binding the receptor. Further included are antibodies that activate the receptor. These antibodies may act as agonists for either all or less than all of the biological activities affected by ligand-mediated receptor activation. The antibodies may be specified as agonists or antagonists for biological activities comprising specific activities disclosed herein. Further included are antibodies that bind to TR9 irrespective of whether TR9 is bound to a TR9 ligand. These antibodies act as TR9 agonists as reflected in an increase in cellular proliferation in response to binding of TR9 to a TR9 ligand in the presence of these antibodies. The above antibody agonists can be made using methods known in the art. See e.g., WO 96/40281; U.S. Pat. No. 5,811,097; Deng, B. et al., Blood 92(6):1981-1988 (1998); Chen, Z. et al., Cancer Res. 58(16):3668-3678 (1998); Harrop, J. A. et al., J. Immunol. 161(4):1786-1794 (1998); Zhu, Z. et al., Cancer Res. 58(15):3209-3214 (1998); Yoon, D. Y. et al., J. Immunol. 160(7):3170-3179 (1998); Prat, M. et al., J. Cell. Sci. 111(Pt2):237-247 (1998); Pitard, V. et al., J. Immunol. Methods 205(2):177-190 (1997); Liautard, J. et al., Cytokinde 9(4):233-241 (1997); Carlson, N. G. et al., J. Biol. Chem. 272(17):11295-11301 (1997); Taryman, R. E. et al., Neuron 14(4):755-762 (1995); Muller, Y. A. et al., Structure 6(9):1153-1167 (1998); Bartunek, P. et al., Cytokine 8(1):14-20 (1996) (said references incorporated by reference in their entireties).

The invention encompasses antibodies that inhibit or reduce the ability of TR9 to bind TR9 ligand in vitro and/or in vivo. In a specific embodiment, antibodies of the invention inhibit or reduce the ability of TR9 to bind TR9 ligand in vitro. In another nonexclusive specific embodiment, antibodies of the invention inhibit or reduce the ability of TR9 to bind TR9 ligand in vivo. Such inhibition can be assayed using techniques described herein or otherwise known in the art.

The invention also encompasses, antibodies that bind specifically to TR9, but do not inhibit the ability of TR9 to bind TR9 ligand in vitro and/or in vivo. In a specific embodiment, antibodies of the invention do not inhibit or reduce the ability of TR9 to bind TR9 ligand in vitro. In another nonexclusive specific embodiment, antibodies of the invention do not inhibit or reduce the ability of TR9 to bind TR9 ligand in vivo.

As described above, the invention encompasses antibodies that inhibit or reduce a TR9-mediated biological activity in vitro and/or in vivo. In a specific embodiment, antibodies of the invention inhibit or reduce TR9-mediated B or T cell proliferation in vitro. Such inhibition can be assayed by routinely modifying B or T cell proliferation assays described herein or otherwise known in the art. In another nonexclusive specific embodiment, antibodies of the invention inhibit or reduce TR9-mediated B or T cell proliferation in vivo.

Alternatively, the invention also encompasses, antibodies that bind specifically to a TR9, but do not inhibit or reduce a TR9-mediated biological activity in vitro and/or in vivo (e.g., stimulation of B or T cell proliferation). In a specific embodiment, antibodies of the invention do not inhibit or reduce a TR9-mediated biological activity in vitro. In another nonexclusive embodiment, antibodies of the invention do not inhibit or reduce a TR9-mediated biological activity in vivo.

As described above, the invention encompasses antibodies that specifically bind to the same epitope as at least one of the antibodies specifically referred to herein, in vitro and/or in vivo.

In a specific embodiment, the specific antibodies described above are humanized using techniques described herein or otherwise known in the art and then used as therapeutics as described herein.

In another specific embodiment, any of the antibodies listed above are used in a soluble form.

In another specific embodiment, any of the antibodies listed above are conjugated to a toxin or a label (as described infra). Such conjugated antibodies are used to kill a particular population of cells or to quantitate a particular population of cells. In a preferred embodiment, such conjugated antibodies are used to kill B cells expressing TR9 on their surface. In another preferred embodiment, such conjugated antibodies are used to quantitate B cells expressing TR9 on their surface. In a preferred embodiment, such conjugated antibodies are used to kill T cells expressing TR9 on their surface. In another preferred embodiment, such conjugated antibodies are used to quantitate T cells expressing TR9 on their surface.

In another specific embodiment, any of the antibodies listed above are conjugated to a toxin or a label (as described infra). Such conjugated antibodies are used to kill a particular population of cells or to quantitate a particular population of cells.

The antibodies of the invention also have uses as therapeutics and/or prophylactics which include, but are not limited to, inactivating lymphocytes or blocking lymphocyte activation and/or killing lymphocyte lineages that express TR9 on their cell surfaces (e.g., to treat, prevent, and/or diagnose myeloid leukemias, lymphocyte based leukemias and lymphomas, lymphocytosis, lymphocytopenia, rheumatoid arthritis, and other diseases or conditions associated with activated lymphocytes). In a specific embodiment, the antibodies of the invention fix complement. In other specific embodiments, as further described herein, the antibodies of the invention (or fragments thereof) are associated with heterologous polypeptides or nucleic acids (e.g. toxins, such as, compounds that bind and activate endogenous cytotoxic effecter systems, and radioisotopes; and cytotoxic prodrugs).

In another embodiment, one or more monoclonal antibodies are produced wherein they recognize or bind TR9 and/or a mutein thereof, but do not recognize or bind TR9 and/or a mutein thereof. In a related embodiment, one or more monoclonal antibodies are produced wherein they recognize or bind TR9 and/or a mutein thereof, but do not recognize or bind TR9 and/or a mutein thereof.

As discussed above, antibodies to the TR9 polypeptides of the invention can, in turn, be utilized to generate anti-idiotype antibodies that "mimic" the TR9, using techniques well known to those skilled in the art. (See, e.g., Greenspan & Bona, FASEB J. 7(5):437-444 (1989), and Nissinoff, J. Immunol. 147(8):2429-2438 (1991)). For example, antibodies which bind to TR9 and competitively inhibit TR9 multimerization and/or binding to ligand can be used to generate anti-idiotypes that "mimic" the TR9 TNF multimerization and/or binding domain and, as a consequence, bind to and neutralize TR9 and/or its ligand. Such neutralizing anti-idiotypes or Fab fragments of such anti-idiotypes can be used in therapeutic regimens to neutralize TR9 ligand. For example, such anti-idiotypic antibodies can be used to bind TR9 on the surface of cells of B or T cell lineage, and thereby block TR9-mediated B or T cell activation, proliferation, and/or differentiation.

Polypeptide Assays

The present invention also relates to diagnostic assays such as quantitative and diagnostic assays for detecting levels of TR9 receptor protein, or the soluble form thereof, in cells and tissues, including determination of normal and abnormal levels. Thus, for instance, a diagnostic assay in accordance with the invention for detecting over-expression of TR9, or soluble form thereof, compared to normal control tissue samples may be used to detect the presence of tumors, for example. Assay techniques that can be used to determine levels of a protein, such as a TR9 protein of the present invention, or a soluble form thereof, in a sample derived from a host are well-known to those of skill in the art. Such assay methods include radioimmunoassays, competitive-binding assays, Western Blot analysis and ELISA assays.

Assaying TR9 protein levels in a biological sample can occur using any art-known method. By "biological sample" is intended any biological sample obtained from an individual, cell line, tissue culture, or other source which contains TR9 receptor protein or mRNA. Preferred for assaying TR9 protein levels in a biological sample are antibody-based techniques. For example, TR9 protein expression in tissues can be studied with classical immunohistological methods. (Jalkanen et al., *J. Cell. Biol.* 101:976-985 (1985); Jalkanen et al., *J. Cell Biol.* 105:3087-3096 (1987)). Other antibody-based methods useful for detecting TR9 receptor gene expression include immunoassays, such as the enzyme linked immunosorbent assay (ELISA) and the radioimmunoassay (RIA).

Suitable labels are known in the art and include enzyme labels, such as, glucose oxidase, and radioisotopes, such as iodine ($^{125}$I, $^{121}$I), carbon ($^{14}$C), sulphur ($^{35}$S), tritium ($^3$H), indium ($^{112}$In), and technetium ($^{99m}$Tc), and fluorescent labels, such as fluorescein and rhodamine, and biotin.

Therapeutics

The tumor necrosis factor (TNF) family ligands are known to be among the most pleiotropic cytokines, inducing a large number of cellular responses, including cytotoxicity, antiviral activity, immunoregulatory activities, and the transcriptional regulation of several genes (D. V. Goeddel et al., "Tumor Necrosis Factors: Gene Structure and Biological Activities," *Symp. Quant. Biol.* 51:597-609 (1986), Cold Spring Harbor; B. Beutler and A. Cerami, *Annu. Rev. Biochem.* 57:505-518 (1988); L. J. Old, *Sci. Am.* 258:59-75 (1988); W. Fiers, *FEBS Lett.* 285:199-224 (1991)). The TNF-family ligands induce such various cellular responses by binding to TNF-family receptors, including the TR9 of the present invention. Cells which express the TR9 polypeptide and are believed to have a potent cellular response to TR9 ligands include fetal liver, PBL, lung, kidney, small intestine, colon, keratinocytes, endothelial cells, and monocyte activated tissue. By "a cellular response to a TNF-family ligand" is intended any genotypic, phenotypic, and/or morphologic change to a cell, cell line, tissue, tissue culture or patient that is induced by a TNF-family ligand. As indicated, such cellular responses include not only normal physiological responses to TNF-family ligands, but also diseases associated with increased apoptosis or the inhibition of apoptosis. Apoptosis-programmed cell death-is a physiological mechanism involved in the deletion of peripheral T lymphocytes of the immune system, and its dysregulation can lead to a number of different pathogenic processes (J. C. Ameisen, *AIDS* 8:1197-1213 (1994); P. H. Krammer et al., *Curr. Opin. Immunol* 6:279-289 (1994)).

Diseases associated with increased cell survival, or the inhibition of apoptosis, include cancers (such as follicular lymphomas, carcinomas with p53 mutations, and hormone-dependent tumors, including, but not limited to colon cancer, cardiac tumors, pancreatic cancer, melanoma, retinoblastoma, glioblastoma, lung cancer, intestinal cancer, testicular cancer, stomach cancer, neuroblastoma, myxoma, myoma, lymphoma, endothelioma, osteoblastoma, osteoclastoma, osteosarcoma, chondrosarcoma, adenoma, breast cancer, prostrate cancer, Kaposi's sarcoma and ovarian cancer); autoimmune disorders (such as multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis rheumatoid arthritis); viral infections (such as herpes viruses, pox viruses and adenoviruses); inflammation; graft vs. host disease; acute graft rejection and chronic graft rejection. In preferred embodiments, TNFR polynucleotides, polypeptides, and/or antagonists of the invention are used to inhibit growth, progression, and/or metasis of cancers, in particular those listed above and in the paragraph that follows.

Additional diseases or conditions associated with increased cell survival include, but are not limited to, progression, and/or metastases of malignancies and related disorders such as leukemia (including acute leukemias (e.g., acute lymphocytic leukemia, acute myelocytic leukemia (including myeloblastic, promyelocytic, myelomonocytic, monocytic, and erythroleukemia)) and chronic leukemias (e.g., chronic myelocytic (granulocytic) leukemia and chronic lymphocytic leukemia)), polycythemia vera, lymphomas (e.g., Hodgkin's disease and non-Hodgkin's disease), multiple myeloma, Waldenstrom's macroglobulinemia, heavy chain disease, and solid tumors including, but not limited to, sarcomas and carcinomas such as fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilm's tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Diseases associated with increased apoptosis include AIDS; neurodegenerative disorders (such as Alzheimer's disease, Parkinson's disease, Amyotrophic lateral sclerosis, Retinitis pigmentosa, Cerebellar degeneration); and brain tumor or prior associated disease); autoimmune disorders (such as, multiple sclerosis, Sjogren's syndrome, Hashimoto's thyroiditis, biliary cirrhosis, Behcet's disease, Crohn's disease, polymyositis, systemic lupus erythematosus and immune-related glomerulonephritis and rheumatoid arthritis) myelodysplastic syndromes (such as aplastic anemia), graft v. host disease, ischemic injury (such as that caused by myocardial infarction, stroke and reperfusion injury), liver injury (e.g., hepatitis related liver injury, ischemia/reperfusion injury, cholestosis (bile duct injury) and liver cancer); toxin-induced liver disease (such as that caused by alcohol), septic shock, cachexia and anorexia. In preferred embodiments, TNFR polynucleotides, polypeptides and/or agonists are used to treat, prevent, diagnose, and/or detect the diseases and disorders listed above.

Immunodeficiencies that may be treated, prevented, diagnosed, and/or prognosed with TR9 polynucleotides or polypeptides or TR9 agonists or antagonists (e.g., anti-TR9 antibodies) of the invention, include, but are not limited to one or more immunodeficiencies selected from: severe combined immunodeficiency (SCID)-X linked, SCID-autosomal, adenosine deaminase deficiency (ADA deficiency), X-linked agammaglobulinemia (XLA), Bruton's disease, congenital agammaglobulinemia, X-linked infantile agammaglobulinemia, acquired agammaglobulinemia, adult onset agammaglobulinemia, late-onset agammaglobulinemia, dysgammaglobulinemia, hypogammaglobulinemia, transient hypogammaglobulinemia of infancy, unspecified hypogammaglobulinemia, agammaglobulinemia, common variable immunodeficiency (CVID) (acquired), Wiskott-Aldrich Syndrome (WAS), X-linked immunodeficiency with hyper IgM, non X-linked immunodeficiency with hyper IgM, selective IgA deficiency, IgG subclass deficiency (with or without IgA deficiency), antibody deficiency with normal or elevated Igs, immunodeficiency with thymoma, Ig heavy chain deletions, kappa chain deficiency, B cell lymphoproliferative disorder (BLPD), selective IgM immunodeficiency, recessive agammaglobulinemia (Swiss type), reticular dysgenesis, neonatal neutropenia, severe congenital leukopenia, thymic alymphoplasia-aplasia or dysplasia with immunodeficiency, ataxia-telangiectasia, short limbed dwarfism, X-linked lymphoproliferative syndrome (XLP), Nezelof syndrome-combined immunodeficiency with Igs, purine nucleoside phosphorylase deficiency (PNP), MHC Class II deficiency (Bare Lymphocyte Syndrome) and severe combined immunodeficiency.

Autoimmune diseases or disorders that may be treated, diagnosed, or prognosed using TR9 polynucleotides or polypeptides or TR9 agonists or antagonists (e.g., anti-TR9 antibodies) of the invention include, but are not limited to, one or more of the following: autoimmune hemolytic anemia, autoimmune neonatal thrombocytopenia, idiopathic thrombocytopenia purpura, autoimmunocytopenia, hemolytic anemia, antiphospholipid syndrome, dermatitis, allergic encephalomyelitis, myocarditis, relapsing polychondritis, rheumatic heart disease, glomerulonephritis (e.g., IgA nephropathy), Multiple Sclerosis, Neuritis, Uveitis Ophthalmia, Polyendocrinopathies, Purpura (e.g., Henloch-Scoenlein purpura), Reiter's Disease, Stiff-Man Syndrome, Autoimmune Pulmonary Inflammation, Guillain-Barre Syndrome, insulin dependent diabetes mellitis, and autoimmune inflammatory eye, autoimmune thyroiditis, hypothyroidism (i.e., Hashimoto's thyroiditis, systemic lupus erythematosus, Goodpasture's syndrome, Pemphigus, Receptor autoimmunities such as, for example, (a) Graves' Disease, (b) Myasthenia Gravis, and (c) insulin resistance, autoimmune hemolytic anemia, autoimmune thrombocytopenic purpura, rheumatoid arthritis, schleroderma with anti-collagen antibodies, mixed connective tissue disease, polymyositis/dermatomyositis, pernicious anemia, idiopathic Addison's disease, infertility, glomerulonephritis such as primary glomerulonephritis and IgA nephropathy, bullous pemphigoid, Sjogren's syndrome, diabetes millitus, and adrenergic drug resistance (including adrenergic drug resistance with asthma or cystic fibrosis), chronic active hepatitis, primary biliary cirrhosis, other endocrine gland failure, vitiligo, vasculitis, post-MI, cardiotomy syndrome, urticaria, atopic dermatitis, asthma, inflammatory myopathies, and other inflammatory, granulamatous, degenerative, and atrophic disorders.

TR9 polynucleotides or polypeptides of the invention, or agonists or antagonists thereof, may be used to diagnose, prognose, treat or prevent one or more of the following diseases or disorders, or conditions associated therewith: primary immuodeficiencies, immune-mediated thrombocytopenia, Kawasaki syndrome, bone marrow transplant (e.g., recent bone marrow transplant in adults or children), chronic B-cell lymphocytic leukemia, HIV infection (e.g., adult or pediatric HIV infection), chronic inflammatory demyelinating polyneuropathy, and post-transfusion purpura.

Additionally, TR9 polynucleotides or polypeptides of the invention, or agonists or antagonists thereof, may be used to diagnose, prognose, treat or prevent one or more of the following diseases, disorders, or conditions associated therewith, Guillain-Barre syndrome, anemia (e.g., anemia associated with parvovirus B19, patients with stable multiple myeloma who are at high risk for infection (e.g., recurrent infection), autoimmune hemolytic anemia (e.g., warm-type autoimmune hemolytic anemia), thrombocytopenia (e.g., neonatal thrombocytopenia), and immune-mediated neutropenia), transplantation (e.g., cytamegalovirus (CMV)-negative recipients of CMV-positive organs), hypogammaglobulinemia (e.g., hypogammaglobulinemic neonates with risk factor for infection or morbidity), epilepsy (e.g., intractable epilepsy), systemic vasculitic syndromes, myasthenia gravis (e.g., decompensation in myasthenia gravis), dermatomyositis, and polymyositis.

Administration to an animal (e.g., mouse, rat, rabbit, hamster, guinea pig, pigs, micro-pig, chicken, camel, goat, horse, cow, sheep, dog, cat, non-human primate, and human, most preferably human) to boost the immune system to produce increased quantities of one or more antibodies (e.g., IgG, IgA, IgM, and IgE), to induce higher affinity antibody production (e.g., IgG, IgA, IgM, and IgE), and/or to increase an immune response. In a specific nonexclusive embodiment, TR9 polypeptides of the invention, and/or agonists thereof, are administered to boost the immune system to produce increased quantities of IgG. In another specific nonexclusive embodiment, TR9 polypeptides of the invention and/or agonists thereof, are administered to boost the immune system to produce increased quantities of IgA. In another specific non-exclusive embodiment, TR9 polypeptides of the invention and/or agonists thereof, are administered to boost the immune system to produce increased quantities of IgM.

Assays available to detect levels of soluble receptors are well known to those of skill in the art, for example, radioimmunoassays, competitive-binding assays, Western blot analysis, and preferably an ELISA assay may be employed.

Thus, in one aspect, the present invention is directed to a method for enhancing apoptosis induced by a TNF-family ligand, which involves administering to a cell which expresses the TR9 polypeptide, an effective amount of TR9 ligand, analog or an agonist capable of increasing TR9 mediated signaling. Preferably, TR9 mediated signaling is increased to treat, prevent, diagnose, and/or detect a disease wherein decreased apoptosis or decreased cytokine and adhesion molecule expression is exhibited. Agonists include, but are not limited to, soluble forms of TR9 and antibodies (preferably monoclonal) directed against the TR9 polypeptide.

In a further aspect, the present invention is directed to a method for inhibiting apoptosis induced by a TNF-family ligand, which involves administering to a cell which expresses the TR9 polypeptide an effective amount of an antagonist capable of decreasing TR9 mediated signaling.

Preferably, TR9 mediated signaling is decreased to treat, prevent, diagnose, and/or detect a disease wherein increased apoptosis, NFkB expression and/or JNK expression is exhibited. Antagonists include, but are not limited to, soluble forms of TR9 polypeptide and antibodies (preferably monoclonal) directed against the TR9 polypeptide.

As disclosed in Example 8, a TR9-Fc fusion protein containing a polypeptide sequence located in the extracellular domain of TR9 activates monocytes and increases monocyte survival. Accordingly, in specific embodiments, the invention encompasses methods of stimulating an inflammatory response, which includes administering to a cell (e.g., monocytes in vitro or in vivo) a polynucleotide, polypeptide, agonist, or antagonist of the invention.

Additionally, the invention encompasses a method of enhancing macrophage activity which involves administering to a cell (e.g., monocytes in vitro or in vivo) a polynucleotide, polypeptide, agonist, or antagonist of the invention. In a specific embodiment, a polynucleotide, polypeptide, agonist, or antagonist of the invention is administered as a prophylactic or therapeutic agent to generate resistance to pathogens.

In another embodiment, a polynucleotide, polypeptide, agonist, or antagonist of the invention, which demonstrates anti-inflammatory activity and/or which acts as an antagonist to a TR9-Fc polypeptide, is administered to treat, prevent, diagnose, and/or detect an inflammatory disease. In another embodiment a polynucleotide, polypeptide, agonist, or antagonist of the invention, which demonstrates anti-inflammatory activity and/or which acts as an antagonist to a TR9-Fc polypeptide, is administered to treat, prevent, diagnose, and/or detect a TH1-associated condition. In a specific embodiment, a polynucleotide, polypeptide, agonist, or antagonist of the invention, which demonstrate anti-inflammatory activity and/or which acts as an antagonist to a TR9-Fc polypeptide is administered to treat, prevent, diagnose, and/or detect autoimmune disorders, such as those disclosed herein.

By "agonist" is intended naturally occurring and synthetic compounds capable of enhancing or potentiating apoptosis. By "antagonist" is intended naturally occurring and synthetic compounds capable of inhibiting apoptosis. Whether any candidate "agonist" or "antagonist" of the present invention can enhance or inhibit apoptosis can be determined using art-known TNF-family ligand/receptor cellular response assays, including those described in more detail below.

One such screening procedure involves the use of melanophores which are transfected to express the receptor of the present invention. Such a screening technique is described in PCT WO 92/01810, published Feb. 6, 1992. Such an assay may be employed, for example, for screening for a compound which inhibits (or enhances) activation of the receptor polypeptide of the present invention by contacting the melanophore cells which encode the receptor with both a TNF-family ligand and the candidate antagonist (or agonist). Inhibition or enhancement of the signal generated by the ligand indicates that the compound is an antagonist or agonist of the ligand/receptor signaling pathway.

Other screening techniques include the use of cells which express the receptor (for example, transfected CHO cells) in a system which measures extracellular pH changes caused by receptor activation, for example, as described in *Science* 246: 181-296 (1989). For example, compounds may be contacted with a cell which expresses the receptor polypeptide of the present invention and a second messenger response, e.g., signal transduction or pH changes, may be measured to determine whether the potential compound activates or inhibits the receptor.

Another such screening technique involves introducing RNA encoding the receptor into *Xenopus* oocytes to transiently express the receptor. The receptor oocytes may then be contacted with the receptor ligand and a compound to be screened, followed by detection of inhibition or activation of a calcium signal in the case of screening for compounds which are thought to inhibit activation of the receptor.

Another screening technique well known in the art involves expressing in cells a construct wherein the receptor is linked to a phospholipase C or D. Exemplary cells include endothelial cells, smooth muscle cells, embryonic kidney cells, etc. The screening may be accomplished as hereinabove described by detecting activation of the receptor or inhibition of activation of the receptor from the phospholipase signal.

Another method involves screening for compounds which inhibit activation of the receptor polypeptide of the present invention antagonists by determining inhibition of binding of labeled ligand to cells which have the receptor on the surface thereof. Such a method involves transfecting a eukaryotic cell with DNA encoding the receptor such that the cell expresses the receptor on its surface and contacting the cell with a compound in the presence of a labeled form of a known ligand. The ligand can be labeled, e.g., by radioactivity. The amount of labeled ligand bound to the receptors is measured, e.g., by measuring radioactivity of the receptors. If the compound binds to the receptor as determined by a reduction of labeled ligand which binds to the receptors, the binding of labeled ligand to the receptor is inhibited.

Soluble forms of the polypeptides of the present invention may be utilized in the ligand binding assay described above. These forms of the TR9 receptors are contacted with ligands in the extracellular medium after they are secreted. A determination is then made as to whether the secreted protein will bind to TR9 receptor ligands.

Further screening assays for agonists and antagonists of the present invention are described in Tartaglia et al., *J. Biol. Chem.* 267:4304-4307(1992).

Thus, in a further aspect, a screening method is provided for determining whether a candidate agonist or antagonist is capable of enhancing or inhibiting a cellular response to a TNF-family ligand. The method involves contacting cells which express the TR9 polypeptide with a candidate compound and a TNF-family ligand, assaying a cellular response, and comparing the cellular response to a standard cellular response, the standard being assayed when contact is made with the ligand in absence of the candidate compound, whereby an increased cellular response over the standard indicates that the candidate compound is an agonist of the ligand/receptor signaling pathway and a decreased cellular response compared to the standard indicates that the candidate compound is an antagonist of the ligand/receptor signaling pathway. By "assaying a cellular response" is intended qualitatively or quantitatively measuring a cellular response to a candidate compound and/or a TNF-family ligand (e.g., determining or estimating an increase or decrease in T cell proliferation or tritiated thymidine labeling). By the invention, a cell expressing the TR9 polypeptide can be contacted with either an endogenous or exogenously administered TNF-family ligand.

Agonist according to the present invention include naturally occurring and synthetic compounds such as, for example, TNF family ligand peptide fragments, transforming growth factor, neurotransmitters (such as glutamate, dopamine, N-methyl-D-aspartate), tumor suppressors (p53), cytolytic T cells and antimetabolites. Preferred agonists include chemotherapeutic drugs such as, for example, cisplatin, doxorubicin, bleomycin, cytosine arabinoside, nitrogen mustard, methotrexate and vincristine. Others include ethanol and -amyloid peptide. (*Science* 267:1457-1458 (1995)). Further preferred agonists include polyclonal and monoclonal antibodies raised against the TR9 polypeptides of the invention, or a fragment thereof. Such agonist antibodies raised against a TNF-family receptor are disclosed in Tartaglia et al., *Proc. Natl. Acad. Sci. USA* 88:9292-9296 (1991); and Tartaglia et al., *J. Biol. Chem.* 267:4304-4307(1992). See, also, PCT Application WO 94/09137.

Antagonists according to the present invention include naturally occurring and synthetic compounds such as, for example, the CD40 ligand, neutral amino acids, zinc, estrogen, androgens, viral genes (such as Adenovirus ElB, Baculovirus p35 and IAP, Cowpox virus crmA, Epstein-Barr virus BHRF1, LMP-1, African swine fever virus LMW5-HL, and Herpesvirus yl 34.5), calpain inhibitors, cysteine protease inhibitors, and tumor promoters (such as PMA, Phenobarbital, and -Hexachlorocyclohexane).

In specific embodiments, antagonists according to the present invention are nucleic acids corresponding to the sequences contained in FIGS. 1A-D, or the complementary strand thereof, and/or to nucleotide sequences contained in the deposited clone. In one embodiment, antisense sequence is generated internally by the organism, in another embodiment, the antisense sequence is separately administered (see, for example, O'Connor, J., *Neurochem.* 56:560 (1991); and *Oligodeoxynucleotides as Antisense Inhibitors of Gene Expression*, CRC Press, Boca Raton, Fla. (1988). Antisense technology can be used to control gene expression through antisense DNA or RNA, or through triple-helix formation. Antisense techniques are discussed for example, in Okano, J., *Neurochem.* 56:560 (1991); *Oligodeoxynucleotides as Antisense Inhibitors of Gene Expression*, CRC Press, Boca Raton, Fla. (1988). Triple helix formation is discussed in, for instance, Lee et al., *Nucleic Acids Research* 6:3073 (1979); Cooney et al., *Science* 241:456 (1988); and Dervan et al., *Science* 251:1300 (1991). The methods are based on binding of a polynucleotide to a complementary DNA or RNA.

For example, the 5' coding portion of a polynucleotide that encodes the mature polypeptide of the present invention may be used to design an antisense RNA polynucleotide of from about 10 to 40 base pairs in length. A DNA polynucleotide is designed to be complementary to a region of the gene involved in transcription thereby preventing transcription and the production of the receptor. The antisense RNA polypeptide hybridizes to the mRNA in vivo and blocks translation of the mRNA molecule into receptor polypeptide. The polynucleotides described herein can also be delivered to cells such that the antisense RNA or DNA may be expressed in vivo to inhibit production of the TR9 receptor.

In one embodiment, the TR9 antisense nucleic acid of the invention is produced intracellularly by transcription from an exogenous sequence. For example, a vector or a portion thereof, is transcribed, producing an antisense nucleic acid (RNA) of the invention. Such a vector would contain a sequence encoding the TR9 antisense nucleic acid. Such a vector can remain episomal or become chromosomally integrated, as long as it can be transcribed to produce the desired antisense RNA. Such vectors can be constructed by recombinant DNA technology methods standard in the art. Vectors can be plasmid, viral, or others know in the art, used for replication and expression in vertebrate cells. Expression of the sequence encoding TR9, or fragments thereof, can be by any promoter known in the art to act in vertebrate, preferably human cells. Such promoters can be inducible or constitutive. Such promoters include, but are not limited to, the SV40 early promoter region (Bernoist and Chambon, *Nature* 29:304-310 (1981), the promoter contained in the 3' long terminal repeat of Rous sarcoma virus (Yamamoto et al., *Cell* 22:787-797 (1980), the herpes thymidine promoter (Wagner et al., *Proc. Natl. Acad. Sci. U.S.A.* 78:1441-1445 (1981), the regulatory sequences of the metallothionein gene (Brinster et al., *Nature* 296:39-42 (1982)), etc.

The antisense nucleic acids of the invention comprise a sequence complementary to at least a portion of an RNA transcript of a TR9 gene. However, absolute complementarity, although preferred, is not required. A sequence "complementary to at least a portion of an RNA," referred to herein, means a sequence having sufficient complementarity to be able to hybridize with the RNA, forming a stable duplex; in the case of double stranded TR9 antisense nucleic acids, a single strand of the duplex DNA may thus be tested, or triplex formation may be assayed. The ability to hybridize will depend on both the degree of complementarity and the length of the antisense nucleic acid Generally, the larger the hybridizing nucleic acid, the more base mismatches with a TR9RNA it may contain and still form a stable duplex (or triplex as the case may be). One skilled in the art can ascertain a tolerable degree of mismatch by use of standard procedures to determine the melting point of the hybridized complex.

Oligonucleotides that are complementary to the 5' end of the message, e.g., the 5' untranslated sequence up to and including the AUG initiation codon, should work most efficiently at inhibiting translation. However, sequences complementary to the 3' untranslated sequences of mRNAs have been shown to be effective at inhibiting translation of mRNAs as well. See generally, Wagner, R., 1994, Nature 372:333-335. Thus, oligonucleotides complementary to either the 5'- or 3'-non-translated, non-coding regions of the TR9 shown in FIGS. 1A-D could be used in an antisense approach to inhibit translation of endogenous TR9 mRNA. Oligonucleotides complementary to the 5' untranslated region of the mRNA should include the complement of the AUG start codon. Antisense oligonucleotides complementary to mRNA coding regions are less efficient inhibitors of translation but could be used in accordance with the invention. Whether designed to hybridize to the 5'-, 3'- or coding region of TR9 mRNA, antisense nucleic acids should be at least six nucleotides in length, and are preferably oligonucleotides ranging from 6 to about 50 nucleotides in length. In specific aspects the oligonucleotide is at least 10 nucleotides, at least 17 nucleotides, at least 25 nucleotides or at least 50 nucleotides.

The polynucleotides of the invention can be DNA or RNA or chimeric mixtures or derivatives or modified versions thereof, single-stranded or double-stranded. The oligonucleotide can be modified at the base moiety, sugar moiety, or phosphate backbone, for example, to improve stability of the molecule, hybridization, etc. The oligonucleotide may include other appended groups such as peptides (e.g., for targeting host cell receptors in vivo), or agents facilitating transport across the cell membrane (see, e.g., Letsinger et al., *Proc. Natl. Acad. Sci. U.S.A.* 86:6553-6556 (1989); Lemaitre et al., *Proc. Natl. Acad. Sci.* 84:648-652 (1987); PCT Publication No. WO88/09810, published Dec. 15, 1988) or the blood-brain barrier (see, e.g., PCT Publication No. WO89/10134, published Apr. 25, 1988), hybridization-triggered cleavage agents. (See, e.g., Krol et al., BioTechniques 6:958-976 (1988)) or intercalating agents. (See, e.g., Zon, *Pharm. Res.* 5:539-549 (1988)). To this end, the oligonucleotide may be conjugated to another molecule, e.g., a peptide, hybridization triggered cross-linking agent, transport agent, hybridization-triggered cleavage agent, etc.

The antisense oligonucleotide may comprise at least one modified base moiety which is selected from the group including, but not limited to, 5-fluorouracil, 5-bromouracil, 5-chlorouracil, 5-iodouracil, hypoxanthine, xantine, 4-acetylcytosine, 5-(carboxyhydroxylmethyl)uracil, 5-carboxymethylaminomethyl-2-thiouridine, 5-carboxymethylaminomethyluracil, dihydrouracil, beta-D-galactosylqueosine, inosine, N6-isopentenyladenine, 1-methylguanine, 1-methylinosine, 2,2-dimethylguanine, 2-methyladenine, 2-methylguanine, 3-methylcytosine, 5-methylcytosine, N6-adenine, 7-methylguanine, 5-methylaminomethyluracil, 5-methoxyaminomethyl-2-thiouracil, beta-D-mannosylqueosine, 5☐-methoxycarboxymethyluracil, 5-methoxyuracil, 2-methylthio-N-6-isopentenyladenine, uracil-5-oxyacetic acid (v), wybutoxosine, pseudouracil, queosine, 2-thiocytosine, 5-methyl-2-thiouracil, 2-thiouracil, 4-thiouracil, 5-methyluracil, uracil-5-oxyacetic acid methylester, uracil-5-oxyacetic acid (v), 5-methyl-2-thiouracil, 3-(3-amino-3-N2-carboxypropyl)uracil, (acp3)w, and 2,6-diaminopurine.

The antisense oligonucleotide may also comprise at least one modified sugar moiety selected from the group including, but not limited to, arabinose, 2-fluoroarabinose, xylulose, and hexose.

In yet another embodiment, the antisense oligonucleotide comprises at least one modified phosphate backbone selected from the group including, but not limited to, a phosphorothioate, a phosphorodithioate, a phosphoramidothioate, a phosphoramidate, a phosphordiamidate, a methylphosphonate, an alkyl phosphotriester, and a formacetal or analog thereof.

In yet another embodiment, the antisense oligonucleotide is an ☐-anomeric oligonucleotide. An alpha-anomeric oligonucleotide forms specific double-stranded hybrids with complementary RNA in which, contrary to the usual beta-units, the strands run parallel to each other (Gautier et al., Nucl. Acids Res. 15:6625-6641 (1987)). The oligonucleotide is a 2☐-0-methylribonucleotide (Inoue et al., Nucl. Acids Res. 15:6131-6148 (1987)), or a chimeric RNA-DNA analogue (Inoue et al., FEBS Lett. 215:327-330 (1987)).

Polynucleotides of the invention may be synthesized by standard methods known in the art, e.g. by use of an automated DNA synthesizer (such as are commercially available from Biosearch, Applied Biosystems, etc.). As examples, phosphorothioate oligonucleotides may be synthesized by the method of Stein et al. (Nucl. Acids Res. 16:3209 (1988)), methylphosphonate oligonucleotides can be prepared by use of controlled pore glass polymer supports (Sarin et al., Proc. Natl. Acad. Sci. U.S.A. 85:7448-7451 (1988)), etc.

While antisense nucleotides complementary to the TR9 coding region sequence could be used, those complementary to the transcribed untranslated region are most preferred.

Potential antagonists according to the invention also include catalytic RNA, or a ribozyme (See, e.g., PCT International Publication WO 90/11364, published Oct. 4, 1990; Sarver et al, *Science* 247:1222-1225 (1990). While ribozymes that cleave mRNA at site specific recognition sequences can be used to destroy TR9 mRNAs, the use of hammerhead ribozymes is preferred. Hammerhead ribozymes cleave mRNAs at locations dictated by flanking regions that form complementary base pairs with the target mRNA. The sole requirement is that the target mRNA have the following sequence of two bases: 5'-UG-3'. The construction and production of hammerhead ribozymes is well known in the art and is described more fully in Haseloff and Gerlach, *Nature* 334:585-591 (1988). There are numerous potential hammerhead ribozyme cleavage sites within the nucleotide sequence of TR9 (FIGS. 1A-D). Preferably, the ribozyme is engineered so that the cleavage recognition site is located near the 5' end of the TR9 mRNA; i.e., to increase efficiency and minimize the intracellular accumulation of non-functional mRNA transcripts.

As in the antisense approach, the ribozymes of the invention can be composed of modified oligonucleotides (e.g. for improved stability, targeting, etc.) and should be delivered to cells which express TR9 in vivo. DNA constructs encoding the ribozyme may be introduced into the cell in the same manner as described above for the introduction of antisense encoding DNA. A preferred method of delivery involves using a DNA construct "encoding" the ribozyme under the control of a strong constitutive promoter, such as, for example, pol III or pol II promoter, so that transfected cells will produce sufficient quantities of the ribozyme to destroy endogenous TR9 messages and inhibit translation. Since ribozymes, unlike antisense molecules are catalytic, a lower intracellular concentration is required for efficiency.

Endogenous gene expression can also be reduced by inactivating or "knocking out" the TR9 gene and/or its promoter using targeted homologous recombination. (E.g., see Smithies et al., Nature 317:230-234 (1985); Thomas & Capecchi, Cell 51:503-512 (1987); Thompson et al., Cell 5:313-321 (1989); each of which is incorporated by reference herein in its entirety). For example, a mutant, non-functional polynucleotide of the invention (or a completely unrelated DNA sequence) flanked by DNA homologous to the endogenous polynucleotide sequence (either the coding regions or regulatory regions of the gene) can be used, with or without a selectable marker and/or a negative selectable marker, to transfect cells that express polypeptides of the invention in vivo. In another embodiment, techniques known in the art are used to generate knockouts in cells that contain, but do not express the gene of interest. Insertion of the DNA construct, via targeted homologous recombination, results in inactivation of the targeted gene. Such approaches are particularly suited in research and agricultural fields where modifications to embryonic stem cells can be used to generate animal offspring with an inactive targeted gene (e.g., see Thomas & Capecchi 1987 and Thompson 1989, supra). However this approach can be routinely adapted for use in humans provided the recombinant DNA constructs are directly administered or targeted to the required site in vivo using appropriate viral vectors that will be apparent to those of skill in the art. The contents of each of the documents recited in this paragraph is herein incorporated by reference in its entirety.

Further antagonists according to the present invention include soluble forms of TR9, (e.g., fragments of the TR9 receptor sequence depicted in FIGS. 1A-D that include the ligand binding domain from the extracellular region of the full length receptor). Such soluble forms of the receptor, which may be naturally occurring or synthetic, antagonize TR9 mediated signaling by competing with the cell surface TR9 for binding to TNF-family ligands. Thus, soluble forms of the receptor that include the ligand binding domain are novel cytokines capable of inhibiting apoptosis induced by TNF-family ligands. These are preferably expressed as dimers or trimers, since these have been shown to be superior to monomeric forms of soluble receptor as antagonists, e.g., IgGFc-TNF receptor family fusions. Other such cytokines are known in the art and include Fas B (a soluble form of the mouse Fas receptor) that acts physiologically to limit apoptosis induced by Fas ligand (Hughes and Crispe, *J. Exp. Med.* 182:1395-1401 (1995)). By a "TNF-family ligand" is intended naturally occurring, recombinant, and synthetic ligands that are capable of binding to a member of the TNF receptor family and inducing and/or blocking the ligand/receptor signaling pathway. Members of the TNF ligand family include, but are not limited to, TNF-a, lymphotoxin-a (LT-a, also known as TNF-b), LT-b (found in complex heterotrimer LT-a2-b), FasL, TNF-gamma (International Publication No. WO 96/14328), AIM-I (International Publication No. WO 97/33899), AIM-II (International Publication No. WO 97/34911), APRIL (J. Exp. Med. 188(6):1185-1190), endokine-alpha (International Publication No. WO 98/07880), neutrokine-alpha (International Publication No. WO 98/18921), CD40L, CD27L, CD30L, 4-1BBL, OX40L and nerve growth factor (NGF). The experiments set forth in Example 5 and 6, indicate that the TR9 receptor, like other homologous proteins, is a death domain-containing molecule capable of triggering apoptosis, which is important in the regulation of the immune system. In addition, the experiments set forth below suggest that TR9-induced apoptosis will be blocked by the inhibitors of ICE-like proteases, CrmA and z-VAD-fmk. Importantly, it is also expected that apoptosis induced by TR9 will be blocked by dominant negative versions of FADD (FADD-DN) or FLICE (FLICE-DN/MACHa1C360S), which were previously shown to inhibit death signaling by Fas/APO-1 and TNFR-1. Thus, inhibitors of ICE-like proteases, FADD-DN and FLICE-DN/MACHa1C360S could also be used as antagonists for TR9 activity.

Antagonists of the present invention also include antibodies specific for TNF-family ligands or the TR9 polypeptides of the invention. The term "antibody" (Ab) or "monoclonal antibody" (mAb) as used herein is meant to include intact molecules as well as fragments thereof (such as, e.g., Fab and F(ab')$_2$ fragments) which are capable of binding an antigen. Fab and F(ab')$_2$ fragments lack the Fc fragment of intact antibody, clear more rapidly from the circulation, and may have less non-specific tissue binding of an intact antibody (Wahl et al., *J. Nucl. Med.* 24:316-325 (1983)).

Antibodies according to the present invention may be prepared by any of a variety of standard methods using TR9 immunogens of the present invention. As indicated, such TR9 immunogens include the full-length (complete) TR9 polypeptide depicted in FIGS. 1A-D (SEQ ID NO:2) (which may or may not include the leader sequence) and TR9 polypeptide fragments comprising, or alternatively consisting of, for example, the ligand binding domain, extracellular domain, transmembrane domain, intracellular domain, death domain, incomplete death domain, or any combination thereof.

Polyclonal and monoclonal antibody agonists or antagonists according to the present invention can be raised according to the methods disclosed herein and/or known in the art, such as, for example, those methods described in Tartaglia and Goeddel, *J. Biol. Chem.* 267(7):4304-4307(1992)); Tartaglia et al., *Cell* 73:213-216 (1993)), and PCT Application WO 94/09137 (the contents of each of these three publications are herein incorporated by reference in their entireties), and are preferably specific to (i.e., bind uniquely to) polypeptides of the invention having the amino acid sequence of SEQ ID NO:2.

In a preferred method, antibodies according to the present invention are mAbs. Such mAbs can be prepared using hybridoma technology (Kohler and Millstein, *Nature* 256:495-497 (1975) and U.S. Pat. No. 4,376,110; Harlow et al., *Antibodies: A Laboratory Manual*, Cold Spring Harbor Laboratory Press, Cold Spring Harbor, N.Y., 1988; *Monoclonal Antibodies and Hybridomas: A New Dimension in Biological Analyses*, Plenum Press, New York, N.Y., 1980; Campbell, "Monoclonal Antibody Technology," In: *Laboratory Techniques in Biochemistry and Molecular Biology*, Volume 13 (Burdon et al., eds.), Elsevier, Amsterdam (1984)).

Proteins and other compounds which bind the TR9 domains are also candidate agonists and antagonists according to the present invention. Such binding compounds can be "captured" using the yeast two-hybrid system (Fields and Song, *Nature* 340:245-246 (1989)). A modified version of the yeast two-hybrid system has been described by Roger Brent and his colleagues (Gyuris, *Cell* 75:791-803 (1993); Zervos et al., *Cell* 72:223-232 (1993)). Preferably, the yeast two-hybrid system is used according to the present invention to capture compounds which bind to the ligand binding domain, extracellular, intracellular, transmembrane, and death domain of the TR9. Such compounds are good candidate agonists and antagonists of the present invention.

Using the two-hybrid assay described above, the intracellular domain of the TR9 receptor, or a portion thereof, may be used to identify cellular proteins which interact with the receptor in vivo. Such an assay may also be used to identify ligands with potential agonistic or antagonistic activity of TR9 receptor function. This screening assay has previously been used to identify protein which interact with the cytoplasmic domain of the murine TNF-RII and led to the identification of two receptor associated proteins. Rothe et al., *Cell* 78:681 (1994). Such proteins and amino acid sequences which bind to the cytoplasmic domain of the TR9 receptors are good candidate agonist and antagonist of the present invention.

Other screening techniques include the use of cells which express the polypeptide of the present invention (for example, transfected CHO cells) in a system which measures extracellular pH changes caused by receptor activation, for example, as described in *Science*, 246:181-296 (1989). In another example, potential agonists or antagonists may be contacted with a cell which expresses the polypeptide of the present invention and a second messenger response, e.g., signal transduction may be measured to determine whether the potential antagonist or agonist is effective.

By a "TNF-family ligand" is intended naturally occurring, recombinant, and synthetic ligands that are capable of binding to a member of the TNF receptor family and inducing the ligand/receptor signaling pathway. Members of the TNF ligand family include, but are not limited to TR9 ligands including TRAIL, TNF-alpha, lymphotoxin-alpha (LT-alpha, also known as TNF-beta), LT-beta (found in complex heterotrimer LT-alpha2-beta), FasL, CD40, CD27, CD30, 4-1BB, OX40, and nerve growth factor (NGF) and other TNF ligand family members described herein.

Representative therapeutic applications of the present invention are discussed in more detail below. The state of immunodeficiency that defines AIDS is secondary to a decrease in the number and function of CD4$^+$ T-lymphocytes. Recent reports estimate the daily loss of CD4$^+$ T cells to be between 3.5×10$^7$ and 2×10$^9$ cells (Wei et al., *Nature* 373:117-122 (1995)). One cause of CD4$^+$ T cell depletion in the setting of HIV infection is believed to be HIV-induced apoptosis. Indeed, HIV-induced apoptotic cell death has been demonstrated not only in vitro but also, more importantly, in infected individuals (Ameisen, J. C., *AIDS* 8:1197-1213 (1994); Finkel and Banda, *Curr. Opin. Immunol.* 6:605-615(1995); Muro-Cacho et al., *J. Immunol* 154:5555-5566 (1995)). Furthermore, apoptosis and CD4$^+$ T-lymphocyte depletion is tightly correlated in different animal models of AIDS (Brunner et al., *Nature* 373:441-444 (1995); Gougeon et al., *AIDS Res. Hum. Retroviruses* 9:553-563 (1993)) and, apoptosis is not observed in those animal models in which viral replication does not result in AIDS. Id. Further data indicates that uninfected but primed or activated T lymphocytes from HIV-infected individuals undergo apoptosis after encountering the TNF-family ligand FasL. Using monocytic cell lines that result in death following HIV infection, it has been demonstrated that infection of U937 cells with HIV results in the de novo expression of FasL and that FasL mediates HIV-induced apoptosis (Badley et al., *J. Virol.* 70:199-206 (1996)). Further, the TNF-family ligand was detectable in uninfected macrophages and its expression was upregulated following HIV infection resulting in selective killing of uninfected CD4 T-lymphocytes. Id. Thus, by the invention, a method for treating, preventing, diagnosing, and/or detecting HIV$^+$ individuals is provided which involves administering an antagonist of the present invention to reduce selective killing of CD4 T-lymphocytes. Modes of administration and dosages are discussed in detail below.

In rejection of an allograft, the immune system of the recipient animal has not previously been primed to respond because the immune system for the most part is only primed by environmental antigens. Tissues from other members of the same species have not been presented in the same way than, for example, viruses and bacteria have been presented. In the case of allograft rejection, immunosuppressive regimens are designed to prevent the immune system from reaching the effector stage. However, the immune profile of xenograft rejection may resemble disease recurrence more than allograft rejection. In the case of disease recurrence, the immune system has already been activated, as evidenced by destruction of the native islet cells. Therefore, in disease recurrence, the immune system is already at the effector stage. Agonists of the present invention are able to suppress the immune response to both allografts and xenografts because lymphocytes activated and differentiated into effector cells will express the TR9 polypeptide, and thereby are susceptible to compounds which enhance apoptosis. Thus, the present invention further provides a method for creating immune privileged tissues.

TR9 antagonists of the invention can further be used in the treatment, prevention, diagnosis, and/or detection of inflammatory diseases and stress response related diseases, such as inflammatory bowel disease, rheumatoid arthritis, osteoarthritis, psoriasis, and septicemia.

In addition, due to lymphoblast expression of TR9, soluble TR9 agonist or antagonist antibodies (e.g., mABs) may be used to treat, prevent, diagnose, and/or detect this form of cancer. Further, soluble TR9 or neutralizing mABs may be used to treat, prevent, diagnose, and/or detect various chronic and acute forms of inflammation such as rheumatoid arthritis, osteoarthritis, psoriasis, septicemia, and inflammatory bowel disease.

Polynucleotides and/or polypeptides of the invention, and/ or agonists and/or antagonists thereof, are useful in the diagnosis and treatment, prevention, diagnosis, and/or detection of a wide range of diseases and/or conditions. Such diseases and conditions include, but are not limited to, cancer (e.g., immune cell related cancers, breast cancer, prostate cancer, ovarian cancer, follicular lymphoma, cancer associated with mutation or alteration of p53, brain tumor, bladder cancer, uterocervical cancer, colon cancer, colorectal cancer, non-small cell carcinoma of the lung, small cell carcinoma of the lung, stomach cancer, etc.), lymphoproliferative disorders (e.g., lymphadenopathy), microbial (e.g., viral, bacterial, etc.) infection (e.g., HIV-1 infection, HIV-2 infection, herpesvirus infection (including, but not limited to, HSV-1, HSV-2, CMV, VZV, HHV-6, HHV-7, EBV), adenovirus infection, poxvirus infection, human papilloma virus infection, hepatitis infection (e.g., HAV, HBV, HCV, etc.), *Helicobacter pylori* infection, invasive Staphylococcia, etc.), parasitic infection, nephritis, bone disease (e.g., osteoporosis), atherosclerosis, pain, cardiovascular disorders (e.g., neovascularization, hypovascularization or reduced circulation (e.g., ischemic disease (e.g., myocardial infarction, stroke, etc.)), AIDS, allergy, inflammation, neurodegenerative disease (e.g., Alzheimer's disease, Parkinson's disease, amyotrophic lateral sclerosis, pigmentary retinitis, cerebellar degeneration, etc.), graft rejection (acute and chronic), graft vs. host disease, diseases due to osteomyelodysplasia (e.g., aplastic anemia, etc.), joint tissue destruction in rheumatism, liver disease (e.g., acute and chronic hepatitis, liver injury, and cirrhosis), autoimmune disease (e.g., multiple sclerosis, rheumatoid arthritis, systemic lupus erythematosus, immune complex glomerulonephritis, autoimmune diabetes, autoimmune thrombocytopenic purpura, Grave's disease, Hashimoto's thyroiditis, etc.), cardiomyopathy (e.g., dilated cardiomyopathy), diabetes, diabetic complications (e.g., diabetic nephropathy, diabetic neuropathy, diabetic retinopathy), influenza, asthma, psoriasis, glomerulonephritis, septic shock, and ulcerative colitis.

Polynucleotides and/or polypeptides of the invention and/ or agonists and/or antagonists thereof are useful in promoting angiogenesis, wound healing (e.g., wounds, burns, and bone fractures).

Polynucleotides and/or polypeptides of the invention and/ or agonists and/or antagonists thereof are also useful as an adjuvant to enhance immune responsiveness to specific antigen and/or anti-viral immune responses.

More generally, polynucleotides and/or polypeptides of the invention and/or agonists and/or antagonists thereof are useful in regulating (i.e., elevating or reducing) immune response. For example, polynucleotides and/or polypeptides of the invention may be useful in preparation or recovery from surgery, trauma, radiation therapy, chemotherapy, and transplantation, or may be used to boost immune response and/or recovery in the elderly and immunocompromised individuals. Alternatively, polynucleotides and/or polypeptides of the invention and/or agonists and/or antagonists thereof are useful as immunosuppressive agents, for example in the treatment, prevention, diagnosis, and/or detection of autoimmune disorders. In specific embodiments, polynucleotides and/or polypeptides of the invention are used to treat, prevent, diagnose, and/or detect chronic inflammatory, allergic or autoimmune conditions, such as those described herein or are otherwise known in the art.

Modes of Administration

The agonist or antagonists described herein can be administered in vitro, ex vivo, or in vivo to cells which express the receptor of the present invention. By administration of an "effective amount" of an agonist or antagonist is intended an amount of the compound that is sufficient to enhance or inhibit a cellular response to a TNF-family ligand and include polypeptides. In particular, by administration of an "effective amount" of an agonist or antagonists is intended an amount effective to enhance or inhibit TR9 mediated apoptosis. Of course, where it is desired for apoptosis to be enhanced, an agonist according to the present invention can be co-administered with a TNF-family ligand. One of ordinary skill will appreciate that effective amounts of an agonist or antagonist can be determined empirically and may be employed in pure form or in pharmaceutically acceptable salt, ester or prodrug form. The agonist or antagonist may be administered in compositions in combination with one or more pharmaceutically acceptable excipients (i.e., carriers).

It will be understood that, when administered to a human patient, the total daily usage of the compounds and compositions of the present invention will be decided by the attending physician within the scope of sound medical judgment. The specific therapeutically effective dose level for any particular patient will depend upon factors well known in the medical arts.

As a general proposition, the total pharmaceutically effective amount of TR9 polypeptide administered parenterally per dose will be in the range of about 1 µg/kg/day to 10 mg/kg/day of patient body weight, although, as noted above, this will be subject to therapeutic discretion. More preferably, this dose is at least 0.01 mg/kg/day, and most preferably for humans between about 0.01 and 1 mg/kg/day for the hormone. If given continuously, the TR9 polypeptide is typically administered at a dose rate of about 1 µg/kg/hour to about 50 µg/kg/hour, either by 1-4 injections per day or by continuous subcutaneous infusions, for example, using a mini-pump. An intravenous bag solution may also be employed.

Dosaging may also be arranged in a patient specific manner to provide a predetermined concentration of an agonist or antagonist in the blood, as determined by the RIA technique. Thus patient dosaging may be adjusted to achieve regular on-going trough blood levels, as measured by RIA, on the order of from 50 to 1000 ng/ml, preferably 150 to 500 ng/ml.

Pharmaceutical compositions are provided comprising an agonist (including TR9 receptor polynucleotides, polypeptides or antibodies of the invention) or agonist (e.g., TR9 polynucleotides, polypeptides of the invention or antibodies thereto) of TR9 and a pharmaceutically acceptable carrier or excipient, which may be administered orally, rectally, parenterally, intracisternally, intravaginally, intraperitoneally, topically (as by powders, ointments, drops or transdermal patch), bucally, or as an oral or nasal spray, In one embodiment "pharmaceutically acceptable carrier" means a non-toxic solid, semisolid or liquid filler, diluent, encapsulating material or formulation auxiliary of any type. In a specific embodiment, "pharmaceutically acceptable" means approved by a regulatory agency of the federal or a state government or listed in the U.S. Pharmacopeia or other generally recognized pharmacopeia for use in animals, and more particularly humans. Nonlimiting examples of suitable pharmaceutical carriers according to this embodiment are provided in "Remington's Pharmaceutical Sciences" by E. W. Martin, and include sterile liquids, such as water and oils, including those of petroleum, animal, vegetable or synthetic origin, such as peanut oil, soybean oil, mineral oil, sesame oil and the like. Water is a preferred carrier when the pharmaceutical composition is administered intravenously. Saline solutions and aqueous dextrose and glycerol solutions can be employed as liquid carriers, particularly for injectable solutions.

The term "parenteral" as used herein refers to modes of administration which include intravenous, intramuscular, intraperitoneal, intrasternal, subcutaneous and intraarticular injection and infusion.

Pharmaceutical compositions of the present invention for parenteral injection can comprise pharmaceutically acceptable sterile aqueous or nonaqueous solutions, dispersions, suspensions or emulsions as well as sterile powders for reconstitution into sterile injectable solutions or dispersions just prior to use.

In addition to soluble TR9 polypeptides, TR9 polypeptides containing the transmembrane region can also be used when appropriately solubilized by including detergents, such as CHAPS or NP-40, with buffer.

The compositions of the invention may be administered alone or in combination with other therapeutic agents. Therapeutic agents that may be administered in combination with the compositions of the invention, include but not limited to, other members of the TNF family, chemotherapeutic agents, antibiotics, steroidal and non-steroidal anti-inflammatories, conventional immunotherapeutic agents, cytokines and/or growth factors. Combinations may be administered either concomitantly, e.g., as an admixture, separately but simultaneously or concurrently; or sequentially. This includes presentations in which the combined agents are administered together as a therapeutic mixture, and also procedures in which the combined agents are administered separately but simultaneously, e.g., as through separate intravenous lines into the same individual. Administration "in combination" further includes the separate administration of one of the compounds or agents given first, followed by the second.

In one embodiment, the compositions of the invention are administered in combination with other members of the TNF family. TNF, TNF-related or TNF-like molecules that may be administered with the compositions of the invention include, but are not limited to, soluble forms of TNF-alpha, lymphotoxin-alpha (LT-alpha, also known as TNF-beta), LT-beta (found in complex heterotrimer LT-alpha2-beta), OPGL, FasL, CD27L, CD30L, CD40L, 4-1BBL, DcR3, OX40L, TNF-gamma (International Publication No. WO 96/14328), AIM-I (International Publication No. WO 97/33899), AIM-II ((International Publication No. WO 97/34911), endokine-alpha (International Publication No. WO 98/07880), TR6 (International Publication No. WO 98/30694), OPG, and neutrokine-alpha (International Publication No. WO 98/18921, OX40, and nerve growth factor (NGF), and soluble forms of Fas, CD30, CD27, CD40 and 4-IBB, TR2 (International Publication No. WO 96/34095), DR3 (International Publication No. WO 97/33904), DR4 (International Publication No. WO 98/32856), TR5 (International Publication No. WO 98/30693), TR6 (International Publication No. WO 98/30694), TR7 (International Publication No. WO 98/41629), TRANK, TR9 (International Publication No. WO 98/56892), TR10 (International Publication No. WO 98/54202), 312C2 (International Publication No. WO 98/06842), and TR11, TR11SV1, TR11SV2, TR12, and soluble forms CD154, CD70, and CD153.

In a preferred embodiment, compositions of the invention are administered in combination with endokine-alpha.

In a preferred embodiment, the compositions of the invention are administered in combination with CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

In a further embodiment, the compositions of the invention are administered in combination with an antibiotic agent. Antibiotic agents that may be administered with the compositions of the invention include, but are not limited to, tetracycline, metronidazole, amoxicillin, beta-lactamases, aminoglycosides, macrolides, quinolones, fluoroquinolones, cephalosporins, erythromycin, ciprofloxacin, and streptomycin.

In certain embodiments, compositions of the invention are administered in combination with antiretroviral agents, nucleoside reverse transcriptase inhibitors, non-nucleoside reverse transcriptase inhibitors, and/or protease inhibitors.

Nucleoside reverse transcriptase inhibitors that may be administered in combination with the compositions of the invention, include, but are not limited to, RETROVIR™ (zidovudine/AZT), VIDEX™ (didanosine/ddI), HIVID™ (zalcitabine/ddC), ZERIT™ (stavudine/d4T), EPIVIR™ (lamivudine/3TC), and COMBIVIR™ (zidovudine/lamivudine). Non-nucleoside reverse transcriptase inhibitors that may be administered in combination with the compositions of the invention, include, but are not limited to, VIRAMUNE™ (nevirapine), RESCRIPTOR™ (delavirdine), and SUSTIVA™ (efavirenz). Protease inhibitors that may be administered in combination with the compositions of the invention, include, but are not limited to, CRIXIVAN™ (indinavir), NORVIR™ (ritonavir), INVIRASE™ (saquinavir), and VIRACEPT™ (nelfinavir). In a specific embodiment, antiretroviral agents, nucleoside reverse transcriptase inhibitors, non-nucleoside reverse transcriptase inhibitors, and/or protease inhibitors may be used in any combination with compositions of the invention to treat AIDS and/or to prevent or treat HIV infection.

In other embodiments, compositions of the invention may be administered in combination with anti-opportunistic infection agents. Anti-opportunistic agents that may be administered in combination with the compositions of the invention, include, but are not limited to, TRIMETHOPRIM-SULFAMETHOXAZOLE™, DAPSONE™, PENTAMIDINE™, ATOVAQUONE™, ISONIAZID™, RIFAMPIN™, PYRAZINAMIDE™, ETHAMBUTOL™, RIFABUTIN™, CLARITHROMYCIN™, AZITHROMYCIN™, GANCICLOVIR™, FOSCARNET™, CIDOFOVIR™, FLUCONAZOLE™, ITRACONAZOLE™, KETOCONAZOLE™, ACYCLOVIR™, FAMCICOLVIR™, PYRIMETHAMINE™, LEUCOVORIN™, NEUPOGEN™ (filgrastim/G-CSF), and LEUKINE™ (sargramostim/GM-CSF). In a specific embodiment, compositions of the invention are used in any combination with TRIMETHOPRIM-SULFAMETHOXAZOLE™, DAPSONE™, PENTAMIDINE™, and/or ATOVAQUONE™ to prophylactically treat or prevent an opportunistic *Pneumocystis carinii* pneumonia infection. In another specific embodiment, compositions of the invention are used in any combination with ISONIAZID™, RIFAMPIN™, PYRAZINAMIDE™, and/or ETHAMBUTOL™ to prophylactically treat or prevent an opportunistic *Mycobacterium avium* complex infection. In another specific embodiment, compositions of the invention are used in any combination with RIFABUTIN™, CLARITHROMYCIN™, and/or AZITHROMYCIN™ to prophylactically treat or prevent an opportunistic *Mycobacterium tuberculosis* infection. In another specific embodiment, compositions of the invention are used in any combination with GANCICLOVIR™, FOSCARNET™, and/or CIDOFOVIR™ to prophylactically treat or prevent an opportunistic cytomegalovirus infection. In another specific embodiment, compositions of the invention are used in any combination with FLUCONAZOLE™, ITRACONAZOLE™, and/or KETOCONAZOLE™ to prophylactically treat or prevent an opportunistic fungal infection. In another specific embodiment, compositions of the invention are used in any combination with ACYCLOVIR™ and/or FAMCICOLVIR™ to prophylactically treat or prevent an opportunistic herpes simplex virus type I and/or type II infection. In another specific embodiment, compositions of the invention are used in any combination with PYRIMETHAMINE™ and/or LEUCOVORIN™ to prophylactically treat or prevent an opportunistic *Toxoplasma gondii* infection. In another specific embodiment, compositions of the invention are used in any combination with LEUCOVORIN™ and/or NEUPOGEN™ to prophylactically treat or prevent an opportunistic bacterial infection.

In a further embodiment, the compositions of the invention are administered in combination with an antiviral agent. Antiviral agents that may be administered with the compositions of the invention include, but are not limited to, acyclovir, ribavirin, amantadine, and remantidine.

In a further embodiment, the compositions of the invention are administered in combination with an antibiotic agent. Antibiotic agents that may be administered with the compositions of the invention include, but are not limited to, amoxicillin, aminoglycosides, beta-lactam (glycopeptide), beta-lactamases, Clindamycin, chloramphenicol, cephalosporins, ciprofloxacin, ciprofloxacin, erythromycin, fluoroquinolones, macrolides, metronidazole, penicillins, quinolones, rifampin, streptomycin, sulfonamide, tetracyclines, trimethoprim, trimethoprim-sulfamthoxazole, and vancomycin.

Conventional nonspecific immunosuppressive agents, that may be administered in combination with the compositions of the invention include, but are not limited to, steroids, cyclosporine, cyclosporine analogs, cyclophosphamide methylprednisone, prednisone, azathioprine, FK-506, 15-deoxyspergualin, and other immunosuppressive agents that act by suppressing the function of responding T cells.

Additionally, immunosuppressants preparations that may be administered with the compositions of the invention include, but are not limited to, ORTHOCLONE™ (OKT3), SANDIMMUNE™/NEORAL™/SANGDYA™ (cyclosporin), PROGRAF™ (tacrolimus), CELLCEPT™ (mycophenolate), Azathioprine, glucorticosteroids, and RAPAMUNE™ (sirolimus). In a specific embodiment, immunosuppressants may be used to prevent rejection of organ or bone marrow transplantation.

In a preferred embodiment, the compositions of the invention are administered in combination with steroid therapy. Steroids that may be administered in combination with the compositions of the invention, include, but are not limited to, oral corticosteroids, prednisone, and methylprednisolone (e.g., IV methylprednisolone). In a specific embodiment, compositions of the invention are administered in combination with prednisone. In a further specific embodiment, the compositions of the invention are administered in combination with prednisone and an immunosuppressive agent. Immunosuppressive agents that may be administered with the compositions of the invention and prednisone are those described herein, and include, but are not limited to, azathioprine, cylophosphamide, and cyclophosphamide IV. In a another specific embodiment, compositions of the invention are administered in combination with methylprednisolone. In a further specific embodiment, the compositions of the invention are administered in combination with methylprednisolone and an immunosuppressive agent. Immunosuppressive agents that may be administered with the compositions of the invention and methylprednisolone are those described herein, and include, but are not limited to, azathioprine, cylophosphamide, and cyclophosphamide IV.

In a preferred embodiment, the compositions of the invention are administered in combination with an antimalarial. Antimalarials that may be administered with the compositions of the invention include, but are not limited to, hydroxychloroquine, chloroquine, and/or quinacrine.

In a preferred embodiment, the compositions of the invention are administered in combination with an NSAID.

In a nonexclusive embodiment, the compositions of the invention are administered in combination with one, two, three, four, five, ten, or more of the following drugs: NRD-101 (Hoechst Marion Roussel), diclofenac (Dimethaid), oxaprozin potassium (Monsanto), mecasermin (Chiron), T-614 (Toyama), pemetrexed disodium (Eli Lilly), atreleuton (Abbott), valdecoxib (Monsanto), eltenac (Byk Gulden), campath, AGM-1470 (Takeda), CDP-571 (Celltech Chiroscience), CM-101 (CarboMed), ML-3000 (Merckle), CB-2431 (KS Biomedix), CBF-BS2 (KS Biomedix), IL-1Ra gene therapy (Valentis), JTE-522 (Japan Tobacco), paclitaxel (Angiotech), DW-166HC (Dong Wha), darbufelone mesylate (Warner-Lambert), soluble TNF receptor 1 (synergen; Amgen), IPR-6001 (Institute for Pharmaceutical Research), trocade (Hoffman-La Roche), EF-5 (Scotia Pharmaceuticals), BIIL-284 (Boehringer Ingelheim), BIIF-1149 (Boehringer Ingelheim), LeukoVax (Inflammatics), MK-663 (Merck), ST-1482 (Sigma-Tau), and butixocort propionate (WarnerLambert).

In a preferred embodiment, the compositions of the invention are administered in combination with one, two, three, four, five or more of the following drugs: methotrexate, sulfasalazine, sodium aurothiomalate, auranofin, cyclosporine, penicillamine, azathioprine, an antimalarial drug (e.g., as described herein), cyclophosphamide, chlorambucil, gold, ENBREL™ (Etanercept), anti-TNF antibody, and prednisolone.

In a more preferred embodiment, the compositions of the invention are administered in combination with an antimalarial, methotrexate, anti-TNF antibody, ENBREL™ and/or sulfasalazine. In one embodiment, the compositions of the invention are administered in combination with methotrexate. In another embodiment, the compositions of the invention are administered in combination with anti-TNF antibody. In another embodiment, the compositions of the invention are administered in combination with methotrexate and anti-TNF antibody. In another embodiment, the compositions of the invention are administered in combination with sulfasalazine. In another specific embodiment, the compositions of the invention are administered in combination with methotrexate, anti-TNF antibody, and sulfasalazine. In another embodiment, the compositions of the invention are administered in combination ENBREL™. In another embodiment, the compositions of the invention are administered in combination with ENBREL™ and methotrexate. In another embodiment, the compositions of the invention are administered in combination with ENBREL™, methotrexate and sulfasalazine. In another embodiment, the compositions of the invention are administered in combination with ENBREL™, methotrexate and sulfasalazine. In other embodiments, one or more antimalarials is combined with one of the above-recited combinations. In a specific embodiment, the compositions of the invention are administered in combination with an antimalarial (e.g., hydroxychloroquine), ENBREL™, methotrexate and sulfasalazine. In another specific embodiment, the compositions of the invention are administered in combination with an antimalarial (e.g., hydroxychloroquine), sulfasalazine, anti-TNF antibody, and methotrexate.

In an additional embodiment, compositions of the invention are administered alone or in combination with one or more intravenous immune globulin preparations. Intravenous immune globulin preparations that may be administered with the compositions of the invention include, but not limited to, GAMMAR™, IVEEGAM™, SANDOGLOBULIN™, GAMMAGARD S/D™, and GAMIMUNE™. In a specific embodiment, compositions of the invention are administered in combination with intravenous immune globulin preparations in transplantation therapy (e.g., bone marrow transplant).

CD40 ligand (CD40L), a soluble form of CD40L (e.g., AVREND™), biologically active fragments, variants, or derivatives of CD40L, anti-CD40L antibodies (e.g., agonistic or antagonistic antibodies), and/or anti-CD40 antibodies (e.g., agonistic or antagonistic antibodies).

In an additional embodiment, the compositions of the invention are administered alone or in combination with an anti-inflammatory agent. Anti-inflammatory agents that may be administered with the compositions of the invention include, but are not limited to, glucocorticoids and the non-steroidal anti-inflammatories, aminoarylcarboxylic acid derivatives, arylacetic acid derivatives, arylbutyric acid derivatives, arylcarboxylic acids, arylpropionic acid derivatives, pyrazoles, pyrazolones, salicylic acid derivatives, thiazinecarboxamides, e-acetamidocaproic acid, S-adenosylmethionine, 3-amino-4-hydroxybutyric acid, amixetrine, bendazac, benzydamine, bucolome, difenpiramide, ditazol, emorfazone, guaiazulene, nabumetone, nimesulide, orgotein, oxaceprol, paranyline, perisoxal, pifoxime, proquazone, proxazole, and tenidap.

In another embodiment, compostions of the invention are administered in combination with a chemotherapeutic agent. Chemotherapeutic agents that may be administered with the compositions of the invention include, but are not limited to, antibiotic derivatives (e.g., doxorubicin, bleomycin, daunorubicin, and dactinomycin); antiestrogens (e.g., tamoxifen); antimetabolites (e.g., fluorouracil, 5-FU, methotrexate, floxuridine, interferon alpha-2b, glutamic acid, plicamycin, mercaptopurine, and 6-thioguanine); cytotoxic agents (e.g., carmustine, BCNU, lomustine, CCNU, cytosine arabinoside, cyclophosphamide, estramustine, hydroxyurea, procarbazine, mitomycin, busulfan, cis-platin, and vincristine sulfate); hormones (e.g., medroxyprogesterone, estramustine phosphate sodium, ethinyl estradiol, estradiol, megestrol acetate, methyltestosterone, diethylstilbestrol diphosphate, chlorotrianisene, and testolactone); nitrogen mustard derivatives (e.g., mephalen, chorambucil, mechlorethamine (nitrogen mustard) and thiotepa); steroids and combinations (e.g., bethamethasone sodium phosphate); and others (e.g., dicarbazine, asparaginase, mitotane, vincristine sulfate, vinblastine sulfate, and etoposide).

In an additional embodiment, the compositions of the invention are administered in combination with cytokines. Cytokines that may be administered with the compositions of the invention include, but are not limited to, IL2, IL3, IL4, IL5, IL6, IL7, IL10, IL12, IL13, IL15, anti-CD40, CD40L, IFN-gamma and TNF-alpha.

In an additional embodiment, the compositions of the invention are administered in combination with angiogenic proteins. Angiogenic proteins that may be administered with the compositions of the invention include, but are not limited to, Glioma Derived Growth Factor (GDGF), as disclosed in European Patent Number EP-399816; Platelet Derived Growth Factor-A (PDGF-A), as disclosed in European Patent Number EP-682110; Platelet Derived Growth Factor-B (PDGF-B), as disclosed in European Patent Number EP-282317; Placental Growth Factor (PlGF), as disclosed in International Publication Number WO 92/06194; Placental Growth Factor-2 (PlGF-2), as disclosed in Hauser et al., Growth Factors, 4:259-268 (1993); Vascular Endothelial Growth Factor (VEGF), as disclosed in International Publication Number WO 90/13649; Vascular Endothelial Growth Factor-A (VEGF-A), as disclosed in European Patent Number EP-506477; Vascular Endothelial Growth Factor-2 (VEGF-2), as disclosed in International Publication Number WO 96/39515; Vascular Endothelial Growth Factor B-186 (VEGF-B186), as disclosed in International Publication Number WO 96/26736; Vascular Endothelial Growth Factor-D (VEGF-D), as disclosed in International Publication Number WO 98/02543; Vascular Endothelial Growth Factor-D (VEGF-D), as disclosed in International Publication Number WO 98/07832; and Vascular Endothelial Growth Factor-E (VEGF-E), as disclosed in German Patent Number DE19639601. The above mentioned references are incorporated herein by reference herein.

In an additional embodiment, the compositions of the invention are administered in combination with Fibroblast Growth Factors. Fibroblast Growth Factors that may be administered with the compositions of the invention include, but are not limited to, FGF-1, FGF-2, FGF-3, FGF-4, FGF-5, FGF-6, FGF-7, FGF-8, FGF-9, FGF-10, FGF-11, FGF-12, FGF-13, FGF-14, and FGF-15.

In additional embodiments, the compositions of the invention are administered in combination with other therapeutic or prophylactic regimens, such as, for example, radiation therapy.

Chromosome Assays

The nucleic acid molecules of the present invention are also valuable for chromosome identification. The sequence is specifically targeted to and can hybridize with a particular location on an individual human chromosome. The mapping of DNAs to chromosomes according to the present invention is an important first step in correlating those sequences with genes associated with disease.

In certain preferred embodiments in this regard, the cDNA herein disclosed is used to clone genomic DNA of a TR9 receptor gene. This can be accomplished using a variety of well known techniques and libraries, which generally are available commercially. The genomic DNA then is used for in situ chromosome mapping using well known techniques for this purpose.

In addition, in some cases, sequences can be mapped to chromosomes by preparing PCR primers (preferably 15-25 bp) from the cDNA. Computer analysis of the 3. untranslated region of the gene is used to rapidly select primers that do not span more than one exon in the genomic DNA, thus complicating the amplification process. These primers are then used for PCR screening of somatic cell hybrids containing individual human chromosomes.

Fluorescence in situ hybridization ("FISH") of a cDNA clone to a metaphase chromosomal spread can be used to provide a precise chromosomal location in one step. This technique can be used with probes from the cDNA as short as 50 or 60 bp. For a review of this technique, see Verma et al., *Human Chromosomes: A Manual Of Basic Techniques*, Pergamon Press, N.Y. (1988).

Once a sequence has been mapped to a precise chromosomal location, the physical position of the sequence on the chromosome can be correlated with genetic map data. Such data are found, for example, in V. McKusick, *Mendelian Inheritance In Man*, available on-line through Johns Hopkins University, Welch Medical Library. The relationship between genes and diseases that have been mapped to the same chromosomal region are then identified through linkage analysis (coinheritance of physically adjacent genes).

Next, it is necessary to determine the differences in the cDNA or genomic sequence between affected and unaffected individuals. If a mutation is observed in some or all of the affected individuals but not in any normal individuals, then the mutation is likely to be the causative agent of the disease.

Having generally described the invention, the same will be more readily understood by reference to the following examples, which are provided by way of illustration and are not intended as limiting.

EXAMPLES

Example 1

Expression and Purification of the TR9 Receptor in *E. coli*

The bacterial expression vector pQE60 is used for bacterial expression in this example. (QIAGEN, Inc., 9259 Eton Avenue, Chatsworth, Calif., 91311). pQE60 encodes ampicillin antibiotic resistance ("Amp$^r$") and contains a bacterial origin of replication ("ori"), an IPTG inducible promoter, a ribosome binding site ("RBS"), six codons encoding histidine residues that allow affinity purification using nickel-nitrilo-tri-acetic acid ("Ni-NTA") affinity resin sold by QIAGEN, Inc., supra, and suitable single restriction enzyme cleavage sites. These elements are arranged such that a DNA fragment encoding a polypeptide may be inserted in such as way as to produce that polypeptide with the six His residues (i.e., a "6xHis tag") covalently linked to the carboxyl terminus of that polypeptide. However, in this example, the polypeptide coding sequence is inserted such that translation of the six His codons is prevented and, therefore, the polypeptide is produced with no 6xHis tag.

The DNA sequence encoding the desired portion of the TR9 receptor protein lacking the hydrophobic leader sequence is amplified from the deposited cDNA clone using PCR oligonucleotide primers which anneal to the amino terminal sequences of the desired portion of the TR9 receptor protein and to sequences in the deposited construct 3' to the cDNA coding sequence. Additional nucleotides containing restriction sites to facilitate cloning in the pQE60 vector are added to the 5' and 3' sequences, respectively.

For cloning the mature protein, the 5' primer has the sequence:

5'-CGC CCATGGCTC AGC CAG AAC AGA AG-3' (SEQ ID NO:11) containing the underlined NcoI restriction site followed by 17 nucleotides complementary to the amino terminal coding sequence of the mature TR9 receptor sequence in FIGS. 1A-D. One of ordinary skill in the art would appreciate, of course, that the point in the protein coding sequence where the 5' primer begins may be varied to amplify a desired portion of the complete protein shorter or longer than the mature form. The 3' primer has the sequence:

5'-CGC AAGCTTTTA GGG CAA ATG CTC ATT G-3' (SEQ ID NO:12) containing the underlined HindIII restriction site followed by 19 nucleotides complementary to the 3' end of the non-coding sequence in the TR9 receptor DNA sequence in FIGS. 1A-D.

The amplified TR9 receptor DNA fragments and the vector pQE60 are digested with NcoI and HindIII, and the digested DNAs are then ligated together. Insertion of the TR9 receptor DNA into the restricted pQE60 vector places the TR9 receptor protein coding region including its associated stop codon downstream from the IPTG-inducible promoter and in-frame with an initiating AUG. The associated stop codon prevents translation of the six histidine codons downstream of the insertion point.

The ligation mixture is transformed into competent *E. coli* cells using standard procedures such as those described in Sambrook et al., *Molecular Cloning: a Laboratory Manual, 2nd Ed.*; Cold Spring Harbor Laboratory Press, Cold Spring Harbor, N.Y. (1989). *E. coli* strain M15/rep4, containing multiple copies of the plasmid pREP4, which expresses the lac repressor and confers kanamycin resistance ("Kan$^r$"), is used in carrying out the illustrative example described herein. This strain, which is only one of many that are suitable for expressing TR9 receptor protein, is available commercially from QIAGEN, Inc., supra. Transformants are identified by their ability to grow on LB plates in the presence of ampicillin and kanamycin. Plasmid DNA is isolated from resistant colonies and the identity of the cloned DNA confirmed by restriction analysis, PCR and DNA sequencing.

Clones containing the desired constructs are grown overnight ("O/N") in liquid culture in LB media supplemented with both ampicillin (100 µg/ml) and kanamycin (25 µg/ml). The O/N culture is used to inoculate a large culture, at a dilution of approximately 1:25 to 1:250. The cells are grown to an optical density at 600 nm ("OD600") of between 0.4 and 0.6. Isopropyl-b-D-thiogalactopyranoside ("IPTG") is then added to a final concentration of 1 mM to induce transcription from the lac repressor sensitive promoter, by inactivating the lacI repressor. Cells subsequently are incubated further for 3 to 4 hours. Cells then are harvested by centrifugation.

The cells are then stirred for 3-4 hours at 4° C. in 6M guanidine-HCl, pH8. The cell debris is removed by centrifugation, and the supernatant containing the TR9 receptor is dialyzed against 50 mM Na-acetate buffer pH6, supplemented with 200 mM NaCl. Alternatively, the protein can be successfully refolded by dialyzing it against 500 mM NaCl, 20% glycerol, 25 mM Tris/HCl pH7.4, containing protease inhibitors. After renaturation the protein can be purified by ion exchange, hydrophobic interaction and size exclusion chromatography. Alternatively, an affinity chromatography step such as an antibody column can be used to obtain pure TR9 receptor protein. The purified protein is stored at 4° C. or frozen at −80° C.

Example 2

Cloning and Expression of the TR9 Receptor Protein in a Baculovirus Expression System In this illustrative example, the plasmid shuttle vector pA2 is used to insert the cloned DNA encoding the complete protein, including its naturally associated secretary signal (leader) sequence, into a baculovirus to express the mature TR9 receptor protein, using standard methods as described in Summers et al., *A Manual of Methods for Baculovirus Vectors and Insect Cell Culture Procedures*, Texas Agricultural Experimental Station Bulletin No. 1555 (1987). This expression vector contains the strong polyhedrin promoter of the *Autographa californica* nuclear polyhedrosis virus (AcMNPV) followed by convenient restriction sites such as BamHI and Asp718. The polyadenylation site of the simian virus 40 ("SV40") is used for efficient polyadenylation. For easy selection of recombinant virus, the plasmid contains the beta-galactosidase gene from *E. coli* under control of a weak *Drosophila* promoter in the same orientation, followed by the polyadenylation signal of the polyhedrin gene. The inserted genes are flanked on both sides by viral sequences for cell-mediated homologous recombination with wild-type viral DNA to generate viable virus that express the cloned polynucleotide.

Many other baculovirus vectors could be used in place of the vector above, such as pAc373, pVL941 and pAcIM1, as one skilled in the art would readily appreciate, as long as the construct provides appropriately located signals for transcription, translation, secretion and the like, including a signal peptide and an in-frame AUG as required. Such vectors are described, for instance, in Luckow et al., *Virology* 170:31-39 (1989).

The cDNA sequence encoding the full length TR9 protein in the deposited clone, including the AUG initiation codon and the naturally associated leader sequence shown in FIGS. 1A-D (SEQ ID NO:2), is amplified using PCR oligonucleotide primers corresponding to the 5' and 3' sequences of the gene. The 5' primer has the sequence: 5'-CGC CCCGGGGCC ATC ATG GGG ACC TCT CCG AGC-3' (SEQ ID NO:13) containing the underlined SmaI restriction enzyme site, an efficient signal for initiation of translation in eukaryotic cells, as described by Kozak, M., *J. Mol. Biol.* 196:947-950 (1987), followed by a number of bases of the sequence of the complete TR9 receptor protein shown in FIGS. 1A-D, beginning with the AUG initiation codon.

The 3' primer (for cloning the soluble form) has the sequence: 5'-CGC GGTACCTTA GGG CAA ATG CTC ATT G-3' (SEQ ID NO:14) containing the underlined Asp718 restriction site followed by nucleotides complementary to the 3' noncoding sequence in FIGS. 1A-D.

The amplified fragment is isolated from a 1% agarose gel using a commercially available kit ("Geneclean," BIO 101 Inc., La Jolla, Calif.). The fragment then is digested with SmaI and Asp718 and again is purified on a 1% agarose gel. This fragment is designated herein "F1".

The plasmid is digested with the restriction enzymes SmaI and Asp718 and optionally, can be dephosphorylated using calf intestinal phosphatase, using routine procedures known in the art. The DNA is then isolated from a 1% agarose gel using a commercially available kit ("Geneclean" BIO 101 Inc., La Jolla, Calif.). This vector DNA is designated herein "V1".

Fragment F1 and the dephosphorylated plasmid V1 are ligated together with T4 DNA ligase. *E. coli* HB101 or other suitable *E. coli* hosts such as XL-1 Blue (Stratagene Cloning Systems, La Jolla, Calif.) cells are transformed with the ligation mixture and spread on culture plates. Bacteria are identified that contain the plasmid with the human TR9 receptor gene using the PCR method, in which one of the primers that is used to amplify the gene and the second primer is from well within the vector so that only those bacterial colonies containing the TR9 receptor gene fragment will show amplification of the DNA. The sequence of the cloned fragment is confirmed by DNA sequencing. This plasmid is designated herein pBacTR9.

Five µg of the plasmid pBacTR9 are co-transfected with 1.0 µg of a commercially available linearized baculovirus DNA ("BaculoGod™ baculovirus DNA", Pharmingen, San Diego, Calif.), using the lipofection method described by Felgner et al., *Proc. Natl. Acad. Sci. USA* 84:7413-7417 (1987). One µg of BaculoGod™ virus DNA and 5 µg of the plasmid pBacTR9 are mixed in a sterile well of a microtiter plate containing 50 µl of serum-free Grace's medium (Life Technologies Inc., Rockville, Md.). Afterwards, 10 µl Lipofectin plus 90 µl Grace's medium are added, mixed and incubated for 15 minutes at room temperature. Then the transfection mixture is added drop-wise to Sf9 insect cells (ATCC CRL 1711) seeded in a 35 mm tissue culture plate with 1 ml Grace's medium without serum. The plate is rocked back and forth to mix the newly added solution. The plate is then incubated for 5 hours at 27° C. After 5 hours the transfection solution is removed from the plate and 1 ml of Grace's insect medium supplemented with 10% fetal calf serum is added. The plate is put back into an incubator and cultivation is continued at 27° C. for four days.

After four days the supernatant is collected and a plaque assay is performed, as described by Summers and Smith, supra. An agarose gel with "Blue Gal" (Life Technologies Inc., Rockville, Md.) is used to allow easy identification and isolation of gal-expressing clones, which produce blue-stained plaques. (A detailed description of a "plaque assay" of this type can also be found in the user's guide for insect cell culture and baculovirology distributed by Life Technologies Inc., Rockville, Md., page 9-10). After appropriate incubation, blue stained plaques are picked with the tip of a micropipettor (e.g., Eppendorf). The agar containing the recombinant viruses is then resuspended in a microcentrifuge tube containing 200 μl of Grace's medium and the suspension containing the recombinant baculovirus is used to infect Sf9 cells seeded in 35 mm dishes. Four days later the supernatants of these culture dishes are harvested and then they are stored at 4° C. The recombinant virus is called V-TR9.

To verify the expression of the V-TR9 gene, Sf9 cells are grown in Grace's medium supplemented with 10% heat inactivated FBS. The cells are infected with the recombinant baculovirus V-TR9 at a multiplicity of infection ("MOI") of about 2. Six hours later the medium is removed and is replaced with SF900 II medium minus methionine and cysteine (available from Life Technologies Inc., Rockville, Md.). If radiolabeled proteins are desired, 42 hours later, 5 μCi of $^{35}$S-methionine and 5 μCi $^{35}$S-cysteine (available from Amersham) are added. The cells are further incubated for 16 hours and then they are harvested by centrifugation. The proteins in the supernatant as well as the intracellular proteins are analyzed by SDS-PAGE followed by autoradiography (if radiolabeled). Microsequencing of the amino acid sequence of the amino terminus of purified protein may be used to determine the amino terminal sequence of the mature protein and thus the cleavage point and length of the secretory signal peptide.

Example 3

Cloning and Expression of TR9 in Mammalian Cells

A typical mammalian expression vector contains the promoter element, which mediates the initiation of transcription of mRNA, the protein coding sequence, and signals required for the termination of transcription and polyadenylation of the transcript. Additional elements include enhancers, Kozak sequences and intervening sequences flanked by donor and acceptor sites for RNA splicing. Highly efficient transcription can be achieved with the early and late promoters from SV40, the long terminal repeats (LTRS) from Retroviruses, e.g., RSV, HTLVI, HIVI and the early promoter of the cytomegalovirus (CMV). However, cellular elements can also be used (e.g., the human actin promoter). Suitable expression vectors for use in practicing the present invention include, for example, vectors such as PSVL and PMSG (Pharmacia, Uppsala, Sweden), pRSVcat (ATCC 37152), pSV2dhfr (ATCC 37146) and pBC12MI (ATCC 67109). Mammalian host cells that could be used include, human Hela 293, H9 and Jurkat cells, mouse NIH3T3 and C127 cells, Cos 1, Cos 7 and CV 1, quail QC1-3 cells, mouse L cells and Chinese hamster ovary (CHO) cells.

Alternatively, the gene can be expressed in stable cell lines that contain the gene integrated into a chromosome. The co-transfection with a selectable marker such as dhfr, gpt, neomycin, or hygromycin allows the identification and isolation of the transfected cells.

The transfected gene can also be amplified to express large amounts of the encoded protein. The dihydrofolate reductase (DHFR) marker is useful to develop cell lines that carry several hundred or even several thousand copies of the gene of interest. Another useful selection marker is the enzyme glutamine synthase (GS) (Murphy et al., *Biochem J.* 227:277-279 (1991); Bebbington et al., *Bio/Technology* 10:169-175 (1992)). Using these markers, the mammalian cells are grown in selective medium and the cells with the highest resistance are selected. These cell lines contain the amplified gene(s) integrated into a chromosome. Chinese hamster ovary (CHO) and NSO cells are often used for the production of proteins.

The expression vectors pC1 and pC4 contain the strong promoter (LTR) of the Rous Sarcoma Virus (Cullen et al., *Molec. Cell. Biol.* 5:438-447 (1985)) plus a fragment of the CMV-enhancer (Boshart et al., *Cell* 41:521-530 (1985)). Multiple cloning sites, e.g., with the restriction enzyme cleavage sites BamHI, XhaI and Asp718, facilitate the cloning of the gene of interest. The vectors contain in addition the 3' intron, the polyadenylation and termination signal of the rat preproinsulin gene.

Example 3(a)

Cloning and Expression in COS Cells

The expression plasmid, pTR9-HA, is made by cloning a cDNA encoding TR9 into the expression vector pcDNAI/Amp or pcDNAIII (which can be obtained from Invitrogen, Inc.).

The expression vector pcDNAI/Amp contains: (1) an *E. coli* origin of replication effective for propagation in *E. coli* and other prokaryotic cells; (2) an ampicillin resistance gene for selection of plasmid-containing prokaryotic cells; (3) an SV40 origin of replication for propagation in eukaryotic cells; (4) a CMV promoter, a polylinker, an SV40 intron; (5) several codons encoding a hemagglutinin fragment (i.e., an "HA" tag to facilitate purification) followed by a termination codon and polyadenylation signal arranged so that a cDNA can be conveniently placed under expression control of the CMV promoter and operably linked to the SV40 intron and the polyadenylation signal by means of restriction sites in the polylinker. The HA tag corresponds to an epitope derived from the influenza hemagglutinin protein described by Wilson et al., *Cell* 37:767-778 (1984). The fusion of the HA tag to the target protein allows easy detection and recovery of the recombinant protein with an antibody that recognizes the HA epitope. pcDNAIII contains, in addition, the selectable neomycin marker.

A DNA fragment encoding the TR9 is cloned into the polylinker region of the vector so that recombinant protein expression is directed by the CMV promoter. The plasmid construction strategy is as follows. The TR9 cDNA of the deposited clone is amplified using primers that contain convenient restriction sites, much as described above for construction of vectors for expression of TR9 in *E. coli*. Suitable primers include the following, which are used in this example.

The 5' primer, containing the underlined SmaI site, a Kozak sequence, an AUG start codon and codons of the 5' coding region of the complete TR9 receptor has the following sequence: 5'-CGC CCCGGGCC ATC ATG GGG ACC TCT CCG AGC-3' (SEQ ID NO: 13).

The 3' primer, containing the underlined XbaI site, a stop codon, and nucleotides of the 3' coding sequence, has the following sequence (at the 3' end): 5'-CGC TCTAGATCA AGC GTA GTC TGG GAC GTC GTA TGG GTA GGG CAA ATG CTC ATT G-3' (SEQ ID NO: 15).

The PCR amplified DNA fragment and the vector, pcDNAI/Amp, are digested with SmaI and XbaI and then ligated. The ligation mixture is transformed into *E. coli* strain SURE (available from Stratagene Cloning Systems, 11099 North Torrey Pines Road, La Jolla, Calif. 92037), and the transformed culture is plated on ampicillin media plates which then are incubated to allow growth of ampicillin resistant colonies. Plasmid DNA is isolated from resistant colonies and examined by restriction analysis or other means for the presence of the TR9-encoding fragment.

For expression of recombinant TR9, COS cells are transfected with an expression vector, as described above, using DEAE-DEXTRAN, as described, for instance, in Sambrook et al., *Molecular Cloning: a Laboratory Manual*, Cold Spring Laboratory Press, Cold Spring Harbor, N.Y. (1989). Cells are incubated under conditions for expression of TR9 by the vector.

Expression of the TR9-HA fusion protein is detected by radiolabeling and immunoprecipitation, using methods described in, for example Harlow et al., *Antibodies: A Laboratory Manual*, 2nd Ed.; Cold Spring Harbor Laboratory Press, Cold Spring Harbor, N.Y. (1988). To this end, two days after transfection, the cells are labeled by incubation in media containing $^{35}$S-cysteine for 8 hours. The cells and the media are collected, and the cells are washed and lysed with detergent-containing RIPA buffer: 150 mM NaCl, 1% NP-40, 0.1% SDS, 0.5% DOC, 50 mM TRIS, pH 7.5, as described by Wilson et al. cited above. Proteins are precipitated from the cell lysate and from the culture media using an HA-specific monoclonal antibody. The precipitated proteins then are analyzed by SDS-PAGE and autoradiography. An expression product of the expected size is seen in the cell lysate, which is not seen in negative controls.

Example 3(b)

Cloning and Expression in CHO Cells

The vector pC4 is used for the expression of TR9 protein. Plasmid pC4 is a derivative of the plasmid pSV2-dhfr (ATCC Accession No. 37146). The plasmid contains the mouse DHFR gene under control of the SV40 early promoter. Chinese hamster ovary- or other cells lacking dihydrofolate activity that are transfected with these plasmids can be selected by growing the cells in a selective medium (alpha minus MEM, Life Technologies, Rockville, Md.) supplemented with the chemotherapeutic agent methotrexate. The amplification of the DHFR genes in cells resistant to methotrexate (MTX) has been well documented (see, e.g., Alt et al., *J. Biol. Chem.* 253:1357-1370 (1978); Hamlin et. al., *Biochem. et Biophys. Acta*, 1097:107-143 (1990); and Page et. al., *Biotechnology* 9:64-68 (1991)). Cells grown in increasing concentrations of MTX develop resistance to the drug by overproducing the target enzyme, DHFR, as a result of amplification of the DHFR gene. If a second gene is linked to the DHFR gene, it is usually co-amplified and over-expressed. It is known in the art that this approach may be used to develop cell lines carrying more than 1,000 copies of the amplified gene(s). Subsequently, when the methotrexate is withdrawn, cell lines are obtained which contain the amplified gene integrated into one or more chromosome(s) of the host cell.

Plasmid pC4 contains for expressing the gene of interest the strong promoter of the long terminal repeat (LTR) of the Rous Sarcoma Virus (Cullen et al., *Molec. Cell. Biol.* 5:438-447 (1985)) plus a fragment isolated from the enhancer of the immediate early gene of human cytomegalovirus (CMV) (Boshart et al., *Cell* 41:521-530 (1985)). Downstream of the promoter are BamHI, XhaI, and Asp718 restriction enzyme cleavage sites that allow integration of the genes. Behind these cloning sites the plasmid contains the 3' intron and polyadenylation site of the rat preproinsulin gene. Other high efficiency promoters can also be used for the expression, e.g., the human β-actin promoter, the SV40 early or late promoters or the long terminal repeats from other retroviruses, e.g., HIV and HTLVI. Clontech's Tet-Off and Tet-On gene expression systems and similar systems can be used to express the TR9 in a regulated way in mammalian cells (Gossen et. al., *Proc. Natl. Acad. Sci. USA* 89:5547-5551 (1992). For the polyadenylation of the mRNA other signals, e.g., from the human growth hormone or globin genes can be used as well. Stable cell lines carrying a gene of interest integrated into the chromosomes can also be selected upon co-transfection with a selectable marker such as gpt, G418 or hygromycin. It is advantageous to use more than one selectable marker in the beginning, e.g., G418 plus methotrexate.

The plasmid pC4 is digested with the restriction enzymes SmaI and Asp718 and then dephosphorylated using calf intestinal phosphatase by procedures known in the art. The vector is then isolated from a 1% agarose gel.

The DNA sequence encoding the complete TR9 protein including its leader sequence is amplified using PCR oligonucleotide primers corresponding to the 5' and 3' sequences of the gene.

The 5' primer has the sequence: 5'-CGC <u>CCCGGGGCC</u> ATC ATG GGG ACC TCT CCG AGC-3' (SEQ ID NO:13) restriction enzyme site, an efficient signal for initiation of translation in eukaryotic cells, as described by Kozak, M., *J. Mol Biol.* 196:947-950 (1987), followed by a number of bases of the coding sequence of the TR9 receptor protein shown in FIGS. 1A-D (SEQ ID NO:1).

The 3' primer (for cloning the soluble form) has the sequence: 5'-CGC <u>GGTACC</u>TTA GGG CAA ATG CTC ATT G-3' (SEQ ID NO:14) containing the underlined Asp718 restriction site followed by nucleotides complementary to the non-translated region of the TR9 receptor gene shown in FIGS. 1A-D (SEQ ID NO:1).

The amplified fragment is digested with the endonucleases SmaI and then purified again on a 1% agarose gel. The isolated fragment and the dephosphorylated vector are then ligated with T4 DNA ligase. *E. coli* HB101 or XL-1 Blue cells are then transformed and bacteria are identified that contain the fragment inserted into plasmid pC4 using, for instance, restriction enzyme analysis.

Chinese hamster ovary cells lacking an active DHFR gene are used for transfection. Five μg of the expression plasmid pC4 is cotransfected with 0.5 μg of the plasmid pSV2-neo using lipofectin (Felgner et al., supra). The plasmid pSV2neo contains a dominant selectable marker, the neo gene from Tn5 encoding an enzyme that confers resistance to a group of antibiotics including G418. The cells are seeded in alpha minus MEM supplemented with 1 mg/ml G418. After 2 days, the cells are trypsinized and seeded in hybridoma cloning plates (Greiner, Germany) in alpha minus MEM supplemented with 10, 25, or 50 ng/ml of methotrexate plus 1 mg/ml G418. After about 10-14 days single clones are trypsinized and then seeded in 6-well petri dishes or 10 ml flasks using different concentrations of methotrexate (50 nM, 100 nM, 200 nM, 400 nM, 800 nM). Clones growing at the highest concentrations of methotrexate are then transferred to new 6-well plates containing even higher concentrations of methotrexate (1 μM, 2 μM, 5 μM, 10 μM, 20 μM). The same procedure is repeated until clones are obtained which grow at a concentration of 100-200 μM. Expression of the desired gene product is analyzed, for instance, by SDS-PAGE and Western blot or by reverse phase HPLC analysis.

Example 4

Tissue Distribution of TR9 mRNA Expression

Northern blot analysis is carried out to examine TR9 gene expression in human tissues, using methods described by, among others, Sambrook et al., supra. A cDNA probe containing the entire nucleotide sequence of the TR9 protein (SEQ ID NO:1) is labeled with $^{32}$P using the rediprime™ DNA labeling system (Amersham Life Science), according to manufacturer's instructions. After labeling, the probe was purified using a CHROMA SPIN-100™ column (Clontech Laboratories, Inc.), according to manufacturer's protocol number PT1200-1. The purified labeled probe is then used to examine various human tissues for TR9 mRNA.

Multiple Tissue Northern (MTN) blots containing various human tissues (H) or human immune system tissues (IM) are obtained from Clontech and are examined with the labeled probe using ExpressHyb™ hybridization solution (Clontech) according to manufacturer's protocol number PT1190-1. Following hybridization and washing, the blots are mounted and exposed to film at −70° C. overnight, and films developed according to standard procedures.

Example 5

TR9 Induced Apoptosis

Overexpression of Fas/APO-1 and TNFR-1 in mammalian cells mimics receptor activation (M. Muzio et al., Cell 85:817-827 (1996); M. P. Boldin et al., Cell 85:803-815 (1996)). Thus, this system is utilized to study the functional role of TR9. Transient expression of TR9 in MCF7 breast carcinoma cells and 293 human embryonic kidney cells is investigated for induction of apoptosis.

Experimental Design

Cell death assays are performed essentially as previously described (A. M. Chinnaiyan et al., Cell 81:505-512 (1995); M. P. Boldin et al., J. Biol. Chem. 270: 7795-8 (1995); F. C. Kischkel et al., EMBO 14:5579-5588 (1995); A. M. Chinnaiyan et al., J. Biol. Chem. 271:4961-4965 (1996)). Briefly, MCF-7 human breast carcinoma clonal cell lines stably transfected with either vector alone, a CrmA expression construct (M. Tewari et al., J. Biol. Chem. 270:3255-60 (1995)), or FADD-DN expression construct (A. M. Chinnaiyan et al., J. Biol. Chem. 271:4961-4965 (1996)) are transiently transfected with pCMV-TR9-galactosidase in the presence of a ten-fold excess of pcDNA3 expression constructs encoding the indicated proteins using lipofectamine (GIBCO-BRL). 293 cells are likewise transfected using the CaPO4 method. The ICE family inhibitor z-VAD-fmk (Enzyme Systems Products, Dublin, Calif.) is added to the cells at a concentration of 10 uM, 5 hrs after transfection. 32 hours following transfection, cells are fixed and stained with X-Gal as previously described (A. M. Chinnaiyan et al., Cell 81:505-12 (1995); M. P. Boldin et al., J. Biol. Chem. 270:7795-8 (1995); F. C. Kischkel et al., EMBO 14:5579-5588 (1995)).

Results

The affected cells will display morphological alterations typical of cells undergoing apoptosis, becoming rounded, condensed, and detaching from the dish. Similar to TNFR-1 and Fas/APO-1 (M. Muzio et al., Cell 85:817-827 (1996); M. P. Boldin et al., Cell 85:803-815 (1996); M. Tewari et al., J. Biol. Chem. 270:3255-60 (1995)), TR9-induced apoptosis is blocked by the inhibitors of ICE-like proteases, CrmA and z-VAD-fmk.

Example 6

Characterization of TR9

Members of the TNF receptor family are crucial modulators of inflammatory and cellular immune responses, and mediate a variety of biological functions, ranging from cell proliferation, differentiation and apoptosis to cell survival (Nagata, S., Cell 88:355-365 (1997); Armitage, R. J., Curr. Opin. Immuno. 6:407-413 (1994); Golstein, P., Curr. Biol. 7:R750-R753 (1997); Baichwal et al., Curr. Biol. 7:R94-R96. (1997); Smith et al., Cell 76: 959-962 (1994); Anderson et al., Nature 390:175-179 (1997); and Cleveland et al., Cell 81:479-482 (1995)). This family of receptors is characterized by several extracellular, cysteine-rich motifs that compose the ligand binding domain (Armitage, R. J., Curr. Opin. Immuno. 6:407-413 (1994); and Smith et al., Cell 76: 959-962 (1994)). Upon ligation by their cognate ligands, these receptors engage a number of signal transduction pathways, including apoptosis, activation of NF□B and JNK pathways that modulate the expression of genes involved in the immune and stress response (Smith et al., Cell 76: 959-962 (1994)).

Within the TNF receptor family, six members have emerged as a distinct subgroup termed death receptors; they contain a cytoplasmic death domain and activation of these receptors leads to engagement of components of the cell death pathway (Nagata, S., Cell 88:355-365 (1997); and Golstein, P., Curr. Biol. 7:R750-R753 (1997)). Transmission of the death signal is mediated by a series of homophilic protein-protein interactions involving the death domain and death effector domain that was originally defined as being present in the adaptor molecule FADD/MORT1 and the death protease caspase-8 (Chinnaiyan et al., Semmin. Immunol. 9:66-67 (1997)). For example, when the death receptor CD95/Fas is ligated by cognate ligand or agonist antibody, the adaptor molecule FADD and the death protease caspase-8 are recruited to the signalling complex through interactions involving death and death effector domains, respectively (Chinnaiyan et al., Semmin. Immunol. 9:66-67 (1997); Muzio et al., Cell 85: 817-827 (1996); and Boldin et al., Cell 85:803-815 (1996)). On approximation, caspase-8 undergoes an autoactivation, initiating activation of the downstream caspases, cleavage of death substrates and demise of the cell (Muzio et al, J. Biol. Chem. 273:2952-2956 (1997); Barinaga, M., Science 280:32-34 (1998); Salvesen et al., Cell 91:443-446 (1997); and Martin et al., Cell 82: 349-352 (1995)). In contrast to CD-95 that directly engages the FADD-caspase-8 pathway (Muzio et al., Cell 85: 817-827 (1996); Boldin et al., Cell 85:803-815 (1996); Chinnaiyan et al., Cell 81:505-512 (1995); and Boldin et al., J. Biol. Chem. 270:7795-7789 (1995)), both TNFR1 and DR3 utilize a primary adaptor molecule termed TRADD, around which assembles the FADD-caspase-8 pathway, an NF□B activating pathway involving the death domain-containing Ser/Thr kinase RIP and a JNK activating pathway that is mediated by the adaptor molecule TRAF2 (Hsu et al., Cell 81:495-504 (1995); Hsu et al., Immunity 4:387-396 (1996); Chinnaiyan et al., Science 274:990-992 (1996); Kitson et al., Nature 384:372-375 (1996); Yeh et al., Immunity 7:715-725 (1997); Lee et al., Immunity 7:703-713 (1997); and Kelliher et al., Immunity 8:297-303 (1998). Finally, there exists a subsidiary death pathway involving the death domain-containing adaptor RAIDD that binds to caspase-2 and has been shown to be part of the TNFR1 receptor complex, although the exact physiologic relevance of this redundant pathway remains unclear (Duan et al., Nature 385:86-89 (1997); and Ahmad et al., Cancer Res. 57:615-619 (1997).

Here, we report the identification and initial characterization of TR9, a new member of the TNF receptor family possessing a cytoplasmic death domain. TR9 induced apoptosis in mammalian cells and was capable of engaging the NF☐B and JNK pathways.

Materials and Methods

Expression Constructs—TR9 (amino acid residues 42-655 as depicted in FIGS. 1A-D; amino acid residues 2-615 as presented in SEQ ID NO:2) and TR9 delta (amino acid residues 42-460 as depicted in FIGS. 1A-D; amino acid residues 2-420 as presented in SEQ ID NO:2) were cloned into pCMV1FLAG (IBI-Kodak) as in frame fusions to a TR9-terminal Preprotrypsin leader sequence and FLAG tag encoded by the vector. cDNAs were obtained by polymerase chain reaction using DNA oligo primers for TR9: 5'-GGA AGATCTGCC AGA ACA GAA GGC CTC GAA T-3' (SEQ ID NO:16) and 5'-CCA TCT TCC TGA CCT GCT GTA GTC TAG AGC C-3' (SEQ ID NO:17) and for TR9 delta: 5'-GGA AGATCTGCC AGA ACA GAA GGC CTC GAA T-3' (SEQ ID NO:16) and 5'-GCC GAC CAC GAG CGG GCC TAG TCTAGAGCC-3' (SEQ ID NO:18). Constructs encoding DR4, FADD, CD95, DR3, TRADD, ICH1-pro, RAIDD and RIP have been described previously (Chinnaiyan et al., *Cell* 81:505-512 (1995); Hsu et al., *Cell* 81:495-504 (1995); Hsu et al., *Immunity* 4:387-396 (1996); Chinnaiyan et al., *Science* 274:990-992 (1996); Kelliher et al., *Immunity* 8:297-303 (1998); and Pan et al., *Science* 276:111-113 (1997)).

Apoptosis Assay—Cell death assays were performed as previously described (Chinnaiyan et al., *Cell* 81:505-512 (1995); and Pan et al., *Science* 276:111-113 (1997)). Both Hela and MCF7 cells were transfected using the lipofectamine procedure (Life Technologies, Inc.) according to the manufacturer's instructions.

Co-immunoprecipitation Assay—In vivo interaction assays have been described elsewhere (Chinnaiyan et al., *Cell* 81:505-512(1995); and Pan et al., *Science* 276:111-113 (1997)). 293 cells were co-transfected with FLAG-TR9, FLAG-TR9 delta, FLAG-CD95, FLAG-DR3, FLAG-TNFR1, and ICH-1pro-FLAG, expression constructs using standard calcium phosphate precipitation. After transfection (at 38-40 hours), cell lysates were prepared and the FLAG-tagged expressed proteins were immunoprecipitated with FLAG M2 affinity gel (IBI-Kodak) and the presence of FADD, myc-tagged TRADD and RIP (myc-TRADD and myc-RIP), or RAIDD detected by immunoblotting with polyclonal antibody to FADD horseradish peroxidase (HRP)-conjugated antibody to myc (BMB), or polyclonal antibody to RAIDD.

NF-☐B Luciferase Assay NF-☐B luciferase assays were done as described elsewhere (Chinnaiyan et al., *Cell* 81:505-512(1995); and Pan et al., *Science* 276:111-113 (1997)).

JNK Activation Assay—293 cells were cultured in MEM containing 10% FBS. Cells were plated in 6-well plates and transfected with TR9 expressing plasmid or vector alone at 60-70% confluency by the lipofectamine method according to the manufacturer's instructions. Forty hours post transfection, cell extracts were prepared in lysis buffer containing 20 mM HEPES, pH 7.4, 2 mM EDTA, 250 mM NaCl, 0.1% NP-40, 2 micrograms/ml leupeptin, 2 micrograms/ml aprotinin, 1 mM PMSF, 0.5 micrograms/ml benzamide, 1 mM DTT and 1 mM orthovanadate. The C-jun kinase assay was performed by a modified method as described (Haridas et al., *Immunol.* 160:3152-3162 (1998)). Briefly, cell extracts (70 micrograms) were subjected to immunoprecipitation with 0.03 µg anti-JNK antibody for 30 min at 4° C. Immunocomplexes were collected by incubation with protein A/G-sepharose beads for 30 min at 4° C. The beads were extensively washed with lysis buffer (4×400 microliters) and kinase buffer (2×400 microliters: 20 mM HEPES, pH 7.4, 1 mM DTT, 25 mM NaCl) and the kinase reaction allowed to proceed for 15 min at 30° C with 2 micrograms GST-Jun (1-79) in 2 microliters containing 20 mM HEPES, pH 7.4, 10 mM MgCl$_2$, 1 mM DTT and 10 microcuries [gamma$^{32}$P]ATP. Reactions were stopped by the addition of 15 microliters SDS-sample buffer and resolved by SDS-polyacrylamide gel electrophoresis. GST-Jun (1-79) was visualized by staining with Coomassie Blue and the dried gel visualized following Phosphorimager analysis (Molecular Dynamics; Sunnyvale, Calif.) and quantitation by ImageQuant Software (Molecular Dynamics). A specific assay for JNK activity involved the co-transfection of 3×10$^6$ 293 cells with vector, or the CD40, TR9, or TR9 delta expression constructs (6.4 micrograms) together with 2.4 micrograms of a JNK-myc expression plasmid using the calcium phosphate precipitation method. After transfection (approximately 36 hours), cell extracts were prepared by lysis in NP 40 buffer (20 mM Tris-Cl, pH 8.0, 137 mM NaCl, 10% Glycerol, 2 mM EDTA, 5 mM Na$_2$VO$_4$, 0.5 mM PMSF and 1% NP40) plus protease inhibitor cocktail (BMB). Immunoprecipitation of JNK-myc was performed using monoclonal anti-myc antibody (10 micrograms, Babco) and immunocomplexes precipitated with 20 microliters protein G-sepharose (50% slurry, Sigma) and detected by blotting with anti-myc-HRP. FLAG tagged CD40, TR9, and TR9 delta were immunoprecipitated with anti-FLAG M2 affinity gel and detected by blotting with anti-FLAG antibody. The kinase assay utilized 2 micrograms GST Jun(1-79) as substrate, 50 mM ATP and 5 microcuries [gamma$^{32}$P]ATP in 30 microliters kinase buffer (30 mM HEPES, pH 7.4, 7 mM MnCl$_2$, 5 mM MgCl$_2$ and 1 mM DTT).

Results and Discussion

TR9 has a putative signal sequence (amino acid residues 1-41 as depicted in FIGS. 1A-D and 4A; amino acid residues −40 to 1 in SEQ ID NO:2), with the mature form predicted to start at amino acids 42 (Gln) as depicted in FIGS. 1A-D and 4A (Nielson et al., *Protein. Eng.* 10:1-6 (1997)). The extracellular portion (amino acid residues 42-350 as depicted in FIGS. 1A-D and 4A; amino acid residues 2-310 in SEQ ID NO:2) contains four TNFR-like cysteine-rich motifs of TR9 (amino acid residues 67-211 as depicted in FIGS. 1A-D; amino acid residues 27-171 in SEQ ID NO:2) that are most related to those of osteoprotegerin (OPG) and TNFR2 with 36% and 42% amino acid identities, respectively (FIG. 4B; data not shown). A transmembrane domain (amino acids 351 to 370 as depicted in FIGS. 1A-D and 4A; residues 311 to 330 of SEQ ID NO:2) is followed by a 285-amino acid long cytoplasmic portion of the molecule that contains a death domain related to those of all known death receptors (FIG. 4C), being most related to the death domain of TNFR1 (27.2%) and least like that of DR5 (19.7%). Curiously, unlike other death receptors that have death domains present in their COOH-terminus, the death domain in TR9 was located adjacent to the transmembrane domain followed by a 150 amino acid tail. Interestingly, following the death domain was a putative leucine zipper sequence overlapping with a proline-rich region reminiscent of a SH3 domain-binding motif (FIG. 4A) (Pawson et al., *Science* 278:2075-2080 (1997)).

TR9 mRNA expression in human tissues and cancer cell lines—A 4-kb TR9 transcript was found in most human adult tissue, immune tissue, and cancer cell lines represented on Northern blots (Clontech) that were probed with TR9 cDNA according to the manufacturers instructions (data not shown). The transcript was abundant in heart, brain, placenta, pancreas, lymph node, thymus and prostate. Lower levels were detected in lung, skeletal muscle, kidney, testis, uterus, small intestine, colon, spleen, bone marrow, and fetal liver. However, adult liver and peripheral blood leukocytes expressed little TR9 mRNA. Additionally, smaller transcripts of 3.1 and 2.4 kb were observed in the testis and fetal liver, respectively.

Among human cancer cell lines, abundant levels of 4-kb transcript was detected in several nonlymphoid tumor cells, including cervical carcinoma Hela S3, colorectal adenocarcinoma SW480, lung carcinoma A549, and melanoma G361 cells. Significantly, less or no expression was observed in lines of hematopoietic origin (e.g., Raji, K562, and HL-60; data not shown).

Figure 5:
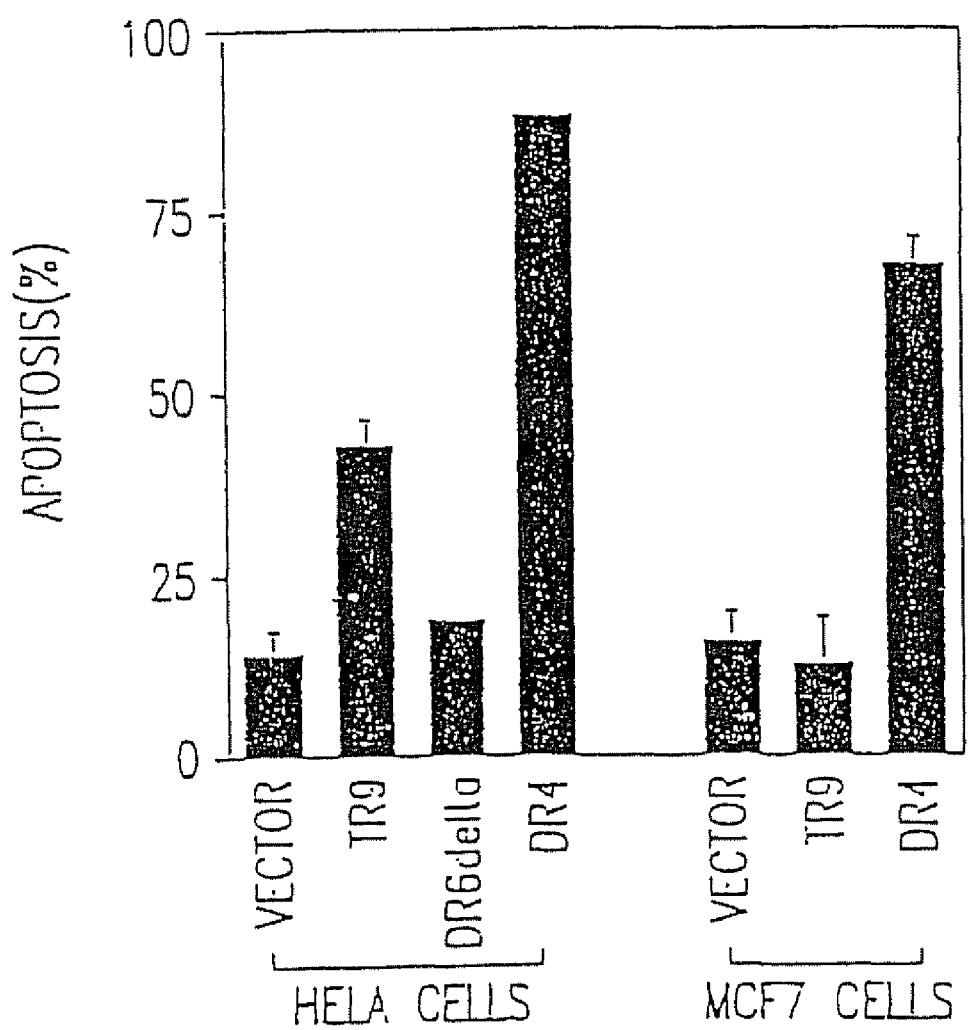
FIG. 5. TR9 induces apoptosis in mammalian cells. Ectopic expression of TR9 induces apoptosis in Hela cells, but not in MCF7 cells. Hela and MCF7 cells were cotransfected with a empty vector, TR9, TR9 delta, or DR4, together with a beta-galactosidase-expressing reporter construct using a lipofectamine method according to the manufacturer's instructions (BRL). Nineteen hours after transfection, cells were stained with 5-bromo-4-chloro-3-indoxyl-beta-D-galactopyranoside (X-Gal) and examined as described in Chinnaiyan et al., Cell 81:505-512 (1995). The data (mean ±SD) represent the percentage of round, apoptotic cells as a function of total beta-galactosidase-positive cells (n=4).

TR9 induces apoptosis in mammalian cells—Since ectopic expression of death receptors can induce cell death in a ligand-independent manner (Chinnaiyan et al., Cell 81:505-512 (1995); Boldin et al., J. Biol. Chem. 270:7795-7789 (1995); Chinnaiyan et al., Science 274:990-992 (1996); Kitson et al., Nature 384:372-375 (1996); and Pan et al., Science 276:111-113 (1997)), we tested if TR9 could induce apoptosis upon overexpression. When Hela S3 cervical carcinoma cells were transfected with a TR9-expressing construct, 43% of the transfected cells underwent morphological changes characteristic of apoptosis (FIG. 5). As expected, deletion of the putative death domain (TR9 delta) abolished its killing activity. Significantly, TR9 was unable to induce cell death in human breast carcinoma MCF7 cells although they were very sensitive to DR4 killing (FIG. 5 and not shown), suggesting that the cell death pathway engaged by TR9 may be distinct from that engaged by other death receptors. Alternatively, the apoptotic activity of TR9 may be modulated by other signaling pathways it activates (see below) or ligand binding may be required to unveil its full killing capacity.

Interaction of TR9 with adaptor molecules in vivo—Death receptors utilize the adaptor molecules FADD (for CD95) or both TRADD and FADD (for TNFR1 and DR3) to transmit the death signal (Chinnaiyan et al., Cell 81:505-512 (1995); Boldin et al., J. Biol. Chem. 270:7795-7789 (1995); Chinnaiyan et al., Science 274:990-992 (1996); and Kitson et al., Nature 384:372-375 (1996)). We thus determined if TR9 could bind any of these adaptor molecules in human embryonic kidney 293 cells. TR9 did not interact with FADD, although the association between CD95 and FADD was readily detected under similar conditions (data not shown). Interestingly, TR9 was found to associate with TRADD, although the interaction was weaker than that between DR3 and TRADD (data not shown). This observation is consistent with the observation that TR9 has a weaker killing ability. Alternatively, TR9 may use a TRADD-related molecule as an adaptor, or the observed association might be bridged by another adaptor protein. Interaction was not detectable between TR9 and RAIDD or RIP, two other adaptor molecules known to be recruited to the TNFR1 and DR3 signalling complexes (data not shown).

TR9 activates nuclear factor-kappab—Both TNFR1 and DR3 can engage a signal transduction pathway that leads to the activation of NF-kappaB (Smith et al., Cell 76: 959-962 (1994); Chinnaiyan et al., Science 274:990-992 (1996); Kitson et al., Nature 384:372-375 (1996); and Baker et al., Oncogene 12:1-9 (1996)). The ability of TR9 to activate NF-kappaB was tested in a luciferase reporter assay and was found to induce NF-kappaB activation in a dose-dependent manner (FIG. 6). Presumably overexpressing the receptor allowed it to achieve an active configuration that was competent to signal the NF-kappaB system. Interestingly, the cytoplasmic deletion of TR9 that abolished its apoptotic activity similarly abrogated its ability to activate NF-kappaB (data not shown), suggesting that these two signaling pathways may be mediated by a common receptor-proximal adapter molecule.

Ectopic expression of TR9 induces JNK activation—JNK activation is known to be induced by several TNF receptors including TNFR1 and CD40 (Smith et al., Cell 76: 959-962 (1994); Yeh et al., Immunity 7:715-725 (1997); Lee et al., Immunity 7:703-713 (1997); and Baker et al., Oncogene 12:1-9 (1996)). We next determined whether overexpression of TR9 could lead to JNK activation using an in vitro kinase assay. TR9 was found to induce JNK activation in a dose-dependent manner (data not shown). The cytoplasmic truncation that attenuated cell death or NF-kappaB activation had surprisingly little effect on JNK activation (data not shown). This would be consistent with the notion that JNK activation is mediated by a cytoplasmic segment different from that responsible for apoptosis and NF-kappaB induction. It is noteworthy that two potential TRAF-binding motifs are present adjacent to the transmembrane domain PRQDP (amino acid residues 381-385 as depicted in FIGS. 1A-D; amino acid residues 341-345 as presented in SEQ ID NO:2), and PTQNR (amino acid residues 400-404 as depicted in FIGS. 1A-D; amino acid residues 360-364 as presented in SEQ ID NO:2) (Gedrich et al., J. Biol. Chem. 271:12852-12858 (1996) and Boucher et al., Biochem. and Biophy. Res. Communi. 233:592-600 (1997).

In conclusion, we have identified a novel death domain-containing TNF receptor designated TR9. TR9 engages a cell death pathway different from those initiated by the CD95, TNFR1 or TRAIL/Apo2L receptors. In addition, TR9 also activates NF-kappaB and JNK, two signaling pathways shared by TNFR1. Thus, it is likely that like the other members of the TNF receptor family, TR9 plays a role in inflammatory responses and immune regulation.

Example 7

Gene Therapy Using Endogenous TR9 Gene

Another method of gene therapy according to the present invention involves operably associating the endogenous TR9 sequence with a promoter via homologous recombination as described, for example, in U.S. Pat. No. 5,641,670, issued Jun. 24, 1997; International Publication Number WO 96/29411, published Sep. 26, 1996; International Publication Number WO 94/12650, published Aug. 4, 1994; Koller et al., Proc. Natl. Acad. Sci. USA 86:8932-8935 (1989); and Zijlstra et al., Nature 342:435-438 (1989). This method involves the activation of a gene which is present in the target cells, but which is not expressed in the cells, or is expressed at a lower level than desired. Polynucleotide constructs are made which contain a promoter and targeting sequences, which are homologous to the 5' non-coding sequence of endogenous TR9, flanking the promoter. The targeting sequence will be sufficiently near the 5' end of TR9 so the promoter will be operably linked to the endogenous sequence upon homologous recombination. The promoter and the targeting sequences can be amplified using PCR. Preferably, the amplified promoter contains distinct restriction enzyme sites on the 5' and 3' ends. Preferably, the 3' end of the first targeting sequence contains the same restriction enzyme site as the 5' end of the amplified promoter and the 5' end of the second targeting sequence contains the same restriction site as the 3' end of the amplified promoter.

The amplified promoter and the amplified targeting sequences are digested with the appropriate restriction enzymes and subsequently treated with calf intestinal phosphatase. The digested promoter and digested targeting sequences are added together in the presence of T4 DNA ligase. The resulting mixture is maintained under conditions appropriate for ligation of the two fragments. The construct is size fractionated on an agarose gel then purified by phenol extraction and ethanol precipitation.

In this Example, the polynucleotide constructs are administered as naked polynucleotides via electroporation. However, the polynucleotide constructs may also be administered with transfection-facilitating agents, such as liposomes, viral sequences, viral particles, precipitating agents, etc. Such methods of delivery are known in the art.

Once the cells are transfected, homologous recombination will take place which results in the promoter being operably linked to the endogenous TR9 sequence. This results in the expression of TR9 in the cell. Expression may be detected by immunological staining, or any other method known in the art.

Fibroblasts are obtained from a subject by skin biopsy. The resulting tissue is placed in DMEM+10% fetal calf serum. Exponentially growing or early stationary phase fibroblasts are trypsinized and rinsed from the plastic surface with nutrient medium. An aliquot of the cell suspension is removed for counting, and the remaining cells are subjected to centrifugation. The supernatant is aspirated and the pellet is resuspended in 5 ml of electroporation buffer (20 mM HEPES pH 7.3, 137 mM NaCl, 5 mM KCl, 0.7 mM Na2 HPO4, 6 mM dextrose). The cells are recentrifuged, the supernatant aspirated, and the cells resuspended in electroporation buffer containing 1 mg/ml acetylated bovine serum albumin. The final cell suspension contains approximately 3×106 cells/ml. Electroporation should be performed immediately following resuspension.

Plasmid DNA is prepared according to standard techniques. For example, to construct a plasmid for targeting to the TR9 locus, plasmid pUC18 (MBI Fermentas, Amherst, N.Y.) is digested with HindIII. The CMV promoter is amplified by PCR with an XbaI site on the 5' end and a BamHI site on the 3' end. Two TR9 non-coding sequences are amplified via PCR: one TR9 non-coding sequence (TR9 fragment 1) is amplified with a HindIII site at the 5' end and an Xba site at the 3' end; the other TR9 non-coding sequence (TR9 fragment 2) is amplified with a BamHI site at the 5' end and a HindIII site at the 3' end. The CMV promoter and TR9 fragments are digested with the appropriate enzymes (CMV promoter—XbaI and BamHI; TR9 fragment 1—XbaI; TR9 fragment 2—BamHI) and ligated together. The resulting ligation product is digested with HindIII, and ligated with the HindIII-digested pUC18 plasmid.

Plasmid DNA is added to a sterile cuvette with a 0.4 cm electrode gap (Bio-Rad). The final DNA concentration is generally at least 120 µg/ml. 0.5 ml of the cell suspension (containing approximately 1.5×106 cells) is then added to the cuvette, and the cell suspension and DNA solutions are gently mixed. Electroporation is performed with a Gene-Pulser apparatus (Bio-Rad). Capacitance and voltage are set at 960 µF and 250-300 V, respectively. As voltage increases, cell survival decreases, but the percentage of surviving cells that stably incorporate the introduced DNA into their genome increases dramatically. Given these parameters, a pulse time of approximately 14-20 mSec should be observed.

Electroporated cells are maintained at room temperature for approximately 5 min, and the contents of the cuvette are then gently removed with a sterile transfer pipette. The cells are added directly to 10 ml of prewarmed nutrient media (DMEM with 15% calf serum) in a 10 cm dish and incubated at 37° C. The following day, the media is aspirated and replaced with 10 ml of fresh media and incubated for a further 16-24 hours.

The engineered fibroblasts are then injected into the host, either alone or after having been grown to confluence on cytodex 3 microcarrier beads. The fibroblasts now produce the protein product. The fibroblasts can then be introduced into a patient as described above Example: 8

TR9 Activates Monocytes and Increases Monocyte Survival

The effects of TR9-Fc (containing amino acids residues M1 to L350 of the sequence depicted in FIGS. 1A-D fused to an ISG1 fc fusion protein) on monocytes were evaluated using monocyte survival and TNF-alpha release functional assays.

Methods:

Monocyte Survival

Monocytes were cultured for 48 hours in polypropilene tubes: in serum-free medium (positive control); in the presence of 100 ng/ml TNF-alpha (negative control); and in the presence of 2 µg/ml and 20 µg/ml of TR9-Fc. The cultured cells were stained with Annexin V and propidium iodide to determine the number of apoptotic and dead cells.

TNF-alpha Release

Monocytes ($5 \times 10^5$) were incubated for 1 day on immobilized TR9-Fc (10 µg/ml). Conditioned media were collected and analyzed in ELISA for TNF-alpha content using R&D Systems kits.

MCP-1 Release

Monocytes ($5 \times 10^5$) were incubated for 1 day on wells coated with TR9-Fc (10 µg/ml). Conditioned media were collected and analyzed for MCP-1 content by ELISA using R&D system kits.

Results:

The effects of TR9-Fc on monocyte activation were examined using the above-described monocyte survival and TNF-alpha release assays.

In the monocyte survival assay, monocytes were cultured in serum free media and serum free media containing TR9-Fc (at concentrations of 2 µg/ml or 20 µg/ml), or TNF-alpha (100 ng/ml). After 48 hours the percentage of apoptotic or dead cells was determined by staining with Annexin V and propidium iodide. The results revealed that 81% of untreated cells were apoptotic or dead, while only 25% of the cells treated with TNF-alpha were killed. Monocytes treated with 20 µg/ml of TR9-Fc were 48% apoptotic, indicating that TR9-Fc enhances monocte survival.

In the TNF-alpha release assay, as described above, monocytes were incubated alone or on immobilized TR9-Fc (10 µg/ml) and the production of TNF-alpha was measured by a standard ELISA assay. The concentration of TNF-alpha release of the TR9-Fc treated monocytes was in all of the four donor lots tested greater than 5 fold than that observed in the absence of TR9-Fc (see Table III). Interestingly, additional experiments conducted as described above, but in the presence or absence of Interferon-gamma (5 ng/ml; Peprotech) revealed that the combination of TR9-Fc and Interferon-gamma results in a synergistic release of TNF-alpha (see Table III, Donor 4).

TABLE III

TR9-Fc-induced TNF-alpha secretion from monocytes

| Treatment | TNF-alpha (pg/ml) |
|---|---|
| Donor 1 | |
| None | 0 |
| TR9-Fc | 331 |
| Donor 2 | |
| None | 0 |
| TR9-Fc | 460 |
| Donor 3 | |
| None | 60 |
| TR9-Fc | 5290 |
| Donor 4 | |
| None | 0 |
| TR9-Fc | 5 |
| IFN-☐ | 25 |
| TR9-Fc + IFN-☐ | 85 |

Monocytes ($5 \times 10^5$) were incubated for 1 day on wells coated with TR9-Fc (10 _g/ml). Conditioned media were collected and analyzed for TNF-alpha content by ELISA.

In the MCP-1 release assay, as described above, monocytes were incubated alone or on immobilized TR9-Fc and the production of MCP-1 was measured by a standard ELISA assay. The concentration of MCP-1 release of the TR9-Fc treated monocytes was greater than that observed in the absence of TR9-Fc (see Table IV).

TABLE IV

TR9-Fc-induced MCP-1 secretion from monocytes

| Treatment | MCP-1 (pg/ml) |
|---|---|
| None | 0 |
| TR9-Fc | 351 |

Monocytes ($5 \times 10^5$) were incubated for 1 day on wells coated with TR9-Fc (10 μg/ml). Conditioned media were collected and analyzed for MCP-1 content by ELISA.

Example: 9

Assays for Monocyte Activation and/or Increased Survival

Assays for molecules that activate (or alternatively, inactivate) monocytes and/or increase monocyte survival (or alternatively, decrease monocyte survival) are known in the art and may routinely be applied to determine whether a molecule of the invention functions as a TR9 agonists (or alternatively, a TR9 antagonist). Three of such assays are described below.

Methods:

Monocyte Survival Assay

Monocytes are cultured for 48 hours in polypropylene tubes in serum-free medium (positive control), in the presence of 100 ng/ml TNF-alpha (negative control), and in the presence of varying concentrations of the compound to be tested. In assays for antagonists, the assays include varying concentrations of the composition to be tested in the presence of 20 μg/ml of TR9-Fc. Monocyte survival is assayed by staining the cells with Annexin V and propidium iodide and determining the number of apoptotic and dead cells.

As exemplified in Example 8, compounds that function as TR9 agonists will enhance monocyte survival when compared to the media alone (i.e., the positive control).

In contrast, compounds that function as TR9 antagonists will decrease monocyte survival when compared to that observed when the cells are contacted with the TR9-Fc protein alone.

TNF-alpha Release

To identify TR9-Fc agonists, monocytes ($5 \times 10^5$) are incubated for 1 day with varying concentrations of the compound to be tested. Culture media are collected and analyzed in ELISA for TNF-alpha content using R&D Systems kits. TR9-Fc agonists will induce a greater concentration of TNF-alpha release when compared to that observed when monocyte cells are incubated for 1 day under the same conditions, but in the absence of the test compound.

To identify TR9-Fc antagonists, monocytes ($5 \times 10^5$) are incubated for 1 day with varying concentrations of the compound to be tested in the presence and absence of immobilized TR9-Fc (10 μg/ml). Culture media are collected and analyzed in ELISA for TNF-alpha content using R&D Systems kits. TR9-Fc antagonists elicit a reduced TNF-alpha release from the monocytes when compared to that observed when monocytes cells are incubated in the presence of immobilized TR9-Fc, but in the absence of the test compound.

MCP-1 Release

To identify TR9-Fc agonists, monocytes ($5 \times 10^5$) are incubated for 1 day with varying concentrations of the compound to be tested. Culture media are collected and analyzed in ELISA for MCP-1 content using R&D Systems kits. TR9-Fc agonists will induce a greater concentration of MCP-1 release when compared to that observed when monocyte cells are incubated for 1 day under the same conditions, but in the absence of the test compound.

To identify TR9-Fc antagonists, monocytes ($5 \times 10^5$) are incubated for 1 day with varying concentrations of the compound to be tested in the presence and absence of immobilized TR9-Fc (10 μg/ml). Culture media are collected and analyzed in ELISA for MCP-1 content using R&D Systems kits. TR9-Fc antagonists elicit a reduced MCP-1 release from the monocytes when compared to that observed when monocytes cells are incubated in the presence of immobilized TR9-Fc, but in the absence of the test compound.

Example 10

Protein Fusions of TR9

TR9 polypeptides of the invention are optionally fused to other proteins. These fusion proteins can be used for a variety of applications. For example, fusion of TR9 polypeptides to His-tag, HA-tag, protein A, IgG domains, and maltose binding protein facilitates purification. (See EP A 394,827; Traunecker, et al., Nature 331:84-86 (1988).) Similarly, fusion to IgG-1, IgG-3, and albumin increases the halflife time in vivo. Nuclear localization signals fused to TR9 polypeptides can target the protein to a specific subcellular localization, while covalent heterodimer or homodimers can increase or decrease the activity of a fusion protein. Fusion proteins can also create chimeric molecules having more than one function. Finally, fusion proteins can increase solubility and/or stability of the fused protein compared to the non-fused protein. All of the types of fusion proteins described above can be made using techniques known in the art or by using or routinely modifying the following protocol, which outlines the fusion of a polypeptide to an IgG molecule.

Briefly, the human Fc portion of the IgG molecule can be PCR amplified, using primers that span the 5' and 3' ends of the sequence described below. These primers also preferably contain convenient restriction enzyme sites that will facilitate cloning into an expression vector, preferably a mammalian expression vector.

For example, if the pC4 (Accession No. 209646) expression vector is used, the human Fc portion can be ligated into the BamHI cloning site. Note that the 3' BamHI site should be destroyed. Next, the vector containing the human Fc portion is re-restricted with BamHI, linearizing the vector, and TR9 polynucleotide, isolated by the PCR protocol described in Example 1, is ligated into this BamHI site. Note that the polynucleotide is cloned without a stop codon, otherwise a fusion protein will not be produced.

If the naturally occurring signal sequence is used to produce the secreted protein, pC4 does not need a second signal peptide. Alternatively, if the naturally occurring signal sequence is not used, the vector can be modified to include a heterologous signal sequence. (See, e.g., WO 96/34891.)

Human IgG Fc Region:

Hybridomas, Elsevier, N.Y., pp. 563-681 (1981)). In general, an animal (preferably a mouse) is immunized with polypeptide(s) of the invention or, more preferably, with a secreted polypeptide-expressing cell. Such polypeptide-expressing cells are cultured in any suitable tissue culture medium, preferably in Earle's modified Eagle's medium supplemented with 10% fetal bovine serum (inactivated at about 56° C.), and supplemented with about 10 g/l of nonessential amino acids, about 1,000 U/ml of penicillin, and about 100 µg/ml of streptomycin.

The splenocytes of such mice are extracted and fused with a suitable myeloma cell line. Any suitable myeloma cell line may be employed in accordance with the present invention; however, it is preferable to employ the parent myeloma cell line (SP2O), available from the ATCC. After fusion, the resulting hybridoma cells are selectively maintained in HAT medium, and then cloned by limiting dilution as described by Wands et al. (Gastroenterology 80:225-232 (1981)). The hybridoma cells obtained through such a selection are then assayed to identify clones which secrete antibodies capable of binding the polypeptide(s) of the invention.

Alternatively, additional antibodies capable of binding to polypeptide(s) of the invention can be produced in a two-step procedure using anti-idiotypic antibodies. Such a method makes use of the fact that antibodies are themselves antigens,

```
GGGATCCGGAGCCCAAATCTTCTGACAAAACTCACACATGCCCACCGTGCCCAGCACCTGAAT    (SEQ ID NO: 27)

TCGAGGGTGCACCGTCAGTCTTCCTCTTCCCCCCAAAACCCAAGGACACCCTCATGATCTCCCGGACTC

CTGAGGTCACATGCGTGGTGGTGGACGTAAGCCACGAAGACCCTGAGGTCAAGTTCAACTGGTACGTG

GACGGCGTGGAGGTGCATAATGCCAAGACAAAGCCGCGGGAGGAGCAGTACAACAGCACGTACCGTG

TGGTCAGCGTCCTCACCGTCCTGCACCAGGACTGGCTGAATGGCAAGGAGTACAAGTGCAAGGTCTCC

AACAAAGCCCTCCCAACCCCCATCGAGAAAACCATCTCCAAAGCCAAAGGGCAGCCCCGAGAACCAC

AGGTGTACACCCTGCCCCCATCCCGGGATGAGCTGACCAAGAACCAGGTCAGCCTGACCTGCCTGGTC

AAAGGCTTCTATCCAAGCGACATCGCCGTGGAGTGGGAGAGCAATGGGCAGCCGGAGAACAACTACA

AGACCACGCCTCCCGTGCTGGACTCCGACGGCTCCTTCTTCCTCTACAGCAAGCTCACCGTGGACAAG

AGCAGGTGGCAGCAGGGGAACGTCTTCTCATGCTCCGTGATGCATGAGGCTCTGCACAACCACTACAC

GCAGAAGAGCCTCTCCCTGTCTCCGGGTAAATGAGTGCGACGGCCGCGACTCTAGAGGAT .
```

Example 11

Production of an Antibody

Hybridoma Technology

The antibodies of the present invention can be prepared by a variety of methods. (See, Current Protocols, Chapter 2.) As one example of such methods, cells expressing polypeptide(s) of the invention are administered to an animal to induce the production of sera containing polyclonal antibodies. In a preferred method, a preparation of polypeptide(s) of the invention is prepared and purified to render it substantially free of natural contaminants. Such a preparation is then introduced into an animal in order to produce polyclonal antisera of greater specific activity.

Monoclonal antibodies specific for polypeptide(s) of the invention are prepared using hybridoma technology. (Kohler et al., Nature 256:495 (1975); Kohler et al., Eur. J. Immunol. 6:511 (1976); Kohler et al., Eur. J. Immunol. 6:292 (1976); Hammerling et al., in: Monoclonal Antibodies and T-Cell and therefore, it is possible to obtain an antibody which binds to a second antibody. In accordance with this method, protein specific antibodies are used to immunize an animal, preferably a mouse. The splenocytes of such an animal are then used to produce hybridoma cells, and the hybridoma cells are screened to identify clones which produce an antibody whose ability to bind to the protein-specific antibody can be blocked by polypeptide(s) of the invention. Such antibodies comprise anti-idiotypic antibodies to the protein-specific antibody and are used to immunize an animal to induce formation of further protein-specific antibodies.

For in vivo use of antibodies in humans, an antibody is "humanized". Such antibodies can be produced using genetic constructs derived from hybridoma cells producing the monoclonal antibodies described above. Methods for producing chimeric and humanized antibodies are known in the art and are discussed herein. (See, for review, Morrison, Science 229:1202 (1985); Oi et al., BioTechniques 4:214 (1986); Cabilly et al., U.S. Pat. No. 4,816,567; Taniguchi et al., EP 171496; Morrison et al., EP 173494; Neuberger et al., WO 8601533; Robinson et al., WO 8702671; Boulianne et al., Nature 312:643 (1984); Neuberger et al., Nature 314:268 (1985).)

Isolation of Antibody Fragments Directed Against Polypeptide(s) from a Library of scFvs Naturally occurring V-genes isolated from human PBLs are constructed into a library of antibody fragments which contain reactivities against polypeptide(s) of the invention to which the donor may or may not have been exposed (see e.g., U.S. Pat. No. 5,885,793 incorporated herein by reference in its entirety).

Rescue of the Library.

A library of scFvs is constructed from the RNA of human PBLs as described in PCT publication WO 92/01047. To rescue phage displaying antibody fragments, approximately 109 E. coli harboring the phagemid are used to inoculate 50 ml of 2×TY containing 1% glucose and 100 µg/ml of ampicillin (2×TY-AMP-GLU) and grown to an O.D. of 0.8 with shaking. Five ml of this culture is used to innoculate 50 ml of 2×TY-AMP-GLU, 2×108 TU of delta gene 3 helper (M13 delta gene III, see PCT publication WO 92/01047) are added and the culture incubated at 37° C. for 45 minutes without shaking and then at 37° C. for 45 minutes with shaking. The culture is centrifuged at 4000 r.p.m. for 10 min. and the pellet resuspended in 2 liters of 2×TY containing 100 µg/ml ampicillin and 50 µg/ml kanamycin and grown overnight. Phage are prepared as described in PCT publication WO 92/01047.

M13 delta gene III is prepared as follows: M13 delta gene III helper phage does not encode gene III protein, hence the phage(mid) displaying antibody fragments have a greater avidity of binding to antigen. Infectious M13 delta gene III particles are made by growing the helper phage in cells harboring a pUC19 derivative supplying the wild type gene III protein during phage morphogenesis. The culture is incubated for 1 hour at 37° C. without shaking and then for a further hour at 37° C. with shaking. Cells are spun down (IEC-Centra 8,400 r.p.m. for 10 min), resuspended in 300 ml 2×TY broth containing 100 µg ampicillin/ml and 25 µg kanamycin/ml (2×TY-AMP-KAN) and grown overnight, shaking at 37° C. Phage particles are purified and concentrated from the culture medium by two PEG-precipitations (Sambrook et al., 1990), resuspended in 2 ml PBS and passed through a 0.45 µm filter (Minisart NML; Sartorius) to give a final concentration of approximately 1013 transducing units/ml (ampicillin-resistant clones).

Panning of the Library.

Immunotubes (Nunc) are coated overnight in PBS with 4 ml of either 100 µg/ml or 10 µg/ml of a polypeptide of the present invention. Tubes are blocked with 2% Marvel-PBS for 2 hours at 37° C. and then washed 3 times in PBS. Approximately 1013 TU of phage is applied to the tube and incubated for 30 minutes at room temperature tumbling on an over and under turntable and then left to stand for another 1.5 hours. Tubes are washed 10 times with PBS 0.1% Tween-20 and 10 times with PBS. Phage are eluted by adding 1 ml of 100 mM triethylamine and rotating 15 minutes on an under and over turntable after which the solution is immediately neutralized with 0.5 ml of 1.0M Tris-HCl, pH 7.4. Phage are then used to infect 10 ml of mid-log E. coli TG1 by incubating eluted phage with bacteria for 30 minutes at 37° C. The E. coli are then plated on TYE plates containing 1% glucose and 100 µg/ml ampicillin. The resulting bacterial library is then rescued with delta gene 3 helper phage as described above to prepare phage for a subsequent round of selection. This process is then repeated for a total of 4 rounds of affinity purification with tube-washing increased to 20 times with PBS, 0.1% Tween-20 and 20 times with PBS for rounds 3 and 4.

Characterization of Binders.

Eluted phage from the 3rd and 4th rounds of selection are used to infect E. coli HB 2151 and soluble scFv is produced (Marks, et al., 1991) from single colonies for assay. ELISAs are performed with microtitre plates coated with either 10 pg/ml of the polypeptide of the present invention in 50 mM bicarbonate pH 9.6. Clones positive in ELISA are further characterized by PCR fingerprinting (see, e.g., PCT publication WO 92/01047) and then by sequencing. These ELISA positive clones may also be further characterized by techniques known in the art, such as, for example, epitope mapping, binding affinity, receptor signal transduction, ability to block or competitively inhibit antibody/antigen binding, and competitive agonistic or antagonistic activity.

Example 12

Method of Determining Alterations in the TR9 Gene

RNA is isolated from entire families or individual patients presenting with a phenotype of interest (such as a disease). cDNA is then generated from these RNA samples using protocols known in the art. (See, Sambrook.) The cDNA is then used as a template for PCR, employing primers surrounding regions of interest in SEQ ID NO:1. Suggested PCR conditions consist of 35 cycles at 95° C. for 30 seconds; 60-120 seconds at 52-58° C.; and 60-120 seconds at 70° C., using buffer solutions described in Sidransky, D., et al., Science 252:706 (1991).

PCR products are then sequenced using primers labeled at their 5' end with T4 polynucleotide kinase, employing SequiTherm Polymerase. (Epicentre Technologies). The intron-exon borders of selected exons of TR9 are also determined and genomic PCR products analyzed to confirm the results. PCR products harboring suspected mutations in TR9 is then cloned and sequenced to validate the results of the direct sequencing.

PCR products of TR9 are cloned into T-tailed vectors as described in Holton, T. A. and Graham, M. W., Nucleic Acids Research, 19:1156 (1991) and sequenced with T7 polymerase (United States Biochemical). Affected individuals are identified by mutations in TR9 not present in unaffected individuals.

Genomic rearrangements are also observed as a method of determining alterations in the TR9 gene. Genomic clones isolated using techniques known in the art are nick-translated with digoxigenindeoxy-uridine 5'-triphosphate (Boehringer Manheim), and FISH performed as described in Johnson, Cg. et al., Methods Cell Biol. 35:73-99 (1991). Hybridization with the labeled probe is carried out using a vast excess of human cot-1 DNA for specific hybridization to the TR9 genomic locus.

Chromosomes are counterstained with 4,6-diamino-2-phenylindole and propidium iodide, producing a combination of C- and R-bands. Aligned images for precise mapping are obtained using a triple-band filter set (Chroma Technology, Brattleboro, Vt.) in combination with a cooled charge-coupled device camera (Photometrics, Tucson, Ariz.) and variable excitation wavelength filters. (Johnson, Cv. et al., Genet. Anal. Tech. Appl., 8:75 (1991).) Image collection, analysis and chromosomal fractional length measurements are performed using the ISee Graphical Program System. (Inovision Corporation, Durham, N.C.) Chromosome alterations of the genomic region of TR9 (hybridized by the probe)

are identified as insertions, deletions, and translocations. These TR9 alterations are used as a diagnostic marker for an associated disease.

Example 13

Method of Detecting Abnormal Levels of TR9 in a Biological Sample

TR9 polypeptides can be detected in a biological sample, and if an increased or decreased level of TR9 is detected, this polypeptide is a marker for a particular phenotype. Methods of detection are numerous, and thus, it is understood that one skilled in the art can modify the following assay to fit their particular needs.

For example, antibody-sandwich ELISAs are used to detect TR9 in a sample, preferably a biological sample. Wells of a microtiter plate are coated with specific antibodies to TR9, at a final concentration of 0.2 to 10 µg/ml. The antibodies are either monoclonal or polyclonal and are produced using technique known in the art. The wells are blocked so that non-specific binding of TR9 to the well is reduced.

The coated wells are then incubated for >2 hours at RT with a sample containing TR9. Preferably, serial dilutions of the sample should be used to validate results. The plates are then washed three times with deionized or distilled water to remove unbounded TR9.

Next, 50 ul of specific antibody-alkaline phosphatase conjugate, at a concentration of 25-400 ng, is added and incubated for 2 hours at room temperature. The plates are again washed three times with deionized or distilled water to remove unbounded conjugate.

75 ul of 4-methylumbelliferyl phosphate (MUP) or p-nitrophenyl phosphate (NPP) substrate solution is then added to each well and incubated 1 hour at room temperature to allow cleavage of the substrate and fluorescence. The fluorescence is measured by a microtiter plate reader. A standard curve is prepared using the experimental results from serial dilutions of a control sample with the sample concentration plotted on the X-axis (log scale) and fluorescence or absorbance on the Y-axis (linear scale). The TR9 polypeptide concentration in a sample is then interpolated using the standard curve based on the measured fluorescence of that sample.

Example 14

Method of Treating Decreased Levels of TR9

The present invention relates to a method for treating an individual in need of a decreased level of TR9 biological activity in the body comprising, administering to such an individual a composition comprising a therapeutically effective amount of TR9 antagonist. Preferred antagonists for use in the present invention are TR9-specific antibodies.

Moreover, it will be appreciated that conditions caused by a decrease in the standard or normal expression level of TR9 in an individual can be treated by administering TR9, preferably in a soluble and/or secreted form. Thus, the invention also provides a method of treatment of an individual in need of an increased level of TR9 polypeptide comprising administering to such an individual a pharmaceutical composition comprising an amount of TR9 to increase the biological activity level of TR9 in such an individual.

For example, a patient with decreased levels of TR9 polypeptide receives a daily dose 0.1-100 µg/kg of the polypeptide for six consecutive days. Preferably, the polypeptide is in a soluble and/or secreted form.

Example 15

Method of Treating Increased Levels of TR9

The present invention also relates to a method for treating an individual in need of an increased level of TR9 biological activity in the body comprising administering to such an individual a composition comprising a therapeutically effective amount of TR9 or an agonist thereof.

Antisense technology is used to inhibit production of TR9. This technology is one example of a method of decreasing levels of TR9 polypeptide, preferably a soluble and/or secreted form, due to a variety of etiologies, such as cancer.

For example, a patient diagnosed with abnormally increased levels of TR9 is administered intravenously antisense polynucleotides at 0.5, 1.0, 1.5, 2.0 and 3.0 mg/kg day for 21 days. This treatment is repeated after a 7-day rest period if the is determined to be well tolerated.

Example 16

Method of Treatment Using Gene Therapy—Ex Vivo

One method of gene therapy transplants fibroblasts, which are capable of expressing soluble and/or mature TR9 polypeptides, onto a patient. Generally, fibroblasts are obtained from a subject by skin biopsy. The resulting tissue is placed in tissue-culture medium and separated into small pieces. Small chunks of the tissue are placed on a wet surface of a tissue culture flask, approximately ten pieces are placed in each flask. The flask is turned upside down, closed tight and left at room temperature over night. After 24 hours at room temperature, the flask is inverted and the chunks of tissue remain fixed to the bottom of the flask and fresh media (e.g., Ham's F12 media, with 10% FBS, penicillin and streptomycin) is added. The flasks are then incubated at 37 degree C. for approximately one week.

At this time, fresh media is added and subsequently changed every several days. After an additional two weeks in culture, a monolayer of fibroblasts emerge. The monolayer is trypsinized and scaled into larger flasks.

pMV-7 (Kirschmeier, P. T. et al., DNA, 7:219-25 (1988)), flanked by the long terminal repeats of the Moloney murine sarcoma virus, is digested with EcoRI and HindIII and subsequently treated with calf intestinal phosphatase. The linear vector is fractionated on agarose gel and purified, using glass beads.

The cDNA encoding TR9 can be amplified using PCR primers which correspond to the 5' and 3' end encoding sequences respectively. Preferably, the 5' primer contains an EcoRI site and the 3' primer includes a HindIII site. Equal quantities of the Moloney murine sarcoma virus linear backbone and the amplified EcoRI and HindIII fragment are added together, in the presence of T4 DNA ligase. The resulting mixture is maintained under conditions appropriate for ligation of the two fragments. The ligation mixture is then used to transform E. coli HB101, which are then plated onto agar containing kanamycin for the purpose of confirming that the vector contains properly inserted TR9.

The amphotropic pA317 or GP+am12 packaging cells are grown in tissue culture to confluent density in Dulbecco's Modified Eagles Medium (DMEM) with 10% calf serum (CS), penicillin and streptomycin. The MSV vector containing the TR9 gene is then added to the media and the packaging cells transduced with the vector. The packaging cells now produce infectious viral particles containing the TR9 gene (the packaging cells are now referred to as producer cells).

Fresh media is added to the transduced producer cells, and subsequently, the media is harvested from a 10 cm plate of confluent producer cells. The spent media, containing the infectious viral particles, is filtered through a millipore filter to remove detached producer cells and this media is then used to infect fibroblast cells. Media is removed from a sub-confluent plate of fibroblasts and quickly replaced with the media from the producer cells. This media is removed and replaced with fresh media. If the titer of virus is high, then virtually all fibroblasts will be infected and no selection is required. If the titer is very low, then it is necessary to use a retroviral vector that has a selectable marker, such as neo or his. Once the fibroblasts have been efficiently infected, the fibroblasts are analyzed to determine whether TR9 protein is produced.

The engineered fibroblasts are then transplanted onto the host, either alone or after having been grown to confluence on cytodex 3 microcarrier beads.

Example 17

Method of Treatment Using Gene Therapy—In Vivo

Another aspect of the present invention is using in vivo gene therapy methods to treat disorders, diseases and conditions. The gene therapy method relates to the introduction of naked nucleic acid (DNA, RNA, and antisense DNA or RNA) TR9 sequences into an animal to increase or decrease the expression of the TR9 polypeptide. The TR9 polynucleotide may be operatively linked to a promoter or any other genetic elements necessary for the expression of the TR9 polypeptide by the target tissue. Such gene therapy and delivery techniques and methods are known in the art, see, for example, WO90/11092, WO98/11779; U.S. Pat. Nos. 5,693,622, 5,705,151, 5,580,859; Tabata H. et al., *Cardiovasc. Res.* 35:470-479 (1997); Chao J. et al., *Pharmacol. Res.* 35:517-522 (1997); Wolff J. A. *Neuromuscul. Disord.* 7:314-318 (1997); Schwartz B. et al., *Gene Ther.* 3:405-411 (1996); Tsurumi Y. et al., *Circulation* 94:3281-3290 (1996) (incorporated herein by reference).

The TR9 polynucleotide constructs may be delivered by any method that delivers injectable materials to the cells of an animal, such as, injection into the interstitial space of tissues (heart, muscle, skin, lung, liver, intestine and the like). The TR9 polynucleotide constructs can be delivered in a pharmaceutically acceptable liquid or aqueous carrier.

The term "naked" polynucleotide, DNA or RNA, refers to sequences that are free from any delivery vehicle that acts to assist, promote, or facilitate entry into the cell, including viral sequences, viral particles, liposome formulations, lipofectin or precipitating agents and the like. However, the TR9 polynucleotides may also be delivered in liposome formulations (such as those taught in Felgner P. L. et al. (1995) Ann. NY Acad. Sci. 772:126-139 and Abdallah B. et al. (1995) Biol. Cell 85(1):1-7) which can be prepared by methods well known to those skilled in the art.

The TR9 polynucleotide vector constructs used in the gene therapy method are preferably constructs that will not integrate into the host genome nor will they contain sequences that allow for replication. Any strong promoter known to those skilled in the art can be used for driving the expression of DNA. Unlike other gene therapies techniques, one major advantage of introducing naked nucleic acid sequences into target cells is the transitory nature of the polynucleotide synthesis in the cells. Studies have shown that non-replicating DNA sequences can be introduced into cells to provide production of the desired polypeptide for periods of up to six months.

The TR9 polynucleotide construct can be delivered to the interstitial space of tissues within the an animal, including of muscle, skin, brain, lung, liver, spleen, bone marrow, thymus, heart, lymph, blood, bone, cartilage, pancreas, kidney, gall bladder, stomach, intestine, testis, ovary, uterus, rectum, nervous system, eye, gland, and connective tissue. Interstitial space of the tissues comprises the intercellular fluid, mucopolysaccharide matrix among the reticular fibers of organ tissues, elastic fibers in the walls of vessels or chambers, collagen fibers of fibrous tissues, or that same matrix within connective tissue ensheathing muscle cells or in the lacunae of bone. It is similarly the space occupied by the plasma of the circulation and the lymph fluid of the lymphatic channels. Delivery to the interstitial space of muscle tissue is preferred for the reasons discussed below. They may be conveniently delivered by injection into the tissues comprising these cells. They are preferably delivered to and expressed in persistent, non-dividing cells which are differentiated, although delivery and expression may be achieved in non-differentiated or less completely differentiated cells, such as, for example, stem cells of blood or skin fibroblasts. In vivo muscle cells are particularly competent in their ability to take up and express polynucleotides.

For the naked TR9 polynucleotide injection, an effective dosage amount of DNA or RNA will be in the range of from about 0.05 g/kg body weight to about 50 mg/kg body weight. Preferably the dosage will be from about 0.005 mg/kg to about 20 mg/kg and more preferably from about 0.05 mg/kg to about 5 mg/kg. Of course, as the artisan of ordinary skill will appreciate, this dosage will vary according to the tissue site of injection. The appropriate and effective dosage of nucleic acid sequence can readily be determined by those of ordinary skill in the art and may depend on the condition being treated and the route of administration. The preferred route of administration is by the parenteral route of injection into the interstitial space of tissues. However, other parenteral routes may also be used, such as, inhalation of an aerosol formulation particularly for delivery to lungs or bronchial tissues, throat or mucous membranes of the nose. In addition, naked TR9 polynucleotide constructs can be delivered to arteries during angioplasty by the catheter used in the procedure.

The dose response effects of injected TR9 polynucleotide in muscle in vivo is determined as follows. Suitable TR9 template DNA for production of mRNA coding for TR9 polypeptide is prepared in accordance with a standard recombinant DNA methodology. The template DNA, which may be either circular or linear, is either used as naked DNA or complexed with liposomes. The quadriceps muscles of mice are then injected with various amounts of the template DNA.

Five to six week old female and male Balb/C mice are anesthetized by intraperitoneal injection with 0.3 ml of 2.5% Avertin. A 1.5 cm incision is made on the anterior thigh, and the quadriceps muscle is directly visualized. The TR9 template DNA is injected in 0.1 ml of carrier in a 1 cc syringe through a 27 gauge needle over one minute, approximately 0.5 cm from the distal insertion site of the muscle into the knee and about 0.2 cm deep. A suture is placed over the injection site for future localization, and the skin is closed with stainless steel clips.

After an appropriate incubation time (e.g., 7 days) muscle extracts are prepared by excising the entire quadriceps. Every fifth 15 um cross-section of the individual quadriceps muscles is histochemically stained for TR9 protein expression. A time course for TR9 protein expression may be done in a similar fashion except that quadriceps from different mice are harvested at different times. Persistence of TR9 DNA in muscle

Example 18

Effect of TR9 on the Expression of MHC Class II, Costimulatory and Adhesion Molecules and Cell Differentiation of Monocytes and Monocyte-Derived Human Dendritic Cells Dendritic cells are generated by the expansion of proliferating precursors found in the peripheral blood: adherent PBMC or elutriated monocytic fractions are cultured for 7-10 days with GM-CSF (50 ng/ml) and IL-4 (20 ng/ml). These dendritic cells have the characteristic phenotype of immature cells (expression of CD1, CD80, CD86, CD40 and MHC class II antigens). Treatment with activating factors, such as TNF-α, causes a rapid change in surface phenotype (increased expression of MHC class I and II, costimulatory and adhesion molecules, downregulation of FCγRII, upregulation of CD83). These changes correlate with increased antigen-presenting capacity and with functional maturation of the dendritic cells.

FACS analysis of surface antigens is performed as follows. Cells are treated 1-3 days with increasing concentrations of TR9 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Effect on the Production of Cytokines.

Cytokines generated by dendritic cells, in particular IL-12, are important in the initiation of T-cell dependent immune responses. IL-12 strongly influences the development of Th1 helper T-cell immune response, and induces cytotoxic T and NK cell function. An ELISA is used to measure the IL-12 release as follows. Dendritic cells ($10^6$/ml) are treated with increasing concentrations of TR9 for 24 hours. LPS (100 ng/ml) is added to the cell culture as positive control. Supernatants from the cell cultures are then collected and analyzed for IL-12 content using commercial ELISA kit (e.g., R & D Systems (Minneapolis, Minn.)). The standard protocols provided with the kits are used.

Effect on the expression of MHC Class II, costimulatory and adhesion molecules. Three major families of cell surface antigens can be identified on monocytes: adhesion molecules, molecules involved in antigen presentation, and Fc receptor. Modulation of the expression of MHC class II antigens and other costimulatory molecules, such as B7 and ICAM-1, may result in changes in the antigen presenting capacity of monocytes and ability to induce T cell activation. Increase expression of Fc receptors may correlate with improved monocyte cytotoxic activity, cytokine release and phagocytosis.

FACS analysis is used to examine the surface antigens as follows. Monocytes are treated 1-5 days with increasing concentrations of TR9 or LPS (positive control), washed with PBS containing 1% BSA and 0.02 mM sodium azide, and then incubated with 1:20 dilution of appropriate FITC- or PE-labeled monoclonal antibodies for 30 minutes at 4° C. After an additional wash, the labeled cells are analyzed by flow cytometry on a FACScan (Becton Dickinson).

Monocyte Activation and/or Increased Survival.

Assays for molecules that activate (or alternatively, inactivate) monocytes and/or increase monocyte survival (or alternatively, decrease monocyte survival) are known in the art and may routinely be applied to determine whether a molecule of the invention functions as an inhibitor or activator of monocytes. TR9, agonists, or antagonists of TR9 can be screened using the three assays described below. For each of these assays, Peripheral blood mononuclear cells (PBMC) are purified from single donor leukopacks (American Red Cross, Baltimore, Md.) by centrifugation through a Histopaque gradient (Sigma). Monocytes are isolated from PBMC by counterflow centrifugal elutriation.

1. Monocyte Survival Assay. Human peripheral blood monocytes progressively lose viability when cultured in absence of serum or other stimuli. Their death results from internally regulated process (apoptosis). Addition to the culture of activating factors, such as TNF-alpha dramatically improves cell survival and prevents DNA fragmentation. Propidium iodide (PI) staining is used to measure apoptosis as follows. Monocytes are cultured for 48 hours in polypropylene tubes in serum-free medium (positive control), in the presence of 100 ng/ml TNF-alpha (negative control), and in the presence of varying concentrations of the compound to be tested. Cells are suspended at a concentration of $2\times10^6$/ml in PBS containing PI at a final concentration of 5 µg/ml, and then incubated at room temperature for 5 minutes before FAC Scan analysis. PI uptake has been demonstrated to correlate with DNA fragmentation in this experimental paradigm.

2. Effect on cytokine release. An important function of monocytes/macrophages is their regulatory activity on other cellular populations of the immune system through the release of cytokines after stimulation. An ELISA to measure cytokine release is performed as follows. Human monocytes are incubated at a density of $5\times10^5$ cells/ml with increasing concentrations of TR9 and under the same conditions, but in the absence of TR9. For IL-12 production, the cells are primed overnight with IFN-□ (100 U/ml) in presence of TR9. LPS (10 ng/ml) is then added. Conditioned media are collected after 24 h and kept frozen until use. Measurement of TNF-□, IL-10, MCP-1 and IL-8 is then performed using a commercially available ELISA kit (e.g., R & D Systems (Minneapolis, Minn.)) applying the standard protocols provided with the kit.

3. Oxidative burst. Purified monocytes are plated in 96-well plate at $2-1\times10^5$ cell/well. Increasing concentrations of TR9 are added to the wells in a total volume of 0.2 ml culture medium (RPMI 1640+10% FCS, glutamine and antibiotics). After 3 days incubation, the plates are centrifuged and the medium is removed from the wells. To the macrophage monolayers, 0.2 ml per well of phenol red solution (140 mM NaCl, 10 mM potassium phosphate buffer pH 7.0, 5.5 mM dextrose, 0.56 mM phenol red and 19 U/ml of HRPO) is added, together with the stimulant (200 nM PMA). The plates are incubated at 37° C. for 2 hours and the reaction is stopped by adding 20 µl 1N NaOH per well. The absorbance is read at 610 nm. To calculate the amount of $H_2O_2$ produced by the macrophages, a standard curve of a $H_2O_2$ solution of known molarity is performed for each experiment.

The studies described in this example tested activity in TR9 protein. However, one skilled in the art could easily modify the exemplified studies to test the activity of TR9 polynucleotides (e.g., gene therapy), agonists, and/or antagonists of TR9.

It will be clear that the invention may be practiced otherwise than as particularly described in the foregoing description and examples.

Numerous modifications and variations of the present invention are possible in light of the above teachings and, therefore, are within the scope of the appended claims.

The entire disclosure of all publications (including patents, patent applications, journal articles, laboratory manuals, books, or other documents) cited herein are hereby incorporated by reference.

Further, the Sequence Listing submitted herewith, and the Sequence Listing submitted with U.S. Provisional Application Ser. No. 60/126,019, filed on Mar. 24, 1999; U.S. Provisional Application Ser. No. 60/134,220, filed on May 14, 1999, U.S. application Ser. No. 09/095,094, filed on Jun. 10, 1998; and U.S. Provisional Application Ser. No. 60/052,991, filed on Jun. 11, 1997, in both computer and paper forms, are each hereby incorporated by reference in its entirety.

What is claimed is:

1. An isolated antibody or fragment thereof that specifically binds to a polypeptide selected from the group consisting of:
   (a) a polypeptide consisting of amino acid residues 1 to 615 of SEQ ID NO:2;
   (b) a polypeptide consisting of amino acid residues 1 to 310 of SEQ ID NO:2;
   (c) a polypeptide consisting of the mature form of the polypeptide encoded by the cDNA contained in ATCC Deposit Number 209037; and
   (d) a polypeptide consisting of the extracellular domain of the polypeptide encoded by the cDNA contained in ATCC Deposit Number 209037.

2. The antibody or fragment thereof of claim 1 wherein said antibody or fragment thereof enhances the apoptotic activity of TR9.

3. The antibody or fragment thereof of claim 1 wherein said antibody or fragment thereof inhibits the apoptotic activity of TR9.

4. The antibody or fragment thereof of claim 1 wherein polypeptide bound by said antibody or fragment thereof is glycosylated.

5. The antibody or fragment thereof of claim 1 wherein said antibody or fragment thereof is polyclonal.

6. The antibody or fragment thereof of claim 1 wherein said antibody or fragment thereof is monoclonal.

7. The antibody or fragment thereof of claim 1 which is selected from the group consisting of:
   (a) a chimeric antibody or fragment thereof;
   (b) a humanized antibody or fragment thereof;
   (c) a human antibody or fragment thereof;
   (d) a single chain antibody; and
   (e) a Fab fragment.

8. The antibody or fragment thereof of claim 1 which is labeled.

9. The antibody or fragment thereof of claim 8 wherein said label is selected from the group consisting of:
   (a) an enzyme,
   (b) a fluorescent label; and
   (c) a radioisotope.

10. The antibody or fragment thereof of claim 1 wherein said antibody or fragment thereof specifically binds to said polypeptide in a Western blot or an ELISA.

11. The antibody or fragment thereof of claim 1 wherein the amino acid sequence of said polypeptide consists of amino acid residues 1 to 310 of SEQ ID NO:2.

12. An isolated cell that produces the antibody or fragment thereof of claim 1.

13. A hybridoma that produces the antibody or fragment thereof of claim 1.

14. A composition comprising the antibody or fragment thereof of claim 1 and a pharmaceutically acceptable carrier.

15. A method of producing the antibody or fragment thereof of claim 1 comprising:
 (a) immunizing an animal with a polypeptide consisting of amino acids 1-615 of SEQ ID NO:2 or an epitope bearing fragment thereof; and
 (b) recovering said antibody or fragment thereof.

16. A method of detecting TR9 polypeptide in a biological sample comprising:
 (a) contacting said biological sample with the antibody or fragment thereof of claim 1; and
 (b) detecting the antibody or fragment thereof bound to said TR9 polypeptide, thereby detecting said TR9 polypeptide in said biological sample.

* * * * *